US012480103B2

(12) United States Patent
Montasser et al.

(10) Patent No.: US 12,480,103 B2
(45) Date of Patent: Nov. 25, 2025

(54) B4GALT1 VARIANTS AND USES THEREOF

(71) Applicants: Regeneron Pharmaceuticals, Inc., Tarrytown, NY (US); University of Maryland, Baltimore, Baltimore, MD (US)

(72) Inventors: May Montasser, Baltimore, MD (US); Cristopher Van Hout, Tarrytown, NY (US); Alan Shuldiner, Tarrytown, NY (US); Giusy Della Gatta, Tarrytown, NY (US); Matthew Healy, Tarrytown, NY (US); Marja Puurunen, Tarrytown, NY (US)

(73) Assignees: Regeneron Pharmaceuticals, Inc., Tarrytown, NY (US); University of Maryland, Baltimore, Baltimore, MD (US)

( * ) Notice: Subject to any disclaimer, the term of this patent is extended or adjusted under 35 U.S.C. 154(b) by 1396 days.

(21) Appl. No.: 16/919,423

(22) Filed: Jul. 2, 2020

(65) Prior Publication Data

US 2020/0399617 A1 Dec. 24, 2020

Related U.S. Application Data

(63) Continuation of application No. 15/996,892, filed on Jun. 4, 2018, now Pat. No. 10,738,284.

(60) Provisional application No. 62/659,344, filed on Apr. 18, 2018, provisional application No. 62/550,161, filed on Aug. 25, 2017, provisional application No. 62/515,140, filed on Jun. 5, 2017.

(51) Int. Cl.
*C12N 9/10* (2006.01)
*C12N 15/86* (2006.01)

(52) U.S. Cl.
CPC .......... *C12N 9/1051* (2013.01); *C12N 15/86* (2013.01); *C12Y 204/01133* (2013.01)

(58) Field of Classification Search
CPC ................. C12N 9/1051; C12N 15/86; C12Y 204/01133
See application file for complete search history.

(56) References Cited

U.S. PATENT DOCUMENTS

| | | | |
|---|---|---|---|
| 7,374,927 | B2 | 5/2008 | Palma et al. |
| 2012/0295815 | A1 | 11/2012 | Lindahl et al. |

FOREIGN PATENT DOCUMENTS

| | | |
|---|---|---|
| RU | 2444378 | 3/2012 |
| WO | 2005108415 | 11/2005 |
| WO | 2009025645 | 2/2009 |
| WO | 2009102820 | 8/2009 |
| WO | 2018226560 | 12/2018 |

OTHER PUBLICATIONS

Cardiovascular Diseases WebMD, Feb. 12, 2024, www.webmd.com/heart-disease/diseases-cardiovascular. Accessed online Apr. 23, 2024. (Year: 2024).*

Lee, K., Conboy, M., Park, H.M. et al. Nanoparticle delivery of Cas9 ribonucleoprotein and donor DNA in vivo induces homology-directed DNA repair. Nat Biomed Eng 1, 889-901 (2017). https://doi.org/10.1038/s41551-017-0137-2 (Year: 2017).*

Chang Liu, Li Zhang, Hao Liu, Kun Cheng, Delivery strategies of the CRISPR-Cas9 gene-editing system for therapeutic applications, Journal of Controlled Release, vol. 266, 2017, pp. 17-26, ISSN 0168-3659 (Year: 2017).*

Luther, D. C., Lee, Y. W., Nagaraj, H., Scaletti, F., & Rotello, V. M. (2018). Delivery approaches for CRISPR/Cas9 therapeutics in vivo: advances and challenges. Expert Opinion on Drug Delivery, 15(9), 905-913. https://doi.org/10.1080/17425247.2018.1517746 (Year: 2018).*

B4GALT1[gene]—ClinVar. Accessed online Apr. 26, 2024. (Year: 2024).*

Yazdanyar A, Newman AB. The burden of cardiovascular disease in the elderly: morbidity, mortality, and costs. Clin Geriatr Med. Nov. 2009;25(4):563-77, vii. doi: 10.1016/j.cger.2009.07.007. PMID: 19944261; PMCID: PMC2797320. (Year: 2009).*

M.A.W. van den Boogert et al. Genetic defects in protein glycosylation as a cause of dyslipidemia, Atherosclerosis, vol. 235, Issue 2, 2014, p. e18, ISSN 0021-9150, https://doi.org/10.1016/j.atherosclerosis.2014.05.021. (Year: 2014).*

Juppner et al. Bone. vol. 17, No. 2 Supplement. Aug. 1995, 39S-42S. (Year: 1995).*

Mohammadsharif Tabebordbar et al. ,In vivo gene editing in dystrophic mouse muscle and muscle stem cells. Science351,407-411(2016). DOI:10.1126/science.aad5177 (Year: 2016).*

Nelson CE et al. In vivo genome editing improves muscle function in a mouse model of Duchenne muscular dystrophy. Science. Jan. 22, 2016;351(6271):403-7. doi: 10.1126/science.aad5143. Epub Dec. 31, 2015. PMID: 26721684; PMCID: PMC4883596. (Year: 2015).*

Long C, Amoasii L, Mireault AA, McAnally JR, Li H, Sanchez-Ortiz E, Bhattacharyya S, Shelton JM, Bassel-Duby R, Olson EN. Postnatal genome editing partially restores dystrophin expression in a mouse model of muscular dystrophy. Science. Jan. 22, 2016;351(6271):400-3. (Year: 2015).*

Nami F, Basiri M, Satarian L, Curtiss C, Baharvand H, Verfaillie C. Strategies for In Vivo Genome Editing in Nondividing Cells. Trends Biotechnol. Aug. 2018;36(8):770-786. doi: 10.1016/j.tibtech.2018.03.004. Epub Apr. 21, 2018. PMID: 29685818. (Year: 2018).*

(Continued)

*Primary Examiner* — Brian Whiteman
*Assistant Examiner* — Amanda M Zahorik
(74) *Attorney, Agent, or Firm* — Armstrong Teasdale LLP

(57) ABSTRACT

Variant B4GALT1 genomic, mRNA, and cDNA nucleic acid molecules, and polypeptides, methods of detecting the presence of these molecules, methods of modulating endogenous B4GALT1 genomic, mRNA, and cDNA nucleic acid molecules, and polypeptides, methods of ascertaining the risk of developing cardiovascular conditions by detecting the presence or absence of the variant B4GALT1 genomic, mRNA, and cDNA nucleic acid molecules, and polypeptides, and methods of treating cardiovascular conditions are provided herein.

14 Claims, 25 Drawing Sheets

Specification includes a Sequence Listing.

(56) References Cited

OTHER PUBLICATIONS

Human Protein Atlas. (n.d.). Tissue expression of B4GALT1—summary—The human protein atlas. https://www.proteinatlas.org/ENSG00000086062-B4GALT1/tissue (Year: 2024).*
Van den Boogert et al. Genetic defects in protein glycosylation as a cause of dyslipidemia. Genomics and proteomics of lipid metabolism, vol. 235, Issue 2, E18, Aug. 2014. (Year: 2014).*
Hansske et al. Deficiency of UDP-galactose: N-acetylglucosamine beta-1,4-galactosyltransferase 1 causes the congenital disorder of glycosylation type IId. J. Clin. Invest. 109: 725-733, 2002. (Year: 2002).*
Database EMBL, "Sequence 357811 from patent U.S. Pat. No. 7,374,927", 2008, EBI: EM_PAT:GC157811.
Database Geneseq, "Human membrane protein cDNA, SEQ ID No. 492, probe SEQ ID No. 2784", 2008, GSN: AEE00070.
EMBL Database, Database accession No. AL161445, 20000316, "Human DNA sequence from clone RP11-326F20 on chromosome 9", 2000.
Mariuzza et al., "The structural basis of antigen-antibody recognition", Ann Rev Biophys Chem, 1987, 16, pp. 139-159.
Pakula et al., "Genetic analysis of protein stability and function", Anna Rev Genet, 1989, 23, pp. 289-310.
Keskin et al., "A new, structurally nonredundant, diverse data set of protein-protein interfaces and its implications", Protein Sci, 2004, 13(4), pp. 1043-1055.
Anonymous, "SNP Detail rs27801608", 2005, http://www.infomatics.jax.org/snp/rs27801608.
Asano et al., "Growth retardation and early death of beta-1,4-galactosyltransferase knockout mice with augmented proliferation and abnormal differentiation of epithelial cells", The EMBO Journal, 1997, 16(8), pp. 1850-1857.
Landers et al., "Porcine beta-1,4-galactosyltransferase-I Sequence and Expression", Reprod Dom Anim, 2009, 44(2), pp. 228-234.
Lee et al., "Genome editing methods in animal models", Animal Cells and Systems, 2020, 24(1), pp. 8-16.
Platt et al., "CRISPR-Cas9 knockin mice for genome editing and cancer modeling", Cell, 2014, 159(2), pp. 440-455.
Montasser et al., "Genetic and functional evidence relates a missense variant in B4GALT1 to lower LDL-C and fibrinogen", bioRxiv, 2019, pp. 1-17.
Rodeheffer et al., "Targeted mutations in beta-1,4-galactosyltransferase I reveal its multiple cellular functions", Biochimica et Biophysica Acta, 2002, 1573 (3), pp. 258-270.
Singh et al., "Efficient In Vivo Liver-Directed Gene Editing Using CRISPR/Cas9", Molecular Therapy, 2018, 26(5), pp. 1241-1254.
International Search Report and Written Opinion mailed May 20, 2021 for International Patent Application No. PCT/US2021/020579.
NCBI Reference sequence NM_022305.4 (6 pages) (Dec. 28, 2019).
NCBI Reference sequence NM_053287.1 (4 pages) (Apr. 11, 2021).
Lu et al., "Targeted Mutation in b1,4-Galactosyltransferase Leads to Pituitary Insufficiency and Neonatal Lethality", Developmental Biology, 1997, 181, pp. 257-267.
Lu et al., "Sperm from b1,4-Galactosyltransferase-null mice are refractory to ZP3-induced acrosome reactions and penetrate the zona pellucida poorly", Developmental Biology, 1997, 181, pp. 4121-4131.
NCBI Reference sequence NP_071641.1 (3 pages) (Apr. 21, 2021).
NCBI Reference sequence NP_001488.2 (4 pages) (May 9, 2021).
BLAST Alignment (Mouse and human B4galt1 aligned).
Anonymous, "dbSNP Detail ss1665638970", 2015, NCBI dsSNP Short genetic variations, pp. 1.
Database Geneseq, "Human mutant beta-4Gal-T1-M34OH-Y285L DNA SEQ ID:1", 2009, GSN: AWI43668.
Database Geneseq, "Encodes a HeLa cell galactosyltransferase enzyme", 1993, XP-0027884507.
Database EMBL, "Human DNA sequence from clone RP11-326F20 on chromosome 9", 2000, XP-002784508.
Database Genseq, "LNCap cells/CL1 cells expressed protein, SED ID 1153", 2015, XP-002784509.
Database Geneseq, "Beta-1,4 galactosyltransferase (beta 4Gal-T1) CDS, SEQ ID:1", 2009, XP-002784510.
Humphreys et al., "Isolation and Immunologic Characterization of a Human B-lymphocyte-specific, cell surface antigen", Journal of Experimental Medicine, 1976, pp. 98-112.
Machingo et al., "A β1,4-galactosyltransferase is required for convergent extension movements in zebrafish", Developmental Biology, 2006, 297, pp. 471-482.
Qasba et al., "Structure and function of beta-1,4-galactosyltransferase 1", Curr Drug Targets, 2008, 9(4), pp. 292-309.
Shen et al., "Familial Defective Apolopoprotein B-100 and Increased Low-Density Lipoprotein Cholesterol and Coronary Artery Calcification in the Old Order Amish", Arch Intern Med, 2010, 170(20), pp. 1850-1855.
Willer et al., "Newly identified loci that influence lipid concentrations and risk of coronary artery disease", Nature Genetics, 2008, 40(2), pp. 1061-4036.
Database Geneseq, "*Homo sapiens* beta-1,4-galactosyltransferase 1 (B4GALT1), mRNA", 2016, NCBI Reference Sequence: NM_001497.3.
Alves et al., "Optimizing Chinese hamster ovary cell line development via targeted control of N-glycosylation", Pharmaceutical Bioprocessing, 2015, 3(7), pp. 1-19.

* cited by examiner

| Haplotype | Copies | 9:31523876 | 9:31599161 | 9:31853653 | 9:32231857 | rs551564683 | 9:33892787 | 9:33971380 |
|---|---|---|---|---|---|---|---|---|
| A | 115 | 1 | 1 | 1 | 1 | 1 | 1 | 1 |
| B | 7 | 1 | 1 | 1 | 1 | 1 | 0 | 0 |
| C | 6 | 0 | 0 | 0 | 0 | 1 | 1 | 1 |
| Haplotype | Copies | 9:33991394 | 9:34066623 | 9:34277757 | 9:34520551 | 9:34860994 | 9:35178756 | 9:35570095 |
| A | 115 | 1 | 1 | 1 | 1 | 1 | 1 | 1 |
| B | 7 | 0 | 0 | 0 | 0 | 0 | 0 | 0 |
| C | 6 | 1 | 1 | 1 | 1 | 1 | 1 | 1 |

Figure 3

| Population | AAF |
|---|---|
| UMD Amish Research Clinic (Amish, 5k) | 0.061 |
| Clinic for Special Children (Amish and Mennonite, 2k) | 0.018 |
| National Institute of Mental illness (Amish, 460) | 0.003 |
| Geisinger Health Center (66k) | 0.000053 |
| All RGC (130k) | 0.0025 |
| ExAC (60k) | 0 |
| deCode (Iceland, 2.5k WGS) | <0.005 |

| Population | Population size | # HET carriers | # HOM carriers | AAF |
|---|---|---|---|---|
| BCH | 580 | 0 | 0 | 0.000000 |
| CNCD | 96 | 0 | 0 | 0.000000 |
| COL-CHUNG | 4064 | 0 | 0 | 0.000000 |
| COL-CHUNG_FBC | 1193 | 0 | 0 | 0.000000 |
| CSC | 2084 | 65 | 5 | 0.017994 |
| DHS | 4654 | 0 | 0 | 0.000000 |
| DRIFT-NIMH | 460 | 3 | 0 | 0.002081 |
| DUKE | 8783 | 2 | 0 | 0.000114 |
| ECO | 858 | 0 | 0 | 0.000000 |
| GHS | 66216 | 7 | 0 | 0.000053 |
| IOWA | 58 | 0 | 0 | 0.000000 |
| MADGC | 2393 | 1 | 0 | 0.000209 |
| MARIO | 127 | 0 | 0 | 0.000000 |
| NIAID | 95 | 0 | 0 | 0.000000 |
| SIMONS | 96 | 0 | 0 | 0.000000 |
| SINAI | 96 | 0 | 0 | 0.000000 |
| TAICHI | 13963 | 0 | 0 | 0.000000 |
| TSK | 3407 | 0 | 0 | 0.000000 |
| UCHC | 1039 | 0 | 0 | 0.000000 |
| UMD | 4725 | 548 | 13 | 0.060741 |
| UPENN | 11451 | 1 | 0 | 0.000044 |
| UTAH | 3688 | 0 | 0 | 0.000000 |
| Total | 130126 | 627 | 18 | 0.002548 |

Figure 5B

| Phenotype | Genotypic Means* | Genotypic Means Unadjusted | Counts (Ref/Het/Alt) | Effect (95% CI) | Pvalue |
|---|---|---|---|---|---|
| Serum lipids | | | | | |
| Cholesterol, mg/dL | 210.6 / 190.9 / 172.7 | 210.4 / 192.3 / 176.2 | 3995/527/12 | -17.18 (-22.4, -11.95) | 1.3E-10 |
| LDL, mg/dL | 134.7 / 117.4 / 103.5 | 134.6 / 118.3 / 103.5 | 3991/526/12 | -14.61 (-19.37, -9.86) | 1.8E-09 |
| HDL, mg/dL | 61.4 / 59.4 / 58.6 | 61.3 / 59.6 / 61.6 | 3995/527/12 | -2.14 (-3.88, -0.41) | 0.0155 |
| Triglycerides (log10), mg/dL | 73.9 / 72.9 / 72.7 | 71.9 / 72.0 / 55.8 | 3995/527/12 | -3.39 (-8.17,1.62) % | 0.1760 |
| Chol/HDL (log10) | 3.39 / 3.15 / 2.94 | 3.39 / 3.16 / 2.87 | 3318/450/11 | -6.67 (-8.80, -2.28) % | 0.0003 |
| NonHDL Cholesterol ,mg/dL | 161.5 / 144.5 / 91.1 | 161.0 / 149.0 / 99.0 | 727/87/1 | -14.33 (-23.57, -5.08) | 0.0025 |

0.0774* Genotypic means are on the clinical scale, removing the effects of Age, Age2, Sex, and Study
** Also adjusted for BMI
*** Result generated at UMD in a model with Age Sex, Study as covariates.

Figure 6

| Phenotype | Genotypic Means* | Genotypic Means Unadjusted | Counts (Ref/Het/Alt) | Effect (95% CI) | Pvalue |
|---|---|---|---|---|---|
| CAD-related traits | | | | | |
| Coronary Calcification (log10) | 0.301 / 0.201 / NA | 0.298 / 0.220 / NA | 202/42/0 | -22.4 (-38.3, -0.92) % | 0.0433 |
| Coronary Calcification (log10)*** | 1.87 / 1.44 / 0 | NA | 546/94/1 | -19 % | 0.1349 |
| Pericardial Fat** | 69.5 / 82.7 / NA | 71.5 / 71.4 / NA | 148/27/0 | 12.76 (1.06, 24.46) | 0.0339 |
| | | | | | |
| Liver traits | | | | | |
| AST (log10), U/L | 18.0 / 18.6 / 35.2 | 18.0 / 18.7 / 34.3 | 3910/517/12 | 7.15 (4.71, 12.20) % | 6.0E-08 |
| ALT (log10), U/L | 17.2 / 16.9 / 20.3 | 17.2 / 16.9 / 19.7 | 3978/530/13 | -0.23 (-4.50, 4.71) % | 0.8920 |
| AlkPhos (log10), U/L | 53.8 / 52.9 / 62.9 | 53.8 / 53.1 / 61.8 | 3987/531/13 | 0.92 (-3.87, 2.09) % | 0.5391 |
| Liver fat (by EBCT) | 1.27 / 1.33 / NA | 1.27 / 1.32 / NA | 166/38/0 | 0.05 (-0.005, 0.110) | |

0.0774* Genotypic means are on the clinical scale, removing the effects of Age, Age2, Sex, and Study
** Also adjusted for BMI
*** Result generated at UMD in a model with Age Sex, Study as covariates.

Figure 6 (cont.)

*B4GALT1* ASN352SER IS HIGHLY ASSOCIATED WITH SERUM LIPIDS AND AST
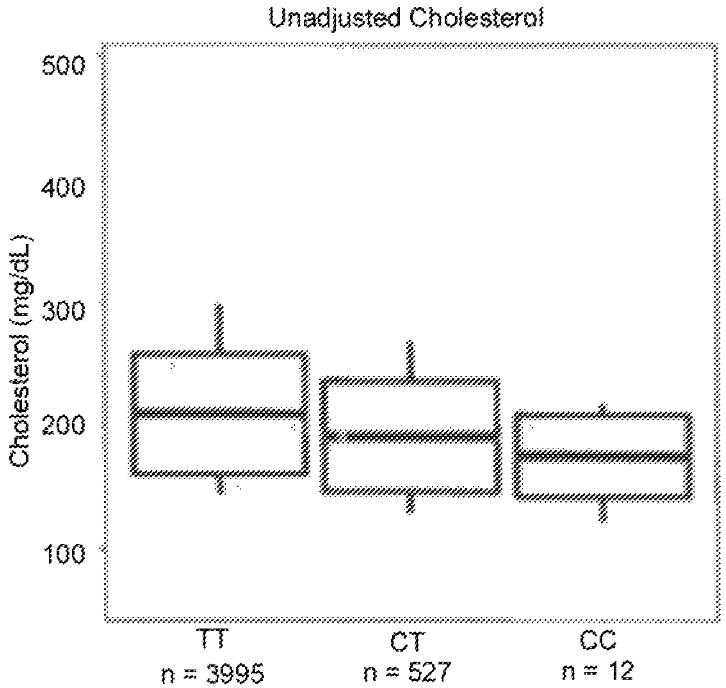
| Model | Effect | PValue | Genotypic Means |
|---|---|---|---|
| Unadjusted | -17.0 | 1.01E-09 | 210.4/192.3/176.2 |
| w/ Covars* | -17.2 | 1.30E-10 | 210.6/190.9/172.7 |
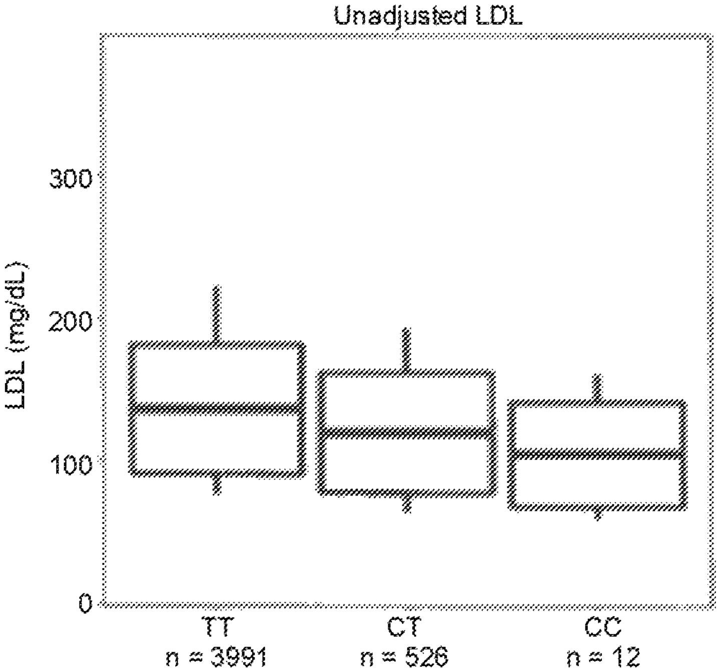
| Model | Effect | PValue | Genotypic Means |
|---|---|---|---|
| Unadjusted | -14.5 | 9.35E-09 | 134.6/118.3/103.5 |
| w/ Covars* | -14.6 | 1.84E-09 | 134.7/117.4/103.5 |
*Statistical models account for Age, $Age^2$, Sex, and Study; further adjustment for R3527Q *APOB* does not appreciably alter results; AST normal reference range = 10-35 U/L
Figure 7A
Figure 7B

*B4GALT1* ASN352SER IS HIGHLY ASSOCIATED WITH SERUM LIPIDS AND AST

| Model | Effect | PValue | Genotypic Means |
|---|---|---|---|
| Unadjusted | 7.9% | 2.10E-07 | 17.99/18.66/34.28 |
| w/ Covars* | 7.9% | 6.02E-08 | 17.99/18.62/35.25 |

*Statistical models account for Age, Age$^2$, Sex, and Study; further adjustment for R3527Q *APOB* does not appreciably alter results; AST normal reference range = 10-35 U/L

*B4GALT1* ASN352SER IS ASSOCIATED WITH DECREASES IN ALL LIPID SUBFRACTIONS
(AMISH HAPI HEART STUDY)

| Phenotype | Genotypic Means* | Genotypic Means Unadjusted | Counts(Ref/Het/Alt) | Effect | Pvalue |
|---|---|---|---|---|---|
| HDL2, mg/dL | 15.9 / 13.5 / 19.6 | 15.9 / 13.7 / 21.0 | 660/74/1 | -2.07 (-3.68, -0.46) | 0.012 |
| HDL2a, mg/dL | 11.2 / 9.7 / 15.3 | 11.2 / 9.8 / 16.4 | 660/74/1 | -1.23 (-2.38, -0.09) | 0.036 |
| HDL2b, mg/dL | 3.2 / 2.9 / 3.6 | 3.2 / 2.9 / 3.9 | 660/74/1 | -0.33 (-0.73, 0.08) | 0.113 |
| HDL2c, mg/dL | 1.5 / 1.1 / 0.1 | 1.5 / 1.1 / 0.2 | 660/74/1 | -0.47 (-0.87, -0.07) | 0.023 |
| HDL3, mg/dL | 39.5 / 36.8 / 39.3 | 39.4 / 37.1 / 41.0 | 660/74/1 | -2.48 (-4.23, -0.72) | 0.006 |
| HDL3a, mg/dL | 14.8 / 12.8 / 17.1 | 14.8 / 12.9 / 18.3 | 660/74/1 | -1.73 (-3, -0.47) | 0.007 |
| HDL3b, mg/dL | 6.2 / 6.4 / 5.8 | 6.2 / 6.4 / 5.9 | 660/74/1 | 0.09 (-0.3, 0.49) | 0.640 |
| HDL3c, mg/dL | 9.5 / 9 / 9.3 | 9.5 / 9.0 / 9.7 | 660/74/1 | -0.49 (-0.96, -0.03) | 0.037 |
| HDL3d, mg/dL | 9 / 8.7 / 7.5 | 8.9 / 8.7 / 7.5 | 660/74/1 | -0.34 (-0.7, 0.03) | 0.070 |
| LDL1, mg/dL | 22.8 / 20.2 / 15.2 | 22.7 / 20.9 / 17.4 | 660/74/1 | -3.17 (-5.89, -0.45) | 0.023 |
| LDL2, mg/dL | 48.3 / 39.4 / 32.1 | 48.2 / 39.7 / 34.4 | 660/74/1 | -8.43 (-14.47, -2.38) | 0.006 |
| LDL3, mg/dL | 45.7 / 43.2 / 18.2 | 45.4 / 44.4 / 18.3 | 660/74/1 | -1.69 (-6.77, 3.38) | 0.513 |
| LipoproteinA, mg/dL | 7.7 / 6.6 / 11.6 | 7.7 / 6.7 / 12.0 | 660/74/1 | -0.66 (-1.56, 0.24) | 0.150 |
| Lpa1 (log10), mg/dL | 3.79 / 3.39 / 5.13 | 3.78 / 3.50 / 5.50 | 220/10/1 | -4.50 (-33.9, 34.9) % | 0.764 |
| Lpa2 (log10), mg/dL | 1.91 / 1.66 / NA | 1.91 / 1.66 / NA | 206/29/0 | -14.9 (-41.1, 23.0) % | 0.395 |
| Lpa3 (log10), mg/dL | 4.58 / 3.72 / NA | 4.58 / 3.72 / NA | 323/47/0 | -18.7 (-30.8, -4.50) % | 0.009 |
| Lpa4 (log10), mg/dL | 3.78 / 3.65 / NA | 3.76 / 3.85 / NA | 204/23/0 | -4.50 (-27.6, 28.8) % | 0.784 |
| Lpa5 (log10), mg/dL | 3.37 / 2.89 / 5.74 | 3.36 / 2.95 / 6.10 | 252/25/1 | -8.80 (-24.1, 9.65) % | 0.339 |

*Statistical models account for Age, $Age^2$, Sex, and Study

Figure 8

*B4GALT1* ASN352SER IS ASSOCIATED WITH DECREASED FIBRINOGEN LEVELS (AMISH PAPI STUDY) + OTHER TRAITS OF POTENTIAL INTEREST

| Phenotype | Genotypic Means* | Genotypic Means Unadjusted | GenoCounts (Ref/Het/Alt) | Effect | Pvalue |
|---|---|---|---|---|---|
| Fibrinogen, drug naïve, mg/dL | 280.8 / 255 / 253.8 | 280.5 / 257.1 / 273.3 | 564/54/3 | -23.97 (-38.35, -9.59) | 1.15E-03 |
| Fibrinogen, post-clopidogrel, mg/dL | 276 / 247.7 / 182 | 275. / 249.7 / 197.0 | 549/54/3 | -32.45 (-47.5, -17.41) | 2.74E-05 |

Of 20+ platelet aggregation measures, pre/post-clopidogrel/post-aspirin, only 2 are nominally significant

| Phenotype | Control Counts (Ref/Het/Alt) | Case Counts (Ref/Het/Alt) | Control Freq | Case Freq | OR (95% CI) | OR Het (95% CI) | OR Hom | Pvalue |
|---|---|---|---|---|---|---|---|---|
| CAD (logistic) | 3535/473/11 | 101/13/0 | 0.061 | 0.057 | 0.78 (0.45, 1.48) | 0.96 (0.54, 1.72) | - | 0.42 |

| Phenotype | Genotypic Means* | Genotypic Means Unadjusted | Counts (Ref/Het/Alt) | Effect | Pvalue |
|---|---|---|---|---|---|
| Creatinine (log10), mg/dL | 0.747 / 0.767 / 0.789 | 0.748 / 0.763 / 0.756 | 3987/531/13 | 2.23 (0.46, 1.04) % | 0.0095 |
| eGFR, mL/min/1.73m$^2$ | 107.2 / 104.1 / 97.0 | 107.2 / 103.5 / 95.5 | 3910/517/12 | -2.86 (-5.10, -0.63) | 0.0121 |
| Basophils (log10), % | 0.402 / 0.376 / 0.369 | 0.402 / 0.378 / 0.370 | 3275/444/11 | -6.67 (-10.87, 0.69) % | 0.0259 |
| Hematocrit, % | 40.5 / 40.8 / 42.8 | 40.5 / 40.7 / 41.4 | 3897/514/12 | 0.34 (0.04, 0.63) | 0.0271 |

*Statistical models account for Age, Age$^2$, Sex, and Study

Figure 9

B4GALT1 VARIANTS AND USES THEREOF

CROSS-REFERENCE TO RELATED APPLICATIONS

This application claims priority to U.S. Application No. 62/659,344, filed Apr. 18, 2018, to U.S. Application No. 62/550,161, filed Aug. 25, 2017, and to U.S. Application No. 62/515,140, filed Jun. 5, 2017, each of which is incorporated herein by reference in its entirety.

REFERENCE TO GOVERNMENT GRANTS

This invention was made with government support under Grant Number HL121007 awarded by the National Institutes of Health. The government has certain rights in the invention.

REFERENCE TO A SEQUENCE LISTING

This application includes a Sequence Listing submitted electronically as a text file named 18923800201SEQ, created on Jun. 4, 2018, with a size of 161 KB. The Sequence Listing is incorporated by reference herein.

FIELD

The present disclosure provides variant B4GALT1 genomic, mRNA, and cDNA nucleic acid molecules, and polypeptides, methods of detecting the presence of these molecules, methods of modulating endogenous B4GALT1 genomic, mRNA, and cDNA nucleic acid molecules, and polypeptides, methods of ascertaining the risk of developing cardiovascular conditions by detecting the presence or absence of the variant B4GALT1 genomic, mRNA, and cDNA nucleic acid molecules, and polypeptides, and methods of treating cardiovascular conditions.

BACKGROUND

Various publications, including patents, published applications, accession numbers, technical articles and scholarly articles are cited throughout the specification. Each cited publication is incorporated by reference herein, in its entirety and for all purposes.

Beta-1,4-galactosyltransferase 1 (B4GALT1) is a member of the beta-1,4-galactosyltransferase gene family which encode type II membrane-bound glycoproteins that play a role in the biosynthesis of different glycoconjugates and saccharide structures. The enzyme encoded by B4GALT1 plays a critical role in the processing of N-linked oligosaccharide moieties in glycoproteins, and protein-linked sugar chains often modulate the biological functions of the glycoprotein. Thus, an impaired B4GALT1 activity has potential to alter the structure of all glycoproteins containing N-linked oligosaccharides. The long form of the B4GALT1 enzyme is localized in the trans-Golgi, where it transfers galactosyl residues to N-acetylglucosamine residues during the course of biosynthetic processing of high-mannose to complex-type N-linked oligosaccharides. Because addition of galactosyl residues is a pre-requisite for addition of sialic acids, a defect in B4GALT1 exerts an indirect effect to block addition of sialic acid residues and, therefore, may alter the half-life of plasma glycoproteins. Defects in glycosylation have been reported to impair intracellular trafficking of various glycoproteins—including the LDL receptor. Further, structural abnormalities in N-linked oligosaccharides have the potential to alter protein folding, which in turn could alter the function of glycoproteins and their secretion. A large percentage of proteins contain N-linked glycosylation, including cell surface receptors (e.g., LDL receptors and insulin receptors) as well as various circulating plasma proteins (e.g., apolipoprotein B and fibrinogen). There have been reports of patients with genetic disease due to homozygosity for protein-truncating mutations in the B4GALT1 gene. One such patient had a severe phenotype characterized by a) severe neurodevelopmental abnormalities (including hydrocephalus), b) myopathy, and c) blood clotting abnormalities. As predicted, oligosaccharides derived from circulating transferrin lacked galactose and sialic acid residues. Two additional patients with the same genetic defect presented with a milder phenotype, characterized by coagulation disturbances, hepatopathy, and dysmorphic features.

Cardiovascular disease is the leading cause of death in the United States and other westernized countries. Major risk factors for atherothrombotic cardiovascular diseases such as stroke and myocardial infarction include increased blood cholesterol and thrombotic tendency. Many proteins that are involved in lipid metabolism and coagulation are glycosylated and, thus, subject to modulation by B4GALT1. Knowledge of genetic factors underlying the development and progression of cardiovascular conditions could improve risk stratification and provide the foundation for novel therapeutic strategies.

SUMMARY

The present disclosure provides nucleic acid molecules comprising a nucleic acid sequence at least about 90% identical to the B4GALT1 variant genomic sequence (that comprises the SNP designated rs551564683), provided that the nucleic acid sequence also comprises nucleotides that encode a serine at the position corresponding to position 352 of the full length/mature B4GALT1 polypeptide.

The present disclosure also provides nucleic acid molecules comprising a nucleic acid sequence at least about 90% identical to the B4GALT1 variant mRNA sequence (that comprises the SNP designated rs551564683), provided that the nucleic acid sequence also encodes a serine at the position corresponding to position 352 of the full length/mature B4GALT1 polypeptide.

The present disclosure also provides cDNA molecules encoding a B4GALT1 polypeptide that comprise a nucleic acid sequence at least about 90% identical to the B4GALT1 variant cDNA sequence (that comprises the SNP designated rs551564683), provided that the nucleic acid sequence also encodes a serine at the position corresponding to position 352 in the full length/mature B4GALT1 polypeptide.

The present disclosure also provides vectors or exogenous donor sequences comprising any one or more of these nucleic acid molecules.

The present disclosure also provides isolated polypeptides comprising an amino acid sequence at least about 90% identical to a B4GALT1 polypeptide having a serine at the position corresponding to position 352 in the full length/mature B4GALT1 polypeptide.

The present disclosure also provides host cells comprising any one of more of these nucleic acid molecules operably linked to a heterologous promoter active in the host cell.

The present disclosure also provides methods of producing the B4GALT1 polypeptide by culturing a host cell containing a nucleic acid molecule encoding the B4GALT1 polypeptide, wherein the nucleic acid molecule is operably linked to a heterologous promoter active in the host cell, whereby the nucleic acid molecule is expressed, and recovering the isolated polypeptide.

The present disclosure also provides compositions comprising these nucleic acid molecules, or polypeptides, and a carrier for increasing their stability.

The present disclosure also provides methods of detecting the presence or absence of a B4GALT1 variant nucleic acid molecule (that comprises the SNP designated rs551564683) in a human subject, comprising performing an assay on a biological sample from the human subject that determines whether a nucleic acid molecule in the biological sample comprises a nucleic acid sequence that encodes a variant B4GALT1 polypeptide having a serine at the position corresponding to position 352 in the full length/mature B4GALT1 polypeptide.

The present disclosure also provides methods of detecting the presence of a variant B4GALT1 polypeptide having a serine at the position corresponding to position 352 in the full length/mature B4GALT1 polypeptide in a human subject, comprising performing an assay on a biological sample from the human subject that determines the presence of the variant B4GALT1 polypeptide.

The present disclosure also provides methods of determining a human subject's susceptibility to developing a cardiovascular condition, comprising: a) performing an assay on a biological sample from the human subject that determines whether a nucleic acid molecule in the biological sample comprises a nucleic acid sequence that encodes a variant B4GALT1 polypeptide having a serine at the position corresponding to position 352 in the full length/mature B4GALT1 polypeptide; and b) classifying the human subject as being at decreased risk for developing the cardiovascular condition if a nucleic acid molecule comprising a nucleic acid sequence that encodes a variant B4GALT1 polypeptide having a serine at the position corresponding to position 352 in the full length/mature B4GALT1 polypeptide is detected in the biological sample, or classifying the human subject as being at increased risk for developing the cardiovascular condition if a nucleic acid molecule comprising a nucleic acid sequence that encodes a variant B4GALT1 polypeptide having a serine at the position corresponding to position 352 in the full length/mature B4GALT1 polypeptide is not detected in the biological sample.

The present disclosure also provides methods of determining a human subject's susceptibility to developing a cardiovascular condition, comprising: a) performing an assay on a biological sample from the human subject that determines whether a B4GALT1 polypeptide in the biological sample comprises a serine at a position corresponding to position 352; and b) classifying the human subject as being at decreased risk for developing the cardiovascular condition if a B4GALT1 polypeptide having a serine at the position corresponding to position 352 in the full length/mature B4GALT1 polypeptide is detected in the biological sample, or classifying the human subject as being at increased risk for developing the cardiovascular condition if a B4GALT1 polypeptide having a serine at the position corresponding to position 352 in the full length/mature B4GALT1 polypeptide is not detected in the biological sample.

The present disclosure also provides guide RNA molecules effective to direct a Cas enzyme to bind to or cleave an endogenous B4GALT1 gene, wherein the guide RNA comprises a DNA-targeting segment that hybridizes to a guide RNA recognition sequence within the endogenous B4GALT1 gene that includes or is proximate (for instance, within a certain number of nucleotides, such as discussed below) to a position corresponding to positions 53575 to 53577 of the wild-type B4GALT1 gene.

The present disclosure also provides methods of modifying an endogenous B4GALT1 gene in a cell, comprising contacting the genome of the cell with: a) a Cas protein; and b) a guide RNA that forms a complex with the Cas protein and hybridizes to a guide RNA recognition sequence within the endogenous B4GALT1 gene, wherein the guide RNA recognition sequence includes or is proximate (for instance, within a certain number of nucleotides, such as discussed below) to a position corresponding to positions 53575 to 53577 of the wild-type B4GALT1 gene, wherein the Cas protein cleaves the endogenous B4GALT1 gene.

The present disclosure also provides methods of modifying an endogenous B4GALT1 gene in a cell, comprising contacting the genome of the cell with: a) a Cas protein; and b) a first guide RNA that forms a complex with the Cas protein and hybridizes to a first guide RNA recognition sequence within the endogenous B4GALT1 gene, wherein the first guide RNA recognition sequence comprises the start codon for the B4GALT1 gene or is within about 1,000 nucleotides of the start codon, wherein the Cas protein cleaves or alters expression of the endogenous B4GALT1 gene.

The present disclosure also provides methods for modifying a cell, comprising introducing an expression vector into the cell, wherein the expression vector comprises a recombinant B4GALT1 gene comprising a nucleotide sequence encoding a B4GALT1 polypeptide having a serine at the position corresponding to position 352 in the full length/mature B4GALT1 polypeptide.

The present disclosure also provides methods for modifying a cell, comprising introducing an expression vector into the cell, wherein the expression vector comprises a nucleic acid molecule encoding a polypeptide that is at least about 90% identical to a B4GALT1 polypeptide having a serine at the position corresponding to position 352 in the full length/mature B4GALT1 polypeptide, wherein the polypeptide also comprises a serine at the position corresponding to position 352 in the full length/mature B4GALT1 polypeptide.

The present disclosure also provides methods for modifying a cell, comprising introducing a polypeptide, or fragment thereof, into the cell, wherein the polypeptide is at least 90% identical to a B4GALT1 polypeptide having a serine at the position corresponding to position 352 in the full length/mature B4GALT1 polypeptide, and wherein the polypeptide also comprises a serine at the position corresponding to position 352 in the full length/mature B4GALT1 polypeptide.

The present disclosure also provides methods of treating a subject who is not a carrier of the B4GALT1 variant nucleic acid molecule or polypeptide (that comprises the SNP designated rs551564683) and has or is susceptible to developing a cardiovascular condition, comprising introducing into the subject: a) a Cas protein or a nucleic acid encoding the Cas protein; b) a guide RNA or a nucleic acid encoding the guide RNA, wherein the guide RNA forms a complex with the Cas protein and hybridizes to a guide RNA recognition sequence within an endogenous B4GALT1 gene, wherein the guide RNA recognition sequence includes or is proximate to a position corresponding to positions 53575 to 53577 of the wild-type B4GALT1 gene; and c) an exogenous donor sequence comprising a 5' homology arm that hybridizes to a target sequence 5' of the positions corresponding to positions 53575 to 53577 of the wild-type B4GALT1 gene, a 3' homology arm that hybridizes to a target sequence 3' of the positions corresponding to positions 53575 to 53577 of the wild-type B4GALT1 gene, and a nucleic acid insert comprising a nucleotide sequence encoding a B4GALT1 polypeptide having a serine at the position corresponding to position 352 in the full length/mature B4GALT1 polypeptide flanked by the 5' homology arm and the 3' homology arm, wherein the Cas protein cleaves the endogenous B4GALT1 gene in a cell in the subject and the exogenous donor sequence recombines with the endogenous B4GALT1 gene in the cell, wherein upon recombination of the exogenous donor sequence with the endogenous B4GALT1 gene, the serine is inserted at nucleotides corresponding to positions 53575 to 53577 of the wild-type B4GALT1 gene.

The present disclosure also provides methods of treating a subject who is not a carrier of the B4GALT1 variant nucleic acid molecule or polypeptide (that comprises the SNP designated rs551564683) and has or is susceptible to developing a cardiovascular condition, comprising introducing into the subject: a) a Cas protein or a nucleic acid encoding the Cas protein; b) a first guide RNA or a nucleic acid encoding the first guide RNA, wherein the first guide RNA forms a complex with the Cas protein and hybridizes to a first guide RNA recognition sequence within the endogenous B4GALT1 gene, wherein the first guide RNA recognition sequence comprises the start codon for the endogenous B4GALT1 gene or is within about 1,000 nucleotides of the start codon; and c) an expression vector comprising a recombinant B4GALT1 gene comprising a nucleotide sequence encoding a B4GALT1 polypeptide having a serine at the position corresponding to position 352 in the full length/mature B4GALT1 polypeptide, wherein the Cas protein cleaves or alters expression of the endogenous B4GALT1 gene in a cell in the subject and the expression vector expresses the recombinant B4GALT1 gene in the cell in the subject.

The present disclosure also provides methods of treating a subject who is not a carrier of the B4GALT1 variant nucleic acid molecule or polypeptide (that comprises the SNP designated rs551564683) and has or is susceptible to developing a cardiovascular condition comprising introducing into the subject an antisense DNA, RNA, an siRNA, or an shRNA that hybridizes to a sequence within the endogenous B4GALT1 gene and decreases expression of B4GALT1 polypeptide in a cell in the subject.

The present disclosure also provides methods of treating a subject who is not a carrier of the B4GALT1 variant nucleic acid molecule or polypeptide (that comprises the SNP designated rs551564683) and has or is susceptible to developing a cardiovascular condition comprising introducing an expression vector into the subject, wherein the expression vector comprises a recombinant B4GALT1 gene comprising a nucleotide sequence encoding a B4GALT1 polypeptide having a serine at the position corresponding to position 352 in the full length/mature B4GALT1 polypeptide, wherein the expression vector expresses the recombinant B4GALT1 gene in a cell in the subject.

The present disclosure also provides methods of treating a subject who is not a carrier of the B4GALT1 variant nucleic acid molecule or polypeptide (that comprises the SNP designated rs551564683) and has or is susceptible to developing a cardiovascular condition comprising introducing an expression vector into the subject, wherein the expression vector comprises a nucleic acid molecule encoding a B4GALT1 polypeptide having a serine at the position corresponding to position 352 in the full length/mature B4GALT1 polypeptide, wherein the expression vector expresses the nucleic acid encoding the B4GALT1 polypeptide in a cell in the subject.

The present disclosure also provides methods of treating a subject who is not a carrier of the B4GALT1 variant nucleic acid molecule or polypeptide (that comprises the SNP designated rs551564683) and has or is susceptible to developing a cardiovascular condition comprising introducing an mRNA into the subject, wherein the mRNA encodes a B4GALT1 polypeptide having a serine at the position corresponding to position 352 in the full length/mature B4GALT1 polypeptide, wherein the mRNA expresses the B4GALT1 polypeptide in a cell in the subject.

The present disclosure also provides methods of treating a subject who is not a carrier of the B4GALT1 variant nucleic acid molecule or polypeptide (that comprises the SNP designated rs551564683) and has or is susceptible to developing a cardiovascular condition comprising introducing a B4GALT1 polypeptide having a serine at the position corresponding to position 352 in the full length/mature B4GALT1 polypeptide or fragment thereof into the subject.

In any of the methods described or exemplified herein, a cardiovascular condition may comprise levels of one or more serum lipids that increase atherosclerotic risk. The serum lipids comprise one or more of cholesterol, LDL, HDL, triglycerides, HDL-cholesterol, and non-HDL cholesterol, or any subfraction thereof (e.g., HDL2, HDL2a, HDL2b, HDL2c, HDL3, HDL3a, HDL3b, HDL3c, HDL3d, LDL1, LDL2, LDL3, lipoprotein A, Lpa1, Lpa1, Lpa3, Lpa4, or Lpa5). A cardiovascular condition may comprise elevated levels of coronary artery calcification. A cardiovascular condition may comprise elevated levels of pericardial fat. A cardiovascular condition may comprise an atherothrombotic condition. The atherothrombotic condition may comprise elevated levels of fibrinogen. The atherothrombotic condition may comprise a fibrinogen-mediated blood clot. A cardiovascular condition may comprise elevated levels of fibrinogen. A cardiovascular condition may comprise a fibrinogen-mediated blood clot. A cardiovascular condition may comprise a blood clot formed from the involvement of fibrinogen activity. A fibrinogen-mediated blood clot or blood clot formed from the involvement of fibrinogen activity may be in any vein or artery in the body.

BRIEF DESCRIPTION OF THE FIGURES

FIG. 3 shows the results of a representative haplotype structure of the top B4GALT1-associated SNPs.

FIGS. 5A and 5B show that the frequency of the variant B4GALT1 gene is greater than 1000-fold enriched in the Amish.

FIG. 6 shows the association of B4GALT1 Asn352Ser with decreased serum lipids.

FIGS. 7A, 7B, and 7C show the high degree of association of B4GALT1 Asn352Ser with decreased serum lipids and increased AST.

FIG. 8 shows the association of B4GALT1 Asn352Ser with all lipid subfractions.

FIG. 9 shows the association of B4GALT1 Asn352Ser with decreased fibrinogen levels.

DETAILED DESCRIPTION

Figure 1:
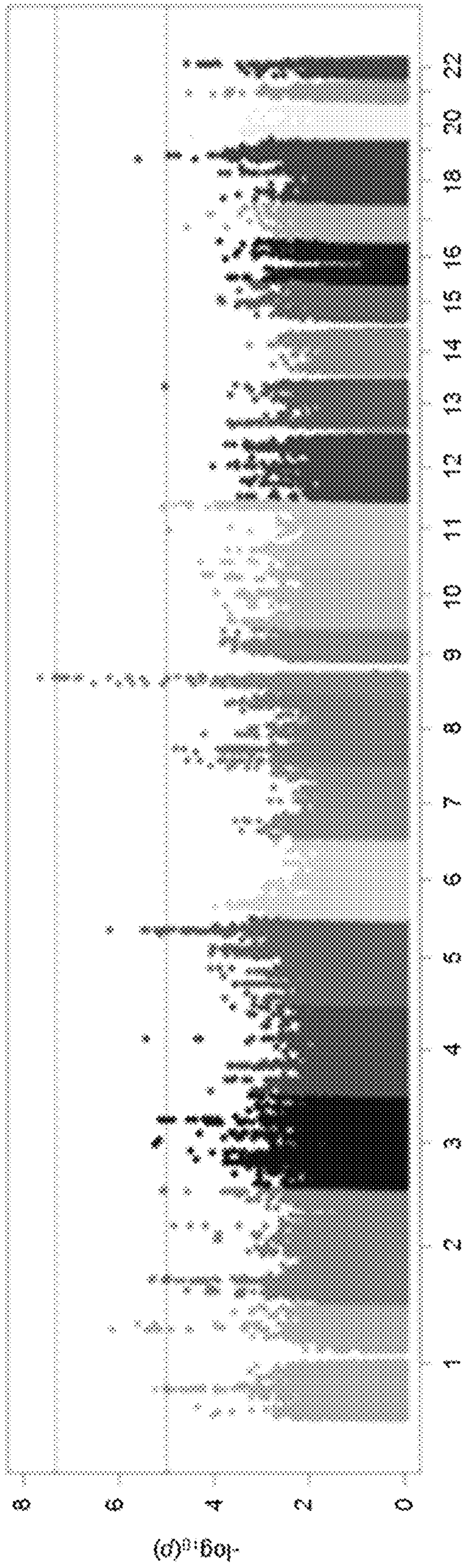
FIG. 1 shows the results of a representative genome-wide association of variant B4GALT1 with LDL.

As set forth herein, sequencing studies have identified a variant of B4GALT1 having a serine at the position corresponding to position 352 in the full length/mature B4GALT1 polypeptide instead of an asparagine present in about 11%-12% of individuals of the Old Order Amish (OOA) (alternate allele frequency=6%), and is extremely rare in the general population. This mutation changes the asparagine to serine in position 352 (N352S) of the 398 amino acid long human protein, or in position 311 of the short isoform. The variant B4GALT1 has been observed to be associated with lower levels of low density lipoprotein cholesterol (LDL), total cholesterol, and fibrinogen and eGFR, increased levels of aspartate transaminase (AST) (but not alanine transaminase (ALT)) and serum levels of creatine kinase and creatinine, expression in muscle tissue (but not liver or red blood cells), and a decrease in basophils. It is believed that the N352S variant is protective against one or more cardiovascular conditions. It is further believed that B4GALT1, including its variant status, may be used to diagnose a patient's risk of developing cardiovascular conditions.

The phrase "corresponding to" when used in the context of the numbering of a given amino acid or polynucleotide sequence refers to the numbering of the residues of a specified reference sequence when the given amino acid or polynucleotide sequence is compared to the reference sequence (with the reference sequence herein being the polynucleotide (gDNA sequence, mRNA sequence, cDNA sequence) or polypeptide of (wild-type/full length) B4GALT1). In other words, the residue number or residue position of a given polymer is designated with respect to the reference sequence rather than by the actual numerical position of the residue within the given amino acid or polynucleotide sequence. For example, a given amino acid sequence can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

As used herein, the singular forms of the articles "a," "an," and "the" include plural references unless the context clearly dictates otherwise.

As used herein, and unless otherwise apparent from the context, "about" encompasses values within a standard margin of error of measurement (e.g., SEM) of a stated value.

As used herein, "and/or" refers to and encompasses any and all possible combinations of one or more of the associated listed items, as well as the lack of combinations when interpreted in the alternative ("or").

As used herein, the terms "comprising" or "including" means that one or more of the recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed subject matter. Thus, the term "consisting essentially of" when used in a claim of the present disclosure is not intended to be interpreted to be equivalent to "comprising."

As used herein, "optional" or "optionally" means that the subsequently described event or circumstance may or may not occur and that the description includes instances in which the event or circumstance occurs and instances in which it does not.

As used herein, "or" refers to any one member of a particular list and also includes any combination of members of that list.

Designation of a range of values includes all integers within or defining the range (including the two endpoint values), and all subranges defined by integers within the range.

It should be appreciated that particular features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

The present disclosure provides isolated B4GALT1 genomic and mRNA variants, B4GALT1 cDNA variants, or any complement thereof, and isolated B4GALT1 polypeptide variants. These variants are believed to be associated with a diminished risk of developing various cardiovascular conditions including, but not limited to, elevated levels of serum lipids, and elevated levels fibrinogen, coronary artery calcification, coronary artery disease (CAD), and increased levels of aspartate aminotransferase (AST), but not alanine transaminase (ALT). Without wishing to be bound by any theory, it is believed that these B4GALT1 variants associate with expression in muscle tissue, and not liver or red blood cells, as evidenced by the experimentally-observed increased levels of AST, but not ALT. Compositions comprising B4GALT1 genomic and mRNA variants, B4GALT1 cDNA variants, and isolated B4GALT1 polypeptide variants are also provided herein. Nucleic acid molecules that hybridize to the B4GALT1 genomic and mRNA variants and B4GALT1 cDNA variants are also provided herein. The present disclosure also provides vectors and cells comprising B4GALT1 genomic and mRNA variants, B4GALT1 cDNA variants, and B4GALT1 polypeptide variants.

The present disclosure also provides methods of detecting the presence of and/or levels of genomic and/or mRNA variants, B4GALT1 cDNA variants, or complement thereof, and/or B4GALT1 polypeptide variants in a biological sample. Also provided are methods for determining a subject's susceptibility to developing a cardiovascular condition, and methods of diagnosing a subject with a cardiovascular condition or at risk for a cardiovascular condition. Also provided are methods for modifying a cell through the use of any combination of nuclease agents, exogenous donor sequences, transcriptional activators, transcriptional repressors, and expression vectors for expressing a recombinant B4GALT1 gene or a nucleic acid encoding an B4GALT1 polypeptide. Also provided are therapeutic and prophylactic methods for treating a subject having or at risk of developing a cardiovascular condition.

The wild-type human genomic B4GALT1 nucleic acid is approximately 56.7 kb in length, includes 6 exons, and is located at chromosome 9 in the human genome. An exemplary wild-type human genomic B4GALT1 sequence is assigned NCBI Accession No. NG_008919.1 (SEQ ID NO:1). A variant of human genomic B4GALT1 is shown in SEQ ID NO:2, and comprises a single nucleotide polymorphism (SNP) (A to G at position 53576; referred to herein as a variant B4GALT1). The variant SNP results in a serine at the position corresponding to position 352 in the full length/mature B4GALT1 polypeptide of the encoded B4GALT1 variant polypeptide, rather than the asparagine encoded by the wild-type B4GALT1 polypeptide. The variant human genomic B4GALT1 nucleic acid comprises, for example, three bases (e.g., "agt") encoding a serine at the positions corresponding to positions 53575 to 53577 of the wild-type human genomic B4GALT1, as opposed to the three bases "aat" at positions 53575 to 53577 of the wild-type human genomic B4GALT1 (comparing SEQ ID NO:2 to SEQ ID NO:1, respectively). In some embodiments, the isolated nucleic acid molecule comprises SEQ ID NO:2. In some embodiments, the isolated nucleic acid molecule consists of SEQ ID NO:2. In some embodiments, the isolated nucleic acid molecule is a complement of any genomic B4GALT1 nucleic acid molecule disclosed herein.

In some embodiments, the isolated nucleic acid molecules comprise or consist of a nucleic acid sequence that is at least about 70%, at least about 75%, at least about 80%, at least about 85%, at least about 90%, at least about 95%, at least about 96%, at least about 97%, at least about 98%, at least about 99%, or 100% identical to SEQ ID NO:2. In some embodiments, such nucleic acid sequence also comprises nucleotides corresponding to positions 53575 to 53577 of SEQ ID NO:2. In some embodiments, the isolated nucleic acid molecules comprise or consist of a nucleic acid sequence that is at least about 70%, at least about 75%, at least about 80%, at least about 85%, at least about 90%, at least about 95%, at least about 96%, at least about 97%, at least about 98%, at least about 99%, or 100% identical to a portion of SEQ ID NO:2 that comprises exons 1 to 6 of the B4GALT1 gene. In some embodiments, such nucleic acid sequence also comprises nucleotides corresponding to positions 53575 to 53577 of SEQ ID NO:2. In some embodiments, the isolated nucleic acid molecules comprise or consist of a nucleic acid sequence that is at least about 70%, at least about 75%, at least about 80%, at least about 85%, at least about 90%, at least about 95%, at least about 96%, at least about 97%, at least about 98%, at least about 99%, or 100% identical to a portion of SEQ ID NO:2 comprising exon 5. In some embodiments, such nucleic acid sequence also comprises nucleotides corresponding to positions 53575 to 53577 of SEQ ID NO:2. In some embodiments, the isolated nucleic acid molecule comprises a nucleic acid sequence at least about 90% identical to SEQ ID NO:2, provided that the nucleic acid sequence comprises nucleotides corresponding to positions 53575 to 53577 of SEQ ID NO:2.

Percent complementarity between particular stretches of nucleic acid sequences within nucleic acids can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

In some embodiments, the isolated nucleic acid molecules comprise less than the entire genomic sequence. In some embodiments, the isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 11000, at least about 12000, at least about 13000, at least about 14000, at least about 15000, at least about 16000, at least about 17000, at least about 18000, at least about 19000, or at least about 20000 contiguous nucleotides of SEQ ID NO:2. In some embodiments, such isolated nucleic acid molecules also comprise nucleotides corresponding to positions 53575 to 53577 of SEQ ID NO:2. In some embodiments, the isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, or at least about 1000 contiguous nucleotides of SEQ ID NO:2. In some embodiments, such isolated nucleic acid molecules also comprise nucleotides corresponding to positions 53575 to 53577 of SEQ ID NO:2. In some embodiments, the isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, or at least about 1000 contiguous nucleotides of exon 5 of SEQ ID NO:2. In some embodiments, such isolated nucleic acid molecules also comprise nucleotides corresponding to positions 53575 to 53577 of SEQ ID NO:2.

For example, in some embodiments, the isolated nucleic acid molecule comprises at least 15 contiguous nucleotides of SEQ ID NO:2, wherein the contiguous nucleotides include nucleotides 53575 to 53577 of SEQ ID NO:2. In some such embodiments, the isolated nucleic acid molecule comprises at least 20, at least 25 or at least 30 contiguous nucleotides of SEQ ID NO:2. In some embodiments, the isolated nucleic acid molecule comprises between 15 and 50 contiguous nucleotides of SEQ ID NO:2, wherein the contiguous nucleotides include nucleotides 53575 to 53577 of SEQ ID NO:2. In some such embodiments, the isolated nucleic acid molecule comprises at least 20, at least 25 or at least 30 contiguous nucleotides of SEQ ID NO:2.

In some embodiments, the disclosure provides an isolated nucleid acid that comprises a nucleic acid sequence that is at least 90% identical to a portion of SEQ ID NO:2, wherein the portion of SEQ ID NO:2 comprises nucleotides 53575 to 53577 of SEQ ID NO:2 and wherein the portion of SEQ ID NO:2 is at least 15 nucleotides in length. In some such embodiments, the portion of SEQ ID NO:2 is at least 20, at least 25, or at least 30 nucleotides in length. In some embodiments, the disclosure provides an isolated nucleid acid that comprises a nucleic acid sequence that is at least 90% identical to a portion of SEQ ID NO:2, wherein the portion of SEQ ID NO:2 comprises nucleotides 53575 to 53577 of SEQ ID NO:2 and wherein the portion of SEQ ID NO:2 is between 15 and 50 nucleotides in length. In some such embodiments, the portion of SEQ ID NO:2 is at least 20, at least 25, or at least 30 nucleotides in length.

In some embodiments, the disclosure provides an isolated nucleid acid that comprises a nucleic acid sequence that is at least 95% identical to a portion of SEQ ID NO:2, wherein the portion of SEQ ID NO:2 comprises nucleotides 53575 to 53577 of SEQ ID NO:2 and wherein the portion of SEQ ID NO:2 is at least 15 nucleotides in length. In some such embodiments, the portion of SEQ ID NO:2 is at least 20, at least 25, or at least 30 nucleotides in length. In some embodiments, the disclosure provides an isolated nucleid acid that comprises a nucleic acid sequence that is at least 95% identical to a portion of SEQ ID NO:2, wherein the portion of SEQ ID NO:2 comprises nucleotides 53575 to 53577 of SEQ ID NO:2 and wherein the portion of SEQ ID NO:2 is between 15 and 50 nucleotides in length. In some such embodiments, the portion of SEQ ID NO:2 is at least 20, at least 25, or at least 30 nucleotides in length.

Such isolated nucleic acid molecules can be used, for example, to express variant B4GALT1 mRNAs and proteins or as exogenous donor sequences. It is understood that gene sequences within a population can vary due to polymorphisms, such as SNPs. The examples provided herein are only exemplary sequences, and other sequences are also possible.

In some embodiments, the isolated nucleic acid molecules comprise a variant B4GALT1 minigene, in which one or more nonessential segments of SEQ ID NO:2 have been deleted with respect to a corresponding wild-type B4GALT1 gene. In some embodiments, the deleted nonessential segments comprise one or more intron sequences. In some embodiments, the B4GALT1 minigenes can comprise, for example, exons corresponding to any one or more of exons 1 to 6, or any combination of such exons, from variant B4GALT1 (SEQ ID NO:2). In some embodiments, the minigene comprises or consists of exon 5 of SEQ ID NO:2. In some embodiments, the B4GALT1 minigene is at least about 70%, at least about 75%, at least about 80%, at least about 85%, at least about 90%, at least about 95%, at least about 96%, at least about 97%, at least about 98%, at least about 99%, or 100% identical to a portion of SEQ ID NO:2 comprising any one or more of exons 1 to 6, or any combination of such exons. In some embodiments, the B4GALT1 minigene is at least 70%, at least 75%, at least 80%, at least 85%, at least 90%, at least 95%, at least 96%, at least 97%, at least 98%, at least 99%, or 100% identical to a portion of SEQ ID NO:2 comprising any one or more of exons 1 to 6, or any combination of such exons and comprise nucleotides corresponding to positions 53575 to 53577 of SEQ ID NO:2. In some embodiments, the B4GALT1 minigene is at least about 70%, at least about 75%, at least about 80%, at least about 85%, at least about 90%, at least about 95%, at least about 96%, at least about 97%, at least about 98%, at least about 99%, or 100% identical to a portion of SEQ ID NO:2 comprising exon 5.

The present disclosure also provides isolated nucleic acid molecules that hybridize to a variant B4GALT1 genomic sequence or a variant B4GALT1 minigene. In some embodiments, such isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 11000, at least about 12000, at least about 13000, at least about 14000, at least about 15000, at least about 16000, at least about 17000, at least about 18000, at least about 19000, or at least about 20000 nucleotides. In some embodiments, such isolated nucleic acid molecules also hybridize to positions 53575 to 53577 of SEQ ID NO:2. In some embodiments, the isolated nucleic acid molecules hybridize to a portion of variant B4GALT1 genome or minigene at a segment that includes or is within about 1000, within about 500, within about 400, within about 300, within about 200, within about 100, within about 50, within about 45, within about 40, within about 35, within about 30, within about 25, within about 20, within about 15, within about 10, or within about 5 nucleotides of positions 53575 to 53577 of SEQ ID NO:2. In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to variant B4GALT1 genomic DNA or minigene. In some embodiments, such isolated nucleic acid molecules also hybridize to positions 53575 to 53577 of SEQ ID NO:2. In some embodiments, the isolated nucleic acid molecules comprise or consist of from about 15 to about 100 nucleotides, or from about 15 to about 35 nucleotides.

For example, in some embodiments, the disclosure provides an isolated nucleic acid molecule that comprises at least 15 nucleotides, wherein the isolated nucleic acid molecule hybridizes to a nucleic acid comprising the sequence of SEQ ID NO:2, wherein the isolated nucleic acid molecule hybridizes to a portion of SEQ ID NO:2, and wherein the portion of SEQ ID NO:2 comprises nucleotides 53575 to 53577 of SEQ ID NO:2. In some such embodiments, the isolated nucleic acid molecule comprises at least 20, at least 25, or at least 30 nucleotides. In some embodiments, the disclosure provides an isolated nucleic acid molecule that comprises 15 to 50 nucleotides, wherein the isolated nucleic acid molecule hybridizes to a nucleic acid comprising the sequence of SEQ ID NO:2, wherein the isolated nucleic acid molecule hybridizes to a portion of SEQ ID NO:2, and wherein the portion of SEQ ID NO:2 comprises nucleotides 53575 to 53577 of SEQ ID NO:2. In some such embodiments, the isolated nucleic acid molecule comprises at least 20, at least 25, or at least 30 nucleotides.

In some embodiments, the isolated nucleic acid molecules hybridize to at least 15 contiguous nucleotides of a nucleic acid, wherein the contiguous nucleotides are at least 90% identical to a portion of SEQ ID NO:2, wherein the contiguous nucleotides comprise nucleotides 53575 to 53577 of SEQ ID NO:2 at positions that correspond to positions 53757 to 53577 of SEQ ID NO:2. In some such embodiments, the contiguous nucleotides are at least 20, at least 25, or at least 30 nucleotides in length. In some embodiments, the isolated nucleic acid molecules hybridize to at least 15 contiguous nucleotides of a nucleic acid, wherein the contiguous nucleotides are at least 95% identical to a portion of SEQ ID NO:2, wherein the contiguous nucleotides comprise nucleotides 53575 to 53577 of SEQ ID NO:2 at positions that correspond to positions 53757 to 53577 of SEQ ID NO:2. In some such embodiments, the contiguous nucleotides are at least 20, at least 25, or at least 30 nucleotides in length. In some embodiments, the isolated nucleic acid molecules hybridize to at least 15 contiguous nucleotides of a nucleic acid, wherein the contiguous nucleotides are at least 100% identical to a portion of SEQ ID NO:2, wherein the contiguous nucleotides comprise nucleotides 53575 to 53577 of SEQ ID NO:2 at positions that correspond to positions 53757 to 53577 of SEQ ID NO:2. In some such embodiments, the contiguous nucleotides are at least 20, at least 25, or at least 30 nucleotides in length.

In some embodiments, the isolated nucleic acid molecules hybridize to 15 to 50 contiguous nucleotides of a nucleic acid, wherein the contiguous nucleotides are at least 90% identical to a portion of SEQ ID NO:2, wherein the contiguous nucleotides comprise nucleotides 53575 to 53577 of SEQ ID NO:2 at positions that correspond to positions 53757 to 53577 of SEQ ID NO:2. In some such embodiments, the contiguous nucleotides are at least 20, at least 25, or at least 30 nucleotides in length. In some embodiments, the isolated nucleic acid molecules hybridize to 15 to 50 contiguous nucleotides of a nucleic acid, wherein the contiguous nucleotides are at least 95% identical to a portion of SEQ ID NO:2, wherein the contiguous nucleotides comprise nucleotides 53575 to 53577 of SEQ ID NO:2 at positions that correspond to positions 53757 to 53577 of SEQ ID NO:2. In some such embodiments, the contiguous nucleotides are at least 20, at least 25, or at least 30 nucleotides in length. In some embodiments, the isolated nucleic acid molecules hybridize to 15 to 50 contiguous nucleotides of a nucleic acid, wherein the contiguous nucleotides are at least 100% identical to a portion of SEQ ID NO:2, wherein the contiguous nucleotides comprise nucleotides 53575 to 53577 of SEQ ID NO:2 at positions that correspond to positions 53757 to 53577 of SEQ ID NO:2. In some such embodiments, the contiguous nucleotides are at least 20, at least 25, or at least 30 nucleotides in length.

Such isolated nucleic acid molecules can be used, for example, as guide RNAs, primers, probes, or exogenous donor sequences.

A representative wild-type B4GALT1 genomic sequence is recited in SEQ ID NO:1. A representative variant B4GALT1 genomic sequence variant is recited in SEQ ID NO:2.

The present disclosure also provides isolated nucleic acid molecules comprising a variant of B4GALT1 mRNA. An exemplary wild-type human B4GALT1 mRNA is assigned NCBI Accession NM_001497 (SEQ ID NO:3), and consists of 4214 nucleotide bases. A variant of human B4GALT1 mRNA is shown in SEQ ID NO:4, and comprises the SNP (A to G at position 1244; referred to herein as a variant B4GALT1), which results in a serine at the position corresponding to position 352 of the encoded B4GALT1 variant polypeptide. The variant human B4GALT1 mRNA comprises, for example, the three bases "agu" encoding a serine at positions corresponding to positions 1243 to 1245 of the wild-type human B4GALT1 mRNA, as opposed to the three bases "aau" at positions 1243 to 1245 of the wild-type human B4GALT1 mRNA (comparing SEQ ID NO:4 to SEQ ID NO:3, respectively). In some embodiments, the isolated nucleic acid molecule comprises SEQ ID NO:4. In some embodiments, the isolated nucleic acid molecule consists of SEQ ID NO:4.

In some embodiments, the isolated nucleic acid molecules comprise or consist of a nucleic acid sequence that is at least about 70%, at least about 75%, at least about 80%, at least about 85%, at least about 90%, at least about 95%, at least about 96%, at least about 97%, at least about 98%, at least about 99%, or 100% identical to SEQ ID NO:4. In some embodiments, such nucleic acid sequences also comprise nucleotides corresponding to positions 1243 to 1245 of SEQ ID NO:4. In some embodiments, the isolated nucleic acid molecules comprise or consist of a nucleotide sequence that is at least about 70%, at least about 75%, at least about 80%, at least about 85%, at least about 90%, at least about 95%, at least about 96%, at least about 97%, at least about 98%, at least about 99%, or 100% identical to a portion of SEQ ID NO:4 comprising exons 1 to 6. In some embodiments, such nucleic acid sequences also comprise nucleotides corresponding to positions 1243 to 1245 of SEQ ID NO:4. In some embodiments, the isolated nucleic acid molecule is a complement of any B4GALT1 mRNA molecule disclosed herein.

In some embodiments, the isolated nucleic acid molecules comprises less than the entire mRNA sequence. In some embodiments, the isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, or at least about 4000 contiguous nucleotides of SEQ ID NO:4. In some embodiments, such isolated nucleic acid molecules also comprise nucleotides corresponding to positions 1243 to 1245 of SEQ ID NO:4. In some embodiments, the isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, or at least about 1000 contiguous nucleotides of SEQ ID NO:4. In some embodiments, such isolated nucleic acid molecules also comprises nucleotides corresponding to positions 1243 to 1245 of SEQ ID NO:4. In some embodiments, the isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, or at least about 1000 contiguous nucleotides of exons 1 to 6 of SEQ ID NO:4. In some embodiments, such isolated nucleic acid molecules also comprise nucleotides corresponding to positions 1243 to 1245 of SEQ ID NO:4.

In some embodiments, the disclosure provides an isolated nucleic acid molecule that comprises a nucleic acid sequence that is at least 90% identical to a portion of SEQ ID NO:4, wherein the portion of SEQ ID NO:4 comprises nucleotides 1243 to 1245 of SEQ ID NO:4 and wherein the portion of SEQ ID NO:4 comprises at least 15 nucleotides of SEQ ID NO:4. In some such embodiments, the portion of SEQ ID NO:4 is at least 20, at least 25 or at least 30 nucleotides of SEQ ID NO:4. In some embodiments, the disclosure provides an isolated nucleic acid molecule that comprises a nucleic acid sequence that is at least 95% identical to a portion of SEQ ID NO:4, wherein the portion of SEQ ID NO:4 comprises nucleotides 1243 to 1245 of SEQ ID NO:4 and wherein the portion of SEQ ID NO:4 comprises at least 15 nucleotides of SEQ ID NO:4. In some such embodiments, the portion of SEQ ID NO:4 is at least 20, at least 25 or at least 30 nucleotides of SEQ ID NO:4. In some embodiments, the disclosure provides an isolated nucleic acid molecule that comprises a nucleic acid sequence that is 100% identical to a portion of SEQ ID NO:4, wherein the portion of SEQ ID NO:4 comprises nucleotides 1243 to 1245 of SEQ ID NO:4 and wherein the portion of SEQ ID NO:4 comprises at least 15 nucleotides of SEQ ID NO:4. In some such embodiments, the portion of SEQ ID NO:4 is at least 20, at least 25 or at least 30 nucleotides of SEQ ID NO:4. In some embodiments, the disclosure provides an isolated nucleic acid molecule that comprises a nucleic acid sequence that is at least 90% identical to a portion of SEQ ID NO:4, wherein the portion of SEQ ID NO:4 comprises nucleotides 1243 to 1245 of SEQ ID NO:4 and wherein the portion of SEQ ID NO:4 comprises 15 to 50 nucleotides of SEQ ID NO:4. In some such embodiments, the portion of SEQ ID NO:4 is at least 20, at least 25 or at least 30 nucleotides of SEQ ID NO:4. In some embodiments, the disclosure provides an isolated nucleic acid molecule that comprises a nucleic acid sequence that is at least 95% identical to a portion of SEQ ID NO:4, wherein the portion of SEQ ID NO:4 comprises nucleotides 1243 to 1245 of SEQ ID NO:4 and wherein the portion of SEQ ID NO:4 comprises 15 to 50 nucleotides of SEQ ID NO:4. In some such embodiments, the portion of SEQ ID NO:4 is at least 20, at least 25 or at least 30 nucleotides of SEQ ID NO:4. In some embodiments, the disclosure provides an isolated nucleic acid molecule that comprises a nucleic acid sequence that is 100% identical to a portion of SEQ ID NO:4, wherein the portion of SEQ ID NO:4 comprises nucleotides 1243 to 1245 of SEQ ID NO:4 and wherein the portion of SEQ ID NO:4 comprises 15 to 50 nucleotides of SEQ ID NO:4. In some such embodiments, the portion of SEQ ID NO:4 is at least 20, at least 25 or at least 30 nucleotides of SEQ ID NO:4.

Such isolated nucleic acid molecules can be used, for example, to express B4GALT1 variant polypeptides or as exogenous donor sequences. It is understood that gene sequences within a population can vary due to polymorphisms such as SNPs. The examples provided herein are only exemplary sequences, and other sequences are also possible.

In some embodiments, the isolated nucleic acid molecules comprise or consist of a nucleic acid sequence encoding a polypeptide at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to the variant Asn352Ser B4GALT1 polypeptide (SEQ ID NO:8), provided that the polypeptide comprises a serine at the position corresponding to position 352. In some embodiments, the isolated nucleic acid molecules comprise or consist of a nucleic acid sequence encoding a polypeptide at least about 90%, identical to SEQ ID NO:8, provided that the polypeptide comprises a serine at the position corresponding to position 352. In some embodiments, the isolated nucleic acid molecules comprise or consist of a nucleic acid sequence encoding a polypeptide at least about 95%, identical to SEQ ID NO:8, provided that the polypeptide comprises a serine at the position corresponding to position 352.

For example, in some embodiments, the isolated nucleic acid molecule comprises a nucleic acid sequence encoding a polypeptide that has an amino acid sequence that is at least 10 amino acids long, wherein the amino acid sequence is 90% identical to a portion of the amino acid sequence of SEQ ID NO:8, wherein the portion comprises a serine at the position corresponding to position 352 of SEQ ID NO:8. In some such embodiments, the nucleic acid sequence encodes a polypeptide that has an amino acid sequence that is at least 15, at least 20 or at least 25 amino acids long. In some embodiments, the isolated nucleic acid molecule comprises a nucleic acid sequence encoding a polypeptide that has an amino acid sequence that is at least 10 amino acids long, wherein the amino acid sequence is 95% identical to a portion of the amino acid sequence of SEQ ID NO:8, wherein the portion comprises a serine at the position corresponding to position 352 of SEQ ID NO:8. In some such embodiments, the nucleic acid sequence encodes a polypeptide that has an amino acid sequence that is at least 15, at least 20 or at least 25 amino acids long. In some embodiments, the isolated nucleic acid molecule comprises a nucleic acid sequence encoding a polypeptide that has an amino acid sequence that is 10 to 50 amino acids long, wherein the amino acid sequence is 90% identical to a portion of the amino acid sequence of SEQ ID NO:8, wherein the portion comprises a serine at the position corresponding to position 352 of SEQ ID NO:8. In some such embodiments, the nucleic acid sequence encodes a polypeptide that has an amino acid sequence that is at least 15, at least 20 or at least 25 amino acids long. In some embodiments, the isolated nucleic acid molecule comprises a nucleic acid sequence encoding a polypeptide that has an amino acid sequence that is 10 to 50 amino acids long, wherein the amino acid sequence is 95% identical to a portion of the amino acid sequence of SEQ ID NO:8, wherein the portion comprises a serine at the position corresponding to position 352 of SEQ ID NO:8. In some such embodiments, the nucleic acid sequence encodes a polypeptide that has an amino acid sequence that is at least 15, at least 20 or at least 25 amino acids long. In some embodiments, the isolated nucleic acid molecules comprise or consist of a nucleic acid sequence encoding a polypeptide identical to SEQ ID NO:8.

The present disclosure also provides isolated nucleic acid molecules that hybridize to a variant B4GALT1 mRNA sequence. In some embodiments, such isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, or at least about 4000 nucleotides. In some embodiments, such isolated nucleic acid molecules also hybridize to positions 1243 to 1245 of SEQ ID NO:4. In some embodiments, the isolated nucleic acid molecules hybridize to a portion of a variant B4GALT1 mRNA at a segment that includes or is within about 1000, within about 500, within about 400, within about 300, within about 200, within about 100, within about 50, within about 45, within about 40, within about 35, within about 30, within about 25, within about 20, within about 15, within about 10, or within about 5 nucleotides of positions 1243 to 1245 of SEQ ID NO:4.

In some embodiments, the isolated nucleic acid molecules comprise or consist of at least 15 nucleotides and hybridize to a portion of a variant B4GALT1 mRNA (for example, SEQ ID NO:4) at a segment that includes or is within 5 nucleotides of positions 1243 to 1245 of SEQ ID NO:4. In some such embodiments, the isolated nucleic acid molecules comprise at least 20, at least 25 or at least 30 nucleotides. In some embodiments, the isolated nucleic acid molecules comprise or consist of at least 15 nucleotides, hybridize to a portion of a variant B4GALT1 mRNA (for example, SEQ ID NO:4) at a segment that includes or is within 5 nucleotides of positions 1243 to 1245 of SEQ ID NO:4 and hybridize to positions 1243 to 1245 of SEQ ID NO:4. In some such embodiments, the isolated nucleic acid molecules comprise at least 20, at least 25 or at least 30 nucleotides. In some embodiments, the isolated nucleic acid molecules comprise 15 to 50 nucleotides and hybridize to a portion of a variant B4GALT1 mRNA (for example, SEQ ID NO:4) at a segment that includes positions 1243 to 1245 of SEQ ID NO:4 and hybridize to positions 1243 to 1245 of SEQ ID NO:4. In some such embodiments, the isolated nucleic acid molecules comprise at least 20, at least 25 or at least 30 nucleotides.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to a variant B4GALT1 mRNA (such as, for example, SEQ ID NO:4). In some embodiments, the isolated nucleic acid molecules also hybridize to positions 1243 to 1245 of SEQ ID NO:4. In some embodiments, the isolated nucleic acid molecules comprise or consist of from about 15 to about 100 nucleotides, or from about 15 to about 35 nucleotides.

In some embodiments, the isolated nucleic acid molecules comprise or consist of at least 15 nucleotides and hybridize to a portion of a variant B4GALT1 mRNA at a segment that includes or is within 5 nucleotides of positions 1243 to 1245 of SEQ ID NO:4, wherein the variant B4GALT1 mRNA is at least 90% identical to a variant B4GALT1 mRNA (such as, for example, SEQ ID NO:4). In some such embodiments, the isolated nucleic acid molecules comprise at least 20, at least 25 or at least 30 nucleotides. In some embodiments, the isolated nucleic acid molecules comprise or consist of at least 15 nucleotides and hybridize to a portion of a variant B4GALT1 mRNA at a segment that includes or is within 5 nucleotides of positions 1243 to 1245 of SEQ ID NO:4, wherein the variant B4GALT1 mRNA is at least 95% identical to a variant B4GALT1 mRNA (such as, for example, SEQ ID NO:4). In some such embodiments, the isolated nucleic acid molecules comprise at least 20, at least 25 or at least 30 nucleotides. In some embodiments, the isolated nucleic acid molecules comprise or consist of at least 15 nucleotides, hybridize to a portion of a variant B4GALT1 mRNA at a segment that includes or is within 5 nucleotides of positions 1243 to 1245 of SEQ ID NO:4 and hybridize to positions 1243 to 1245 of SEQ ID NO:4, wherein the variant B4GALT1 mRNA is at least 90% identical to a variant B4GALT1 mRNA (such as, for example, SEQ ID NO:4). In some such embodiments, the isolated nucleic acid molecules comprise at least 20, at least 25 or at least 30 nucleotides. In some embodiments, the isolated nucleic acid molecules comprise or consist of at least 15 nucleotides, hybridize to a portion of a variant B4GALT1 mRNA at a segment that includes or is within 5 nucleotides of positions 1243 to 1245 of SEQ ID NO:4 and hybridize to positions 1243 to 1245 of SEQ ID NO:4, wherein the variant B4GALT1 mRNA is at least 95% identical to a variant B4GALT1 mRNA (such as, for example, SEQ ID NO:4). In some such embodiments, the isolated nucleic acid molecules comprise at least 20, at least 25 or at least 30 nucleotides. In some embodiments, the isolated nucleic acid molecules comprise or consist of from 15 to 100 nucleotides, or from 15 to 35 nucleotides.

Such isolated nucleic acid molecules can be used, for example, as guide RNAs, primers, probes, or exogenous donor sequences.

A representative wild-type B4GALT1 mRNA sequence is recited in SEQ ID NO:3. A representative variant B4GALT1 mRNA sequence is recited in SEQ ID NO:4.

The present disclosure also provides nucleic acid molecules comprising a variant of B4GALT1 cDNA encoding all or part of a B4GALT1 variant polypeptide. An exemplary wild-type human B4GALT1 cDNA (e.g., coding region of mRNA written as DNA) consists of 1197 nucleotide bases (SEQ ID NO:5). A variant of human B4GALT1 cDNA is shown in SEQ ID NO:6, and comprises the SNP (A to G at position 1055; referred to herein as a variant B4GALT1), which results in a serine at the position corresponding to position 352 of the encoded B4GALT1 variant polypeptide. The variant human B4GALT1 cDNA comprises, for example, "agt" encoding a serine at positions corresponding to positions 1054 to 1056 of the full length/mature wild-type human B4GALT1 cDNA, as opposed to the three bases "aat" of the wild-type human B4GALT1 cDNA at positions 1054 to 1056 (comparing SEQ ID NO:6 to SEQ ID NO:5, respectively). In some embodiments, the nucleic acid molecule comprises SEQ ID NO:6. In some embodiments, the nucleic acid molecule consists of SEQ ID NO:6. In some embodiments, the cDNA molecules are isolated.

In some embodiments, the cDNA molecules comprise or consist of a nucleic acid sequence that is at least about 70%, at least about 75%, at least about 80%, at least about 85%, at least about 90%, at least about 95%, at least about 96%, at least about 97%, at least about 98%, at least about 99%, or 100% identical to SEQ ID NO:6. In some embodiments, the cDNA molecules also comprise nucleotides corresponding to positions 1054 to 1056 of SEQ ID NO:6. In some embodiments, the isolated nucleic acid molecule is a complement of any B4GALT1 cDNA molecule disclosed herein.

In some embodiments, the cDNA molecules comprise less than the entire cDNA sequence. In some embodiments, the cDNA molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, or at least about 1100 contiguous nucleotides of SEQ ID NO:6. In some embodiments, such cDNA molecules also comprise nucleotides corresponding to positions 1054 to 1056 of SEQ ID NO:6. In some embodiments, the cDNA molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, or at least about 500 contiguous nucleotides of SEQ ID NO:6. In some embodiments, such cDNA molecules also comprise nucleotides corresponding to positions 1054 to 1056 of SEQ ID NO:6.

For example, in some embodiments, the cDNA molecule comprises at least 15 contiguous nucleotides of SEQ ID NO:6, wherein the contiguous nucleotides include nucleotides 1054 to 1056 of SEQ ID NO:6. In some such embodiments, the isolated nucleic acid molecule comprises at least 20, at least 25 or at least 30 contiguous nucleotides of SEQ ID NO:6. In some embodiments, the cDNA molecule comprises 15 to 50 contiguous nucleotides of SEQ ID NO:6, wherein the contiguous nucleotides include nucleotides 1054 to 1056 of SEQ ID NO:6. In some such embodiments, the isolated nucleic acid molecule comprises at least 20, at least 25 or at least 30 contiguous nucleotides of SEQ ID NO:6. In some embodiments, the disclosure provides a cDNA molecule that comprises a nucleic acid sequence that is at least 90% identical to a portion of SEQ ID NO:6, wherein the portion of SEQ ID NO:6 comprises nucleotides 1054 to 1056 of SEQ ID NO:6 and wherein the portion of SEQ ID NO:6 comprises at least 15 contiguous nucleotides nucleotides of SEQ ID NO:6. In some such embodiments, the portion of SEQ ID NO:6 is at least 20, at least 25 or at least 30 contiguous nucleotides of SEQ ID NO:6. In some embodiments, the disclosure provides a cDNA molecule that comprises a nucleic acid sequence that is at least 95% identical to a portion of SEQ ID NO:6, wherein the portion of SEQ ID NO:6 comprises nucleotides 1054 to 1056 of SEQ ID NO:6 and wherein the portion of SEQ ID NO:6 comprises at least 15 contiguous nucleotides nucleotides of SEQ ID NO:6. In some such embodiments, the portion of SEQ ID NO:6 is at least 20, at least 25 or at least 30 contiguous nucleotides of SEQ ID NO:6. In some embodiments, the disclosure provides a cDNA molecule that comprises a nucleic acid sequence that is at least 90% identical to a portion of SEQ ID NO:6, wherein the portion of SEQ ID NO:6 comprises nucleotides 1054 to 1056 of SEQ ID NO:6 and wherein the portion of SEQ ID NO:6 comprises 15 to 50 contiguous nucleotides nucleotides of SEQ ID NO:6. In some such embodiments, the portion of SEQ ID NO:6 is at least 20, at least 25 or at least 30 contiguous nucleotides of SEQ ID NO:6. In some embodiments, the disclosure provides a cDNA molecule that comprises a nucleic acid sequence that is at least 95% identical to a portion of SEQ ID NO:6, wherein the portion of SEQ ID NO:6 comprises nucleotides 1054 to 1056 of SEQ ID NO:6 and wherein the portion of SEQ ID NO:6 comprises 15 to 50 contiguous nucleotides nucleotides of SEQ ID NO:6. In some such embodiments, the portion of SEQ ID NO:6 is at least 20, at least 25 or at least 30 contiguous nucleotides of SEQ ID NO:6. In some embodiments, the disclosure provides a cDNA molecule that comprises nucleotides 1054 to 1056 of SEQ ID NO:6 at positions corresponding to nucleotides 1054 to 1056 of SEQ ID NO:6, wherein the cDNA molecule comprises a nucleic acid sequence that is at least 90% identical to a portion of SEQ ID NO:6, wherein the portion of SEQ ID NO:6 comprises nucleotides 1054 to 1056 of SEQ ID NO:6 and wherein the portion of SEQ ID NO:6 comprises at least 15 contiguous nucleotides nucleotides of SEQ ID NO:6. In some such embodiments, the portion of SEQ ID NO:6 is at least 20, at least 25 or at least 30 contiguous nucleotides of SEQ ID NO:6. In some embodiments, the disclosure provides a cDNA molecule that comprises nucleotides 1054 to 1056 of SEQ ID NO:6 at positions corresponding to nucleotides 1054 to 1056 of SEQ ID NO:6, wherein the cDNA molecule comprises a nucleic acid sequence that is at least 95% identical to a portion of SEQ ID NO:6, wherein the portion of SEQ ID NO:6 comprises nucleotides 1054 to 1056 of SEQ ID NO:6 and wherein the portion of SEQ ID NO:6 comprises at least 15 contiguous nucleotides nucleotides of SEQ ID NO:6. In some such embodiments, the portion of SEQ ID NO:6 is at least 20, at least 25 or at least 30 contiguous nucleotides of SEQ ID NO:6. In some embodiments, the disclosure provides a cDNA molecule that comprises nucleotides 1054 to 1056 of SEQ ID NO:6 at positions corresponding to nucleotides 1054 to 1056 of SEQ ID NO:6, wherein the cDNA molecule comprises a nucleic acid sequence that is at least 90% identical to a portion of SEQ ID NO:6, wherein the portion of SEQ ID NO:6 comprises nucleotides 1054 to 1056 of SEQ ID NO:6 and wherein the portion of SEQ ID NO:6 comprises 15 to 50 contiguous nucleotides nucleotides of SEQ ID NO:6. In some such embodiments, the portion of SEQ ID NO:6 is at least 20, at least 25 or at least 30 contiguous nucleotides of SEQ ID NO:6. In some embodiments, the disclosure provides a cDNA molecule that comprises nucleotides 1054 to 1056 of SEQ ID NO:6 at positions corresponding to nucleotides 1054 to 1056 of SEQ ID NO:6, wherein the cDNA molecule comprises a nucleic acid sequence that is at least 95% identical to a portion of SEQ ID NO:6, wherein the portion of SEQ ID NO:6 comprises nucleotides 1054 to 1056 of SEQ ID NO:6 and wherein the portion of SEQ ID NO:6 comprises 15 to 50 contiguous nucleotides nucleotides of SEQ ID NO:6. In some such embodiments, the portion of SEQ ID NO:6 is at least 20, at least 25 or at least 30 contiguous nucleotides of SEQ ID NO:6.

Such cDNA molecules can be used, for example, to express B4GALT1 variant proteins or as exogenous donor sequences. It is understood that gene sequences within a population can vary due to polymorphisms such as SNPs. The examples provided herein are only exemplary sequences, and other sequences are also possible.

In some embodiments, the cDNA molecules comprise or consist of a nucleic acid sequence encoding a polypeptide at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to the variant Asn352Ser B4GALT1 polypeptide (SEQ ID NO:8), provided that the polypeptide comprises a serine at the position corresponding to position 352. In some embodiments, the cDNA molecules comprise or consist of a nucleic acid sequence encoding a polypeptide at least about 90%, identical to SEQ ID NO:8, provided that the polypeptide comprises a serine at the position corresponding to position 352. In some embodiments, the cDNA molecules comprise or consist of a nucleic acid sequence encoding a polypeptide at least about 95%, identical to SEQ ID NO:8, provided that the polypeptide comprises a serine at the position corresponding to position 352. In some embodiments, the cDNA molecule comprises or consists of a nucleic acid sequence encoding a polypeptide identical to SEQ ID NO:8.

The present disclosure also provides isolated nucleic acid molecules that hybridize to a variant B4GALT1 cDNA sequence. In some embodiments, such isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, or at least about 1100 nucleotides. In some embodiments, such isolated nucleic acid molecules also hybridize to positions 1054 to 1056 of SEQ ID NO:6. In some embodiments, such isolated nucleic acid molecules hybridize to a portion of a variant B4GALT1 cDNA at a segment that includes or is within about 600, within about 500, within about 400, within about 300, within about 200, within about 100, within about 50, within about 45, within about 40, within about 35, within about 30, within about 25, within about 20, within about 15, within about 10, or within about 5 nucleotides of positions 1054 to 1056 of SEQ ID NO:6. In some embodiments, the isolated nucleic acid molecules hybridize to at least about 15 contiguous nucleotides of a cDNA molecule that is at least about 70%, at least about 75%, at least about 80%, at least about 85%, at least about 90%, at least about 95%, at least about 96%, at least about 97%, at least about 98%, at least about 99%, or 100% identical to a variant B4GALT1 cDNA (such as, for example, SEQ ID NO:6). In some embodiments, the isolated nucleic acid molecules also hybridize to positions 1054 to 1056 of SEQ ID NO:6. In some embodiments, the isolated nucleic acid molecules comprise or consist of from about 15 to about 100 nucleotides, or from about 15 to about 35 nucleotides.

In some embodiments, the isolated nucleic acid molecules comprise or consist of at least 15 nucleotides and hybridize to a portion of a variant B4GALT1 cDNA at a segment that includes or is within 5 nucleotides of positions 1054 to 1056 of SEQ ID NO:6, wherein the variant B4GALT1 cDNA is at least 90% identical to a variant B4GALT1 cDNA (such as, for example, SEQ ID NO:6). In some embodiments, the isolated nucleic acid molecules comprise or consist of at least 15 nucleotides and hybridize to a portion of a variant B4GALT1 cDNA at a segment that includes or is within 5 nucleotides of positions 1054 to 1056 of SEQ ID NO:6, wherein the variant B4GALT1 cDNA is at least 95% identical to a variant B4GALT1 cDNA (such as, for example, SEQ ID NO:6). In some embodiments, the isolated nucleic acid molecules comprise or consist of at least 15 nucleotides and hybridize to a portion of a variant B4GALT1 cDNA at a segment that includes or is within 5 nucleotides of positions 1054 to 1056 of SEQ ID NO:6, wherein the variant B4GALT1 cDNA is 100% identical to a variant B4GALT1 cDNA (such as, for example, SEQ ID NO:6). In some embodiments, the isolated nucleic acid molecules comprise or consist of at least 15 nucleotides, hybridize to a portion of a variant B4GALT1 cDNA at a segment that includes or is within 5 nucleotides of positions 1054 to 1056 of SEQ ID NO:6 and hybridize to positions 1054 to 1056 of SEQ ID NO:6, wherein the variant B4GALT1 cDNA is at least 90% identical to a variant B4GALT1 cDNA (such as, for example, SEQ ID NO:6). In some embodiments, the isolated nucleic acid molecules comprise or consist of at least 15 nucleotides, hybridize to a portion of a variant B4GALT1 cDNA at a segment that includes or is within 5 nucleotides of positions 1054 to 1056 of SEQ ID NO:6 and hybridize to positions 1054 to 1056 of SEQ ID NO:6, wherein the variant B4GALT1 cDNA is at least 95% identical to a variant B4GALT1 cDNA (such as, for example, SEQ ID NO:6). In some embodiments, the isolated nucleic acid molecules comprise or consist of at least 15 nucleotides, hybridize to a portion of a variant B4GALT1 cDNA at a segment that includes or is within 5 nucleotides of positions 1054 to 1056 of SEQ ID NO:6 and hybridize to positions 1054 to 1056 of SEQ ID NO:6, wherein the variant B4GALT1 cDNA is 100% identical to a variant B4GALT1 cDNA (such as, for example, SEQ ID NO:6). In some embodiments, the isolated nucleic acid molecules comprise or consist of from 15 to 100 nucleotides, or from 15 to 35 nucleotides.

Such isolated nucleic acid molecules can be used, for example, as guide RNAs, primers, probes, exogenous donor sequences, antisense RNAs, siRNAs, or shRNAs.

A representative wild-type B4GALT1 cDNA sequence is recited in SEQ ID NO:5. A representative variant B4GALT1 cDNA sequence is recited in SEQ ID NO:6.

The nucleic acid molecules disclosed herein can comprise a nucleic acid sequence of a naturally occurring B4GALT1 gene or mRNA transcript, or can comprise a non-naturally occurring sequence. In some embodiments, the naturally occurring sequence can differ from the non-naturally occurring sequence due to synonymous mutations or mutations that do not affect the encoded B4GALT1 polypeptide. For example, the sequence can be identical with the exception of synonymous mutations or mutations that do not affect the encoded B4GALT1 polypeptide. A synonymous mutation or substitution is the substitution of one nucleotide for another in an exon of a gene coding for a protein such that the produced amino acid sequence is not modified. This is possible because of the degeneracy of the genetic code, with some amino acids being coded for by more than one three-base pair codon. Synonymous substitutions are used, for example, in the process of codon optimization. The nucleic acid molecules disclosed herein can be codon optimized.

Also provided herein are functional polynucleotides that can interact with the disclosed nucleic acid molecules. Functional polynucleotides are nucleic acid molecules that have a specific function, such as binding a target molecule or catalyzing a specific reaction. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

Antisense molecules are designed to interact with a target nucleic acid molecule through either canonical or non-canonical base pairing. The interaction of the antisense molecule and the target molecule is designed to promote the destruction of the target molecule through, for example, RNase-H-mediated RNA-DNA hybrid degradation. Alternately, the antisense molecule is designed to interrupt a processing function that normally would take place on the target molecule, such as transcription or replication. Antisense molecules can be designed based on the sequence of the target molecule. Numerous methods for optimization of antisense efficiency by identifying the most accessible regions of the target molecule exist. Exemplary methods include, but are not limited to, in vitro selection experiments and DNA modification studies using DMS and DEPC. Antisense molecules generally bind the target molecule with a dissociation constant ($k_d$) less than or equal to about $10^{-6}$, less than or equal to about $10^{-8}$, less than or equal to about $10^{-10}$, or less than or equal to about $10^{-12}$. A representative sample of methods and techniques which aid in the design and use of antisense molecules can be found in the following non-limiting list of U.S. Pat. Nos. 5,135,917; 5,294,533; 5,627,158; 5,641,754; 5,691,317; 5,780,607; 5,786,138; 5,849,903; 5,856,103; 5,919,772; 5,955,590; 5,990,088; 5,994,320; 5,998,602; 6,005,095; 6,007,995; 6,013,522; 6,017,898; 6,018,042; 6,025,198; 6,033,910; 6,040,296; 6,046,004; 6,046,319; and 6,057,437. Examples of antisense molecules include, but are not limited to, antisense RNAs, small interfering RNAs (siRNAs), and short hairpin RNAs (shRNAs).

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be in a vector or exogenous donor sequence comprising the isolated nucleic acid molecule and a heterologous nucleic acid sequence. The isolated nucleic acid molecules can also be linked or fused to a heterologous label, such as a fluorescent label. Other examples of labels are disclosed elsewhere herein.

The label can be directly detectable (e.g., fluorophore) or indirectly detectable (e.g., hapten, enzyme, or fluorophore quencher). Such labels can be detectable by spectroscopic, photochemical, biochemical, immunochemical, or chemical means. Such labels include, for example, radiolabels that can be measured with radiation-counting devices; pigments, dyes or other chromogens that can be visually observed or measured with a spectrophotometer; spin labels that can be measured with a spin label analyzer; and fluorescent labels (e.g., fluorophores), where the output signal is generated by the excitation of a suitable molecular adduct and that can be visualized by excitation with light that is absorbed by the dye or can be measured with standard fluorometers or imaging systems. The label can also be, for example, a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term "label" can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidate (HRP) to bind to the tag, and then use a calorimetric substrate (e.g., tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels are known and include, for example, particles, fluorophores, haptens, enzymes and their calorimetric, fluorogenic and chemiluminescent substrates and other labels.

The disclosed nucleic acid molecules can be made up of, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxynnethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain nucleotide analogs such as, for example, 5-substituted pyrimidines, 6-azapyrimidines, and N-2, N-6 and 0-6 substituted purines including, but not limited to, 2-aminopropyladenine, 5-propynyluracil, 5-propynylcytosine, and 5-methylcytosine can increase the stability of duplex formation. Often, base modifications can be combined with, for example, a sugar modification, such as 2'-O-methoxyethyl, to achieve unique properties such as increased duplex stability.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, $—O[(CH_2)_nO]_mCH_3$, $—O(CH_2)_nOCH_3$, $—O(CH_2)_nNH_2$, $—O(CH_2)_nCH_3$, $—O(CH_2)_n—ONH_2$, and $—O(CH_2)_nON[(CH_2)_nCH_3)]_2$, where n and m are from 1 to about 10.

Other modifications at the 2' position include, but are not limited to, $C_{1-10}$alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as $CH_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included.

Nucleotide substitutes include molecules having similar functional properties to nucleotides, but which do not contain a phosphate moiety, such as peptide nucleic acid (PNA). Nucleotide substitutes include molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes also include nucleotides or nucleotide analogs that have had the phosphate moiety or sugar moieties replaced. In some embodiments, nucleotide substitutes may not contain a standard phosphorus atom. Substitutes for the phosphate can be, for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts.

It is also understood in a nucleotide substitute that both the sugar and the phosphate moieties of the nucleotide can be replaced by, for example, an amide type linkage (aminoethylglycine) (PNA).

It is also possible to link other types of molecules (conjugates) to nucleotides or nucleotide analogs to enhance, for example, cellular uptake. Conjugates can be chemically linked to the nucleotide or nucleotide analogs. Such conjugates include, for example, lipid moieties such as a cholesterol moiety, cholic acid, a thioether such as hexyl-S-tritylthiol, a thiocholesterol, an aliphatic chain such as dodecandiol or undecyl residues, a phospholipid such as di-hexadecyl-rac-glycerol or triethylammonium 1,2-di-O-hexadecyl-rac-glycero-3-H-phosphonate, a polyamine or a polyethylene glycol chain, adamantane acetic acid, a palmityl moiety, or an octadecylamine or hexylamino-carbonyl-oxycholesterol moiety.

The present disclosure also provides vectors comprising any one or more of the nucleic acid molecules disclosed herein. In some embodiments, the vectors comprise any one or more of the nucleic acid molecules disclosed herein and a heterologous nucleic acid. The vectors can be viral or nonviral vectors capable of transporting a nucleic acid molecule. In some embodiments, the vector is a plasmid or cosmid (e.g., a circular double-stranded DNA into which additional DNA segments can be ligated). In some embodiments, the vector is a viral vector, wherein additional DNA segments can be ligated into the viral genome. In some embodiments, the vector can autonomously replicate in a host cell into which it is introduced (e.g., bacterial vectors having a bacterial origin of replication and episomal mammalian vectors). In some embodiments, the vector (e.g., non-episomal mammalian vectors) can be integrated into the genome of a host cell upon introduction into the host cell and thereby are replicated along with the host genome. Moreover, particular vectors can direct the expression of genes to which they are operatively linked. Such vectors are referred to herein as "recombinant expression vectors" or "expression vectors." Such vectors can also be targeting vectors (i.e., exogenous donor sequences).

In some embodiments, the proteins encoded by the various genetic variants disclosed herein are expressed by inserting nucleic acid molecules encoding the disclosed genetic variants into expression vectors, such that the genes are operatively linked to expression control sequences, such as transcriptional and translational control sequences. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and the like. In some embodiments, nucleic acid molecules comprising the disclosed genetic variants can be ligated into a vector such that transcriptional and translational control sequences within the vector serve their intended function of regulating the transcription and translation of the genetic variant. The expression vector and expression control sequences are chosen to be compatible with the expression host cell used. Nucleic acid sequences comprising the disclosed genetic variants can be inserted into separate vectors or into the same expression vector as the variant genetic information. A nucleic acid sequence comprising the disclosed genetic variants can be inserted into the expression vector by standard methods (e.g., ligation of complementary restriction sites on the nucleic acid comprising the disclosed genetic variants and vector, or blunt end ligation if no restriction sites are present).

In addition to a nucleic acid sequence comprising the disclosed genetic variants, the recombinant expression vectors can carry regulatory sequences that control the expression of the genetic variant in a host cell. The design of the expression vector, including the selection of regulatory sequences can depend on such factors as the choice of the host cell to be transformed, the level of expression of protein desired, and so forth. Desired regulatory sequences for mammalian host cell expression can include, for example, viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. Methods of expressing polypeptides in bacterial cells or fungal cells (e.g., yeast cells) are also well known.

A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772.

Examples of inducible promoters include, for example, chemically regulated promoters and physically-regulated promoters. Chemically regulated promoters include, for example, alcohol-regulated promoters (e.g., an alcohol dehydrogenase (alcA) gene promoter), tetracycline-regulated promoters (e.g., a tetracycline-responsive promoter, a tetracycline operator sequence (tetO), a tet-On promoter, or a tet-Off promoter), steroid regulated promoters (e.g., a rat glucocorticoid receptor, a promoter of an estrogen receptor, or a promoter of an ecdysone receptor), or metal-regulated promoters (e.g., a metalloprotein promoter). Physically regulated promoters include, for example temperature-regulated promoters (e.g., a heat shock promoter) and light-regulated promoters (e.g., a light-inducible promoter or a light-repressible promoter).

Tissue-specific promoters can be, for example, neuron-specific promoters, glia-specific promoters, muscle cell-specific promoters, heart cell-specific promoters, kidney cell-specific promoters, bone cell-specific promoters, endothelial cell-specific promoters, or immune cell-specific promoters (e.g., a B cell promoter or a T cell promoter).

Developmentally regulated promoters include, for example, promoters active only during an embryonic stage of development, or only in an adult cell.

In addition to a nucleic acid sequence comprising the disclosed genetic variants and regulatory sequences, the recombinant expression vectors can carry additional sequences, such as sequences that regulate replication of the vector in host cells (e.g., origins of replication) and selectable marker genes. A selectable marker gene can facilitate selection of host cells into which the vector has been introduced (see e.g., U.S. Pat. Nos. 4,399,216; 4,634,665; and 5,179,017). For example, a selectable marker gene can confer resistance to drugs, such as G418, hygromycin, or methotrexate, on a host cell into which the vector has been introduced. Exemplary selectable marker genes include, but are not limited to, the dihydrofolate reductase (DHFR) gene (for use in dhfr-host cells with methotrexate selection/amplification), the neo gene (for G418 selection), and the glutamate synthetase (GS) gene.

The present disclosure also provides isolated polypeptides comprising a variant B4GALT1 polypeptide (Asn352Ser). An exemplary wild-type human B4GALT1 polypeptide is assigned UniProt Accession No. P15291 (SEQ ID NO:7), and consists of 398 amino acids. A human variant B4GALT1 polypeptide comprises a serine at the position corresponding to position 352 of the full length/mature B4GALT1 polypeptide (SEQ ID NO:8), as opposed to an asparagine at the same position in the wild-type human B4GALT1 (comparing SEQ ID NO:8 to SEQ ID NO:7, respectively). In some embodiments, the isolated polypeptide comprises SEQ ID NO:8. In some embodiments, the isolated polypeptide consists of SEQ ID NO:8.

In some embodiments, the isolated polypeptides comprise or consist of an amino acid sequence that is at least about 70%, at least about 75%, at least about 80%, at least about 85%, at least about 90%, at least about 95%, at least about 96%, at least about 97%, at least about 98%, at least about 99%, or 100% identical to SEQ ID NO:8. In some embodiments, the isolated polypeptides comprise a serine at the position corresponding to position 352 of SEQ ID NO:8. In some embodiments, the isolated polypeptides comprise or consist of an amino acid sequence that is at least about 90%, at least about 95%, at least about 96%, at least about 97%, at least about 98%, at least about 99%, or 100% identical to SEQ ID NO:8. In some embodiments, the isolated polypeptides comprise a serine at the position corresponding to position 352 of SEQ ID NO:8. In some embodiments, the isolated polypeptides comprise or consist of an amino acid sequence that is at least about 90% identical to SEQ ID NO:8. In some embodiments, the isolated polypeptides comprise or consist of an amino acid sequence that is at least about 90% identical to SEQ ID NO:8 and comprise a serine at the position corresponding to position 352 of SEQ ID NO:8. In some embodiments, the isolated polypeptides comprise or consist of an amino acid sequence that is at least about 90% identical to SEQ ID NO:8, provided that the isolated polypeptides comprise a serine at the position corresponding to position 352 of SEQ ID NO:8.

In some embodiments, the isolated polypeptides comprise a serine at the position corresponding to position 352 of SEQ ID NO:8. In some embodiments, the isolated polypeptides comprise or consist of an amino acid sequence that is at least about 95% identical to SEQ ID NO:8. In some embodiments, the isolated polypeptides comprise or consist of an amino acid sequence that is at least about 95% identical to SEQ ID NO:8 and comprise a serine at the position corresponding to position 352 of SEQ ID NO:8. In some embodiments, the isolated polypeptides comprise or consist of an amino acid sequence that is at least about 95% identical to SEQ ID NO:8, provided that the isolated polypeptides comprise a serine at the position corresponding to position 352 of SEQ ID NO:8. In some embodiments, the isolated polypeptides comprise a serine at the position corresponding to position 352 of SEQ ID NO:8. In some embodiments, the isolated polypeptides comprise or consist of an amino acid sequence that is at least about 98% identical to SEQ ID NO:8. In some embodiments, the isolated polypeptides comprise or consist of an amino acid sequence that is at least about 98% identical to SEQ ID NO:8 and comprise a serine at the position corresponding to position 352 of SEQ ID NO:8. In some embodiments, the isolated polypeptides comprise or consist of an amino acid sequence that is at least about 98% identical to SEQ ID NO:8, provided that the isolated polypeptides comprise a serine at the position corresponding to position 352 of SEQ ID NO:8. In some embodiments, the isolated polypeptides comprise a serine at the position corresponding to position 352 of SEQ ID NO:8. In some embodiments, the isolated polypeptides comprise or consist of an amino acid sequence that is at least about 99% identical to SEQ ID NO:8. In some embodiments, the isolated polypeptides comprise or consist of an amino acid sequence that is at least about 99% identical to SEQ ID NO:8 and comprise a serine at the position corresponding to position 352 of SEQ ID NO:8. In some embodiments, the isolated polypeptides comprise or consist of an amino acid sequence that is at least about 99% identical to SEQ ID NO:8, provided that the isolated polypeptides comprise a serine at the position corresponding to position 352 of SEQ ID NO:8.

In some embodiments, the isolated polypeptides comprise or consist of at least about 15, at least about 20, at least about 25, at least about 30, at least about 35, at least about 40, at least about 45, at least about 50, at least about 60, at least about 70, at least about 80, at least about 90, at least about 100, at least about 150, at least about 200, at least about 250, at least about 300, or at least about 350 contiguous amino acids of SEQ ID NO:8. In some embodiments, the isolated polypeptides also comprise a serine at a position corresponding to position 352 of SEQ ID NO:8. In some embodiments, the isolated polypeptides comprise or consist of an amino acid sequence at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to at least about 8, at least about 10, at least about 15, at least about 20, at least about 25, at least about 30, at least about 35, at least about 40, at least about 45, at least about 50, at least about 60, at least about 70, at least about 80, at least about 90, at least about 100, at least about 150, at least about 200, at least about 250, at least about 300, or at least about 350 contiguous amino acids of SEQ ID NO:8. In some embodiments, the isolated polypeptides also comprise a serine at a position corresponding to position 352 of SEQ ID NO:8. In some embodiments, the isolated polypeptides comprise or consist of an amino acid sequence at least about 90%, at least about 91%, at least about 92%, at least about 93%, at least about 94%, at least about 95%, at least about 96%, at least about 97%, at least about 98%, at least about 99%, or 100% identical to at least about 8, at least about 10, at least about 15, at least about 20, at least about 25, at least about 30, at least about 35, at least about 40, at least about 45, at least about 50, at least about 60, at least about 70, at least about 80, at least about 90, at least about 100, at least about 150, at least about 200, at least about 250, at least about 300, or at least about 350 contiguous amino acids of SEQ ID NO:8. In some embodiments, the isolated polypeptides also comprise a serine at a position corresponding to position 352 of SEQ ID NO:8.

In some embodiments, the isolated polypeptides comprise or consist of an amino acid sequence at least 90% identical to at least 300 contiguous amino acids of SEQ ID NO:8. In some embodiments, the isolated polypeptides comprise or consist of an amino acid sequence at least 90% identical to at least 300 contiguous amino acids of SEQ ID NO:8 and the isolated polypeptides also comprise a serine at a position corresponding to position 352 of SEQ ID NO:8. In some embodiments, the isolated polypeptides comprise or consist of an amino acid sequence at least 95% identical to at least 300 contiguous amino acids of SEQ ID NO:8. In some embodiments, the isolated polypeptides comprise or consist of an amino acid sequence at least 95% identical to at least 300 contiguous amino acids of SEQ ID NO:8 and the isolated polypeptides also comprise a serine at a position corresponding to position 352 of SEQ ID NO:8. In some embodiments, the isolated polypeptides comprise or consist of an amino acid sequence at least 98% identical to at least 300 contiguous amino acids of SEQ ID NO:8. In some embodiments, the isolated polypeptides comprise or consist of an amino acid sequence at least 98% identical to at least 300 contiguous amino acids of SEQ ID NO:8 and the isolated polypeptides also comprise a serine at a position corresponding to position 352 of SEQ ID NO:8. In some embodiments, the isolated polypeptides comprise or consist of an amino acid sequence at least 99% identical to at least 300 contiguous amino acids of SEQ ID NO:8. In some embodiments, the isolated polypeptides comprise or consist of an amino acid sequence at least 99% identical to at least 300 contiguous amino acids of SEQ ID NO:8 and the isolated polypeptides also comprise a serine at a position corresponding to position 352 of SEQ ID NO:8.

In some embodiments, the isolated polypeptides comprise or consist of at least about 15, at least about 20, at least about 25, at least about 30, at least about 35, at least about 40, at least about 45, at least about 50, at least about 60, at least about 70, at least about 80, at least about 90, or at least about 100 contiguous amino acids of SEQ ID NO:8. In some embodiments, the isolated polypeptides also comprise a serine at a position corresponding to position 352 of SEQ ID NO:8. In some embodiments, the isolated polypeptides comprise or consist of an amino acid sequence at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to at least about 8, at least about 10, at least about 15, at least about 20, at least about 25, at least about 30, at least about 35, at least about 40, at least about 45, at least about 50, at least about 60, at least about 70, at least about 80, at least about 90, or at least about 100 contiguous amino acids of SEQ ID NO:8. In some embodiments, the isolated polypeptides also comprise a serine at a position corresponding to position 352 of SEQ ID NO:8. In some embodiments, the isolated polypeptides comprise or consist of an amino acid sequence at least about 90%, at least about 91%, at least about 92%, at least about 93%, at least about 94%, at least about 95%, at least about 96%, at least about 97%, at least about 98%, at least about 99%, or 100% identical to at least about 8, at least about 10, at least about 15, at least about 20, at least about 25, at least about 30, at least about 35, at least about 40, at least about 45, at least about 50, at least about 60, at least about 70, at least about 80, at least about 90, or at least about 100 contiguous amino acids of SEQ ID NO:8. In some embodiments, the isolated polypeptides also comprise a serine at a position corresponding to position 352 of SEQ ID NO:8.

A representative wild-type B4GALT1 polypeptide sequence is recited in SEQ ID NO:7. A representative B4GALT1 variant polypeptide sequence is recited in SEQ ID NO:8.

The isolated polypeptides disclosed herein can comprise an amino acid sequence of a naturally occurring B4GALT1 polypeptide, or can comprise a non-naturally occurring sequence. In some embodiments, the naturally occurring sequence can differ from the non-naturally occurring sequence due to conservative amino acid substitutions. For example, the sequence can be identical with the exception of conservative amino acid substitutions.

In some embodiments, the isolated polypeptides disclosed herein are linked or fused to heterologous polypeptides or heterologous molecules or labels, numerous examples of which are disclosed elsewhere herein. For example, the proteins can be fused to a heterologous polypeptide providing increased or decreased stability. The fused domain or heterologous polypeptide can be located at the N-terminus, the C-terminus, or internally within the polypeptide. A fusion partner may, for example, assist in providing T helper epitopes (an immunological fusion partner), or may assist in expressing the protein (an expression enhancer) at higher yields than the native recombinant polypeptide. Certain fusion partners are both immunological and expression enhancing fusion partners. Other fusion partners may be selected to increase the solubility of the polypeptide or to facilitate targeting the polypeptide to desired intracellular compartments. Some fusion partners include affinity tags, which facilitate purification of the polypeptide.

In some embodiments, a fusion protein is directly fused to the heterologous molecule or is linked to the heterologous molecule via a linker, such as a peptide linker. Suitable peptide linker sequences may be chosen, for example, based on the following factors: 1) the ability to adopt a flexible extended conformation; 2) the resistance to adopt a secondary structure that could interact with functional epitopes on the first and second polypeptides; and 3) the lack of hydrophobic or charged residues that might react with the polypeptide functional epitopes. For example, peptide linker sequences may contain Gly, Asn and Ser residues. Other near neutral amino acids, such as Thr and Ala may also be used in the linker sequence. Amino acid sequences which may be usefully employed as linkers include those disclosed in, for example, Maratea et al., *Gene,* 1985, 40, 39-46; Murphy et al., *Proc. Natl. Acad. Sci. USA,* 1986, 83, 8258-8262; and U.S. Pat. Nos. 4,935,233 and 4,751,180. A linker sequence may generally be, for example, from 1 to about 50 amino acids in length. Linker sequences are generally not required when the first and second polypeptides have non-essential N-terminal amino acid regions that can be used to separate the functional domains and prevent steric interference.

In some embodiments, the polypeptides are operably linked to a cell-penetrating domain. For example, the cell-penetrating domain can be derived from the HIV-1 TAT protein, the TLM cell-penetrating motif from human hepatitis B virus, MPG, Pep-1, VP22, a cell-penetrating peptide from Herpes simplex virus, or a polyarginine peptide sequence. See, e.g., WO 2014/089290. The cell-penetrating domain can be located at the N-terminus, the C-terminus, or anywhere within the protein.

In some embodiments, the polypeptides are operably linked to a heterologous polypeptide for ease of tracking or purification, such as a fluorescent protein, a purification tag, or an epitope tag. Examples of fluorescent proteins include, but are not limited to, green fluorescent proteins (e.g., GFP, GFP-2, tagGFP, turboGFP, eGFP, Emerald, Azami Green, Monomeric Azami Green, CopGFP, AceGFP, ZsGreenI), yellow fluorescent proteins (e.g., YFP, eYFP, Citrine, Venus, YPet, PhiYFP, ZsYellowI), blue fluorescent proteins (e.g. eBFP, eBFP2, Azurite, mKalamaI, GFPuv, Sapphire, T-sapphire), cyan fluorescent proteins (e.g. eCFP, Cerulean, CyPet, AmCyanI, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRedI, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include, but are not limited to, glutathione-S-transferase (GST), chitin binding protein (CBP), maltose binding protein, thioredoxin (TRX), poly (NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, 51, T7, V5, VSV-G, histidine (His), biotin carboxyl carrier protein (BCCP), and calmodulin. In some embodiments, the heterologous molecule is an immunoglobulin Fc domain, a peptide tag, a transduction domain, poly(ethylene glycol), polysialic acid, or glycolic acid.

In some embodiments, the isolated polypeptides comprise non-natural or modified amino acids or peptide analogs. For example, there are numerous D-amino acids or amino acids which have a different functional substituent than the naturally occurring amino acids. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site-specific way.

In some embodiments, the isolated polypeptides are peptide mimetics, which can be produced to resemble peptides, but which are not connected via a natural peptide linkage. For example, linkages for amino acids or amino acid analogs include, but are not limited to, —$CH_2$NH—, —$CH_2$S—, —$CH_2$—, —CH═CH— (cis and trans), —$COCH_2$—, —CH(OH)$CH_2$—, and —$CHH_2$SO—. Peptide analogs can have more than one atom between the bond atoms, such as b-alanine, gaminobutyric acid, and the like. Amino acid analogs and peptide analogs often have enhanced or desirable properties, such as, more economical production, greater chemical stability, enhanced pharmacological properties (half-life, absorption, potency, efficacy, and so forth), altered specificity (e.g., a broad-spectrum of biological activities), reduced antigenicity, and others desirable properties.

In some embodiments, the isolated polypeptides comprise D-amino acids, which can be used to generate more stable peptides because D amino acids are not recognized by peptidases. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations (see, e.g., Rizo and Gierasch, Ann. Rev. Biochem., 1992, 61, 387).

The present disclosure also provides nucleic acid molecules encoding any of the polypeptides disclosed herein. This includes all degenerate sequences related to a specific polypeptide sequence (i.e., all nucleic acids having a sequence that encodes one particular polypeptide sequence as well as all nucleic acids, including degenerate nucleic acids, encoding the disclosed variants and derivatives of the protein sequences). Thus, while each particular nucleic acid sequence may not be written out herein, each and every sequence is in fact disclosed and described herein through the disclosed polypeptide sequences.

The present disclosure also provides compositions comprising any one or more of the nucleic acid molecules and/or any one or more of the polypeptides disclosed herein. In some embodiments, the compositions comprise a carrier. In some embodiments, the carrier increases the stability of the nucleic acid molecule and/or polypeptide (e.g., prolonging the period under given conditions of storage (e.g., −20° C., 4° C., or ambient temperature) for which degradation products remain below a threshold, such as below 0.5% by weight of the starting nucleic acid or protein; or increasing the stability in vivo). Examples of carriers include, but are not limited to, poly(lactic acid) (PLA) microspheres, poly (D,L-lactic-coglycolic-acid) (PLGA) microspheres, liposomes, micelles, inverse micelles, lipid cochleates, and lipid microtubules.

The present disclosure also provides methods of producing any of the B4GALT1 polypeptides or fragments thereof disclosed herein. Such B4GALT1 polypeptides or fragments thereof can be produced by any suitable method. For example, B4GALT1 polypeptides or fragments thereof can be produced from host cells comprising nucleic acid molecules (e.g., recombinant expression vectors) encoding such B4GALT1 polypeptides or fragments thereof. Such methods can comprise culturing a host cell comprising a nucleic acid molecule (e.g., recombinant expression vector) encoding an B4GALT1 polypeptide or fragment thereof under conditions sufficient to produce the B4GALT1 polypeptide or fragment thereof, thereby producing the B4GALT1 polypeptide or fragment thereof. The nucleic acid can be operably linked to a promoter active in the host cell, and the culturing can be carried out under conditions whereby the nucleic acid is expressed. Such methods can further comprise recovering the expressed B4GALT1 polypeptide or fragment thereof. The recovering can further comprise purifying the B4GALT1 polypeptide or fragment thereof.

Examples of suitable systems for protein expression include host cells such as, for example: bacterial cell expression systems (e.g., *Escherichia coli, Lactococcus lactis*), yeast cell expression systems (e.g., *Saccharomyces cerevisiae, Pichia pastoris*), insect cell expression systems (e.g., baculovirus-mediated protein expression), and mammalian cell expression systems.

Examples of nucleic acid molecules encoding B4GALT1 polypeptides or fragments thereof are disclosed in more detail elsewhere herein. In some embodiments, the nucleic acid molecules are codon optimized for expression in the host cell. In some embodiments, the nucleic acid molecules are operably linked to a promoter active in the host cell. The promoter can be a heterologous promoter (i.e., a promoter than is not a naturally occurring B4GALT1 promoter). Examples of promoters suitable for *Escherichia coli* include, but are not limited to, arabinose, lac, tac, and T7 promoters. Examples of promoters suitable for *Lactococcus lactis* include, but are not limited to, P170 and nisin promoters. Examples of promoters suitable for *Saccharomyces cerevisiae* include, but are not limited to, constitutive promoters such as alcohol dehydrogenase (ADHI) or enolase (ENO) promoters or inducible promoters such as PHO, CUP1, GAL1, and G10. Examples of promoters suitable for *Pichia pastoris* include, but are not limited to, the alcohol oxidase I (AOX I) promoter, the glyceraldehyde 3 phosphate dehydrogenase (GAP) promoter, and the glutathione dependent formaldehyde dehydrogenase (FLDI) promoter. An example of a promoter suitable for a baculovirus-mediated system is the late viral strong polyhedrin promoter.

In some embodiments, the nucleic acid molecules encode a tag in frame with the B4GALT1 polypeptide or fragment thereof to facilitate protein purification. Examples of tags are disclosed elsewhere herein. Such tags can, for example, bind to a partner ligand (e.g., immobilized on a resin) such that the tagged protein can be isolated from all other proteins (e.g., host cell proteins). Affinity chromatography, high performance liquid chromatography (HPLC), and size exclusion chromatography (SEC) are examples of methods that can be used to improve the purity of the expressed protein.

Other methods can also be used to produce B4GALT1 polypeptides or fragments thereof. For example, two or more peptides or polypeptides can be linked together by protein chemistry techniques. For example, peptides or polypeptides can be chemically synthesized using either Fmoc (9-fluorenylmethyloxycarbonyl) or Boc (tert-butyloxycarbonoyl) chemistry. Such peptides or polypeptides can be synthesized by standard chemical reactions. For example, a peptide or polypeptide can be synthesized and not cleaved from its synthesis resin, whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively. Alternately, the peptide or polypeptide can be independently synthesized in vivo as described herein. Once isolated, these independent peptides or polypeptides may be linked to form a peptide or fragment thereof via similar peptide condensation reactions.

In some embodiments, enzymatic ligation of cloned or synthetic peptide segments allow relatively short peptide fragments to be joined to produce larger peptide fragments, polypeptides, or whole protein domains (Abrahmsen et al., *Biochemistry,* 1991, 30, 4151). Alternately, native chemical ligation of synthetic peptides can be utilized to synthetically construct large peptides or polypeptides from shorter peptide fragments. This method can consist of a two-step chemical reaction (see, Dawson et al., *Science,* 1994, 266, 776-779). The first step can be the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate can undergo spontaneous, rapid intramolecular reaction to form a native peptide bond at the ligation site.

In some embodiments, unprotected peptide segments can be chemically linked where the bond formed between the peptide segments as a result of the chemical ligation is an unnatural (non-peptide) bond (see, Schnolzer et al., *Science,* 1992, 256, 221).

The present disclosure also provides cells (e.g., recombinant host cells) comprising any one or more of the nucleic acid molecules and/or any one or more of the polypeptides disclosed herein. The cells can be in vitro, ex vivo, or in vivo. Nucleic acid molecules can be linked to a promoter and other regulatory sequences so they are expressed to produce an encoded protein.

In some embodiments, the cell is a totipotent cell or a pluripotent cell (e.g., an embryonic stem (ES) cell such as a rodent ES cell, a mouse ES cell, or a rat ES cell). Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

In some embodiments, the cell is a primary somatic cell, or a cell that is not a primary somatic cell. Somatic cells can include any cell that is not a gamete, germ cell, gametocyte, or undifferentiated stem cell. In some embodiments, the cell can also be a primary cell. Primary cells include cells or cultures of cells that have been isolated directly from an organism, organ, or tissue. Primary cells include cells that are neither transformed nor immortal. Primary cells include any cell obtained from an organism, organ, or tissue which was not previously passed in tissue culture or has been previously passed in tissue culture but is incapable of being indefinitely passed in tissue culture. Such cells can be isolated by conventional techniques and include, for example, somatic cells, hematopoietic cells, endothelial cells, epithelial cells, fibroblasts, mesenchymal cells, keratinocytes, melanocytes, monocytes, mononuclear cells, adipocytes, preadipocytes, neurons, glial cells, hepatocytes, skeletal myoblasts, and smooth muscle cells. For example, primary cells can be derived from connective tissues, muscle tissues, nervous system tissues, or epithelial tissues.

In some embodiments, the cells may normally not proliferate indefinitely but, due to mutation or alteration, have evaded normal cellular senescence and instead can keep undergoing division. Such mutations or alterations can occur naturally or be intentionally induced. Examples of immortalized cells include, but are not limited to, Chinese hamster ovary (CHO) cells, human embryonic kidney cells (e.g., HEK 293 cells), and mouse embryonic fibroblast cells (e.g., 3T3 cells). Numerous types of immortalized cells are well known. Immortalized or primary cells include cells that are typically used for culturing or for expressing recombinant genes or proteins. In some embodiments, the cell is a differentiated cell, such as a liver cell (e.g., a human liver cell).

The cell can be from any source. For example, the cell can be a eukaryotic cell, an animal cell, a plant cell, or a fungal (e.g., yeast) cell. Such cells can be fish cells or bird cells, or such cells can be mammalian cells, such as human cells, non-human mammalian cells, rodent cells, mouse cells or rat cells. Mammals include, but are not limited to, humans, non-human primates, monkeys, apes, cats dogs, horses, bulls, deer, bison, sheep, rodents (e.g., mice, rats, hamsters, guinea pigs), livestock (e.g., bovine species such as cows, steer, etc.; ovine species such as sheep, goats, etc.; and porcine species such as pigs and boars). Birds include, but are not limited to, chickens, turkeys, ostrich, geese, ducks, etc. Domesticated animals and agricultural animals are also included. The term "non-human animal" excludes humans.

The present disclosure also provides methods for detecting the presence of a B4GALT1 variant gene, mRNA, cDNA, and/or polypeptide in a biological sample from a subject human. It is understood that gene sequences within a population and mRNAs and proteins encoded by such genes can vary due to polymorphisms such as single-nucleotide polymorphisms. The sequences provided herein for the B4GALT1 gene, mRNA, cDNA, and polypeptide are only exemplary sequences. Other sequences for the B4GALT1 gene, mRNA, cDNA, and polypeptide are also possible.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting a variant B4GALT1 nucleic acid molecule, preliminary processing designed to isolate or enrich the sample for the genomic DNA can be employed. A variety of known techniques may be used for this purpose. When detecting the level of B4GALT1 mRNA, different techniques can be used enrich the biological sample with mRNA. Various methods to detect the presence or level of a mRNA or the presence of a particular variant genomic DNA locus can be used.

In some embodiments, the disclosure provides methods of detecting the presence or absence of a variant B4GALT1 nucleic acid molecule comprising sequencing at least a portion of a nucleic acid in a biological sample to determine whether the nucleic acid comprises nucleotides 53757 to 53577 of SEQ ID NO:2 at positions that correspond to positions 53757 to 53577 of SEQ ID NO:2.

In some embodiments, the disclosure provides methods of detecting the presence or absence of a variant B4GALT1 nucleic acid molecule comprising sequencing at least a portion of a nucleic acid in a biological sample to determine whether the nucleic acid comprises nucleotides 1243 to 1245 of SEQ ID NO:4 at positions that correspond to positions 1243 to 1245 of SEQ ID NO:4.

In some embodiments, the disclosure provides methods of detecting the presence or absence of a variant B4GALT1 nucleic acid molecule comprising sequencing at least a portion of a nucleic acid in a biological sample to determine whether the nucleic acid comprises nucleotides 1054 to 1056 of SEQ ID NO:6 at positions that correspond to positions 1054 to 1056 of SEQ ID NO:6.

In some embodiments, the methods of detecting the presence or absence of a variant B4GALT1 nucleic acid molecule (e.g., gene, mRNA, or cDNA) in a human subject, comprise: performing an assay on a biological sample from the human subject that determines whether a nucleic acid molecule in the biological sample comprises a nucleic acid sequence that encodes a serine at position 352 of SEQ ID NO:8. In some embodiments, the biological sample comprises a cell or cell lysate. Such methods can comprise, for example, obtaining a biological sample from the subject comprising a B4GALT1 gene, mRNA, or cDNA and performing an assay on the biological sample that determines that a position of the B4GALT1 gene, mRNA, or cDNA corresponding to positions 53757 to 53577 of SEQ ID NO:2 (gene), positions 1243 to 1245 of SEQ ID NO:4 (mRNA), or positions 1054 to 1056 of SEQ ID NO:6 (cDNA) encodes a serine instead of an asparagine at a position corresponding to position 352 of the variant B4GALT1 polypeptide. Such assays can comprise, for example determining the identity of these positions of the particular B4GALT1 nucleic acid molecule.

In some embodiments, the assay comprises: sequencing a portion of the B4GALT1 genomic sequence of a nucleic acid molecule in the biological sample from the human subject, wherein the portion sequenced includes positions corresponding to positions 53575 to 53577 of SEQ ID NO:2; sequencing a portion of the B4GALT1 mRNA sequence of a nucleic acid molecule in the biological sample from the human subject, wherein the portion sequenced includes positions corresponding to positions 1243 to 1245 of SEQ ID NO:4; or sequencing a portion of the B4GALT1 cDNA sequence of a nucleic acid molecule in the biological sample from the human subject, wherein the portion sequenced includes positions corresponding to positions 1054 to 1056 of SEQ ID NO:6.

In some embodiments, the assay comprises: a) contacting the biological sample with a primer hybridizing to: i) a portion of the B4GALT1 genomic sequence that is proximate to a position of the B4GALT1 genomic sequence corresponding to positions 53575 to 53577 of SEQ ID NO:2; ii) a portion of the B4GALT1 mRNA sequence that is proximate to a position of the B4GALT1 mRNA corresponding to positions 1243 to 1245 of SEQ ID NO:4; or iii) a portion of the B4GALT1 cDNA sequence that is proximate to a position of the B4GALT1 cDNA corresponding to positions 1054 to 1056 of SEQ ID NO:6; b) extending the primer at least through: i) the position of the B4GALT1 genomic sequence corresponding to positions 53575 to 53577; ii) the position of the B4GALT1 mRNA corresponding to positions 1243 to 1245; or iii) the position of the B4GALT1 cDNA corresponding to positions 1054 to 1056; and c) determining whether the extension product of the primer comprises nucleotides at positions: i) corresponding to positions 53575 to 53577 of the B4GALT1 genomic sequence; ii) corresponding to positions 1243 to 1245 of the B4GALT1 mRNA; or iii) corresponding to positions 1054 to 1056 of the B4GALT1 cDNA; that encode a serine at position 352 of SEQ ID NO:8. In some embodiments, only B4GALT1 genomic DNA is analyzed. In some embodiments, only B4GALT1 mRNA is analyzed. In some embodiments, only B4GALT1 cDNA is analyzed.

In some embodiments, the assay comprises contacting the biological sample with a primer or probe that specifically hybridizes to a variant B4GALT1 genomic sequence, mRNA sequence, or cDNA sequence and not the corresponding wild-type B4GALT1 sequence under stringent conditions, and determining whether hybridization has occurred.

In some embodiments, the assays described above comprise RNA sequencing (RNA-Seq). In some embodiments, the assays also comprise reverse transcription polymerase chain reaction (RT-PCR).

In some embodiments, the methods utilize probes and primers of sufficient nucleotide length to bind to the target nucleic acid sequence and specifically detect and/or identify a polynucleotide comprising a variant B4GALT1 gene, mRNA, or cDNA. The hybridization conditions or reaction conditions can be determined by the operator to achieve this result. This length may be any length that is sufficient to be useful in a detection method of choice. Generally, for example, about 8, about 11, about 14, about 16, about 18, about 20, about 22, about 24, about 26, about 28, about 30, about 40, about 50, about 75, about 100, about 200, about 300, about 400, about 500, about 600, or about 700 nucleotides, or more, or from about 11 to about 20, from about 20 to about 30, from about 30 to about 40, from about 40 to about 50, from about 50 to about 100, from about 100 to about 200, from about 200 to about 300, from about 300 to about 400, from about 400 to about 500, from about 500 to about 600, from about 600 to about 700, or from about 700 to about 800, or more nucleotides in length are used. Such probes and primers can hybridize specifically to a target sequence under high stringency hybridization conditions. Probes and primers may have complete nucleic acid sequence identity of contiguous nucleotides with the target sequence, although probes differing from the target nucleic acid sequence and that retain the ability to specifically detect and/or identify a target nucleic acid sequence may be designed by conventional methods. Accordingly, probes and primers can share about 80%, about 85%, about 90%, about 91%, about 92%, about 93%, about 94%, about 95%, about 96%, about 97%, about 98%, about 99%, or 100% sequence identity or complementarity to the target nucleic acid molecule.

In some embodiments, specific primers can be used to amplify the variant B4GALT1 locus and/or B4GALT1 variant mRNA or cDNA to produce an amplicon that can be used as a specific probe or can itself be detected for identifying the variant B4GALT1 locus or for determining the level of specific B4GALT1 mRNA or cDNA in a biological sample. The B4GALT1 variant locus can be used to denote a genomic nucleic acid sequence including a position corresponding to positions 53575 to 53577 in SEQ ID NO:2. When the probe is hybridized with a nucleic acid molecule in a biological sample under conditions that allow for the binding of the probe to the nucleic acid molecule, this binding can be detected and allow for an indication of the presence of the variant B4GALT1 locus or the presence or the level of variant B4GALT1 mRNA or cDNA in the biological sample. Such identification of a bound probe has been described. The specific probe may comprise a sequence of at least about 80%, from about 80% to about 85%, from about 85% to about 90%, from about 90% to about 95%, and from about 95% to about 100% identical (or complementary) to a specific region of a variant B4GALT1 gene. The specific probe may comprise a sequence of at least about 80%, from about 80% to about 85%, from about 85% to about 90%, from about 90% to about 95%, and from about 95% to about 100% identical (or complementary) to a specific region of a variant B4GALT1 mRNA. The specific probe may comprise a sequence of at least about 80%, from about 80% to about 85%, from about 85% to about 90%, from about 90% to about 95%, and from about 95% to about 100% identical (or complementary) to a specific region of a variant B4GALT1 cDNA.

In some embodiments, to determine whether the nucleic acid complement of a biological sample comprises the serine encoding nucleotides at positions 53575 to 53577 in the variant B4GALT1 gene locus (SEQ ID NO:2), the biological sample may be subjected to a nucleic acid amplification method using a primer pair that includes a first primer derived from the 5' flanking sequence adjacent to positions 53575 to 53577 and a second primer derived from the 3' flanking sequence adjacent to positions 53575 to 53577 to produce an amplicon that is diagnostic for the presence of the SNP at positions 53575 to 53577 in the variant B4GALT1 gene locus (SEQ ID NO:2). In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions 53575 to 53577 and at least 1, 2, 3, 4, 5, 6, 7, 8, 9, 10, or more nucleotides on each side of positions 53575 to 53577. Similar amplicons can be generated from the mRNA and/or cDNA sequences.

Representative methods for preparing and using probes and primers are described, for example, in *Molecular Cloning: A Laboratory Manual,* 2nd Ed., Vol. 1-3, ed. Sambrook et al., Cold Spring Harbor Laboratory Press, Cold Spring Harbor, N.Y. 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990). PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using known guidelines.

As described in further detail below, any conventional nucleic acid hybridization or amplification or sequencing method can be used to specifically detect the presence of the variant B4GALT1 gene locus and/or the level of variant B4GALT1 mRNA or cDNA. In some embodiments, the nucleic acid molecule can be used either as a primer to amplify a region of the B4GALT1 nucleic acid or the nucleic acid molecule can be used as a probe that hybridizes under stringent conditions to a nucleic acid molecule comprising the variant B4GALT1 gene locus or a nucleic acid molecule comprising a variant B4GALT1 mRNA or cDNA.

A variety of nucleic acid techniques are known, including, for example, nucleic acid sequencing, nucleic acid hybridization, and nucleic acid amplification. Illustrative examples of nucleic acid sequencing techniques include, but are not limited to, chain terminator (Sanger) sequencing and dye terminator sequencing.

Other methods involve nucleic acid hybridization methods other than sequencing, including using labeled primers or probes directed against purified DNA, amplified DNA, and fixed cell preparations (fluorescence in situ hybridization). In some methods, a target nucleic acid may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

Any method can be used for detecting either the non-amplified or amplified polynucleotides including, for example, Hybridization Protection Assay (HPA), quantitative evaluation of the amplification process in real-time, and determining the quantity of target sequence initially present in a sample, but which is not based on a real-time amplification.

Also provided are methods for identifying nucleic acids which do not necessarily require sequence amplification and are based on, for example, the known methods of Southern (DNA:DNA) blot hybridizations, in situ hybridization (ISH), and fluorescence in situ hybridization (FISH) of chromosomal material, using appropriate probes. Southern blotting can be used to detect specific nucleic acid sequences. In such methods, nucleic acid that is extracted from a sample is fragmented, electrophoretically separated on a matrix gel, and transferred to a membrane filter. The filter bound nucleic acid is subject to hybridization with a labeled probe complementary to the sequence of interest. Hybridized probe bound to the filter is detected.

In hybridization techniques, stringent conditions can be employed such that a probe or primer will specifically hybridize to its target. In some embodiments, a polynucleotide primer or probe under stringent conditions will hybridize to its target sequence (e.g., the variant B4GALT1 gene locus, mRNA, or cDNA) to a detectably greater degree than to other sequences (e.g., the corresponding wild-type B4GALT1 locus, mRNA, or cDNA), such as at least 2-fold over background or 10-fold over background. Stringent conditions are sequence-dependent and will be different in different circumstances. By controlling the stringency of the hybridization and/or washing conditions, target sequences that are 100% complementary to the probe can be identified (homologous probing). Alternately, stringency conditions can be adjusted to allow some mismatching in sequences so that lower degrees of identity are detected (heterologous probing). Generally, a probe is less than about 1000 nucleotides in length or less than about 500 nucleotides in length.

Appropriate stringency conditions which promote DNA hybridization, for example, 6× sodium chloride/sodium citrate (SSC) at about 45° C., followed by a wash of 2×SSC at 50° C., are known or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for longer probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In hybridization reactions, specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.,* 1984, 138, 267-284: $T_m$=81.5° C.+16.6 (log M)+0.41 (% GC) −0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1° C., 2° C., 3° C., or 4° C. lower than the thermal melting point ($T_m$); moderately stringent conditions can utilize a hybridization and/or wash at 6° C., 7° C., 8° C., 9° C., or 10° C. lower than the thermal melting point ($T_m$); low stringency conditions can utilize a hybridization and/or wash at 11° C., 12° C., 13° C., 14° C., 15° C., or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used.

Also provided are methods for detecting the presence or levels of variant B4GALT1 polypeptide in a biological sample, including, for example, protein sequencing and immunoassays. In some embodiments, the method of detecting the presence of B4GALT1 Asn352Ser in a human subject, comprises performing an assay on a biological sample from the human subject that determines the presence of B4GALT1 Asn352Ser in the biological sample.

Illustrative non-limiting examples of protein sequencing techniques include, but are not limited to, mass spectrometry and Edman degradation. Illustrative examples of immunoassays include, but are not limited to, immunoprecipitation, Western blot, immunohistochemistry, ELISA, immunocytochemistry, flow cytometry, and immuno-PCR. Polyclonal or monoclonal antibodies detectably labeled using various known techniques (e.g., calorimetric, fluorescent, chemiluminescent, or radioactive) are suitable for use in the immunoassays.

The present disclosure also provides methods for determining a subject's susceptibility to developing a cardiovascular condition or risk of developing a cardiovascular condition. The subject can be any organism, including, for example, a human, a non-human mammal, a rodent, a mouse, or a rat. In some embodiments, the methods comprise detecting the presence of the variant B4GALT1 genomic DNA, mRNA, or cDNA in a biological sample from the subject. It is understood that gene sequences within a population and mRNAs encoded by such genes can vary due to polymorphisms such as SNPs. The sequences provided herein for the B4GALT1 gene, mRNA, cDNA, and polypeptide are only exemplary sequences and other such sequences are also possible.

Non-limiting examples of a cardiovascular condition include an elevated level of one or more serum lipids. The serum lipids comprise one or more of cholesterol, LDL, HDL, triglycerides, HDL-cholesterol, and non-HDL cholesterol, or any subfraction thereof (e.g., HDL2, HDL2a, HDL2b, HDL2c, HDL3, HDL3a, HDL3b, HDL3c, HDL3d, LDL1, LDL2, LDL3, lipoprotein A, Lpa1, Lpa1, Lpa3, Lpa4, or Lpa5). A cardiovascular condition may comprise elevated levels of coronary artery calcification. A cardiovascular condition may comprise Type IId glycosylation (CDG-IId). A cardiovascular condition may comprise elevated levels of pericardial fat. A cardiovascular condition may also comprise coronary artery disease (CAD), myocardial infarction (MI), peripheral artery disease (PAD), stroke, pulmonary embolism, deep vein thrombosis (DVT), and bleeding diatheses and coagulopathies. A cardiovascular condition may comprise an atherothrombotic condition. The atherothrombotic condition may comprise elevated levels of fibrinogen. The atherothrombotic condition may comprises a fibrinogen-mediated blood clot. A cardiovascular condition may comprise elevated levels of fibrinogen. A cardiovascular condition may comprise a fibrinogen-mediated blood clot. A cardiovascular condition may comprise a blood clot formed from the involvement of fibrinogen activity. A fibrinogen-mediated blood clot or blood clot formed from the involvement of fibrinogen activity may be in any vein or artery in the body.

In some embodiments, the methods of determining a human subject's susceptibility to developing a cardiovascular condition, comprise: a) performing an assay on a biological sample from the human subject that determines whether a nucleic acid molecule in the biological sample comprises a nucleic acid sequence that encodes a serine at the position corresponding to position 352 of the full length/mature variant B4GALT1 Asn352Ser polypeptide; and b) classifying the human subject as being at decreased risk for developing the cardiovascular condition if a nucleic acid molecule comprising a nucleic acid sequence that encodes a serine at position 352 of the full length/mature variant B4GALT1 Asn352Ser polypeptide is detected in the biological sample, or classifying the human subject as being at increased risk for developing the cardiovascular condition if a nucleic acid molecule comprising a nucleic acid sequence that encodes a serine at position 352 of the full length/mature variant B4GALT1 Asn352Ser polypeptide is not detected in the biological sample. In some embodiments, the variant B4GALT1 Asn352Ser polypeptide comprises SEQ ID NO:8. In some embodiments, the nucleic acid molecule in the biological sample is genomic DNA, mRNA, or cDNA.

In some embodiments, the disclosure provides methods of determining a human subject's susceptibility to developing a cardiovascular condition, comprising: a) performing an assay on a biological sample from the human subject that determines whether a nucleic acid molecule in the biological sample comprises nucleotides 53757 to 53577 of SEQ ID NO:2 at positions that correspond to positions 53757 to 53577 of SEQ ID NO:2; and b) classifying the human subject as being at decreased risk for developing the cardiovascular condition if a nucleic acid molecule comprising nucleotides 53757 to 53577 of SEQ ID NO:2 at positions that correspond to positions 53757 to 53577 of SEQ ID NO:2 is detected in the biological sample, or classifying the human subject as being at increased risk for developing the cardiovascular condition if a nucleic acid molecule comprising nucleotides 53757 to 53577 of SEQ ID NO:2 at positions that correspond to positions 53757 to 53577 of SEQ ID NO:2 is not detected in the biological sample.

In some embodiments, the disclosure provides methods of determining a human subject's susceptibility to developing a cardiovascular condition, comprising: a) performing an assay on a biological sample from the human subject that determines whether a nucleic acid molecule in the biological sample comprises nucleotides 1243 to 1245 of SEQ ID NO:4 at positions that correspond to positions 1243 to 1245 of SEQ ID NO:4; and b) classifying the human subject as being at decreased risk for developing the cardiovascular condition if a nucleic acid molecule comprising nucleotides 1243 to 1245 of SEQ ID NO:4 at positions that correspond to positions 1243 to 1245 of SEQ ID NO:4 is detected in the biological sample, or classifying the human subject as being at increased risk for developing the cardiovascular condition if a nucleic acid molecule comprising nucleotides 1243 to 1245 of SEQ ID NO:4 at positions that correspond to positions 1243 to 1245 of SEQ ID NO:4 is not detected in the biological sample.

In some embodiments, the disclosure provides methods of determining a human subject's susceptibility to developing a cardiovascular condition, comprising: a) performing an assay on a biological sample from the human subject that determines whether a nucleic acid molecule in the biological sample comprises nucleotides 1054 to 1056 of SEQ ID NO:6 at positions that correspond to positions 1054 to 1056 of SEQ ID NO:6; and b) classifying the human subject as being at decreased risk for developing the cardiovascular condition if a nucleic acid molecule comprising nucleotides 1054 to 1056 of SEQ ID NO:6 at positions that correspond to positions 1054 to 1056 of SEQ ID NO:6 is detected in the biological sample, or classifying the human subject as being at increased risk for developing the cardiovascular condition if a nucleic acid molecule comprising nucleotides 1054 to 1056 of SEQ ID NO:6 at positions that correspond to positions 1054 to 1056 of SEQ ID NO:6 is not detected in the biological sample.

In some embodiments, the methods comprise detecting the presence of a variant B4GALT1 genomic DNA in a biological sample. In some embodiments, such methods comprise determining a subject's susceptibility to developing a cardiovascular condition or risk of developing a cardiovascular condition, comprising: a) obtaining a biological sample from the subject that comprises genomic DNA; b) performing an assay on the genomic DNA that determines the identity of the nucleotides in the DNA occupying positions corresponding to positions 53575 to 53577 of the variant B4GALT1 gene (see, for example, SEQ ID NO:2); and c) classifying the subject as being at decreased risk for developing the cardiovascular condition if the positions in the genomic DNA corresponding to positions 53575 to 53577 of the variant B4GALT1 gene encodes a serine rather than an asparagine. Alternately, the subject can be classified as being at increased risk for developing the cardiovascular condition if the positions in the genomic DNA corresponding to positions 53575 to 53577 of the variant B4GALT1 gene do not encode a serine rather than an asparagine.

In some embodiments, such methods comprise diagnosing a subject with cardiovascular condition, comprising: a) obtaining a biological sample from the subject that comprises genomic DNA; b) performing an assay on the genomic DNA that determines the identity of the nucleotides in the DNA occupying positions corresponding to positions 53575 to 53577 of the variant B4GALT1 gene (see, for example, SEQ ID NO:2); and c) classifying the subject as having a cardiovascular condition if the positions in the genomic DNA corresponding to positions 53575 to 53577 of the variant B4GALT1 gene encodes a serine rather than an asparagine. Alternately, the subject can be classified as not having a cardiovascular condition if the positions in the genomic DNA corresponding to positions 53575 to 53577 of the variant B4GALT1 gene do not encode a serine rather than an asparagine.

In some embodiments, the methods comprise detecting the presence of a variant B4GALT1 mRNA in a biological sample. In some embodiments, such methods comprise determining a subject's susceptibility to developing a cardiovascular condition or risk of developing a cardiovascular condition, comprising: a) obtaining a biological sample from the subject that comprises mRNA; b) performing an assay on the mRNA that determines the identity of the nucleotides in the mRNA occupying positions corresponding to positions 1243 to 1245 of the variant B4GALT1 mRNA (see, for example, SEQ ID NO:4); and c) classifying the subject as being at decreased risk for developing the cardiovascular condition if the positions in the mRNA corresponding to positions 1243 to 1245 of the variant B4GALT1 mRNA encodes a serine rather than an asparagine. Alternately, the subject can be classified as being at increased risk for developing the cardiovascular condition if the positions in the mRNA corresponding to positions 1243 to 1245 of the variant B4GALT1 mRNA do not encode a serine rather than an asparagine.

In some embodiments, such methods comprise diagnosing a subject with cardiovascular condition, comprising: a) obtaining a biological sample from the subject that comprises mRNA; b) performing an assay on the mRNA that determines the identity of the nucleotides in the mRNA occupying positions corresponding to positions 1243 to 1245 of the variant B4GALT1 mRNA (see, for example, SEQ ID NO:4); and c) classifying the subject as having a cardiovascular condition if the positions in the mRNA corresponding to positions 1243 to 1245 of the variant B4GALT1 mRNA encodes a serine rather than an asparagine. Alternately, the subject can be classified as not having a cardiovascular condition if the positions in the mRNA corresponding to positions 1243 to 1245 of the variant B4GALT1 mRNA do not encode a serine rather than an asparagine.

In some embodiments, the methods comprise detecting the presence of a variant B4GALT1 cDNA in a biological sample. In some embodiments, such methods comprise determining a subject's susceptibility to developing a cardiovascular condition or risk of developing a cardiovascular condition, comprising: a) obtaining a biological sample from the subject that comprises cDNA; b) performing an assay on the cDNA that determines the identity of the nucleotides in the cDNA occupying positions corresponding to positions 1054 to 1056 of the variant B4GALT1 cDNA (see, for example, SEQ ID NO:6); and c) classifying the subject as being at decreased risk for developing the cardiovascular condition if the positions in the cDNA corresponding to positions 1054 to 1056 of the variant B4GALT1 cDNA encodes a serine rather than an asparagine. Alternately, the subject can be classified as being at increased risk for developing the cardiovascular condition if the positions in the cDNA corresponding to positions 1054 to 1056 of the variant B4GALT1 cDNA do not encode a serine rather than an asparagine.

In some embodiments, such methods comprise diagnosing a subject with cardiovascular condition, comprising: a) obtaining a biological sample from the subject that comprises cDNA; b) performing an assay on the cDNA that determines the identity of the nucleotides in the cDNA occupying positions corresponding to positions 1054 to 1056 of the variant B4GALT1 cDNA (see, for example, SEQ ID NO:6); and c) classifying the subject as having a cardiovascular condition if the positions in the cDNA corresponding to positions 1054 to 1056 of the variant B4GALT1 cDNA encodes a serine rather than an asparagine. Alternately, the subject can be classified as not having a cardiovascular condition if the positions in the cDNA corresponding to positions 1054 to 1056 of the variant B4GALT1 cDNA do not encode a serine rather than an asparagine.

In some embodiments, the assay comprises: sequencing a portion of the B4GALT1 genomic sequence of a nucleic acid molecule in the biological sample from the human subject, wherein the portion sequenced includes positions corresponding to positions 53575 to 53577 of SEQ ID NO:2; sequencing a portion of the B4GALT1 mRNA sequence of a nucleic acid molecule in the biological sample from the human subject, wherein the portion sequenced includes positions corresponding to positions 1243 to 1245 of SEQ ID NO:4; or sequencing a portion of the B4GALT1 cDNA sequence of a nucleic acid molecule in the biological sample from the human subject, wherein the portion sequenced includes positions corresponding to positions 1054 to 1056 of SEQ ID NO:6.

In some embodiments, the assay comprises: a) contacting the biological sample with a primer hybridizing to: i) a portion of the B4GALT1 genomic sequence that is proximate to a position of the B4GALT1 genomic sequence corresponding to positions 53575 to 53577 of SEQ ID NO:2; ii) a portion of the B4GALT1 mRNA sequence that is proximate to a position of the B4GALT1 mRNA corresponding to positions 1243 to 1245 of SEQ ID NO:4; or iii) a portion of the B4GALT1 cDNA sequence that is proximate to a position of the B4GALT1 cDNA corresponding to positions 1054 to 1056 of SEQ ID NO:6; b) extending the primer at least through: i) the position of the B4GALT1 genomic sequence corresponding to positions 53575 to 53577; ii) the position of the B4GALT1 mRNA corresponding to positions 1243 to 1245; or iii) the position of the B4GALT1 cDNA corresponding to positions 1054 to 1056; and c) determining the whether the extension product of the primer comprises nucleotides at positions: i) corresponding to positions 53575 to 53577 of the B4GALT1 genomic sequence; ii) corresponding to positions 1243 to 1245 of the B4GALT1 mRNA; or iii) corresponding to positions 1054 to 1056 of the B4GALT1 cDNA; that encode a serine at position 352 of SEQ ID NO:8.

In some embodiments, the assay comprises contacting the biological sample with a primer or probe that specifically hybridizes to the variant B4GALT1 genomic sequence, mRNA sequence, or cDNA sequence and not the corresponding wild-type B4GALT1 sequence under stringent conditions, and determining whether hybridization has occurred. In some embodiments, the primer or probe specifically hybridizes to positions within the genomic DNA in the biological sample that corresponds to positions 53575 to 53577 of SEQ ID NO:2. In some embodiments, the primer or probe specifically hybridizes to positions within the mRNA in the biological sample that corresponds to positions 1243 to 1245 of SEQ ID NO:4. In some embodiments, the primer or probe specifically hybridizes to positions within the cDNA in the biological sample that corresponds to positions 1054 to 1056 of SEQ ID NO:6.

Other assays that can be used in the methods disclosed herein include, for example, reverse transcription polymerase chain reaction (RT-PCR) or quantitative RT-PCR (qRT-PCR). Yet other assays that can be used in the methods disclosed herein include, for example, RNA sequencing (RNA-Seq) followed by determination of the presence and quantity of variant mRNA or cDNA in the biological sample.

The present disclosure also provides methods of determining a human subject's susceptibility to developing a cardiovascular condition or diagnosing a subject with cardiovascular condition, comprising: a) performing an assay on a biological sample from the human subject that determines whether a B4GALT1 polypeptide in the biological sample comprises a serine at a position corresponding to position 352 of SEQ ID NO:8; and b) classifying the human subject as being at decreased risk for developing the cardiovascular condition if a B4GALT1 polypeptide comprising a serine at a position corresponding to position 352 of SEQ ID NO:8 is detected in the biological sample, or classifying the human subject as being at increased risk for developing the cardiovascular condition if a B4GALT1 polypeptide comprising a serine at a position corresponding to position 352 of SEQ ID NO:8 is not detected in the biological sample. In some embodiments, the methods further comprise obtaining a biological sample from the subject.

In some embodiments, where a subject has been diagnosed with a cardiovascular condition or as having an increased risk for developing a cardiovascular condition, a therapeutic or prophylactic agent that treats or prevents the cardiovascular condition is administered to the subject. Alternately, the method can further comprise administering a therapeutic agent tailored to prevent or alleviate one or more symptoms associated with progression to more clinically advanced stages of cardiovascular condition, particularly in patients with increased LDL levels and/or those patients who have had or are at increased risk of thrombotic events.

The present disclosure also provides methods for modifying a cell through use of any combination of nuclease agents, exogenous donor sequences, transcriptional activators, transcriptional repressors, antisense molecules such as antisense RNA, siRNA, and shRNA, B4GALT1 polypeptides or fragments thereof, and expression vectors for expressing a recombinant B4GALT1 gene or a nucleic acid encoding an B4GALT1 polypeptide. The methods can occur in vitro, ex vivo, or in vivo. The nuclease agents, exogenous donor sequences, transcriptional activators, transcriptional repressors, antisense molecules such as antisense RNA, siRNA, and shRNA, B4GALT1 polypeptides or fragments thereof, and expression vectors can be introduced into the cell in any form and by any means as described elsewhere herein, and all or some can be introduced simultaneously or sequentially in any combination. Some methods involve only altering an endogenous B4GALT1 gene in a cell. Some methods involve only altering expression of an endogenous B4GALT1 gene through use of transcriptional activators or repressors or through use of antisense molecules such as antisense RNA, siRNA, and shRNA. Some methods involve only introducing a recombinant B4GALT1 gene or nucleic acid encoding a B4GALT1 polypeptide or fragment thereof into a cell. Some methods involve only introducing a B4GALT1 polypeptide or fragment thereof into a cell (e.g., any one of or any combination of the B4GALT1 polypeptides or fragments thereof disclosed herein). Other methods involve both altering an endogenous B4GALT1 gene in a cell and introducing a B4GALT1 polypeptide or fragment thereof or recombinant B4GALT1 gene or nucleic acid encoding a B4GALT1 polypeptide or fragment thereof into the cell. Other methods involve both altering expression of an endogenous B4GALT1 gene in a cell and introducing a B4GALT1 polypeptide or fragment thereof or recombinant B4GALT1 gene or nucleic acid encoding a B4GALT1 polypeptide or fragment thereof into the cell.

The present disclosure provides methods for modifying an endogenous B4GALT1 gene in a genome within a cell (e.g., a pluripotent cell or a differentiated cell) through use of nuclease agents and/or exogenous donor sequences. The methods can occur in vitro, ex vivo, or in vivo. The nuclease agent can be used alone or in combination with an exogenous donor sequence. Alternately, the exogenous donor sequence can be used alone or in combination with a nuclease agent.

Repair in response to double-strand breaks (DSBs) occurs principally through two conserved DNA repair pathways: non-homologous end joining (NHEJ) and homologous recombination (HR) (see, Kasparek & Humphrey, *Seminars in Cell & Dev. Biol.*, 2011, 22, 886-897). Repair of a target nucleic acid (e.g., an endogenous B4GALT1 gene) mediated by an exogenous donor sequence can include any process of exchange of genetic information between the two polynucleotides. For example, NHEJ can also result in the targeted integration of an exogenous donor sequence through direct ligation of the break ends with the ends of the exogenous donor sequence (i.e., NHEJ-based capture). Repair can also occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target.

Targeted genetic modifications to an endogenous B4GALT1 gene in a genome can be generated by contacting a cell with an exogenous donor sequence comprising a 5' homology arm that hybridizes to a 5' target sequence at a target genomic locus within the endogenous B4GALT1 gene and a 3' homology arm that hybridizes to a 3' target sequence at the target genomic locus within the endogenous B4GALT1 gene. The exogenous donor sequence can recombine with the target genomic locus to generate the targeted genetic modification to the endogenous B4GALT1 gene. As one example, the 5' homology arm can hybridize to a target sequence 5' of the position corresponding to positions 53575 to 53577 of SEQ ID NO:1, and the 3' homology arm can hybridize to a target sequence 3' of the position corresponding to positions 53575 to 53577 of SEQ ID NO:1. Such methods can result, for example, in a B4GALT1 gene which contains a nucleotide sequence that encodes a serine at the position corresponding to position 352 of the full length/mature polypeptide produced therefrom. Examples of exogenous donor sequences are disclosed elsewhere herein.

For example, targeted genetic modifications to an endogenous B4GALT1 gene in a genome can be generated by contacting a cell or the genome of a cell with a Cas protein and one or more guide RNAs that hybridize to one or more guide RNA recognition sequences within a target genomic locus in the endogenous B4GALT1 gene. For example, such methods can comprise contacting a cell with a Cas protein and a guide RNA that hybridizes to a guide RNA recognition sequence within the endogenous B4GALT1 gene. In some embodiments, the guide RNA recognition sequence is located within a region corresponding to exon 5 of SEQ ID NO:1. In some embodiments, the guide RNA recognition sequence can include or is proximate to a position corresponding to positions 53575 to 53577 of SEQ ID NO:1. For example, the guide RNA recognition sequence can be within about 1000, within about 500, within about 400, within about 300, within about 200, within about 100, within about 50, within about 45, within about 40, within about 35, within about 30, within about 25, within about 20, within about 15, within about 10, or within about 5 nucleotides of the position corresponding to positions 53575 to 53577 of SEQ ID NO:1. As yet another example, the guide RNA recognition sequence can include or be proximate to the start codon of an endogenous B4GALT1 gene or the stop codon of an endogenous B4GALT1 gene. For example, the guide RNA recognition sequence can be within about 10, within about 20, within about 30, within about 40, within about 50, within about 100, within about 200, within about 300, within about 400, within about 500, or within about 1,000 nucleotides of the start codon or the stop codon. The Cas protein and the guide RNA form a complex, and the Cas protein cleaves the guide RNA recognition sequence. Cleavage by the Cas protein can create a double-strand break or a single-strand break (e.g., if the Cas protein is a nickase). Such methods can result, for example, in an endogenous B4GALT1 gene in which the region corresponding to exon 5 of SEQ ID NO:1 is disrupted, the start codon is disrupted, the stop codon is disrupted, or the coding sequence is deleted. Examples and variations of Cas (e.g., Cas9) proteins and guide RNAs that can be used in the methods are described elsewhere herein.

In some embodiments, two or more nuclease agents can be used. For example, two nuclease agents can be used, each targeting a nuclease recognition sequence within a region corresponding to exon 5 of SEQ ID NO:1, or including or proximate to a position corresponding to positions 53575 to 53577 of SEQ ID NO:1 (e.g., within about 1000, within about 500, within about 400, within about 300, within about 200, within about 100, within about 50, within about 45, within about 40, within about 35, within about 30, within about 25, within about 20, within about 15, within about 10, or within about 5 nucleotides of the positions corresponding to positions 53575 to 53577 of SEQ ID NO:1). As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. As yet another example, three or more nuclease agents can be used, with one or more (e.g., two) targeting nuclease recognition sequences including or proximate to the start codon, and one or more (e.g., two) targeting nuclease recognition sequences including or proximate to the stop codon, wherein cleavage by the nuclease agents can result in deletion of the coding region between the nuclease recognition sequences including or proximate to the start codon and the nuclease recognition sequence including or proximate to the stop codon.

In some embodiments, the cell can be further contacted with one or more additional guide RNAs that hybridize to additional guide RNA recognition sequences within the target genomic locus in the endogenous B4GALT1 gene. By contacting the cell with one or more additional guide RNAs (e.g., a second guide RNA that hybridizes to a second guide RNA recognition sequence), cleavage by the Cas protein can create two or more double-strand breaks or two or more single-strand breaks (e.g., if the Cas protein is a nickase).

In some embodiments, the cell can additionally be contacted with one or more exogenous donor sequences which recombine with the target genomic locus in the endogenous B4GALT1 gene to generate a targeted genetic modification. Examples and variations of exogenous donor sequences that can be used in the methods are disclosed elsewhere herein.

The Cas protein, guide RNA(s), and exogenous donor sequence(s) can be introduced into the cell in any form and by any means as described elsewhere herein, and all or some of the Cas protein, guide RNA(s), and exogenous donor sequence(s) can be introduced simultaneously or sequentially in any combination.

In some embodiments, the repair of the target nucleic acid (e.g., the endogenous B4GALT1 gene) by the exogenous donor sequence occurs via homology-directed repair (HDR). Homology-directed repair can occur when the Cas protein cleaves both strands of DNA in the endogenous B4GALT1 gene to create a double-strand break, when the Cas protein is a nickase that cleaves one strand of DNA in the target nucleic acid to create a single-strand break, or when Cas nickases are used to create a double-strand break formed by two offset nicks. In such methods, the exogenous donor sequence comprises 5' and 3' homology arms corresponding to 5' and 3' target sequences. The guide RNA recognition sequence(s) or cleavage site(s) can be adjacent to the 5' target sequence, adjacent to the 3' target sequence, adjacent to both the 5' target sequence and the 3' target sequence, or adjacent to neither the 5' target sequence nor the 3' target sequence. In some embodiments, the exogenous donor sequence can further comprise a nucleic acid insert flanked by the 5' and 3' homology arms, and the nucleic acid insert is inserted between the 5' and 3' target sequences. If no nucleic acid insert is present, the exogenous donor sequence can function to delete the genomic sequence between the 5' and 3' target sequences. Examples of exogenous donor sequences are disclosed elsewhere herein.

Alternately, the repair of the endogenous B4GALT1 gene mediated by the exogenous donor sequence can occur via non-homologous end joining (NHEJ)-mediated ligation. In such methods, at least one end of the exogenous donor sequence comprises a short single-stranded region that is complementary to at least one overhang created by Cas-mediated cleavage in the endogenous B4GALT1 gene. The complementary end in the exogenous donor sequence can flank a nucleic acid insert. For example, each end of the exogenous donor sequence can comprise a short single-stranded region that is complementary to an overhang created by Cas-mediated cleavage in the endogenous B4GALT1 gene, and these complementary regions in the exogenous donor sequence can flank a nucleic acid insert.

Overhangs (i.e., staggered ends) can be created by resection of the blunt ends of a double-strand break created by Cas-mediated cleavage. Such resection can generate the regions of microhomology needed for fragment joining, but this can create unwanted or uncontrollable alterations in the B4GALT1 gene. Alternately, such overhangs can be created by using paired Cas nickases. For example, the cell can be contacted with first and second nickases that cleave opposite strands of DNA, whereby the genome is modified through double nicking. This can be accomplished by contacting a cell with a first Cas protein nickase, a first guide RNA that hybridizes to a first guide RNA recognition sequence within the target genomic locus in the endogenous B4GALT1 gene, a second Cas protein nickase, and a second guide RNA that hybridizes to a second guide RNA recognition sequence within target genomic locus in the endogenous B4GALT1 gene. The first Cas protein and the first guide RNA form a first complex, and the second Cas protein and the second guide RNA form a second complex. The first Cas protein nickase cleaves a first strand of genomic DNA within the first guide RNA recognition sequence, the second Cas protein nickase cleaves a second strand of genomic DNA within the second guide RNA recognition sequence, and optionally the exogenous donor sequence recombines with the target genomic locus in the endogenous B4GALT1 gene to generate the targeted genetic modification.

The first nickase can cleave a first strand of genomic DNA (i.e., the complementary strand), and the second nickase can cleave a second strand of genomic DNA (i.e., the non-complementary strand). The first and second nickases can be created, for example, by mutating a catalytic residue in the RuvC domain (e.g., the D10A mutation described elsewhere herein) of Cas9 or mutating a catalytic residue in the HNH domain (e.g., the H840A mutation described elsewhere herein) of Cas9. In such methods, the double nicking can be employed to create a double-strand break having staggered ends (i.e., overhangs). The first and second guide RNA recognition sequences can be positioned to create a cleavage site such that the nicks created by the first and second nickases on the first and second strands of DNA create a double-strand break. Overhangs are created when the nicks within the first and second CRISPR RNA recognition sequences are offset. The offset window can be, for example, at least about 5 bp, at least about 10 bp, at least about 20 bp, at least about 30 bp, at least about 40 bp, at least about 50 bp, at least about 60 bp, at least about 70 bp, at least about 80 bp, at least about 90 bp, at least about 100 bp, or more. See, e.g., Ran et al., *Cell,* 2013, 154, 1380-1389; Mali et al., *Nat. Biotech.,* 213, 31, 833-838; and Shen et al., *Nat. Methods,* 2014, 11, 399-404.

Various types of targeted genetic modifications can be introduced using the methods described herein. Such targeted modifications can include, for example, additions of one or more nucleotides, deletions of one or more nucleotides, substitutions of one or more nucleotides, a point mutation, or a combination thereof. For example, at least 1, at least 2, at least 3, at least 4, at least 5, at least 7, at least 8, at least 9, or at least 10, or more nucleotides can be changed (e.g., deleted, inserted, or substituted) to form the targeted genomic modification.

Such targeted genetic modifications can result in disruption of a target genomic locus. Disruption can include alteration of a regulatory element (e.g., promoter or enhancer), a missense mutation, a nonsense mutation, a frame-shift mutation, a truncation mutation, a null mutation, or an insertion or deletion of small number of nucleotides (e.g., causing a frameshift mutation), and it can result in inactivation (i.e., loss of function) or loss of an allele. For example, a targeted modification can comprise disruption of the start codon of an endogenous B4GALT1 gene such that the start codon is no longer functional.

In some embodiments, a targeted modification can comprise a deletion between the first and second guide RNA recognition sequences or Cas cleavage sites. If an exogenous donor sequence (e.g., repair template or targeting vector) is used, the modification can comprise a deletion between the first and second guide RNA recognition sequences or Cas cleavage sites as well as an insertion of a nucleic acid insert between the 5' and 3' target sequences.

In some embodiments, if an exogenous donor sequence is used, alone or in combination with a nuclease agent, the modification can comprise a deletion between the 5' and 3' target sequences as well as an insertion of a nucleic acid insert between the 5' and 3' target sequences in the pair of first and second homologous chromosomes, thereby resulting in a homozygous modified genome. Alternately, if the exogenous donor sequence comprises 5' and 3' homology arms with no nucleic acid insert, the modification can comprise a deletion between the 5' and 3' target sequences.

The deletion between the first and second guide RNA recognition sequences or the deletion between the 5' and 3' target sequences can be a precise deletion wherein the deleted nucleic acid consists of only the nucleic acid sequence between the first and second nuclease cleavage sites or only the nucleic acid sequence between the 5' and 3' target sequences such that there are no additional deletions or insertions at the modified genomic target locus. The deletion between the first and second guide RNA recognition sequences can also be an imprecise deletion extending beyond the first and second nuclease cleavage sites, consistent with imprecise repair by non-homologous end joining (NHEJ), resulting in additional deletions and/or insertions at the modified genomic locus. For example, the deletion can extend about 1 bp, about 2 bp, about 3 bp, about 4 bp, about 5 bp, about 10 bp, about 20 bp, about 30 bp, about 40 bp, about 50 bp, about 100 bp, about 200 bp, about 300 bp, about 400 bp, about 500 bp, or more beyond the first and second Cas protein cleavage sites. Likewise, the modified genomic locus can comprise additional insertions consistent with imprecise repair by NHEJ, such as insertions of about 1 bp, about 2 bp, about 3 bp, about 4 bp, about 5 bp, about 10 bp, about 20 bp, about 30 bp, about 40 bp, about 50 bp, about 100 bp, about 200 bp, about 300 bp, about 400 bp, about 500 bp, or more.

The targeted genetic modification can be, for example, a biallelic modification or a monoallelic modification. Biallelic modifications include events in which the same modification is made to the same locus on corresponding homologous chromosomes (e.g., in a diploid cell), or in which different modifications are made to the same locus on corresponding homologous chromosomes. In some embodiments, the targeted genetic modification is a monoallelic modification. A monoallelic modification includes events in which a modification is made to only one allele (i.e., a modification to the endogenous B4GALT1 gene in only one of the two homologous chromosomes). Homologous chromosomes include chromosomes that have the same genes at the same loci but possibly different alleles (e.g., chromosomes that are paired during meiosis).

A monoallelic mutation can result in a cell that is heterozygous for the targeted B4GALT1 modification. Heterozygosity includes situation in which only one allele of the B4GALT1 gene (i.e., corresponding alleles on both homologous chromosomes) have the targeted modification.

A biallelic modification can result in homozygosity for a targeted modification. Homozygosity includes situations in which both alleles of the B4GALT1 gene (i.e., corresponding alleles on both homologous chromosomes) have the targeted modification. Alternately, a biallelic modification can result in compound heterozygosity (e.g., hemizygosity) for the targeted modification. Compound heterozygosity includes situations in which both alleles of the target locus (i.e., the alleles on both homologous chromosomes) have been modified, but they have been modified in different ways (e.g., a targeted modification in one allele and inactivation or disruption of the other allele).

The methods disclosed herein can further comprise identifying a cell having a modified B4GALT1 gene. Various methods can be used to identify cells having a targeted genetic modification, such as a deletion or an insertion. Such methods can comprise identifying one cell having the targeted genetic modification in the B4GALT1 gene. Screening can be performed to identify such cells with modified genomic loci. The screening step can comprise a quantitative assay for assessing modification of allele (MOA) (e.g., loss-of-allele (LOA) and/or gain-of-allele (GOA) assays) of a parental chromosome.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE' probe technology. Conventional assays for screening for targeted modifications, such as long-range PCR, Southern blotting, or Sanger sequencing, can also be used. Such assays typically are used to obtain evidence for a linkage between the inserted targeting vector and the targeted genomic locus. For example, for a long-range PCR assay, one primer can recognize a sequence within the inserted DNA while the other recognizes a target genomic locus sequence beyond the ends of the targeting vector's homology arms.

Next generation sequencing (NGS) can also be used for screening. Next-generation sequencing can also be referred to as "NGS" or "massively parallel sequencing" or "high throughput sequencing." In some embodiments, it is not necessary to screen for targeted cells using selection markers. For example, the MOA and NGS assays described herein can be relied on without using selection cassettes.

The present disclosure also provides methods for altering expression of nucleic acids encoding B4GALT1 polypeptides. In some embodiments, expression is altered through cleavage with a nuclease agent to cause disruption of the nucleic acid encoding the endogenous B4GALT1 polypeptide, as described in further detail elsewhere herein. In some embodiments, expression is altered through use of a DNA-binding protein fused or linked to a transcription activation domain or a transcription repression domain. In some embodiments, expression is altered through use of RNA interference compositions, such as antisense RNA, shRNA, or siRNA.

In some embodiments, expression of an endogenous B4GALT1 gene or a nucleic acid encoding a B4GALT1 polypeptide can be modified by contacting a cell or the genome within a cell with a nuclease agent that induces one or more nicks or double-strand breaks at a recognition sequence at a target genomic locus within the endogenous B4GALT1 gene or nucleic acid encoding a B4GALT1 polypeptide. Such cleavage can result in disruption of expression of the endogenous B4GALT1 gene or nucleic acid encoding a B4GALT1 polypeptide. For example, the nuclease recognition sequence can include or be proximate to the start codon of the endogenous B4GALT1 gene. For example, the recognition sequence can be within about 10, within about 20, within about 30, within about 40, within about 50, within about 100, within about 200, within about 300, within about 400, within about 500, or within about 1,000 nucleotides of the start codon, and cleavage by the nuclease agent can disrupt the start codon. In some embodiments, two or more nuclease agents can be used, each targeting a nuclease recognition sequence including or proximate to the start codon. In some embodiments, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. In some embodiments, three or more nuclease agents can be used, with one or more (e.g., two) targeting nuclease recognition sequences including or proximate to the start codon, and one or more (e.g., two) targeting nuclease recognition sequences including or proximate to the stop codon, wherein cleavage by the nuclease agents can result in deletion of the coding region between the nuclease recognition sequences including or proximate to the start codon and the nuclease recognition sequence including or proximate to the stop codon. Other examples of modifying an endogenous B4GALT1 gene or a nucleic acid encoding a B4GALT1 polypeptide are disclosed elsewhere herein.

In some embodiments, expression of an endogenous B4GALT1 gene or a nucleic acid encoding a B4GALT1 polypeptide can be modified by contacting a cell or the genome within a cell with a DNA-binding protein that binds to a target genomic locus within the endogenous B4GALT1 gene. The DNA-binding protein can be, for example, a nuclease-inactive Cas protein fused to a transcriptional activator domain or a transcriptional repressor domain. Other examples of DNA-binding proteins include zinc finger proteins fused to a transcriptional activator domain or a transcriptional repressor domain, or Transcription Activator-Like Effector (TALE) proteins fused to a transcriptional activator domain or a transcriptional repressor domain. Examples of such proteins are disclosed elsewhere herein.

The recognition sequence (e.g., guide RNA recognition sequence) for the DNA-binding protein can be anywhere within the endogenous B4GALT1 gene or a nucleic acid encoding a B4GALT1 polypeptide suitable for altering expression. In some embodiments, the recognition sequence can be within a regulatory element, such as an enhancer or promoter, or can be in proximity to a regulatory element. For example, the recognition sequence can include or be proximate to the start codon of an endogenous B4GALT1 gene.

In some embodiments, the recognition sequence can be within about 10, within about 20, within about 30, within about 40, within about 50, within about 100, within about 200, within about 300, within about 400, within about 500, or within about 1,000 nucleotides of the start codon.

In some embodiments, antisense molecules can be used to alter expression of an endogenous B4GALT1 gene or a nucleic acid encoding a B4GALT1 polypeptide. Examples of antisense molecules include, but are not limited to, antisense RNAs, siRNAs, and shRNAs. Such antisense RNAs, siRNAs, or shRNAs can be designed to target any region of an mRNA. For example, the antisense RNAs, siRNAs, or shRNAs can be designed to target a region unique of the B4GALT1 mRNA.

The nucleic acids and proteins disclosed herein can be introduced into a cell by any means. In some embodiments, the introducing can be accomplished by any means, and one or more of the components (e.g., two of the components, or all of the components) can be introduced into the cell simultaneously or sequentially in any combination. For example, an exogenous donor sequence can be introduced prior to the introduction of a nuclease agent, or it can be introduced following introduction of nuclease agent (e.g., the exogenous donor sequence can be administered about 1, about 2, about 3, about 4, about 8, about 12, about 24, about 36, about 48, or about 72 hours before or after introduction of the nuclease agent). Contacting the genome of a cell with a nuclease agent or exogenous donor sequence can comprise introducing one or more nuclease agents or nucleic acids encoding nuclease agents (e.g., one or more Cas proteins or nucleic acids encoding one or more Cas proteins, and one or more guide RNAs or nucleic acids encoding one or more guide RNAs (i.e., one or more CRISPR RNAs and one or more tracrRNAs)) and/or one or more exogenous donor sequences into the cell. Contacting the genome of cell (i.e., contacting a cell) can comprise introducing only one of the above components, one or more of the components, or all of the components into the cell.

A nuclease agent can be introduced into the cell in the form of a protein or in the form of a nucleic acid encoding the nuclease agent, such as an RNA (e.g., messenger RNA (mRNA)) or DNA. When introduced in the form of a DNA, the DNA can be operably linked to a promoter active in the cell. Such DNAs can be in one or more expression constructs. In some embodiments, a Cas protein can be introduced into the cell in the form of a protein, such as a Cas protein complexed with a gRNA, or in the form of a nucleic acid encoding the Cas protein, such as an RNA (e.g., messenger RNA (mRNA)) or DNA. A guide RNA can be introduced into the cell in the form of an RNA or in the form of a DNA encoding the guide RNA. When introduced in the form of a DNA, the DNA encoding the Cas protein and/or the guide RNA can be operably linked to a promoter active in the cell. Such DNAs can be in one or more expression constructs. For example, such expression constructs can be components of a single nucleic acid molecule. Alternately, they can be separated in any combination among two or more nucleic acid molecules (i.e., DNAs encoding one or more CRISPR RNAs, DNAs encoding one or more tracrRNAs, and DNA encoding a Cas protein can be components of separate nucleic acid molecules).

In some embodiments, DNA encoding a nuclease agent (e.g., a Cas protein and a guide RNA) and/or DNA encoding an exogenous donor sequence can be introduced into a cell via DNA minicircles. DNA minicircles are supercoiled DNA molecules that can be used for non-viral gene transfer that have neither an origin of replication nor an antibiotic selection marker. Thus, DNA minicircles are typically smaller in size than plasmid vector. These DNAs are devoid of bacterial DNA, and thus lack the unmethylated CpG motifs found in bacterial DNA.

The methods described herein do not depend on a particular method for introducing a nucleic acid or protein into the cell, only that the nucleic acid or protein gains access to the interior of a least one cell. Methods for introducing nucleic acids and proteins into various cell types are known and include, but are not limited to, stable transfection methods, transient transfection methods, and virus-mediated methods.

Transfection protocols as well as protocols for introducing nucleic acids or proteins into cells may vary. Non-limiting transfection methods include chemical-based transfection methods using liposomes, nanoparticles, calcium, dendrimers, and cationic polymers such as DEAE-dextran or polyethylenimine. Non-chemical methods include electroporation, sono-poration, and optical transfection. Particle-based transfection includes the use of a gene gun, or magnet-assisted transfection. Viral methods can also be used for transfection.

Introduction of nucleic acids or proteins into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In some embodiments, nucleofection is performed using the LONZA® NUCLEOFECTOR™ system.

Introduction of nucleic acids or proteins into a cell can also be accomplished by microinjection. Microinjection of an mRNA is usually into the cytoplasm (e.g., to deliver mRNA directly to the translation machinery), while microinjection of a protein or a DNA encoding a DNA encoding a Cas protein is usually into the nucleus. Alternately, microinjection can be carried out by injection into both the nucleus and the cytoplasm: a needle can first be introduced into the nucleus and a first amount can be injected, and while removing the needle from the cell a second amount can be injected into the cytoplasm. If a nuclease agent protein is injected into the cytoplasm, the protein may comprise a nuclear localization signal to ensure delivery to the nucleus/pronucleus.

Other methods for introducing nucleic acid or proteins into a cell can include, for example, vector delivery, particle-mediated delivery, exosome-mediated delivery, lipid-nanoparticle-mediated delivery, cell-penetrating-peptide-mediated delivery, or implantable-device-mediated delivery. Methods of administering nucleic acids or proteins to a subject to modify cells in vivo are disclosed elsewhere herein. Introduction of nucleic acids and proteins into cells can also be accomplished by hydrodynamic delivery (HDD).

Other methods for introducing nucleic acid or proteins into a cell can include, for example, vector delivery, particle-mediated delivery, exosome-mediated delivery, lipid-nanoparticle-mediated delivery, cell-penetrating-peptide-mediated delivery, or implantable-device-mediated delivery. In some embodiments, a nucleic acid or protein can be introduced into a cell in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule.

The introduction of nucleic acids or proteins into the cell can be performed one time or multiple times over a period of time. In some embodiments, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

In some embodiments, the cells employed in the methods and compositions have a DNA construct stably incorporated into their genome. In such cases, the contacting can comprise providing a cell with the construct already stably incorporated into its genome. In some embodiments, a cell employed in the methods disclosed herein may have a preexisting Cas-encoding gene stably incorporated into its genome (i.e., a Cas-ready cell). In some embodiments, the polynucleotide integrates into the genome of the cell and is capable of being inherited by progeny thereof. Any protocol may be used for the stable incorporation of the DNA constructs or the various components of the targeted genomic integration system.

Any nuclease agent that induces a nick or double-strand break into a desired recognition sequence or any DNA-binding protein that binds to a desired recognition sequence can be used in the methods and compositions disclosed herein. A naturally occurring or native nuclease agent can be employed so long as the nuclease agent induces a nick or double-strand break in a desired recognition sequence. Likewise, a naturally occurring or native DNA-binding protein can be employed so long as the DNA-binding protein binds to the desired recognition sequence. Alternately, a modified or engineered nuclease agent or DNA-binding protein can be employed. An engineered nuclease agent or DNA-binding protein can be derived from a native, naturally occurring nuclease agent or DNA-binding protein or it can be artificially created or synthesized. The engineered nuclease agent or DNA-binding protein can recognize a recognition sequence, for example, wherein the recognition sequence is not a sequence that would have been recognized by a native (non-engineered or non-modified) nuclease agent or DNA-binding protein. The modification of the nuclease agent or DNA-binding protein can be as few as one amino acid in a protein cleavage agent or one nucleotide in a nucleic acid cleavage agent.

Recognition sequences for a nuclease agent includes a DNA sequence at which a nick or double-strand break is induced by a nuclease agent. Likewise, recognition sequences for a DNA-binding protein include a DNA sequence to which a DNA-binding protein will bind. The recognition sequence can be endogenous (or native) to the cell or the recognition sequence can be exogenous to the cell. The recognition sequence can also exogenous to the polynucleotides of interest that one desires to be positioned at the target locus. In some embodiments, the recognition sequence is present only once in the genome of the host cell.

Active variants and fragments of the exemplified recognition sequences are also provided. Such active variants can comprise at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the given recognition sequence, wherein the active variants retain biological activity and are capable of being recognized and cleaved by a nuclease agent in a sequence-specific manner. Assays to measure the double-strand break of a recognition sequence by a nuclease agent are known (e.g., TAQMAN® qPCR assay, Frendewey et al., *Methods in Enzymology,* 2010, 476, 295-307).

The length of the recognition sequence can vary, and includes, for example, recognition sequences that are from about 30 to about 36 bp for a zinc finger protein or zinc finger nuclease (ZFN) pair (i.e., from about 15 to about 18 bp for each ZFN), about 36 bp for a TALE protein or Transcription Activator-Like Effector Nuclease (TALEN), or about 20 bp for a CRISPR/Cas9 guide RNA.

The recognition sequence of the DNA-binding protein or nuclease agent can be positioned anywhere in or near the target genomic locus. The recognition sequence can be located within a coding region of a gene (e.g., the B4GALT1 gene), or within regulatory regions that influence the expression of the gene. A recognition sequence of the DNA-binding protein or nuclease agent can be located in an intron, an exon, a promoter, an enhancer, a regulatory region, or any non-protein coding region.

One type of DNA-binding protein that can be employed in the various methods and compositions disclosed herein is a TALE. A TALE can be fused or linked to, for example, an epigenetic modification domain, a transcriptional activation domain, or a transcriptional repressor domain. Examples of such domains are described with respect to Cas proteins, below, and can also be found, for example, in PCT Publication WO 2011/145121. Correspondingly, one type of nuclease agent that can be employed in the various methods and compositions disclosed herein is a TALEN. Transcription activator-like (TAL) effector nucleases are a class of sequence-specific nucleases that can be used to make double-strand breaks at specific target sequences in the genome of a prokaryotic or eukaryotic organism. TAL effector nucleases are created by fusing a native or engineered TAL effector, or functional part thereof, to the catalytic domain of an endonuclease such as FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. Examples of suitable TAL nucleases, and methods for preparing suitable TAL nucleases, are disclosed, for example, in U.S. Patent Application Publications 2011/0239315; 2011/0269234; 2011/0145940; 2003/0232410; 2005/0208489; 2005/0026157; 2005/0064474; 2006/0188987; and 2006/0063231.

In some TALENs, each monomer of the TALEN comprises from about 33 to about 35 TAL repeats that recognize a single base pair via two hypervariable residues. In some TALENs, the nuclease agent is a chimeric protein comprising a TAL-repeat-based DNA binding domain operably linked to an independent nuclease such as a FokI endonuclease. For example, the nuclease agent can comprise a first TAL-repeat-based DNA binding domain and a second TAL-repeat-based DNA binding domain, wherein each of the first and the second TAL-repeat-based DNA binding domains is operably linked to a FokI nuclease, wherein the first and the second TAL-repeat-based DNA binding domain recognize two contiguous target DNA sequences in each strand of the target DNA sequence separated by a spacer sequence of varying length (from about 12 to about 20 bp), and wherein the FokI nuclease subunits dimerize to create an active nuclease that makes a double strand break at a target sequence.

Another example of a DNA-binding protein is a zinc finger protein. Such zinc finger proteins can be linked or fused to, for example, an epigenetic modification domain, a transcriptional activation domain, or a transcriptional repressor domain. Examples of such domains are described with respect to Cas proteins, below, and can also be found, for example, in PCT Publication WO 2011/145121. Correspondingly, another example of a nuclease agent that can be employed in the various methods and compositions disclosed herein is a ZFN. In some ZFNs, each monomer of the ZFN comprises three or more zinc finger-based DNA binding domains, wherein each zinc finger-based DNA binding domain binds to a 3 bp subsite. In other ZFNs, the ZFN is a chimeric protein comprising a zinc finger-based DNA binding domain operably linked to an independent nuclease such as a FokI endonuclease. For example, the nuclease agent can comprise a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5 to about 7 bp spacer, and wherein the FokI nuclease subunits dimerize to create an active nuclease that makes a double strand break.

Other suitable DNA-binding proteins and nuclease agents for use in the methods and compositions described herein include CRISPR-Cas systems, which are described elsewhere herein.

The DNA-binding protein or nuclease agent may be introduced into the cell by any known means. A polypeptide encoding the DNA-binding protein or nuclease agent may be directly introduced into the cell. Alternately, a polynucleotide encoding the DNA-binding protein or nuclease agent can be introduced into the cell. When a polynucleotide encoding the DNA-binding protein or nuclease agent is introduced into the cell, the DNA-binding protein or nuclease agent can be transiently, conditionally, or constitutively expressed within the cell. For example, the polynucleotide encoding the DNA-binding protein or nuclease agent can be contained in an expression cassette and be operably linked to a conditional promoter, an inducible promoter, a constitutive promoter, or a tissue-specific promoter. Such promoters are discussed in further detail elsewhere herein. In some embodiments, the DNA-binding protein or nuclease agent can be introduced into the cell as an mRNA encoding a DNA-binding protein or a nuclease agent.

A polynucleotide encoding a DNA-binding protein or nuclease agent can be stably integrated in the genome of the cell and operably linked to a promoter active in the cell. Alternately, a polynucleotide encoding a DNA-binding protein or nuclease agent can be in a targeting vector or in a vector or a plasmid that is separate from the targeting vector comprising the insert polynucleotide.

When the DNA-binding protein or nuclease agent is provided to the cell through the introduction of a polynucleotide encoding the DNA-binding protein or nuclease agent, such a polynucleotide encoding a DNA-binding protein or nuclease agent can be modified to substitute codons having a higher frequency of usage in the cell of interest, as compared to the naturally occurring polynucleotide sequence encoding the DNA-binding protein or nuclease agent. In some embodiments, the polynucleotide encoding the DNA-binding protein or nuclease agent can be modified to substitute codons having a higher frequency of usage in a given prokaryotic or eukaryotic cell of interest, including a bacterial cell, a yeast cell, a human cell, a non-human cell, a mammalian cell, a rodent cell, a mouse cell, a rat cell or any other host cell of interest, as compared to the naturally occurring polynucleotide sequence.

The methods disclosed herein can utilize Clustered Regularly Interspersed Short Palindromic Repeats (CRISPR)/CRISPR-associated (Cas) systems or components of such systems to modify a genome within a cell. CRISPR-Cas systems include transcripts and other elements involved in the expression of, or directing the activity of, Cas genes. A CRISPR-Cas system can be a type I, a type II, or a type III system. Alternately a CRISPR/Cas system can be, for example, a type V system (e.g., subtype V-A or subtype V-B). The methods and compositions disclosed herein can employ CRISPR-Cas systems by utilizing CRISPR complexes (comprising a guide RNA (gRNA) complexed with a Cas protein) for site-directed cleavage of nucleic acids.

The CRISPR-Cas systems used in the methods disclosed herein are non-naturally occurring. For example, some CRISPR-Cas systems employ non-naturally occurring CRISPR complexes comprising a gRNA and a Cas protein that do not naturally occur together.

Cas proteins generally comprise at least one RNA recognition or binding domain that can interact with guide RNAs (gRNAs, described in more detail below). Cas proteins can also comprise nuclease domains (e.g., DNase or RNase domains), DNA binding domains, helicase domains, protein-protein interaction domains, dimerization domains, and other domains. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. A wild-type Cas9 protein will typically create a blunt cleavage product. Alternately, a wild-type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break in the endogenous B4GALT1 gene (e.g., a double-strand break with blunt ends), or it can be a nickase that creates a single-strand break in the endogenous B4GALT1 gene.

Examples of Cas proteins include, but are not limited to, Cas1, Cas1B, Cast, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (Cas6), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

In some embodiments, the Cas protein is a Cas9 protein or is derived from a Cas9 protein from a type II CRISPR-Cas system. Cas9 proteins are from a type II CRISPR-Cas system and typically share four key motifs with a conserved architecture. Motifs 1, 2, and 4 are RuvC-like motifs, and motif 3 is an HNH motif. Exemplary Cas9 proteins include, but are not limited to, those are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acido-*

*caldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus*, or *Acaryochloris marina*. Additional examples of the Cas9 family members are described in PCT Publication WO 2014/131833. Cas9 from *S. pyogenes* (assigned SwissProt accession number Q99ZW2) is an exemplary enzyme. Cas9 from *S. aureus* (assigned UniProt accession number J7RUA5) is another exemplary enzyme.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. Exemplary Cpf1 proteins include, but are not limited to, those from *Francisella tularensis* 1, *Francisella tularensis* subsp. *novicida, Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens*, and *Porphyromonas macacae*. Cpf1 from *Francisella novicida* U112 (FnCpf1; assigned UniProt accession number A0Q7Q2) is an exemplary enzyme.

Cas proteins can be wild-type proteins (i.e., those that occur in nature), modified Cas proteins (i.e., Cas protein variants), or fragments of wild-type or modified Cas proteins. Cas proteins can also be active variants or fragments of wild-type or modified Cas proteins. Active variants or fragments can comprise at least 80%, at least 85%, at least 90%, at least 91%, at least 92%, at least 93%, at least 94%, at least 95%, at least 96%, at least 97%, at least 98%, or at least 99%, or 100% sequence identity to the wild-type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can comprise at least one nuclease domain, such as a DNase domain. For example, a wild-type Cpf1 protein generally comprises a RuvC-like domain that cleaves both strands of target DNA, perhaps in a dimeric configuration. Cas proteins can comprise at least two nuclease domains, such as DNase domains. For example, a wild-type Cas9 protein generally comprises a RuvC-like nuclease domain and an HNH-like nuclease domain. The RuvC and HNH domains can each cut a different strand of double-stranded DNA to make a double-stranded break in the DNA.

Cas proteins (e.g., nuclease-active Cas proteins or nuclease-inactive Cas proteins) can also be operably linked to heterologous polypeptides as fusion proteins. For example, a Cas protein can be fused to a cleavage domain, an epigenetic modification domain, a transcriptional activation domain, or a transcriptional repressor domain. Examples of transcriptional activation domains include a herpes simplex virus VP16 activation domain, VP64 (which is a tetrameric derivative of VP16), a NFκB p65 activation domain, p53 activation domains 1 and 2, a CREB (cAMP response element binding protein) activation domain, an E2A activation domain, and an NFAT (nuclear factor of activated T-cells) activation domain. Other examples include, but are not limited to, activation domains from Oct1, Oct-2A, SP1, AP-2, CTF1, P300, CBP, PCAF, SRC1, PvALF, ERF-2, OsGAI, HALF-1, C1, AP1, ARF-5, ARF-6, ARF-7, ARF-8, CPRF1, CPRF4, MYC-RP/GP, TRAB1PC4, and HSF1. See, e.g., U.S. Patent Application Publication 2016/0237456, European Patent EP3045537, and PCT Publication WO 2011/145121.

In some embodiments, a transcriptional activation system can be used comprising a dCas9-VP64 fusion protein paired with MS2-p65-HSF1. Guide RNAs in such systems can be designed with aptamer sequences appended to sgRNA tetraloop and stem-loop 2 designed to bind dimerized MS2 bacteriophage coat proteins. See, e.g., Konermann et al., *Nature,* 2015, 517, 583-588. Examples of transcriptional repressor domains include inducible cAMP early repressor (ICER) domains, Kruppel-associated box A (KRAB-A) repressor domains, YY1 glycine rich repressor domains, Sp1-like repressors, E(spl) repressors, IκB repressor, and MeCP2. Other examples include, but are not limited to, transcriptional repressor domains from A/B, KOX, TGF-beta-inducible early gene (TIEG), v-erbA, SID, SID4X, MBD2, MBD3, DNMT1, DNMG3A, DNMT3B, Rb, ROM2, See, e.g., European Patent EP3045537 and PCT Publication WO 2011/145121. Cas proteins can also be fused to a heterologous polypeptide providing increased or decreased stability. The fused domain or heterologous polypeptide can be located at the N-terminus, the C-terminus, or internally within the Cas protein.

An example of a Cas fusion protein is a Cas protein fused to a heterologous polypeptide that provides for subcellular localization. Such heterologous polypeptides can include, for example, one or more nuclear localization signals (NLS) such as the SV40 NLS for targeting to the nucleus, a mitochondrial localization signal for targeting to the mitochondria, an ER retention signal, and the like. Such subcellular localization signals can be located at the N-terminus, the C-terminus, or anywhere within the Cas protein. An NLS can comprise a stretch of basic amino acids, and can be a monopartite sequence or a bipartite sequence.

Cas proteins can also be operably linked to a cell-penetrating domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreenI), yellow fluorescent proteins (e.g., YFP, eYFP, Citrine, Venus, YPet, PhiYFP, ZsYellowI), blue fluorescent proteins (e.g. eBFP, eBFP2, Azurite, mKalamaI, GFPuv, Sapphire, T-sapphire), cyan fluorescent proteins (e.g. eCFP, Cerulean, CyPet, AmCyanI, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRedI, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly (NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, 51, T7, V5, VSV-G, histidine (His), biotin carboxyl carrier protein (BCCP), and calmodulin.

Cas9 proteins can also be tethered to exogenous donor sequences or labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The exogenous donor sequence or labeled nucleic acid can be tethered to the C-terminus, the N-terminus, or to an internal region within the Cas9 protein. In some embodiments, the exogenous donor sequence or labeled nucleic acid is tethered to the C-terminus or the N-terminus of the Cas9 protein. Likewise, the Cas9 protein can be tethered to the 5' end, the 3' end, or to an internal region within the exogenous donor sequence or labeled nucleic acid. In some embodiments, the Cas9 protein is tethered to the 5' end or the 3' end of the exogenous donor sequence or labeled nucleic acid.

Cas proteins can be provided in any form. For example, a Cas protein can be provided in the form of a protein, such as a Cas protein complexed with a gRNA. Alternately, a Cas protein can be provided in the form of a nucleic acid encoding the Cas protein, such as an RNA (e.g., messenger RNA (mRNA)) or DNA. In some embodiments, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. When a nucleic acid encoding the Cas protein is introduced into the cell, the Cas protein can be transiently, conditionally, or constitutively expressed in the cell.

Nucleic acids encoding Cas proteins can be stably integrated in the genome of the cell and operably linked to a promoter active in the cell. Alternately, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a targeting vector comprising a nucleic acid insert and/or a vector comprising a DNA encoding a gRNA. Alternately, it can be in a vector or plasmid that is separate from the targeting vector comprising the nucleic acid insert and/or separate from the vector comprising the DNA encoding the gRNA. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, or a zygote. Such promoters can be, for example, conditional promoters, inducible promoters, constitutive promoters, or tissue-specific promoters. In some embodiments, the promoter can be a bidirectional promoter driving expression of both a Cas protein in one direction and a guide RNA in the other direction. Such bidirectional promoters can consist of: 1) a complete, conventional, unidirectional Pol III promoter that contains 3 external control elements: a distal sequence element (DSE), a proximal sequence element (PSE), and a TATA box; and 2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. Use of a bidirectional promoter to express genes encoding a Cas protein and a guide RNA simultaneously allow for the generation of compact expression cassettes to facilitate delivery.

The present disclosure also provides guide RNA (gRNA) that binds to a Cas protein (e.g., Cas9 protein) and targets the Cas protein to a specific location within a target DNA (e.g., the B4GALT1 gene). In some embodiments, the guide RNA is effective to direct a Cas enzyme to bind to or cleave an endogenous B4GALT1 gene, wherein the guide RNA comprises a DNA-targeting a segment that hybridizes to a guide RNA recognition sequence within the endogenous B4GALT1 gene that includes or is proximate to, for example, positions 53575 to 53577 of SEQ ID NO:1. For example, the guide RNA recognition sequence can be within about 5, within about 10, within about 15, within about 20, within about 25, within about 30, within about 35, within about 40, within about 45, within about 50, within about 100, within about 200, within about 300, within about 400, within about 500, or within about 1,000 nucleotides of positions 53575 to 53577 of SEQ ID NO:1. Other exemplary guide RNAs comprise a DNA-targeting segment that hybridizes to a guide RNA recognition sequence within the endogenous B4GALT1 gene that is within a region corresponding to exon 5 of SEQ ID NO:1. Other exemplary guide RNAs comprise a DNA-targeting segment that hybridizes to a guide RNA recognition sequence within the endogenous B4GALT1 gene that includes or is proximate to the start codon of the endogenous B4GALT1 gene or includes or is proximate to the stop codon of the endogenous B4GALT1 gene. For example, the guide RNA recognition sequence can be within about 5, within about 10, within about 15, within about 20, within about 25, within about 30, within about 35, within about 40, within about 45, within about 50, within about 100, within about 200, within about 300, within about 400, within about 500, or within about 1,000 nucleotides of the start codon or within about 5, within about 10, within about 15, within about 20, within about 25, within about 30, within about 35, within about 40, within about 45, within about 50, within about 100, within about 200, within about 300, within about 400, within about 500, or within about 1,000 nucleotides of the stop codon. The endogenous B4GALT1 gene can be a B4GALT1 gene from any organism. For example, the B4GALT1 gene can be a human B4GALT1 gene or an ortholog from another organism, such as a non-human mammal, a rodent, a mouse, or a rat.

In some embodiments, guide RNA recognition sequences are present at the 5' end of the human B4GALT1 gene. In some embodiments, guide RNA recognition sequences are adjacent to the transcription start site (TSS) of the human B4GALT1 gene. In some embodiments, guide RNA recognition sequences are present at the 3' end of the human B4GALT1 gene. In some embodiments, guide RNA recognition sequences are proximate to positions 53575 to 53577 of SEQ ID NO:1. Exemplary guide RNA recognition sequences proximate to positions 53575 to 53577 of SEQ ID NO:1 include, but are not limited to, ATTAGTTTTTAGAGGCATGT (SEQ ID NO:9) and GGCTCTCAGGCCAAGTGTAT (SEQ ID NO:10) (both 5' to positions 53575 to 53577 of SEQ ID NO:1) and TACTCCTTCCCCCTTTAGGA (SEQ ID NO:11) and GTCCGAGGCTCTGGGCCTAG (SEQ ID NO:12) (both 3' to positions 53575 to 53577 of SEQ ID NO:1).

Guide RNAs can comprise two segments: a DNA-targeting segment and a protein-binding segment. Some gRNAs comprise two separate RNA molecules: an activator-RNA (e.g., tracrRNA) and a targeter-RNA (e.g., CRISPR RNA or crRNA). Other gRNAs are a single RNA molecule (single RNA polynucleotide; single-molecule gRNA, single-guide RNA, or sgRNA). For Cas9, for example, a single-guide RNA can comprise a crRNA fused to a tracrRNA (e.g., via a linker). For Cpf1, for example, only a crRNA is needed to achieve cleavage. gRNAs include both double-molecule (i.e., modular) gRNAs and single-molecule gRNAs.

The DNA-targeting segment (crRNA) of a given gRNA comprises a nucleotide sequence that is complementary to a sequence (i.e., the guide RNA recognition sequence) in a target DNA. The DNA-targeting segment of a gRNA interacts with a target DNA (e.g., the B4GALT1 gene) in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR-Cas system and organism but often contain a targeting segment from about 21 to about 72 nucleotides length, flanked by two direct repeats (DR) of a length from about 21 to about 46 nucleotides. In the case of *S. pyogenes*, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have a length of at least about 12 nucleotides, at least about 15 nucleotides, at least about 17 nucleotides, at least about 18 nucleotides, at least about 19 nucleotides, at least about 20 nucleotides, at least about 25 nucleotides, at least about 30 nucleotides, at least about 35 nucleotides, or at least about 40 nucleotides. Such DNA-targeting segments can have a length from about 12 nucleotides to about 100 nucleotides, from about 12 nucleotides to about 80 nucleotides, from about 12 nucleotides to about 50 nucleotides, from about 12 nucleotides to about 40 nucleotides, from about 12 nucleotides to about 30 nucleotides, from about 12 nucleotides to about 25 nucleotides, or from about 12 nucleotides to about 20 nucleotides. For example, the DNA targeting segment can be from about 15 nucleotides to about 25 nucleotides (e.g., from about 17 nucleotides to about 20 nucleotides, or about 17 nucleotides, about 18 nucleotides, about 19 nucleotides, or about 20 nucleotides). See, e.g., U.S. Application Publication 2016/0024523. For Cas9 from *S. pyogenes*, a typical DNA-targeting segment is from about 16 to about 20 nucleotides in length or from about 17 to about 20 nucleotides in length. For Cas9 from *S. aureus*, a typical DNA-targeting segment is from about 21 to about 23 nucleotides in length. For Cpf1, a typical DNA-targeting segment is at least about 16 nucleotides in length or at least about 18 nucleotides in length.

The percent complementarity between the DNA-targeting sequence and the guide RNA recognition sequence within the target DNA can be at least about 60%, at least about 65%, at least about 70%, at least about 75%, at least about 80%, at least about 85%, at least about 90%, at least about 95%, at least about 97%, at least about 98%, at least about 99%, or 100%). The percent complementarity between the DNA-targeting sequence and the guide RNA recognition sequence within the target DNA can be at least about 60% over about 20 contiguous nucleotides. As an example, the percent complementarity between the DNA-targeting sequence and the guide RNA recognition sequence within the target DNA is about 100% over about 14 contiguous nucleotides at the 5' end of the guide RNA recognition sequence within the complementary strand of the target DNA and as low as about 0% over the remainder. In such a case, the DNA-targeting sequence can be considered to be about 14 nucleotides in length. As another example, the percent complementarity between the DNA-targeting sequence and the guide RNA recognition sequence within the target DNA is about 100% over the seven contiguous nucleotides at the 5' end of the guide RNA recognition sequence within the complementary strand of the target DNA and as low as about 0% over the remainder. In such a case, the DNA-targeting sequence can be considered to be about 7 nucleotides in length. In some guide RNAs, at least about 17 nucleotides within the DNA-target sequence are complementary to the target DNA. For example, the DNA-targeting sequence can be about 20 nucleotides in length and can comprise 1, 2, or 3 mismatches with the target DNA (the guide RNA recognition sequence). In some embodiments, the mismatches are not adjacent to a protospacer adjacent motif (PAM) sequence (e.g., the mismatches are in the 5' end of the DNA-targeting sequence, or the mismatches are at least 2, at least 3, at least 4, at least 5, at least 6, at least 7, at least 8, at least 9, at least 10, at least 11, at least 12, at least 13, at least 14, at least 15, at least 16, at least 17, at least 18, or at least 19 base pairs away from the PAM sequence).

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. For example, gRNAs can be prepared by in vitro transcription using, for example, T7 RNA polymerase. Guide RNAs can also be prepared by chemical synthesis.

The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively. When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternately, DNAs encoding gRNAs can be operably linked to a promoter in an expression construct. For example, the DNA encoding the gRNA can be in a vector comprising a heterologous nucleic acid. The vector can further comprise an exogenous donor sequence and/or the vector can further comprise a nucleic acid encoding a Cas protein. Alternately, the DNA encoding the gRNA can be in a vector or a plasmid that is separate from the vector comprising an exogenous donor sequence and/or the vector comprising the nucleic acid encoding the Cas protein. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem cell, or a zygote. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

The present disclosure also provides compositions comprising one or more guide RNAs (e.g., 1, 2, 3, 4, or more guide RNAs) disclosed herein and a carrier increasing the stability of the isolated nucleic acid or protein (e.g., prolonging the period under given conditions of storage (e.g., –,20° C., 4° C., or ambient temperature) for which degradation products remain below a threshold, such below 0.5% by weight of the starting nucleic acid or protein; or increasing the stability in vivo). Examples of such carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid microtubules. Such compositions can further comprise a Cas protein, such as a Cas9 protein, or a nucleic acid encoding a Cas protein. Such compositions can further comprise one or more (e.g., 1, 2, 3, 4, or more) exogenous donor sequences and/or one or more (e.g., 1, 2, 3, 4, or more) targeting vectors and/or one or more (e.g., 1, 2, 3, 4, or more) expression vectors as disclosed elsewhere herein.

Guide RNA recognition sequences include nucleic acid sequences present in a target DNA (e.g., the B4GALT1 gene) to which a DNA-targeting segment of a gRNA will bind, provided sufficient conditions for binding exist. For example, guide RNA recognition sequences include sequences to which a guide RNA is designed to have complementarity, where hybridization between a guide RNA recognition sequence and a DNA targeting sequence promotes the formation of a CRISPR complex. Full complementarity is not necessarily required, provided that there is sufficient complementarity to cause hybridization and promote formation of a CRISPR complex. Guide RNA recognition sequences also include cleavage sites for Cas proteins, described in more detail below. A guide RNA recognition sequence can comprise any polynucleotide, which can be located, for example, in the nucleus or cytoplasm of a cell or within an organelle of a cell, such as a mitochondrion or chloroplast.

The guide RNA recognition sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions are known.

The Cas protein can cleave the nucleic acid at a site within or outside of the nucleic acid sequence present in the target DNA to which the DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to a guide RNA recognition sequence and complexed with a Cas protein) can result in cleavage of one or both strands in or near (e.g., within 1, within 2, within 3, within 4, within 5, within 6, within 7, within 8, within 9, within 10, within 20, or within 50, or more base pairs from) the nucleic acid sequence present in a target DNA to which a DNA-targeting segment of a gRNA will bind. The cleavage site can be on only one strand or on both strands of a nucleic acid. Cleavage sites can be at the same position on both strands of the nucleic acid (producing blunt ends) or can be at different sites on each strand (producing staggered ends (i.e., overhangs)). In some embodiments, the guide RNA recognition sequence of the nickase on the first strand is separated from the guide RNA recognition sequence of the nickase on the second strand by at least 2, at least 3, at least 4, at least 5, at least 6, at least 7, at least 8, at least 9, at least 10, at least 15, at least 20, at least 25, at least 30, at least 40, at least 50, at least 75, at least 100, at least 250, at least 500, or at least 1,000 base pairs.

Site-specific cleavage of target DNA by Cas proteins can occur at locations determined by both i) base-pairing complementarity between the gRNA and the target DNA and ii) a short motif, called the protospacer adjacent motif (PAM), in the target DNA. The PAM can flank the guide RNA recognition sequence. In some embodiments, the guide RNA recognition sequence can be flanked on the 3' end by the PAM. Alternately, the guide RNA recognition sequence can be flanked on the 5' end by the PAM. For example, the cleavage site of Cas proteins can be about 1 to about 10, or about 2 to about 5 base pairs (e.g., 3 base pairs) upstream or downstream of the PAM sequence. In some cases (e.g., when Cas9 from *S. pyogenes* or a closely related Cas9 is used), the PAM sequence of the non-complementary strand can be 5'-$N_1$GG-3', where $N_1$ is any DNA nucleotide and is immediately 3' of the guide RNA recognition sequence of the non-complementary strand of the target DNA. As such, the PAM sequence of the complementary strand would be 5'-CC$N_2$-3', where $N_2$ is any DNA nucleotide and is immediately 5' of the guide RNA recognition sequence of the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from *S. aureus*, the PAM can be NNGRRT (SEQ ID NO:13) or NNGRR (SEQ ID NO:14) where N can A, G, C, or T, and R can be G or A. In some cases (e.g., for FnCpf1), the PAM sequence can be upstream of the 5' end and have the sequence 5'-TTN-3'.

Examples of guide RNA recognition sequences include a DNA sequence complementary to the DNA-targeting segment of a gRNA, or such a DNA sequence in addition to a PAM sequence. For example, the target motif can be a 20-nucleotide DNA sequence immediately preceding an NGG motif recognized by a Cas9 protein, such as G$N_{19}$NGG (SEQ ID NO:15) or $N_{20}$NGG (SEQ ID NO:16) (see, e.g., PCT Publication WO 2014/165825). The guanine at the 5' end can facilitate transcription by RNA polymerase in cells. Other examples of guide RNA recognition sequences can include two guanine nucleotides at the 5' end (e.g., GG$N_{20}$NGG; SEQ ID NO:17) to facilitate efficient transcription by T7 polymerase in vitro. See, e.g., PCT Publication WO 2014/065596. Other guide RNA recognition sequences can have from about 4 to about 22 nucleotides in length, including the 5' G or GG and the 3' GG or NGG. In some embodiments, the guide RNA recognition sequences can have from about 14 to about 20 nucleotides in length.

The guide RNA recognition sequence can be any nucleic acid sequence endogenous or exogenous to a cell. The guide RNA recognition sequence can be a sequence coding a gene product (e.g., a protein) or a non-coding sequence (e.g., a regulatory sequence) or can include both.

In some embodiments, the guide RNA recognition sequence can be within a region corresponding to exon 5 of SEQ ID NO:1. In some embodiments, the guide RNA recognition sequence can includes or is proximate to positions 53575 to 53577 of SEQ ID NO:1. For example, the guide RNA recognition sequence can be within about 1000, within about 500, within about 400, within about 300, within about 200, within about 100, within about 50, within about 45, within about 40, within about 35, within about 30, within about 25, within about 20, within about 15, within about 10, or within about 5 nucleotides of the position corresponding to positions 53575 to 53577 of SEQ ID NO:1. In some embodiments, the guide RNA recognition sequence can include or be proximate to the start codon of an endogenous B4GALT1 gene or the stop codon of an endogenous B4GALT1 gene. For example, the guide RNA recognition sequence can be within about 10, within about 20, within about 30, within about 40, within about 50, within about 100, within about 200, within about 300, within about 400, within about 500, or within about 1,000 nucleotides of the start codon or the stop codon.

The methods and compositions disclosed herein can utilize exogenous donor sequences (e.g., targeting vectors or repair templates) to modify an endogenous B4GALT1 gene, either without cleavage of the endogenous B4GALT1 gene or following cleavage of the endogenous B4GALT1 gene with a nuclease agent. An exogenous donor sequence refers to any nucleic acid or vector that includes the elements that are required to enable site-specific recombination with a target sequence. Using exogenous donor sequences in combination with nuclease agents may result in more precise modifications within the endogenous B4GALT1 gene by promoting homology-directed repair.

In such methods, the nuclease agent cleaves the endogenous B4GALT1 gene to create a single-strand break (nick) or double-strand break, and the exogenous donor sequence recombines with the endogenous B4GALT1 gene via non-homologous end joining (NHEJ)-mediated ligation or through a homology-directed repair event. Repair with the exogenous donor sequence may remove or disrupt the nuclease cleavage site so that alleles that have been targeted cannot be re-targeted by the nuclease agent.

Exogenous donor sequences can comprise deoxyribonucleic acid (DNA) or ribonucleic acid (RNA), they can be single-stranded or double-stranded, and they can be in linear or circular form. For example, an exogenous donor sequence can be a single-stranded oligodeoxynucleotide (ssODN). An exemplary exogenous donor sequence is from about 50 nucleotides to about 5 kb in length, from about 50 nucleotides to about 3 kb in length, or from about 50 to about 1,000 nucleotides in length. Other exemplary exogenous donor sequences are from about 40 to about 200 nucleotides in length. For example, an exogenous donor sequence can be from about 50 to about 60, from about 60 to about 70, from about 70 to about 80, from about 80 to about 90, from about 90 to about 100, from about 100 to about 110, from about 110 to about 120, from about 120 to about 130, from about 130 to about 140, from about 140 to about 150, from about 150 to about 160, from about 160 to about 170, from about 170 to about 180, from about 180 to about 190, or from about 190 to about 200 nucleotides in length. Alternately, an exogenous donor sequence can be from about 50 to about 100, from about 100 to about 200, from about 200 to about 300, from about 300 to about 400, from about 400 to about 500, from about 500 to about 600, from about 600 to about 700, from about 700 to about 800, from about 800 to about 900, or from about 900 to about 1,000 nucleotides in length. Alternately, an exogenous donor sequence can be from about 1 kb to about 1.5 kb, from about 1.5 kb to about 2 kb, from about 2 kb to about 2.5 kb, from about 2.5 kb to about 3 kb, from about 3 kb to about 3.5 kb, from about 3.5 kb to about 4 kb, from about 4 kb to about 4.5 kb, or from about 4.5 kb to about 5 kb in length. Alternately, an exogenous donor sequence can be, for example, no more than about 5 kb, no more than about 4.5 kb, no more than about 4 kb, no more than about 3.5 kb, no more than about 3 kb, no more than about 2.5 kb, no more than about 2 kb, no more than about 1.5 kb, no more than about 1 kb, no more than about 900 nucleotides, no more than about 800 nucleotides, no more than about 700 nucleotides, no more than about 600 nucleotides, no more than about 500 nucleotides, no more than about 400 nucleotides, no more than about 300 nucleotides, no more than about 200 nucleotides, no more than about 100 nucleotides, or no more than about 50 nucleotides in length.

In some embodiments, an exogenous donor sequence is a ssODN that is from about 80 nucleotides to about 200 nucleotides in length (e.g., about 120 nucleotides in length). In another example, an exogenous donor sequences is a ssODN that is from about 80 nucleotides to about 3 kb in length. Such an ssODN can have homology arms, for example, that are each from about 40 nucleotides to about 60 nucleotides in length. Such a ssODN can also have homology arms, for example, that are each from about 30 nucleotides to 100 nucleotides in length. The homology arms can be symmetrical (e.g., each about 40 nucleotides or each about 60 nucleotides in length), or they can be asymmetrical (e.g., one homology arm that is about 36 nucleotides in length, and one homology arm that is about 91 nucleotides in length).

Exogenous donor sequences can include modifications or sequences that provide for additional desirable features (e.g., modified or regulated stability; tracking or detecting with a fluorescent label; a binding site for a protein or protein complex; and so forth). Exogenous donor sequences can comprise one or more fluorescent labels, purification tags, epitope tags, or a combination thereof. For example, an exogenous donor sequence can comprise one or more fluorescent labels (e.g., fluorescent proteins or other fluorophores or dyes), such as at least 1, at least 2, at least 3, at least 4, or at least 5 fluorescent labels. Exemplary fluorescent labels include fluorophores such as fluorescein (e.g., 6-carboxyfluorescein (6-FAM)), Texas Red, HEX, Cy3, Cy5, Cy5.5, Pacific Blue, 5-(and-6)-carboxytetramethylrhodamine (TAMRA), and Cy7. A wide range of fluorescent dyes are available commercially for labeling oligonucleotides (e.g., from Integrated DNA Technologies). Such fluorescent labels (e.g., internal fluorescent labels) can be used, for example, to detect an exogenous donor sequence that has been directly integrated into a cleaved endogenous B4GALT1 gene having protruding ends compatible with the ends of the exogenous donor sequence. The label or tag can be at the 5' end, the 3' end, or internally within the exogenous donor sequence. For example, an exogenous donor sequence can be conjugated at 5' end with the IR700 fluorophore from Integrated DNA Technologies (5'IRDYE®700).

Exogenous donor sequences can also comprise nucleic acid inserts including segments of DNA to be integrated into the endogenous B4GALT1 gene. Integration of a nucleic acid insert in the endogenous B4GALT1 gene can result in addition of a nucleic acid sequence of interest in the endogenous B4GALT1 gene, deletion of a nucleic acid sequence of interest in the endogenous B4GALT1 gene, or replacement of a nucleic acid sequence of interest in the endogenous B4GALT1 gene (i.e., deletion and insertion). Some exogenous donor sequences are designed for insertion of a nucleic acid insert in the endogenous B4GALT1 gene without any corresponding deletion in the endogenous B4GALT1 gene. Other exogenous donor sequences are designed to delete a nucleic acid sequence of interest in the endogenous B4GALT1 gene without any corresponding insertion of a nucleic acid insert. Other exogenous donor sequences are designed to delete a nucleic acid sequence of interest in the endogenous B4GALT1 gene and replace it with a nucleic acid insert.

The nucleic acid insert and the corresponding nucleic acid in the endogenous B4GALT1 gene being deleted and/or replaced can be various lengths. An exemplary nucleic acid insert or corresponding nucleic acid in the endogenous B4GALT1 gene being deleted and/or replaced is from about 1 nucleotide to about 5 kb in length or is from about 1 nucleotide to about 1,000 nucleotides in length. For example, a nucleic acid insert or a corresponding nucleic acid in the endogenous B4GALT1 gene being deleted and/or replaced can be from about 1 to about 10, from about 10 to about 20, from about 20 to about 30, from about 30 to about 40, from about 40 to about 50, from about 50 to about 60, from about 60 to about 70, from about 70 to about 80, from about 80 to about 90, from about 90 to about 100, from about 100 to about 110, from about 110 to about 120, from about 120 to about 130, from about 130 to about 140, from about 140 to about 150, from about 150 to about 160, from about 160 to about 170, from about 170 to about 180, from about 180 to about 190, or from about 190 to about 200 nucleotides in length. Likewise, a nucleic acid insert or a corresponding nucleic acid in the endogenous B4GALT1 gene being deleted and/or replaced can be from about 1 to about 100, from about 100 to about 200, from about 200 to about 300, from about 300 to about 400, from about 400 to about 500, from about 500 to about 600, from about 600 to about 700, from about 700 to about 800, from about 800 to about 900, or from about 900 to about 1,000 nucleotides in length. Likewise, a nucleic acid insert or a corresponding nucleic acid in the endogenous B4GALT1 gene being deleted and/or replaced can be from about 1 kb to about 1.5 kb, from about 1.5 kb to about 2 kb, from about 2 kb to about 2.5 kb, from about 2.5 kb to about 3 kb, from about 3 kb to about 3.5 kb, from about 3.5 kb to about 4 kb, from about 4 kb to about 4.5 kb, or from about 4.5 kb to about 5 kb in length.

The nucleic acid insert can comprise genomic DNA or any other type of DNA. For example, the nucleic acid insert can comprise cDNA.

The nucleic acid insert can comprise a sequence that is homologous to all or part of the endogenous B4GALT1 gene (e.g., a portion of the gene encoding a particular motif or region of a B4GALT1 polypeptide). For example, the nucleic acid insert can comprise a sequence that comprises one or more point mutations (e.g., 1, 2, 3, 4, 5, or more) or one or more nucleotide insertions or deletions compared with a sequence targeted for replacement in the endogenous B4GALT1 gene.

The nucleic acid insert or the corresponding nucleic acid in the endogenous B4GALT1 gene being deleted and/or replaced can be a coding region such as an exon; a non-coding region such as an intron, an untranslated region, or a regulatory region (e.g., a promoter, an enhancer, or a transcriptional repressor-binding element); or any combination thereof.

Nucleic acid inserts can also comprise a polynucleotide encoding a selection marker. Alternately, the nucleic acid inserts can lack a polynucleotide encoding a selection marker. The selection marker can be contained in a selection cassette. In some embodiments, the selection cassette can be a self-deleting cassette. As an example, the self-deleting cassette can comprise a Cre gene (comprises two exons encoding a Cre recombinase, which are separated by an intron) operably linked to a mouse Prm1 promoter and a neomycin resistance gene operably linked to a human ubiquitin promoter. Exemplary selection markers include neomycin phosphotransferase ($neo^r$), hygromycin B phosphotransferase ($hyg^r$), puromycin-N-acetyltransferase ($puro^r$), blasticidin S deaminase ($bsr^r$), xanthine/guanine phosphoribosyl transferase (gpt), or herpes simplex virus thymidine kinase (HSV-k), or a combination thereof. The polynucleotide encoding the selection marker can be operably linked to a promoter active in a cell being targeted. Examples of promoters are described elsewhere herein.

The nucleic acid insert can also comprise a reporter gene. Exemplary reporter genes include those encoding luciferase, β-galactosidase, green fluorescent protein (GFP), enhanced green fluorescent protein (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, ZsGreen, MmGFP, mPlum, mCherry, tdTomato, mStrawberry, J-Red, mOrange, mKO, mCitrine, Venus, YPet, Emerald, CyPet, Cerulean, T-Sapphire, and alkaline phosphatase. Such reporter genes can be operably linked to a promoter active in a cell being targeted. Examples of promoters are described elsewhere herein.

The nucleic acid insert can also comprise one or more expression cassettes or deletion cassettes. A particular cassette can comprise one or more of a nucleotide sequence of interest, a polynucleotide encoding a selection marker, and a reporter gene, along with various regulatory components that influence expression. Examples of selectable markers and reporter genes that can be included are discussed in detail elsewhere herein.

The nucleic acid insert can comprise a nucleic acid flanked with site-specific recombination target sequences. Alternately, the nucleic acid insert can comprise one or more site-specific recombination target sequences. Although the entire nucleic acid insert can be flanked by such site-specific recombination target sequences, any region or individual polynucleotide of interest within the nucleic acid insert can also be flanked by such sites. Site-specific recombination target sequences, which can flank the nucleic acid insert or any polynucleotide of interest in the nucleic acid insert can include, for example, loxP, lox511, lox2272, lox66, lox71, loxM2, lox5171, FRT, FRT11, FRT71, attp, att, FRT, rox, or a combination thereof. In some embodiments, the site-specific recombination sites flank a polynucleotide encoding a selection marker and/or a reporter gene contained within the nucleic acid insert. Following integration of the nucleic acid insert into the endogenous B4GALT1 gene, the sequences between the site-specific recombination sites can be removed. In some embodiments, two exogenous donor sequences can be used, each with a nucleic acid insert comprising a site-specific recombination site. The exogenous donor sequences can be targeted to 5' and 3' regions flanking a nucleic acid of interest. Following integration of the two nucleic acid inserts into the target genomic locus, the nucleic acid of interest between the two inserted site-specific recombination sites can be removed.

Nucleic acid inserts can also comprise one or more restriction sites for restriction endonucleases (i.e., restriction enzymes), which include Type I, Type II, Type III, and Type IV endonucleases. Type I and Type III restriction endonucleases recognize specific recognition sequences, but typically cleave at a variable position from the nuclease binding site, which can be hundreds of base pairs away from the cleavage site (recognition sequence). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sequences and cleave outside of the recognition sequence, Type IIb enzymes cut sequences twice with both sites outside of the recognition sequence, and Type IIs enzymes recognize an asymmetric recognition sequence and cleave on one side and at a defined distance of about 1 to about 20 nucleotides from the recognition sequence. Type IV restriction enzymes target methylated DNA.

In some embodiments, the exogenous donor sequences have short single-stranded regions at the 5' end and/or the 3' end that are complementary to one or more overhangs created by nuclease-mediated or Cas-protein-mediated cleavage at the target genomic locus (e.g., in the B4GALT1 gene). These overhangs can also be referred to as 5' and 3' homology arms. For example, some exogenous donor sequences have short single-stranded regions at the 5' end and/or the 3' end that are complementary to one or more overhangs created by Cas-protein-mediated cleavage at 5' and/or 3' target sequences at the target genomic locus. In some embodiments, such exogenous donor sequences have a complementary region only at the 5' end or only at the 3' end. For example, some such exogenous donor sequences have a complementary region only at the 5' end complementary to an overhang created at a 5' target sequence at the target genomic locus or only at the 3' end complementary to an overhang created at a 3' target sequence at the target genomic locus. Other such exogenous donor sequences have complementary regions at both the 5' and 3' ends. For example, other such exogenous donor sequences have complementary regions at both the 5' and 3' ends e.g., complementary to first and second overhangs, respectively, generated by Cas-mediated cleavage at the target genomic locus. For example, if the exogenous donor sequence is double-stranded, the single-stranded complementary regions can extend from the 5' end of the top strand of the donor sequence and the 5' end of the bottom strand of the donor sequence, creating 5' overhangs on each end. Alternately, the single-stranded complementary region can extend from the 3' end of the top strand of the donor sequence and from the 3' end of the bottom strand of the template, creating 3' overhangs.

The complementary regions can be of any length sufficient to promote ligation between the exogenous donor sequence and the endogenous B4GALT1 gene. Exemplary complementary regions are from about 1 to about 5 nucleotides in length, from about 1 to about 25 nucleotides in length, or from about 5 to about 150 nucleotides in length. For example, a complementary region can be at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides in length. Alternately, the complementary region can be about 5 to about 10, about 10 to about 20, about 20 to about 30, about 30 to about 40, about 40 to about 50, about 50 to about 60, about 60 to about 70, about 70 to about 80, about 80 to about 90, about 90 to about 100, about 100 to about 110, about 110 to about 120, about 120 to about 130, about 130 to about 140, about 140 to about 150 nucleotides in length, or longer.

Such complementary regions can be complementary to overhangs created by two pairs of nickases. Two double-strand breaks with staggered ends can be created by using first and second nickases that cleave opposite strands of DNA to create a first double-strand break, and third and fourth nickases that cleave opposite strands of DNA to create a second double-strand break. For example, a Cas protein can be used to nick first, second, third, and fourth guide RNA recognition sequences corresponding with first, second, third, and fourth guide RNAs. The first and second guide RNA recognition sequences can be positioned to create a first cleavage site such that the nicks created by the first and second nickases on the first and second strands of DNA create a double-strand break (i.e., the first cleavage site comprises the nicks within the first and second guide RNA recognition sequences). Likewise, the third and fourth guide RNA recognition sequences can be positioned to create a second cleavage site such that the nicks created by the third and fourth nickases on the first and second strands of DNA create a double-strand break (i.e., the second cleavage site comprises the nicks within the third and fourth guide RNA recognition sequences). In some embodiments, the nicks within the first and second guide RNA recognition sequences and/or the third and fourth guide RNA recognition sequences can be off-set nicks that create overhangs. The offset window can be, for example, at least about 5 bp, at least about 10 bp, at least about 20 bp, at least about 30 bp, at least about 40 bp, at least about 50 bp, at least about 60 bp, at least about 70 bp, at least about 80 bp, at least about 90 bp, or at least about 100 bp or more. In such embodiments, a double-stranded exogenous donor sequence can be designed with single-stranded complementary regions that are complementary to the overhangs created by the nicks within the first and second guide RNA recognition sequences and by the nicks within the third and fourth guide RNA recognition sequences. Such an exogenous donor sequence can then be inserted by non-homologous-end-joining-mediated ligation.

In some embodiments, the exogenous donor sequences (i.e., targeting vectors) comprise homology arms. If the exogenous donor sequence also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous donor sequence.

A homology arm and a target sequence correspond to one another when the two regions share a sufficient level of sequence identity to one another to act as substrates for a homologous recombination reaction. The sequence identity between a particular target sequence and the corresponding homology arm found in the exogenous donor sequence can be any degree of sequence identity that allows for homologous recombination to occur. For example, the amount of sequence identity shared by the homology arm of the exogenous donor sequence (or a fragment thereof) and the target sequence (or a fragment thereof) can be at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity, such that the sequences undergo homologous recombination. Moreover, a corresponding region of homology between the homology arm and the corresponding target sequence can be of any length that is sufficient to promote homologous recombination. Exemplary homology arms are from about 25 nucleotides to about 2.5 kb in length, from about 25 nucleotides to about 1.5 kb in length, or from about 25 to about 500 nucleotides in length. For example, a given homology arm (or each of the homology arms) and/or corresponding target sequence can comprise corresponding regions of homology that are from about 25 to about 30, from about 30 to about 40, from about 40 to about 50, from about 50 to about 60, from about 60 to about 70, from about 70 to about 80, from about 80 to about 90, from about 90 to about 100, from about 100 to about 150, from about 150 to about 200, from about 200 to about 250, from about 250 to about 300, from about 300 to about 350, from about 350 to about 400, from about 400 to about 450, or from about 450 to about 500 nucleotides in length, such that the homology arms have sufficient homology to undergo homologous recombination with the corresponding target sequences within the endogenous B4GALT1 gene. Alternately, a particular homology arm (or each homology arm) and/or corresponding target sequence can comprise corresponding regions of homology that are from about 0.5 kb to about 1 kb, from about 1 kb to about 1.5 kb, from about 1.5 kb to about 2 kb, or from about 2 kb to about 2.5 kb in length. For example, the homology arms can each be about 750 nucleotides in length. The homology arms can be symmetrical (each about the same size in length), or they can be asymmetrical (one longer than the other).

The homology arms can correspond to a locus that is native to a cell (e.g., the targeted locus). Alternately, they can correspond to a region of a heterologous or exogenous segment of DNA that was integrated into the genome of the cell, including, for example, transgenes, expression cassettes, or heterologous or exogenous regions of DNA. In some embodiments, the homology arms of the targeting vector can correspond to a region of a yeast artificial chromosome (YAC), a bacterial artificial chromosome (BAC), a human artificial chromosome, or any other engineered region contained in an appropriate host cell. In some embodiments, the homology arms of the targeting vector can correspond to or be derived from a region of a BAC library, a cosmid library, or a P1 phage library, or can be derived from synthetic DNA.

When a nuclease agent is used in combination with an exogenous donor sequence, the 5' and 3' target sequences are generally located in sufficient proximity to the nuclease cleavage site so as to promote the occurrence of a homologous recombination event between the target sequences and the homology arms upon a single-strand break (nick) or double-strand break at the nuclease cleavage site. Nuclease cleavage sites include a DNA sequence at which a nick or double-strand break is created by a nuclease agent (e.g., a Cas9 protein complexed with a guide RNA). The target sequences within the endogenous B4GALT1 gene that correspond to the 5' and 3' homology arms of the exogenous donor sequence are "located in sufficient proximity" to a nuclease cleavage site if the distance is such as to promote the occurrence of a homologous recombination event between the 5' and 3' target sequences and the homology arms upon a single-strand break or double-strand break at the nuclease cleavage site. Thus, the target sequences corresponding to the 5' and/or 3' homology arms of the exogenous donor sequence can be, for example, within at least 1 nucleotide of a given nuclease cleavage site or within at least 10 nucleotides to about 1,000 nucleotides of a particular nuclease cleavage site. In some embodiments, the nuclease cleavage site can be immediately adjacent to at least one or both of the target sequences.

The spatial relationship of the target sequences that correspond to the homology arms of the exogenous donor sequence and the nuclease cleavage site can vary. In some embodiments, the target sequences can be located 5' to the nuclease cleavage site, target sequences can be located 3' to the nuclease cleavage site, or the target sequences can flank the nuclease cleavage site.

The present disclosure also provides therapeutic methods and methods of treatment or prophylaxis of a cardiovascular condition in a subject having or at risk of having the disease using the methods disclosed herein for modifying or altering expression of an endogenous B4GALT1 gene. The present disclosure also provides therapeutic methods and methods of treatment or prophylaxis of a cardiovascular condition in a subject having or at risk for the disease using methods for decreasing expression of endogenous B4GALT1 mRNA or using methods for providing recombinant nucleic acids encoding B4GALT1 polypeptides, providing mRNAs encoding B4GALT1 polypeptides, or providing B4GALT1 polypeptides to the subject. The methods can comprise introducing one or more nucleic acid molecules or proteins into the subject, into an organ of the subject, or into a cell of the subject (e.g., in vivo or ex vivo).

In some embodiments, the disclosure provides mRNAs encoding B4GALT1 polypeptides (e.g. polynucleotides as discussed herein, for example an mRNA that comprises the sequence of SEQ ID NO:4) for use in therapy. In some such embodiments, the therapy is treating or preventing a cardiovascular condition.

In some embodiments, the disclosure provides B4GALT1 polypeptides (e.g. polypeptides as discussed herein, for example polypeptides that comprise the sequence of SEQ ID NO:8) for use in therapy. In some such embodiments the therapy is treating or preventing a cardiovascular condition.

Subjects include human and other mammalian subjects (e.g., feline, canine, rodent, mouse, or rat) or non-mammalian subjects (e.g., poultry) that receive either prophylactic or therapeutic treatment. Such subjects can be, for example, a subject (e.g., a human) who is not a carrier of the variant B4GALT1 (or is only a heterozygous carrier of the variant B4GALT1) and has or is susceptible to developing a cardiovascular condition.

Non-limiting examples of a cardiovascular condition include an elevated level of one or more serum lipids. The serum lipids comprise one or more of cholesterol, LDL, HDL, triglycerides, HDL-cholesterol, and non-HDL cholesterol, or any subfraction thereof (e.g., HDL2, HDL2a, HDL2b, HDL2c, HDL3, HDL3a, HDL3b, HDL3c, HDL3d, LDL1, LDL2, LDL3, lipoprotein A, Lpa1, Lpa1, Lpa3, Lpa4, or Lpa5). A cardiovascular condition may comprise elevated levels of coronary artery calcification. A cardiovascular condition may comprise Type IId glycosylation (CDG-IId). A cardiovascular condition may comprise elevated levels of pericardial fat. A cardiovascular condition may comprise an atherothrombotic condition. The atherothrombotic condition may comprise elevated levels of fibrinogen. The atherothrombotic condition may comprises a fibrinogen-mediated blood clot. A cardiovascular condition may comprise elevated levels of fibrinogen. A cardiovascular condition may comprise a fibrinogen-mediated blood clot. A cardiovascular condition may comprise a blood clot formed from the involvement of fibrinogen activity. A fibrinogen-mediated blood clot or blood clot formed from the involvement of fibrinogen activity may be in any vein or artery in the body.

Such methods can comprise genome editing or gene therapy. For example, an endogenous B4GALT1 gene that is not the variant B4GALT1 can be modified to comprise the variation associated with the variant B4GALT1 (i.e., replacement of asparagine with a serine at the position corresponding to position 352 of the full length/mature B4GALT1 polypeptide). As another example, an endogenous B4GALT1 gene that is not the variant B4GALT1 can be knocked out or inactivated. Likewise, an endogenous B4GALT1 gene that is not the variant B4GALT1 can be knocked out or inactivated, and an B4GALT1 gene comprising the modification associated with the variant B4GALT1 (e.g., the complete variant B4GALT1 or a minigene comprising the modification) can be introduced and expressed. Similarly, an endogenous B4GALT1 gene that is not the variant B4GALT1 can be knocked out or inactivated, and a recombinant DNA encoding the B4GALT1 variant polypeptide can be introduced and expressed, an mRNA encoding the B4GALT1 variant polypeptide can be introduced and expressed (e.g., intracellular protein replacement therapy), and/or a variant B4GALT1 polypeptide can be introduced (e.g., protein replacement therapy).

In some embodiments, the methods comprise introducing and expressing a recombinant B4GALT1 gene comprising the modification associated with the B4GALT1 rs551564683 variant (e.g., the complete variant B4GALT1 or a minigene comprising the modification), introducing and expressing recombinant nucleic acids (e.g., DNA) encoding the variant B4GALT1 polypeptide or fragments thereof, introducing and expressing one or more mRNAs encoding the variant B4GALT1 polypeptide or fragments thereof (e.g., intracellular protein replacement therapy), or introducing the variant B4GALT1 polypeptide or fragments thereof (e.g., protein replacement therapy) without knocking out or inactivating an endogenous B4GALT1 gene that is not the variant B4GALT1. In some embodiments, such methods can also be carried out in combination with methods in which endogenous B4GALT1 mRNA that is not the variant B4GALT1 is targeted for reduced expression, such as through use of antisense RNA, siRNA, or shRNA.

A B4GALT1 gene or minigene or a DNA encoding the variant B4GALT1 polypeptide or fragments thereof can be introduced and expressed in the form of an expression vector that does not modify the genome, it can be introduced in the form of a targeting vector such that it genomically integrates into an endogenous B4GALT1 locus, or it can be introduced such that it genomically integrates into a locus other than the endogenous B4GALT1 locus, such as a safe harbor locus. The genomically integrated B4GALT1 gene can be operably linked to a B4GALT1 promoter or to another promoter, such as an endogenous promoter at the site of integration. Safe harbor loci are chromosomal sites where transgenes can be stably and reliably expressed in all tissues of interest without adversely affecting gene structure or expression. Safe harbor loci can have, for example, one or more or all of the following characteristics: 1) a distance of greater than about 50 kb from the 5' end of any gene; a distance of greater than about 300 kb from any cancer-related gene; a distance of greater than about 300 kb from any microRNA; outside a gene transcription unit, and outside of ultra-conserved regions. Examples of suitable safe harbor loci include, but are not limited to, adeno-associated virus site 1 (AAVS1), the chemokine (CC motif) receptor 5 (CCR5) gene locus, and the human orthologue of mouse ROSA26 locus.

In some embodiments, the methods comprise a method of treating a subject who is not a carrier of the variant B4GALT1 (or is only a heterozygous carrier of the variant B4GALT1) and has or is susceptible to developing a cardiovascular condition, comprising introducing into the subject or introducing into a cell in the subject: a) a nuclease agent (or nucleic acid encoding) that binds to a nuclease recognition sequence within an endogenous B4GALT1 gene, wherein the nuclease recognition sequence includes or is proximate to positions 53575 to 53577 of SEQ ID NO:1; and b) an exogenous donor sequence comprising a 5' homology arm that hybridizes to a target sequence 5' of positions 53575 to 53577 of SEQ ID NO:1, and a nucleic acid insert comprising a nucleic acid sequence encoding a serine flanked by the 5' homology arm and the 3' homology arm. The nuclease agent can cleave the endogenous B4GALT1 gene in a cell in the subject, and the exogenous donor sequence can recombine with the endogenous B4GALT1 gene in the cell, wherein upon recombination of the exogenous donor sequence with the endogenous B4GALT1 gene, the nucleic acid sequence encoding a serine is inserted at nucleotides corresponding to positions 53575 to 53577 of SEQ ID NO:1. Examples of nuclease agents (e.g., a Cas9 protein and a guide RNA) that can be used in such methods are disclosed elsewhere herein.

In some embodiments, the methods comprise a method of treating a subject who is not a carrier of the variant B4GALT1 (or is only a heterozygous carrier of the variant B4GALT1) and has or is susceptible to developing a cardiovascular condition, comprising introducing into the subject or introducing into a cell in the subject an exogenous donor sequence comprising a 5' homology arm that hybridizes to a target sequence 5' of the position corresponding to positions 53575 to 53577 of SEQ ID NO:1, a 3' homology arm that hybridizes to a target sequence 3' of positions 53575 to 53577 of SEQ ID NO:1, and a nucleic acid insert comprising a nucleotide sequence encoding a serine flanked by the 5' homology arm and the 3' homology arm. The exogenous donor sequence can recombine with the endogenous B4GALT1 gene in the cell, wherein upon recombination of the exogenous donor sequence with the endogenous B4GALT1 gene, the nucleotide sequence encoding a serine is inserted at nucleotides corresponding to positions 53575 to 53577 of SEQ ID NO:1.

Some such methods comprise a method of treating a subject who is not a carrier of the variant B4GALT1 ant (or is only a heterozygous carrier of the variant B4GALT1) and has or is susceptible to developing a cardiovascular condition, comprising introducing into the subject or introducing into a cell in the subject: a) a nuclease agent (or nucleic acid encoding) that binds to a nuclease recognition sequence within an endogenous B4GALT1 gene, wherein the nuclease recognition sequence comprises the start codon for the endogenous B4GALT1 gene or is within about 10, about 20, about 30, about 40, about 50, about 100, about 200, about 300, about 400, about 500, or about 1,000 nucleotides of the start codon or is selected from SEQ ID NOS:9-12. The nuclease agent can cleave and disrupt expression of the endogenous B4GALT1 gene in a cell in the subject.

In some embodiments, the methods comprise a method of treating a subject who is not a carrier of the variant B4GALT1 (or is only a heterozygous carrier of the variant B4GALT1) and has or is susceptible to developing a cardiovascular condition, comprising introducing into the subject or introducing into a cell in the subject: a) a nuclease agent (or nucleic acid encoding) that binds to a nuclease recognition sequence within an endogenous B4GALT1 gene, wherein the nuclease recognition sequence comprises the start codon for the endogenous B4GALT1 gene or is within about 10, within about 20, within about 30, within about 40, within about 50, within about 100, within about 200, within about 300, within about 400, within about 500, or within about 1,000 nucleotides of the start codon or is selected from SEQ ID NOS:9-12; and b) an expression vector comprising a recombinant B4GALT1 gene comprising a nucleotide sequence at positions 53575 to 53577 encoding a serine at the position corresponding to position 352 of the full length/mature B4GALT1 polypeptide. The expression vector can be one that does not genomically integrate. Alternately, a targeting vector (i.e., exogenous donor sequence) can be introduced comprising a recombinant B4GALT1 gene comprising a nucleotide sequence at positions 53575 to 53577 encoding a serine at the position corresponding to position 352 of the full length/mature B4GALT1 polypeptide. The nuclease agent can cleave and disrupt expression of the within B4GALT1 gene in a cell in the subject, and the expression vector can express the recombinant B4GALT1 gene in the cell in the subject. Alternately, the genomically integrated, recombinant B4GALT1 gene can be expressed in the cell in the subject. Examples of nuclease agents (e.g., a nuclease-active Cas9 protein and guide RNA) that can be used in such methods are disclosed elsewhere herein. Examples of suitable guide RNAs and guide RNA recognition sequences are also disclosed elsewhere herein. Step b) can alternately comprise introducing an expression vector or targeting vector comprising a nucleic acid (e.g., DNA) encoding a B4GALT1 polypeptide that is at least 90%, at least 95%, at least 96%, at least 97%, at least 98%, at least 99%, or 100% identical to the variant B4GALT1 Asn352Ser polypeptide or a fragment thereof and/or comprising a sequence that is at least 90%, at least 95%, at least 96%, at least 97%, at least 98%, at least 99%, or 100% identical to the variant B4GALT1 mRNA or a fragment thereof. Likewise, step b) can also comprise introducing an mRNA encoding a B4GALT1 Asn352Ser polypeptide that is at least 90%, at least 95%, at least 96%, at least 97%, at least 98%, at least 99%, or 100% identical to the variant B4GALT1 Asn352Ser polypeptide or a fragment thereof and/or having a complementary DNA (or a portion thereof) that is at least 90%, at least 95%, at least 96%, at least 97%, at least 98%, at least 99%, or 100% identical to the variant B4GALT1 mRNA or a fragment thereof. Likewise, step b) can also comprise introducing a protein comprising an amino acid sequence that is at least 90%, at least 95%, at least 96%, at least 97%, at least 98%, at least 99%, or 100% identical to the variant B4GALT1 Asn352Ser polypeptide or a fragment thereof.

In some embodiments, a second nuclease agent is also introduced into the subject or into the cell in the subject, wherein the second nuclease agent binds to a second nuclease recognition sequence within the endogenous B4GALT1 gene, wherein the second nuclease recognition sequence comprises the stop codon for the endogenous B4GALT1 gene or is within about 10, within about 20, within about 30, within about 40, within about 50, within about 100, within about 200, within about 300, within about 400, within about 500, or within about 1,000 nucleotides of the stop codon or is selected from SEQ ID NOS:9-12, wherein the nuclease agent cleaves the endogenous B4GALT1 gene in the cell within both the first nuclease recognition sequence and the second nuclease recognition sequence, wherein the cell is modified to comprise a deletion between the first nuclease recognition sequence and the second nuclease recognition sequence. In some embodiments, the second nuclease agent can be a Cas9 protein and a guide RNA. Suitable guide RNAs and guide RNA recognition sequences in proximity to the stop codon are disclosed elsewhere herein.

In some embodiments, the methods can also comprise a method of treating a subject who is not a carrier of the variant B4GALT1 (or is only a heterozygous carrier of the variant B4GALT1) and has or is susceptible to developing a cardiovascular condition, comprising introducing into the subject or introducing into a cell in the subject: an antisense RNA, an siRNA, or an shRNA that hybridizes to a sequence within a region of within endogenous B4GALT1 mRNA. For example, the antisense RNA, siRNA, or shRNA can hybridize to sequence within a region in exon 5 of SEQ ID NO:3 (B4GALT1 mRNA) and decrease expression of B4GALT1 mRNA in a cell in the subject. In some embodiments, such methods can further comprise introducing into the subject an expression vector comprising a recombinant B4GALT1 gene comprising a nucleotide sequence encoding a serine inserted at positions 53575 to 53577 of SEQ ID NO:2. The expression vector can be one that does not genomically integrate. Alternately, a targeting vector (i.e., exogenous donor sequence) can be introduced comprising a recombinant B4GALT1 gene comprising nucleic acid sequence encoding a serine at positions corresponding to positions 53575 to 53577 of SEQ ID NO:2. In methods in which an expression vector is used, the expression vector can express the recombinant B4GALT1 gene in the cell in the subject. Alternately, in methods in which a recombinant B4GALT1 gene is genomically integrated, the recombinant B4GALT1 gene can express in the cell in the subject.

In some embodiments, such methods can alternately comprise introducing an expression vector or targeting vector comprising a nucleic acid (e.g., DNA) encoding a B4GALT1 polypeptide that is at least 90%, at least 95%, at least 96%, at least 97%, at least 98%, at least 99%, or 100% identical to the variant B4GALT1 Asn352Ser polypeptide or a fragment thereof and/or comprising a sequence that is at least 90%, at least 95%, at least 96%, at least 97%, at least 98%, at least 99%, or 100% identical to variant B4GALT1 mRNA or a fragment thereof. Likewise, such methods can alternately comprise introducing an mRNA encoding a polypeptide that is at least 90%, at least 95%, at least 96%, at least 97%, at least 98%, at least 99%, or 100% identical to the variant B4GALT1 Asn352Ser polypeptide or a fragment thereof and/or having a complementary DNA (or a portion thereof) that is at least 90%, at least 95%, at least 96%, at least 97%, at least 98%, at least 99%, or 100% identical to the variant B4GALT1 mRNA or a fragment thereof. Likewise, such methods can alternately comprise introducing a polypeptide comprising a sequence that is at least 90%, at least 95%, at least 96%, at least 97%, at least 98%, at least 99%, or 100% identical to the variant B4GALT1 Asn352Ser polypeptide or a fragment thereof.

In some embodiments, such methods can comprise methods of treating a subject who is not a carrier of the variant B4GALT1 (or is only a heterozygous carrier of the variant B4GALT1) and has or is susceptible to developing a cardiovascular condition, comprising introducing into the subject or introducing into a cell in the subject an expression vector, wherein the expression vector comprises a recombinant B4GALT1 gene comprising a nucleotide sequence at positions 53575 to 53577 that encode a serine at the position corresponding to position 352 of the full length/mature B4GALT1 polypeptide, wherein the expression vector expresses the recombinant B4GALT1 gene in a cell in the subject. The expression vector can be one that does not genomically integrate. Alternately, a targeting vector (i.e., exogenous donor sequence) can be introduced comprising a recombinant B4GALT1 gene comprising a nucleotide sequence at positions 53575 to 53577 of SEQ ID NO:2 that encode a serine at the position corresponding to position 352 of the full length/mature B4GALT1 polypeptide. In methods in which an expression vector is used, the expression vector can express the recombinant B4GALT1 gene in the cell in the subject. Alternately, in methods in which a recombinant B4GALT1 gene is genomically integrated, the recombinant B4GALT1 gene can express in the cell in the subject.

Such methods can alternately comprise introducing an expression vector or targeting vector comprising a nucleic acid (e.g., DNA) encoding a B4GALT1 polypeptide that is at least 90%, at least 95%, at least 96%, at least 97%, at least 98%, at least 99%, or 100% identical to the variant B4GALT1 Asn352Ser polypeptide or a fragment thereof and/or comprising a sequence that is at least 90%, at least 95%, at least 96%, at least 97%, at least 98%, at least 99%, or 100% identical to the variant B4GALT1 mRNA or a fragment thereof. Likewise, such methods can alternately comprise introducing an mRNA encoding a polypeptide that is at least 90%, at least 95%, at least 96%, at least 97%, at least 98%, at least 99%, or 100% identical to the variant B4GALT1 polypeptide or a fragment thereof and/or having a complementary DNA (or a portion thereof) that is at least 90%, at least 95%, at least 96%, at least 97%, at least 98%, at least 99%, or 100% identical to the variant B4GALT1 mRNA or a fragment thereof. Likewise, such methods can alternately comprise introducing a protein comprising a sequence that is at least 90%, at least 95%, at least 96%, at least 97%, at least 98%, at least 99%, or 100% identical to the variant B4GALT1 Asn352Ser polypeptide or a fragment thereof.

Suitable expression vectors and recombinant B4GALT1 genes for use in any of the above methods are disclosed elsewhere herein. For example, the recombinant B4GALT1 gene can be the complete B4GALT1 variant gene or can be a B4GALT1 minigene in which one or more nonessential segments of the gene have been deleted with respect to a corresponding wild-type B4GALT1 gene. As an example, the deleted segments can comprise one or more intronic sequences, and the minigene can comprise exons 1 through 6. An example of a complete B4GALT1 variant gene is one that is at least 90%, at least 95%, at least 96%, at least 97%, at least 98%, at least 99%, or 100% identical to SEQ ID NO:2.

In some embodiments, such methods comprise a method of modifying a cell in a subject having or susceptible to developing a cardiovascular condition. In such methods, the nuclease agents and/or exogenous donor sequences and/or recombinant expression vectors can be introduced into the cell via administration in an effective regime meaning a dosage, route of administration and frequency of administration that delays the onset, reduces the severity, inhibits further deterioration, and/or ameliorates at least one sign or symptom of a cardiovascular condition being treated. The term "symptom" refers to a subjective evidence of a disease as perceived by the subject, and a "sign" refers to objective evidence of a disease as observed by a physician. If a subject is already suffering from a disease, the regime can be referred to as a therapeutically effective regime. If the subject is at elevated risk of the disease relative to the general population but is not yet experiencing symptoms, the regime can be referred to as a prophylactically effective regime. In some instances, therapeutic or prophylactic efficacy can be observed in an individual patient relative to historical controls or past experience in the same subject. In other instances, therapeutic or prophylactic efficacy can be demonstrated in a preclinical or clinical trial in a population of treated subjects relative to a control population of untreated subjects.

Delivery can be any suitable method, as disclosed elsewhere herein. For example, the nuclease agents or exogenous donor sequences or recombinant expression vectors can be delivered by, for example, vector delivery, viral delivery, particle-mediated delivery, nanoparticle-mediated delivery, liposome-mediated delivery, exosome-mediated delivery, lipid-mediated delivery, lipid-nanoparticle-mediated delivery, cell-penetrating-peptide-mediated delivery, or implantable-device-mediated delivery. Specific examples include hydrodynamic delivery, virus-mediated delivery, and lipid-nanoparticle-mediated delivery.

Administration can be by any suitable route including, but not limited to, parenteral, intravenous, oral, subcutaneous, intra-arterial, intracranial, intrathecal, intraperitoneal, topical, intranasal, or intramuscular. A specific example which is often used, for example, for protein replacement therapies is intravenous infusion. The frequency of administration and the number of dosages can depend on the half-life of the nuclease agents or exogenous donor sequences or recombinant expression vectors, the condition of the subject, and the route of administration among other factors. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

Other such methods comprise an ex vivo method in a cell from a subject having or susceptible to developing a cardiovascular condition. The cell with the targeted genetic modification can then be transplanted back into the subject.

The present disclosure provides methods of decreasing LDL in a subject in need thereof, by reducing expression of endogenous wild-type B4GALT1 or increasing expression of B4GALT1 Asn352Ser, by any of the methods described herein. The present disclosure provides methods of decreasing total cholesterol in a subject in need thereof, by reducing expression of endogenous wild-type B4GALT1 or increasing expression of B4GALT1 Asn352Ser, by any of the methods described herein. The present disclosure provides methods of decreasing fibrinogen in a subject in need thereof, by reducing expression of endogenous wild-type B4GALT1 or increasing expression of B4GALT1 Asn352Ser, by any of the methods described herein. The present disclosure provides methods of decreasing eGFR in a subject in need thereof, by reducing expression of endogenous wild-type B4GALT1 or increasing expression of B4GALT1 Asn352Ser, by any of the methods described herein. The present disclosure provides methods of increasing AST, but not ALT, in a subject in need thereof, by reducing expression of endogenous wild-type B4GALT1 or increasing expression of B4GALT1 Asn352Ser, by any of the methods described herein. The present disclosure provides methods of increasing creatinine in a subject in need thereof, by reducing expression of endogenous wild-type B4GALT1 or increasing expression of B4GALT1 Asn352Ser, by any of the methods described herein.

The present disclosure also provides methods of diagnosing the risk of developing a cardiovascular condition, or diagnosing the risk of developing a cardiovascular condition and treating the same in a subject in need thereof, comprising: requesting a test providing the results of an analysis of a sample from the subject for the presence or absence of variant B4GALT1 gene, mRNA, cDNA, or polypeptide, as described herein; and, in those subjects not having the variant B4GALT1 gene, mRNA, cDNA, or polypeptide, administering a therapeutic agent, such as described herein, to the subject. Any of the tests described herein whereby the presence or absence of variant B4GALT1 gene, mRNA, cDNA, or polypeptide is determined can be used.

The present disclosure also provides uses of any of the variant B4GALT1 genes, mRNAs, cDNAs, polypeptides, and hybridizing nucleic acid molecules disclosed herein in the manufacture of a medicament for decreasing LDL, decreasing total cholesterol, decreasing fibrinogen, decreasing eGFR, increasing AST (but not ALT), and increasing creatinine in a subject in need thereof. The present disclosure also provides uses of any of the variant B4GALT1 genes, mRNAs, cDNAs, polypeptides, and hybridizing nucleic acid molecules in the manufacture of a medicament for treating coronary artery disease, coronary artery calcification, and related disorders.

The present disclosure also provides uses of any of the variant B4GALT1 genes, mRNAs, cDNAs, polypeptides, and hybridizing nucleic acid molecules disclosed herein for decreasing LDL, decreasing total cholesterol, decreasing fibrinogen, decreasing eGFR, increasing AST (but not ALT), and increasing creatinine in a subject in need thereof.

The present disclosure also provides uses of any of the variant B4GALT1 genes, mRNAs, cDNAs, polypeptides, and hybridizing nucleic acid molecules for treating coronary artery disease, coronary artery calcification, Type IId glycosylation (CDG-IId), and related disorders.

The present disclosure also provides uses of any of the variant B4GALT1 genes, mRNAs, cDNAs, polypeptides, and hybridizing nucleic acid molecules disclosed herein for modifying a B4GALT1 gene in a cell in a subject in need thereof.

The present disclosure also provides uses of any of the variant B4GALT1 genes, mRNAs, cDNAs, polypeptides, and hybridizing nucleic acid molecules disclosed herein for altering expression of a B4GALT1 gene in a cell in a subject in need thereof.

The present disclosure also provides uses of any of the variant B4GALT1 genes, mRNAs, cDNAs, polypeptides, and hybridizing nucleic acid molecules disclosed herein for diagnosing the risk of developing any of the cardiovascular conditions disclosed herein.

The present disclosure also provides uses of any of the variant B4GALT1 genes, mRNAs, cDNAs, polypeptides, and hybridizing nucleic acid molecules disclosed herein for diagnosing a subject of having any of the cardiovascular conditions disclosed herein.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The nucleotide and amino acid sequences recited herein are shown using standard letter abbreviations for nucleotide bases, and one-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

The following examples are provided to describe the embodiments in greater detail. They are intended to illustrate, not to limit, the claimed embodiments.

EXAMPLES

Example 1: Determination of a Novel Locus on Chromosome 9p.21 Associated with Serum Lipid Traits at Genome-Wide Statistical Significance

Materials and Methods

Chip genotyping and QC: Genomic DNA was extracted from whole blood from individuals of the 00A, and quantitated using picogreen. Genome-wide genotyping was performed with Affymetrix 500K and 6.0 chips at the University of Maryland Biopolymer Core Facility. The BRLMM algorithm was used for genotype calling. Samples with call rate <0.93, high level of Mendelian error, or gender mismatch were excluded. SNPs with call rate <0.95, HWEpval <1.0E-6, or MAF <0.01 were excluded. SNPs on chromosomes X and Y, and the mitochondrial genome were also excluded.

WGS and QC: Library preparation and whole genome sequencing was performed by the Broad Institute of MIT and Harvard. The NHLBI Informatics Resource Core at the University of Michigan performed alignment, base calling, and sequence quality scoring of all TOPMed samples and delivered bcf files for all variants passing all quality filters with read depth at least 10, which was used for the analysis. Further QC applied to this files including removing all sites in LCR, or X chromosomes. Variants with >5% missing rates, HWE p-value <1.0E-09 and MAF <0.1% were also removed. Sample QC was performed to remove samples with >5% missing rates, high level of Mendelian error (in some instances), or identical (MZ) twins (one of each pair).

WES and QC: Exome capturing and sequencing was performed at the Regeneron Genetics Center (RGC) as described below in more detail. Briefly, the captured libraries were sequenced on the Illumina HiSeq 2500 platform with v4 chemistry using paired-end 75 bp reads. Paired-end sequencing of the captured bases was performed so that >85% of the bases were covered at 20× or greater, which is sufficient for calling heterozygous variants across most of the targeted bases. Read alignment and variant calling were performed using BWA-MEM and GATK as implemented in the RGC DNAseq analysis pipeline. Samples with call rate <0.90, high level of Mendelian errors, identical (MZ) twins (one of each pair), or gender mismatch were excluded. SNPs with call rate <0.90, and monomorphic SNPs were also excluded. SNPs in chromosomes X and Y, and the mitochondrial genome were also excluded.

Association analysis: Fasting blood samples were collected and used for lipid analysis. LDL was calculated using the Friedewald formula, and in some analyses with subjects on lipid lowering medication adjusted by dividing their LDL levels by 0.7. The genetic association analysis was performed using linear mixed models to account for familial correlation using the pedigree based kinship matrix and/or familial correction that estimates kinship from WES. The analysis was also adjusted for age, age squared, sex, cohort, and APOB R3527Q genotype. APOB R3527Q is enriched in the Amish and was previously identified to have a strong effect on LDL levels (58 mg/dl) (Shen et al., Arch Intern. Med., 2010, 170, 1850-1855), and, therefore, the effect of this variant in the LDL analysis was taken into consideration. Genome-wide corrected p-value of 5.0E-08 was used as the significance threshold.

Identifying the Association Between Chromosome 9p Region and LDL Using Genome Wide Association Study (GWAS):

To identify causative variants in novel genes associated with cardiovascular risk factors, a genome-wide association analysis was performed using 1852 Old Order Amish subjects genotyped with Affymetrix 500K and 6.0 chips. The basic characteristics of these participants are shown in Table 1.

TABLE 1

Basic characteristics of the study populations

| | GWAS Discovery | WGS Fine mapping | WES Confirmation |
|---|---|---|---|
| N | 1852 | 1083 | 4565 |
| Male (%) | 48 | 50 | 43 |
| Age (years) | 51.1 ± 16.3 | 50.4 ± 16.8 | 41.7 ± 15.2 |
| BMI (kg/m$^2$) | 27.4 ± 5.0 | 26.9 ± 4.5 | 26.6 ± 4.9 |
| SBP (mmHg) | 121.1 ± 16.0 | 120.9 ± 15.6 | 115.1 ± 16.1 |
| DBP (mmHg) | 73.6 ± 9.4 | 74.4 ± 9.6 | 71.6 ± 9.6 |
| Cholesterol (mg/dl) | 210.6 ± 46.3 | 211.8 ± 46.9 | 208.2 ± 49.2 |
| HDL (mg/dl) | 56.1 ± 14.8 | 55.9 ± 15.6 | 60.9 ± 16.4 |
| LDL (mg/dl) | 138.2 ± 42.1 | 140.4 ± 43.2 | 132.7 ± 44.9 |
| Triglycerides (mg/dl) | 80.4 ± 53.0 | 77.7 ± 48.8 | 72.1 ± 45.6 |
| Cholesterol lowering med. (%) | 2.4 | 3.2 | 1.9 |
| Diabetes (%) | 2.6 | 2.4 | 2.2 |

Almost all of WGS fine mapping samples (96%) were included in GWAS discovery samples.

Only 30% of WES samples were included in GWAS or WGS samples.

As shown in FIG. 1, a strong novel association signal between LDL and a locus on chromosome 9p was discovered. The lead associated SNP was rs855453 (p=2.2E-08) and had a frequency of 15% in the Amish and 25% in the general population. The minor 'T' allele was associated with a 10 mg/dl lower LDL level. Thus, this GWAS SNP is common in both Amish and non-Amish and has large effect size, but has never been identified in any of the large GWAS meta analyses. These characteristics match those of previous studies (APOC3 and LIPE), and based on that it was concluded that this GWAS SNP was not the causal/functional variant in this region but rather in linkage disequilibrium (LD) with another variant that is rare in the general population but common in the Amish population. Furthermore, multiple studies based on 5 independent crosses of multiple strains also found the syntenic region of the rat genome, located on rat chromosome 5, harbors a QTL for serum cholesterol and triglyceride level (The Rat Genome Database (RGD). Scl12.26. 35. 44, 54 and Stl 28).

Confirmation Using Whole Exome Sequencing (WES):

High quality QC'd WES for 4,565 Amish individuals, the basic characteristics of which are shown in Table 1, were subsequently used. The results of a mixed model exome wide analysis of LDL identified the B4GALT1 rs551564683 missense variant as the most significant association with a p-value of 3.3E-18 and effect size of 14.7 mg/dl lower LDL. The rs551564683 variant had a MAF of 6% in the Amish while extremely rare in the general population. The variant is in dbSNP without frequency or population information, does not exist in the ExAC database (60,000 samples), and only one copy was found in the WGS from 15,387 non-Amish in the NHLBI Trans-Omics for Precision Medicine (TOPMed) dataset. Moreover, in a collective data set of other population cohorts available to the investigators—totaling 125,401 individuals—only 79 heterozygotes and 5 homozygotes of this variant were found (showing over one thousand-fold enrichment in the Amish population). This missense variant is 500 Kb away from the GWAS variant with an r2 estimate of LD of 0.5. There are no perfectly correlated variants with r5551564683; in fact, the next most significant SNP is rs149557496 with p-value E-14. Thus, not only does the strength of the rs551564683 association confirm that the chromosome 9 GWAS locus is real, but rs551564683 has all the characteristics expected of the casual variant.

Fine-Mapping the Chromosome 9p Region Using Whole Genome Sequencing (WGS):

WGS available on a smaller sample was used to fill in the gaps in the exome sequencing to provide further evidence that rs551564683 is causal. WGS data for 1083 OOA was generated as part of the TOPMed program. Basic characteristics of the WGS samples are shown in Table 1. WGS captures all the SNPs and Indels (insertion/deletion)—both coding and non-coding—that might be correlated with the top variants in the region of interest. Since the top variants are ~6% frequency, it is very unlikely there would be insufficient sequence reads to cause the variant caller to miss a variant. However, there may be variants excluded during the QC procedure. By investigating the variants that did not pass QC, 2 additional variants were added in the analysis. The association analysis identified the missense SNP (N352S) rs551564683 in the B4GALT1 gene as the most significantly associated variant with LDL in this region with p-value of 2.9E-06 and effect size of −16.4 mg/dl (see, Table 2).

TABLE 2

Mean (n) LDL levels (mg/dl) by rs551564683-containing genotype in the OOA

| Cohort | TT | TC | CC | p-value |
|---|---|---|---|---|
| WES Confirmation (n = 4,565) | 135 (n = 4025) | 118 (n = 529) | 103 (n = 12) | $3.3 \times 10^{-18}$ |
| WGS Fine mapping (n = 1,083) | 144 (n = 952) | 128 (n = 130) | 87 (n = 1) | $2.9 \times 10^{-6}$ |

Figure 2:
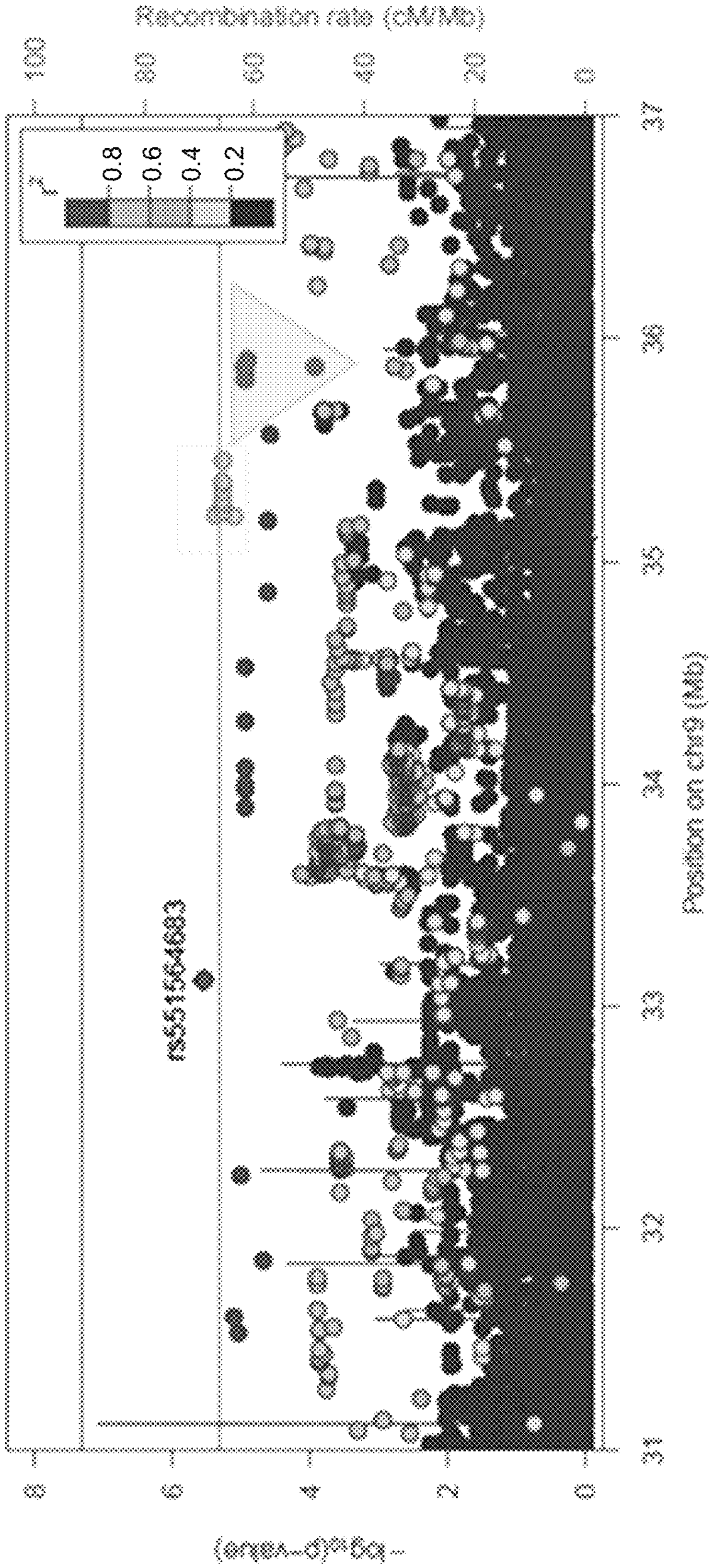
FIG. 2 shows the results of a representative TOPMed WGS association of variant B4GALT1 with LDL.

The TOPMed WGS data set provided 20 variants associated with LDL with p-values from 2.9E-06 to 2.5E-05, and highly, but not perfectly, correlated with the top hit rs551564683 (r2=0.83-0.94) (see, red in FIG. 2). Conditional analysis adjusting for rs551564683 completely abolished the association signal of the 20 variants and did not reveal any other signal in this region, strongly implicating a single causal variant.

By carefully investigating these 20 variants (see, red in FIG. 2) the variants were split into 2 groups: 7 red variants inside the shaded triangle and 13 unshaded red variants. The 7 red variants in the shaded triangle were almost fully correlated with each other and had r2 of 0.83 with the top hit rs551564683. These 7 variants were safely excluded as causal/functional based on three reasons: 1) they are relatively common outside the OOA (maf >1%), 2) they did not show any association with LDL in 3877 samples from Framingham Heart Study (FHS) within TOPMed, and 3) one of these 7 variants had an LDL association p-value of 6.3E-14 vs 3.3E-18 for the top hit rs551564683 in the WES data of 4,565 OOA subjects.

Another group of variants in the shaded rectangle in FIG. 2 also had association p-values only of about 10E-6 and were fully correlated with each other and had r2 of 0.68 with the top hit rs551564683. This group was also excluded as causal/functional because they are common outside the OOA (maf 4%), and did not show any association with LDL in 3877 samples from FHS within TOPMed.

The top hit rs551564683 and 13 unshaded red variants in FIG. 2, which extend over 4 Mb on the short arm of chromosome 9 from 31.5 Mb to 35.5 Mb, remained. As described above, these 13 variants were almost fully correlated with each other and had r2 of 0.91-0.94 with the top hit rs551564683. Among these variants, the top hit rs551564683 was the only coding variant, and it was classified as damaging or deleterious by 5 out of 9 algorithms that predict the effect of a variant on protein function. The top hit rs551564683 and these 13 variants had maf of 6% in the OOA while being almost not existent in the general population.

Haplotype Analysis:

Imperfect r2 between distinct loci is a result of recombination events. A detailed analysis of the primary 14-SNP haplotypes was undertaken. FIG. 3 shows 3 main haplotypes in this 4 Mb region. There are 115 subjects (1 homozygote, and 114 heterozygotes) with Haplotype A, which had identical genotypes at the 14 SNPs, provided no information as to which SNP might be causal. Six subjects had haplotype B, which contained heterozygote genotypes at rs551564683 plus 4 upstream SNPs, and 7 subjects had haplotype C, which contained heterozygote genotypes at rs551564683 plus 9 downstream SNPs. The recombinant haplotypes B and C clustered in related subjects, providing evidence they are not artifacts of genotyping error. Table 3 shows the p-values of rs551564683 after adding individuals with haplotypes B and C into a single group compared to individuals with haplotype A.

TABLE 3

Haplotype analysis results

| | A | B | C | B + C |
|---|---|---|---|---|
| Carriers | 115 | 7 | 6 | 13 |
| Total N | 1063 | 1070 | 1069 | 1076 |
| rs551564683 | 3.43E−05 | 1.40E−05 | 1.18E−05 | 4.82E−06 |

Adding each of haplotypes B and C individually improved the p-value and adding both of them improved the p-value even more. The improved p-values indicated that both haplotypes B and C carry the causal allele. The only SNP in common between B and C was rs551564683, which was considered to be the causal variant.

B4GALT1 Congenital Disorder of Glycosylation Supports Rs551564683 Functional Role:

A phenotype-wide association study (PheWAS) was performed to test the association of rs551564683 with all traits in the Amish database. The strongest association after LDL (p=3.3E-18) and total cholesterol (p=3.0E-18) was found with aspartate transaminase (AST) (p=3.0E-8) where the minor allele homozygotes had a two-fold increase in AST levels over wild-type homozygotes. Higher AST was previously reported in a Congenital Disorder of Glycosylation (CGD) case caused by a frame shift insertion in the B4GALT1 that resulted in a truncated dysfunctional protein. Moreover, a strong association was observed with fibrinogen levels (p=5.0E-4) where the minor homozygote level was about 20% lower than the wild-type, consistent with a blood clotting defect in the same CDG patient. Moreover, in a small experiment, a 50% increase (p=0.02) in creatine kinase serum levels was found in 13 minor allele homozygotes compared to 13 wild-type homozygotes. This consistency in the phenotype associated with the missense SNP and those caused by a truncating insertion in B4GALT1 further strengthen the evidence that B4GALT1 rs551564683 SNP is the causal/functional gene and variant in this region.

The association between lipid subfractions and rs551564683 was examined in a subset of 759 Amish individuals, and an association with lower levels of almost all subfractions with significant or non significant p-values was found, as shown in Table 4.

Coronary calcification score, aortic calcification score, and pericardial fat showed trend of association with lower levels, but with no significant p-values.

PheWAS also found rs551564683 to be associated with higher creatinine and lower eGFR, as well as higher hematocrit and lower basophils.

TABLE 4

Association between rs551564683 and lipid subfractions in 759 OOA individuals

| TRAIT | effect size | p-value |
|---|---|---|
| Chol | −1.66E+01 | 3.79E−04 |
| HDL | −4.16E+00 | 8.72E−03 |
| HDL2 | −1.51E+00 | 4.53E−02 |
| HDL2a | −9.26E−01 | 9.93E−02 |
| HDL2b | −1.94E−01 | 2.96E−01 |
| HDL2c | −2.64E−01 | 2.14E−01 |
| HDL3 | −2.64E+00 | 3.98E−03 |
| HDL3a | −1.51E+00 | 2.00E−02 |
| HDL3b | −1.68E−01 | 4.16E−01 |
| HDL3c | −5.93E−01 | 1.47E−02 |
| HDL3d | −4.44E−01 | 2.48E−02 |
| IDL | −7.31E−01 | 4.92E−01 |
| IDL1 | −1.19E−02 | 9.73E−01 |
| IDL2 | −7.65E−01 | 3.37E−01 |
| LDL | −1.23E+01 | 2.37E−03 |
| LDL1 | −2.22E+00 | 7.20E−02 |
| LDL2 | −5.64E+00 | 3.99E−02 |
| LDL3 | −3.81E+00 | 1.32E−01 |
| LDL4 | −3.96E−02 | 9.65E−01 |
| LDLReal | −1.12E+01 | 9.53E−04 |
| Lpa | −2.15E−01 | 6.34E−01 |
| Lpa1 | −2.91E−01 | 3.00E−01 |
| Lpa2 | 4.67E−02 | 8.27E−01 |
| Lpa3 | 2.31E−01 | 5.04E−01 |
| Lpa4 | −2.91E−02 | 9.19E−01 |
| Lpa5 | −2.48E−01 | 3.11E−01 |
| RennnantLipoprotien | −7.23E−01 | 5.97E−01 |
| TCHDLRatio | −3.29E−02 | 7.68E−01 |
| TotalNonHDL | −1.24E+01 | 3.97E−03 |
| TotalVLDL | −1.03E−01 | 8.70E−01 |
| Triglyceride | 2.19E+00 | 6.46E−01 |
| VLDL1Plus2 | −4.10E−02 | 8.86E−01 |
| VLDL3 | 6.15E−03 | 9.86E−01 |
| VLDL3a | 2.28E−02 | 8.97E−01 |
| VLDL3b | −6.57E−02 | 7.30E−01 |

Example 2: Sample Preparation and Sequencing

Genomic DNA sample concentrations were obtained from the Amish subjects, and then transferred to an in-house facility and stored at −80° C. (LiCONiC TubeStore) until sequence analysis. Sample quantity was determined by fluorescence (Life Technologies) and quality was assessed by running 100 ng of sample on a 2% pre-cast agarose gel (Life Technologies).

DNA samples were normalized and a sample of each was sheared to an average fragment length of 150 base pairs using focused acoustic energy (Covaris LE220). The sheared genomic DNA was prepared for exome capture with a custom reagent kit from Kapa Biosystems using a fully-automated approach developed in house. A unique 6 base pair barcode was added to each DNA fragment during library preparation to facilitate multiplexed exome capture and sequencing. Equal amounts of sample were pooled prior to exome capture on the xGen design available from IDT with some modifications. The multiplexed samples were sequenced using 75 bp paired-end sequencing on an Illumina v4 HiSeq 2500.

Raw sequence data generated on the Illumina Hiseq 2500 platform was uploaded to the high-performance computing resource in DNAnexus (DNAnexus Inc., Mountain View, Calif.), and automated workflows processed the raw .bcl files into annotated variant calls. Raw reads were assigned to appropriate samples for analysis based on sample specific barcodes using CASAVA software (Illumina Inc., San Diego, Calif.).

The sample specific reads were then aligned to the reference sequence using BWA-mem (Li and Durbin, Bioinformatics, 2009, 25, 1754-1760). This produced a binary alignment file (BAM) for each sample with all of a particular sample's reads and the genomic coordinates to which each read mapped. Once aligned, a sample's reads were evaluated to identify and flag duplicate reads with the Picard MarkDuplicates tool (picard.sourceforge.net), producing an alignment file with each duplicate read marked (duplicatesMarked.BAM).

The Genome Analysis Toolkit (GATK) (Van der Auwera, Cur. Protocols in Bioinformatics, 2013, 11, 11-33; McKenna, Genome Res., 2010, 20, 1297-1303) was then used to conduct local realignment of the aligned and duplicate-marked reads of each sample. The GATK HaplotypeCaller was then used to process the realigned, duplicate-marked reads and to identify all exonic positions at which the sample varies from the genome reference, including single nucleotide variations and INDELs, and the zygosity of the variant within a sample at any position where that particular sample differs from the reference.

Associated metrics, including read counts assigned to both reference and alternate allele, genotype quality representing the confidence of the genotype call, and the overall quality of the variant call at that position were output at every variant site. Variant Quality Score Recalibration (VQSR) from GATK was then employed to evaluate the overall quality score of a sample's variants using training datasets to assess and recalculate this score to increase specificity. Metric statistics were captured for each sample to evaluate capture performance, alignment performance, and variant calling. Following completion of cohort sequencing, a project-level VCF was generated by joint-genotyping using GATK to produce genotype and the associated metric information for all samples at any site where any sample in the cohort carries a variant from the reference genome. It was this project-level VCF that was used for down-stream statistical analyses. In addition to VQSR, variants were annotated with the Quality By Depth (QD) metric using GATK, and bi-allelic variants with QD >2.0, missingness rates <1%, and with Hardy-Weinberg equilibrium p-values $>1.0\times10^{-6}$ were retained for further analysis.

Prior to downstream sequence data analysis, samples with reported gender that was discordant with genetically determined gender, samples with high rates of heterozygosity, low sequence coverage (defined as 20× coverage of less than 75% of targeted bases), or unusually high degree of cryptic relatedness, and genetically identified sample duplicates were excluded.

Sequence variants were annotated using an annotation pipeline that uses ANNOVAR (Wang et al., Nuc. Acids Res., 2010, 38, e164) and other customized algorithms for annotation and analysis. Variants were classified according to their potential functional effects, and subsequently filtered by their observed frequencies in publicly available population control databases, and databases in order to filter out common polymorphisms and high frequency, likely benign variants. Algorithms for bioinformatic prediction of functional effects of variants along with conservation scores based on multiple species alignments were incorporated as part of the annotation process of variants and used to inform on the potential deleteriousness of identified candidate variants.

Example 3: B4GALT1 rs551564683 N3525 Frequency is Enriched in the Amish

Figure 4:
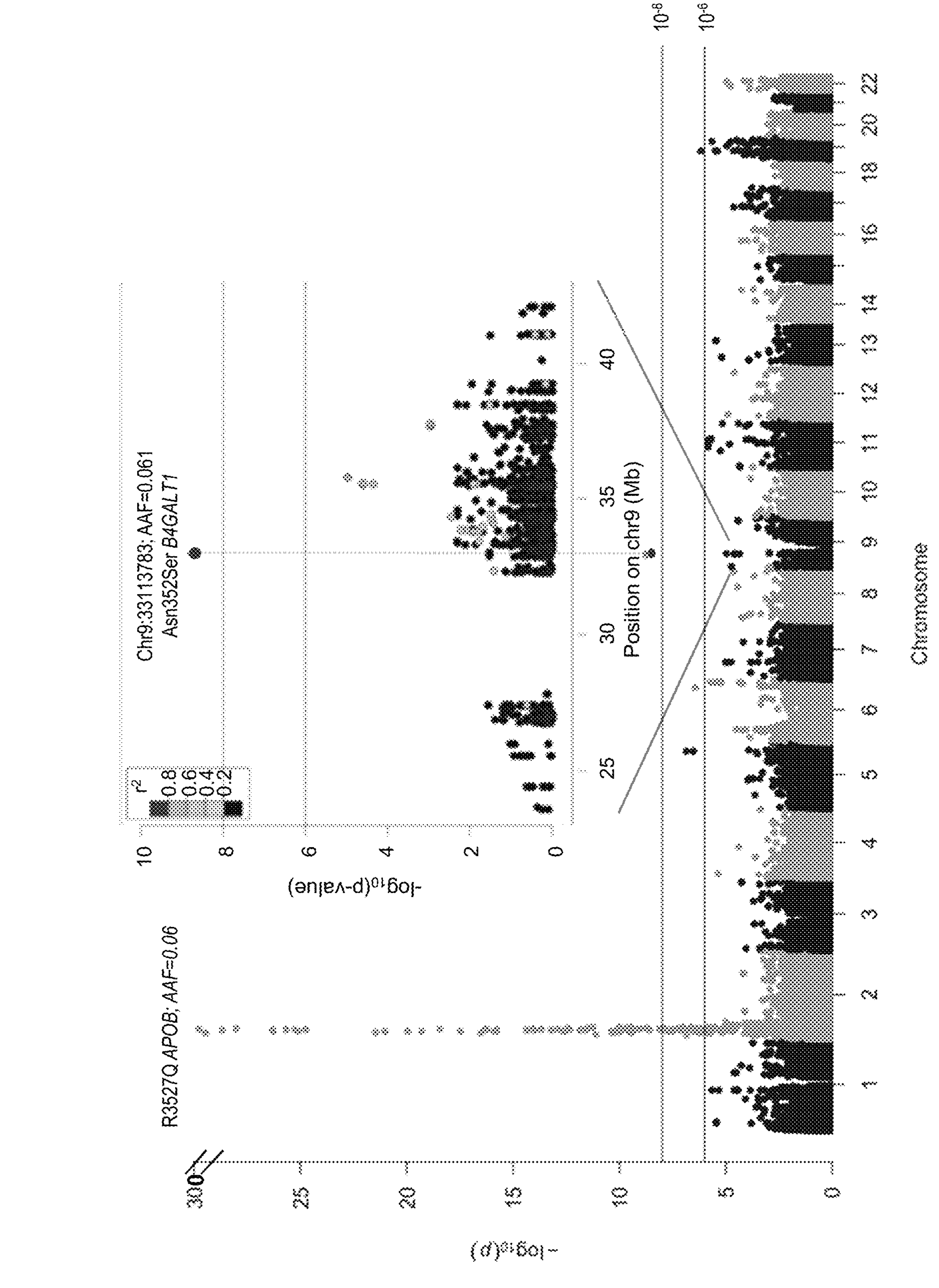
FIG. 4 shows the association of the variant B4GALT1 gene with LDL in the Amish identified by exome sequencing.

Through exome sequencing and association analysis in 4700 Amish subjects, rs551564683 on chromosome 9 was found to be highly associated with total cholesterol levels (p=1.3E-10)(see, FIG. 4). RS551564683 encodes a missense variant in which serine is changed to asparagine at position 352 in the B4GALT1 protein. The next most highly LDL-associated variant in the region was rs149557496 with a p-value of only $10^{-5}$ suggesting the N352S variant as being the most likely causative variant. Referring specifically to FIG. 4, in exome sequence data, the variant in highest LD with Asn352Ser B4GALT1 was rs149557496 in HRCT1, 2.8 Mb distant, $R^2$ 0.78, P-value with LDL in Amish of $10^{-5}$. Whole genome sequence data in the Amish (TOPMED) failed to identify a variant more highly associated with LDL-C in this region.

Figure 5A:
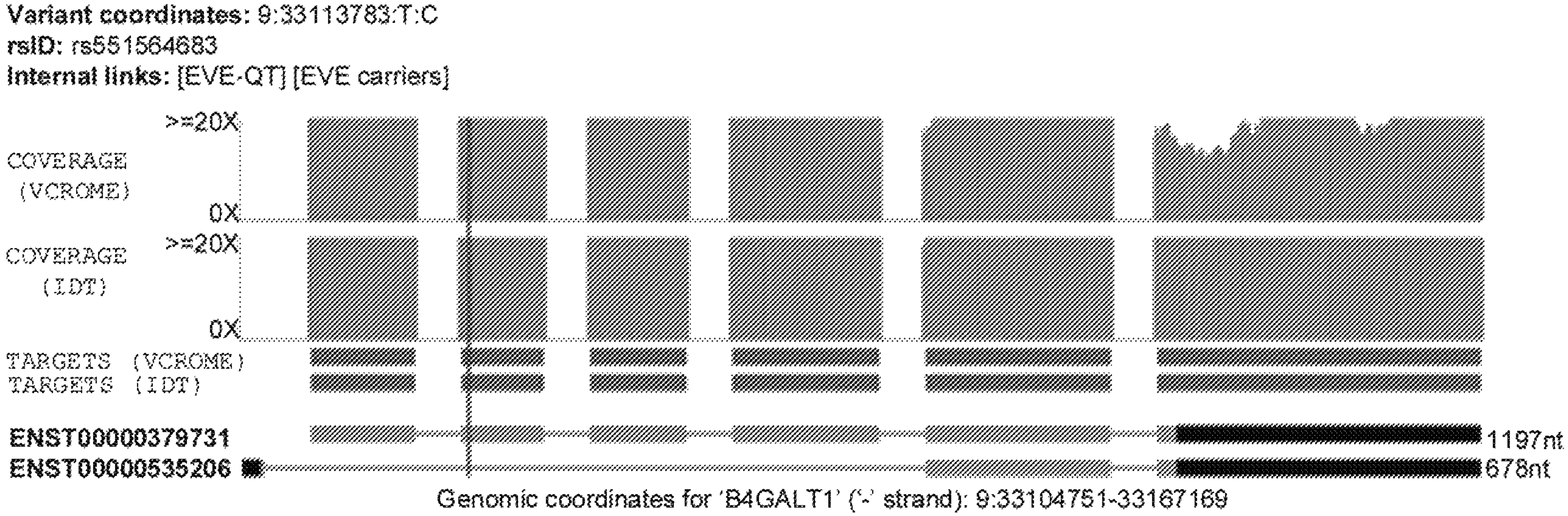

Further analysis revealed that the B4GALT1 N352S variant frequency was over one thousand-fold enriched in the Amish population (see, FIG. 5). The data showed that in the cohort of 4725 Amish, 548 heterozygous carriers for the rs551564683-containing allele were identified, and 13 carriers were homozygous for the allele (see, FIG. 5). In comparison, a collective data set of other population cohorts available to the investigators—totaling 125,401 individuals—was analyzed, and only 79 heterozygotes and 5 homozygotes were identified in this collective data set. The allele frequency in the Amish cohort was estimated to be about 0.06, compared to about 0.0025 in the collective date set (see, FIG. 5). It is believed that genetic drift may account for the higher frequency of this allele in the Amish.

Example 4: B4GALT1 N3525 Associates with Decreased Serum Lipids and Increased AST Association of the B4GALT1 N352S variation with various phenotypes, including serum lipids, coronary artery disease (CAD), and liver traits was assessed. The associations were carried out based on the Amish cohort, with individuals who were homozygous for the reference allele, who were heterozygous for the alternate allele, and who were homozygous for the alternate allele. The genotypic means for the lipid and liver traits and risk of CAD were determined, with the effect measures adjusted by removing the effects of subject age and age squared, subject sex, and study (since the phenotype data were collected from several studies over a period of years). In the case of pericardial fat, the genotypic means were further adjusted for BMI. The effect sizes of the variation on the measured phenotypes were measured at the 95% confidence interval. The traits and the results are presented in FIG. 6, FIG. 7, and FIG. 8.

Figure 7C:
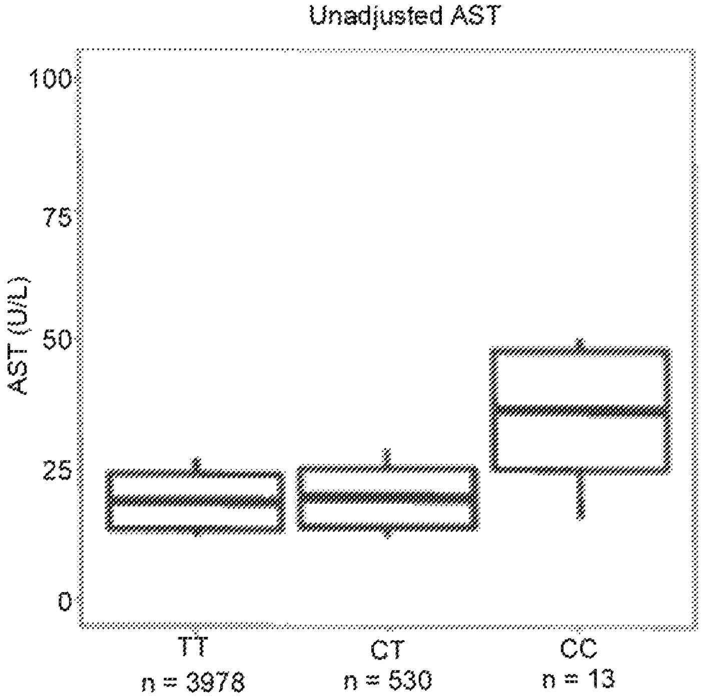

As shown in FIG. 6, the presence of the N352S variation generally correlated with decreased serum lipids, particularly for total cholesterol (p-value $1.3\times10^{-10}$) and LDL (p-value $1.8\times10^{-9}$) levels, which achieved strong statistical significance. Individuals heterozygous and homozygous for this alteration showed 17.3 mg/dL and 31.2 mg/dL reduction, respectively, for LDL levels. There was a trend between the variant and decreased coronary artery calcification. In addition, the presence of this variation correlated with increased aspartate aminotransferase (AST) levels (p-value $6.0\times10^{-8}$). The recessive model p-value for the AST levels was determined to be $9\times10^{-23}$. The variation did not appear to correlate with increased alanine aminotransferase (ALT) levels, alkaline phosphatase levels, or liver fat levels. The cholesterol, LDL, and AST levels are shown graphically in FIG. 7. In FIG. 7, the levels of cholesterol, LDL, and AST are shown for subjects who were homozygous (TT) for the reference allele, heterozygous (CT) for the alternate allele, and homozygous (CC) for the alternate allele. Values shown are unadjusted. The values were recalculated based on adjustments for subject age and age squared, sex, and study (tabulated in the bottom of the FIG. 7).

The effect of the N352S alteration on lipid subfractions was also assessed. These results are shown in FIG. 8. The associations were carried out based on the Amish cohort, with individuals who were homozygous for the reference allele, who were heterozygous for the alternate allele, and who were homozygous for the alternate allele. The results in FIG. 8 show that the B4GALT1 N352S alteration associates with decreases in all lipid subfractions tested.

Example 5: B4GALT1 N3525 Associates with Decreased Fibrinogen Levels

Association of the B4GALT1 N352S variation with fibrinogen levels was also assessed in a subset of samples. As for the serum lipids, CAD, and liver traits assessed in Example 4, the association with fibrinogen levels was carried out based on the Amish cohort, with individuals who were homozygous for the alternate allele, who were heterozygous for the reference allele, and who were homozygous for the alternate allele. The genotypic means for fibrinogen levels were determined in two subgroups of individuals—individuals not on a clopidogrel regimen (drug naïve) and individuals on a clopidogrel regimen (on-clopidogrel) and, as part of the analysis, the mean levels in each group were adjusted by removing the effects of subject age and age squared, subject sex, and study. The effect sizes of the variation on fibrinogen levels was measured at the 95% confidence interval. As shown in FIG. 9, the presence of the N352S variation was associated with decreased fibrinogen levels in each of the drug naïve (p-value $1.15\times10^{-3}$) and on-clopidogrel (p-value $2.74\times10^{-5}$) groups. The drug naïve subgroup showed a decrease of approximately 24 mg/dL of fibrinogen (see, FIG. 9). The on-clopidogrel subgroup showed a decrease of approximately 32.5 mg/dL of fibrinogen (see, FIG. 9).

Example 6: Additional B4GALT1 N3525 Associations

Within the Amish cohort, assessment of associations between the B4GALT1 N352S variation and other traits, including creatinine levels, estimated glomerular filtration rate (eGFR), basophil levels, and hematocrit percentage was also carried out. As shown in FIG. 9, the variant weakly associated with a small increase in creatinine levels, but did not significantly associate with eGFR, basophil levels, or the hematocrit percentage.

Example 7: b4galt1 Ortholog Knockdown in Zebrafish

In parallel to the evidence in cell-based assays, a zebrafish model was pursued to investigate the effect of B4GALT1 p.Asn352Ser on LDL.

Zebrafish Husbandry, Morpholino Injection and Validation

Wild-type (Tubingen) zebrafish stocks were used to generate embryos for morpholino injection. Adult fish were maintained and bred at 27-29° C. and embryos were raised at 28.5° C. All animals were housed and maintained in accordance with protocols approved by the University of Maryland Institutional Animal Care and Use Committee. Morpholino antisense oligonucleotides (MOs) were obtained (Gene Tools, Inc.) based on previously published MOs targeted against b4galt1 (Machingo et al., Dev. Biol., 2006, 297, 471-482). MOs were injected at the 1-2 cell stage and validated by qRT-PCR quantification of wild type b4galt1 transcript. Off-target toxicity was assessed by qRT-PCR quantification of the delta113 isoform of p53 (Robu et al., PLoS Genet., 2007, 3, e78). For mRNA rescue experiments, human B4GALT1 mRNA was transcribed from a pCS2$^+$ plasmid vector containing the open reading frame (ORF) of the wild-type or N352S variant of the gene. mRNA was mixed with MO at varying concentrations and co-injected into 1-2 cell stage embryos. For each injection experiment, a total of 200-400 embryos were injected and each experiment was repeated a minimum of three times.

LDL Quantification in Zebrafish

One hundred 5 days post fertilization (dpf) larvae were homogenized per experiment in 400 μl of ice-cold 10 μM butylated hydroxytoluene. The homogenate was filtered through a 0.45 μm Dura PVDF membrane filter (Millipore) in preparation for lipid extraction. Using the HDL and LDL/VLDL Cholesterol Assay Kit (Cell Biolabs, Inc.), the homogenate was processed as per manufacturer's protocol. After precipitation and dilution, samples were analyzed by fluorimetric analysis using a SpectraMax Gemini EM plate reader and SoftMax Pro microplate data acquisition and analysis software (Molecular Devices).

Figure 10:
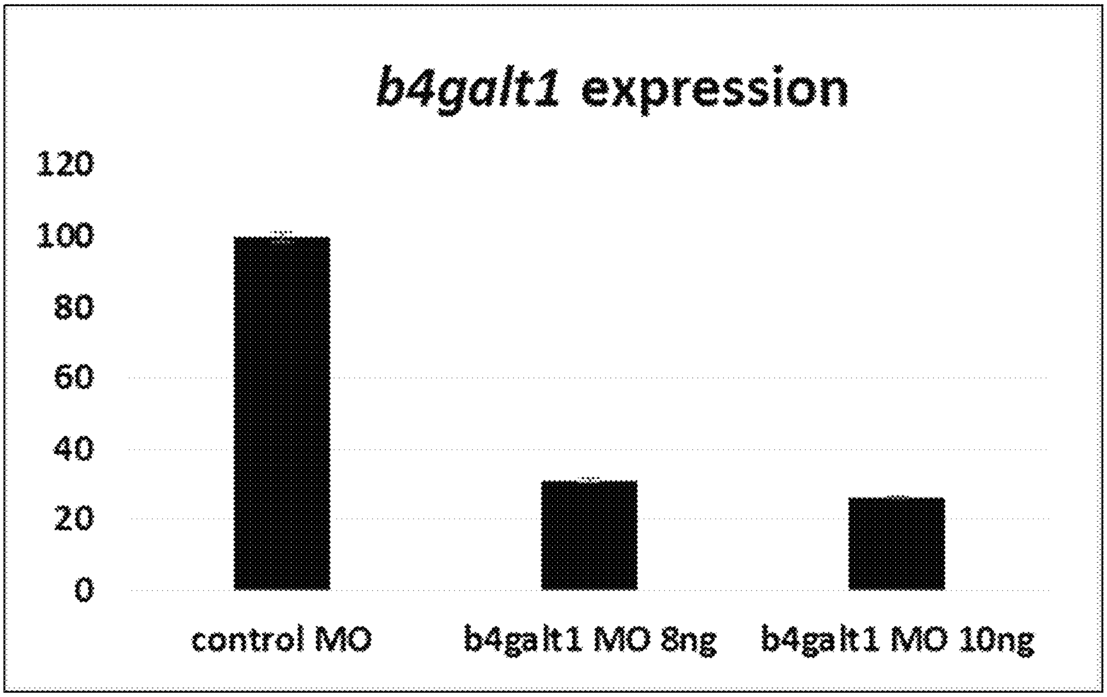
FIG. 10 shows reduced b4galt1 transcript in 5 days post fertilization of zebrafish larvae injected with antisense morpholino oligonucleotide at the indicated concentrations.
Figure 11:
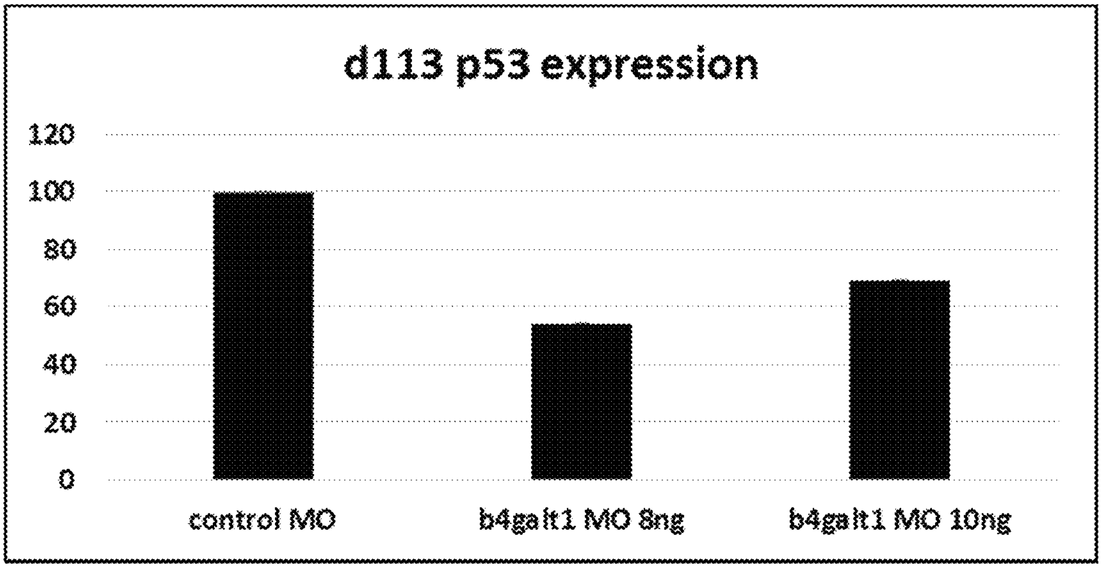
FIG. 11 shows diagnostic marker of antisense morpholino oligonucleotide off-target effects in 5 days post fertilization zebrafish larvae injected with antisense morpholino oligonucleotide at the indicated concentrations.
Figure 12:
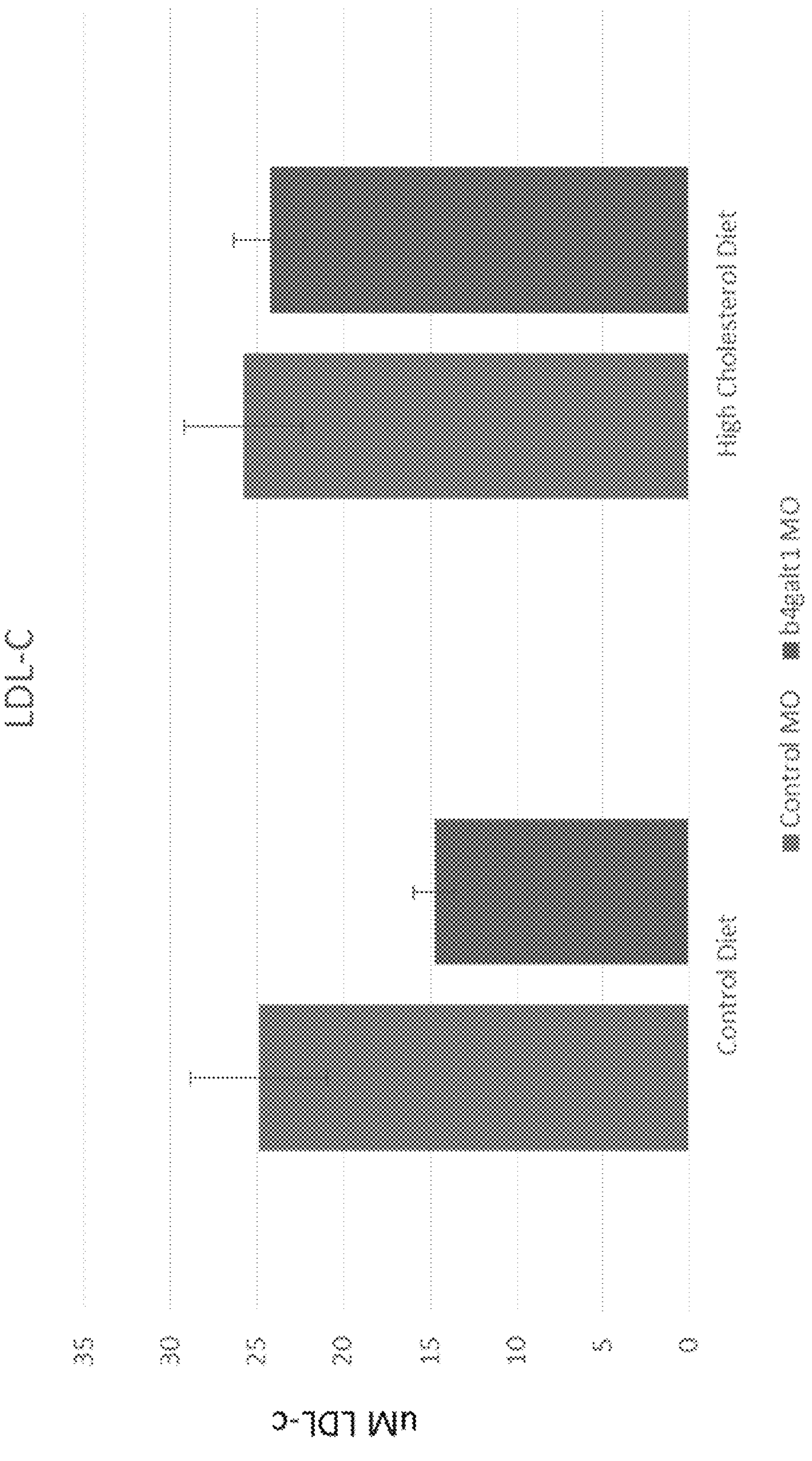
FIG. 12 shows average LDL concentration in homogenates of 100 5 days post fertilization zebrafish larvae per experiment.
Figure 13:
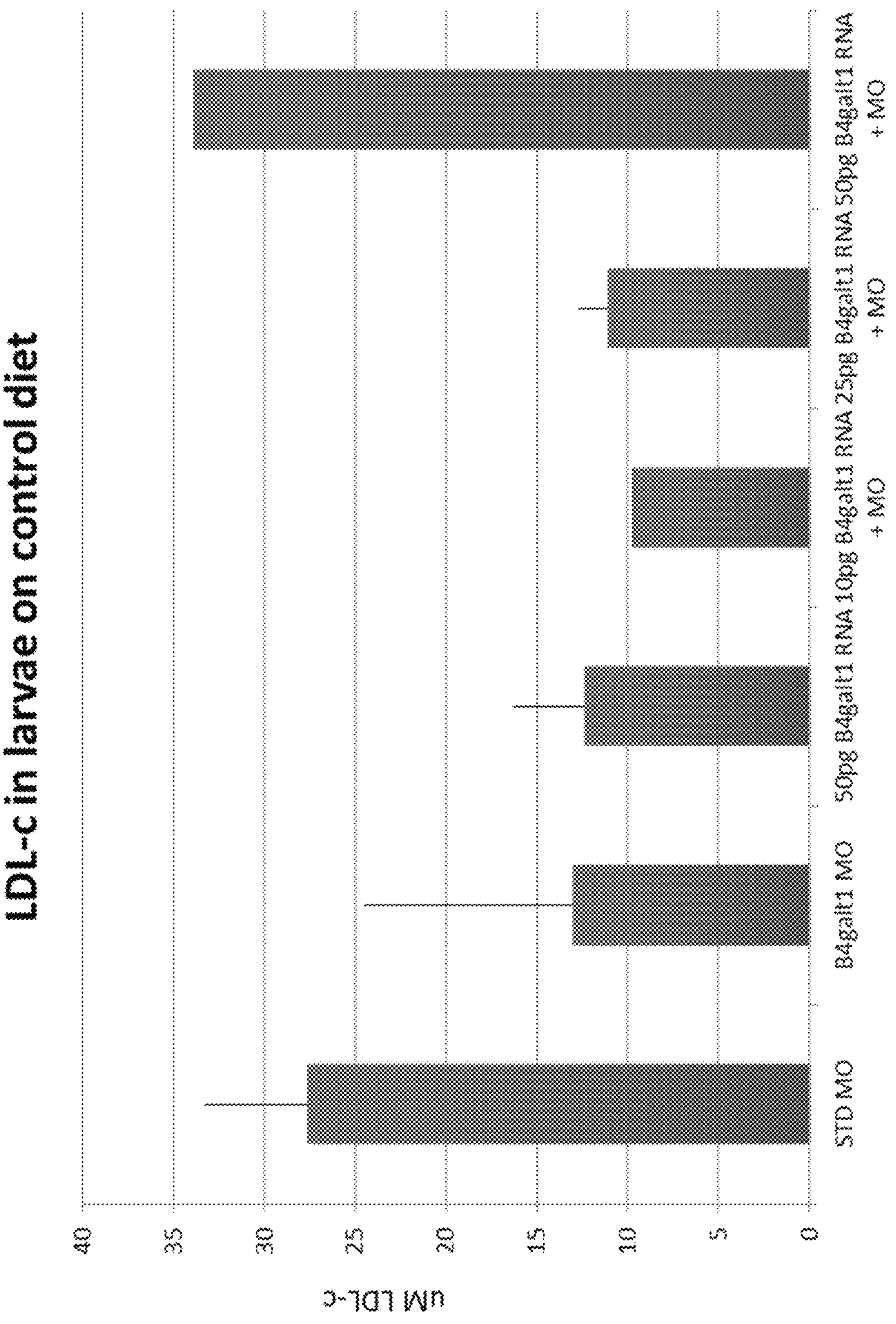
FIG. 13 shows a rescue of LDL-c phenotype by co-expression of 50 pg human B4GALT1 mRNA in the zebrafish.

A genomic knockout of the zebrafish ortholog (b4galt1) was generated using CRISPR/Cas9-mediated targeting of exon 2. Consistent with mouse reports of embryonic lethality in knockout animals, injected F0 animals were not viable to adulthood and consistently died at juvenile stages. To circumvent the lack of viability, a knockdown approach using a previously reported splice-blocking antisense morpholino oligonucleotide (MO) injected into embryos (Machingo et al., Dev. Biol., 2006, 297, 471-482) was employed. The efficacy of the MO was validated at two different concentrations by qRT-PCR (see, FIG. 10) and ruled out the possibility of off-target toxicity (see, FIG. 11). To quantify changes in LDL levels, 8 ng of MO was injected and injected embryos were cultured until 5 days post fertilization (dpf), at which stage larvae were assayed for total LDL as per previously published protocols (O'Hare et al., J. Lipid Res., 2014, 55, 2242-2253). A significant decrease in LDL in MO-injected larvae was observed compared to control larvae consistent with a role for b4galt1 in LDL homeostasis (see, FIG. 12). This result was confirmed using a second splice-blocking MO targeting exon 2 which produced a reduction in LDL concentration upon injection of 2 ng of MO (data not shown). To validate the specificity of these observations and to test the functionality of human B4GALT1 in zebrafish, full length capped mRNA encoding the human gene was generated by in vitro transcription from a pCS2$^+$ plasmid carrying the open reading frame (ORF) of the human gene. To assess the capacity of the wild type human mRNA to rescue the knockdown phenotype, it was co-injected with b4galt1 MO into embryos and LDL in unfed larvae was assessed. Three concentrations of mRNA (10 pg, 25 pg, and 50 pg) were co-injected with 8 ng of MO. Co-injection of 50 pg of B4GALT1 mRNA resulted in LDL levels that were statistically indistinguishable from those in larvae injected only with a control MO (p-value=0.14), suggesting that the human mRNA could rescue the effects of knockdown of the zebrafish gene (see, FIG. 12; larvae were treated with MO against b4galt1, MO co-injected with WT human B4GALT1 mRNA (WT rescue), or MO co-injected with B4GALT1 mRNA encoding the Asn352Ser mutation (N352S rescue)).

These data support the use of this system for functional interpretation of variants in human B4GALT1, and suggest that human wild type B4GALT1 mRNA is functional in zebrafish with respect to regulation of systemic LDL levels. The impact of p.Asn352Ser on B4GALT1 function was further investigated. Using site-directed mutagenesis (O'Hare et al., Hepatology, 2017, 65, 1526-1542), a T to C change was introduced in the coding sequence of the human B4GALT1 ORF construct to generate full length mRNA. Co-injection of the B4GALT1 p.352Ser mRNA with MO resulted in a reduced capacity for rescue of the LDL phenotype. The resulting LDL concentration was 15% lower than that resulting from co-injection of wild type mRNA with MO, a statistically significant effect (39.9 μM compared to 46.6 μM, p-value=0.02). This level of LDL was also statistically greater, however, than b4galt1 MO alone (p-value=0.01) (see, FIG. 12), suggesting a partial defect in function introduced by the missense variant.

Example 8: Targeted Genotyping

Figure 14:
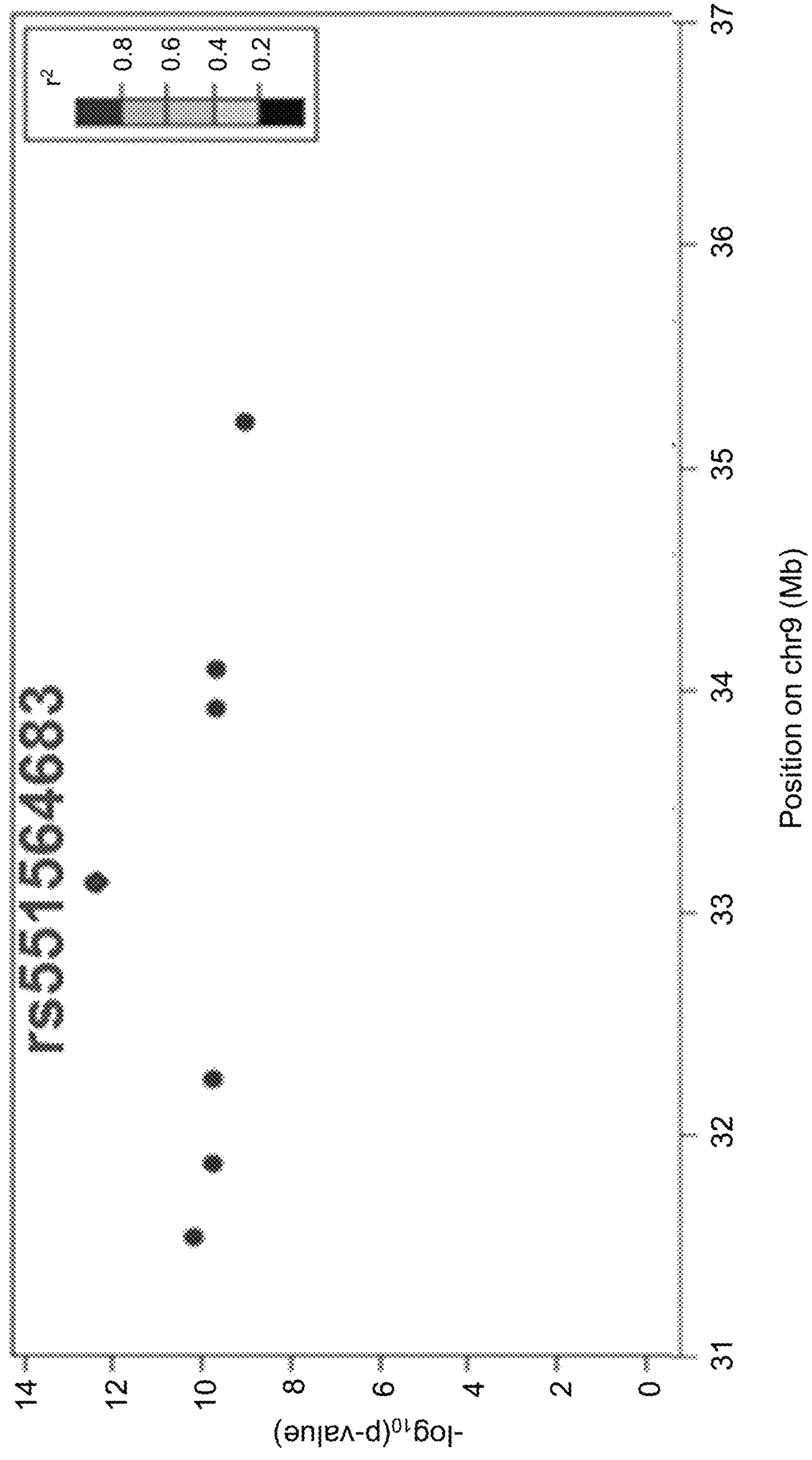
FIG. 14 shows the genetic association results between B4GALT1 N352S and LDL using targeted genotyping.

Targeted SNP genotyping using the QuantStudio system (Thermo Fisher Scientific) was performed for 3,236 OOA subjects. Based on the LD structure of the 14 SNPs, seven SNPs were selected for genotyping, and the association evidence for rs551564683 was 4.1E-13, while it was about E-10 for the other SNPs (FIG. 14), confirming that rs551564683 is the causal variant in this region.

Figure 15:
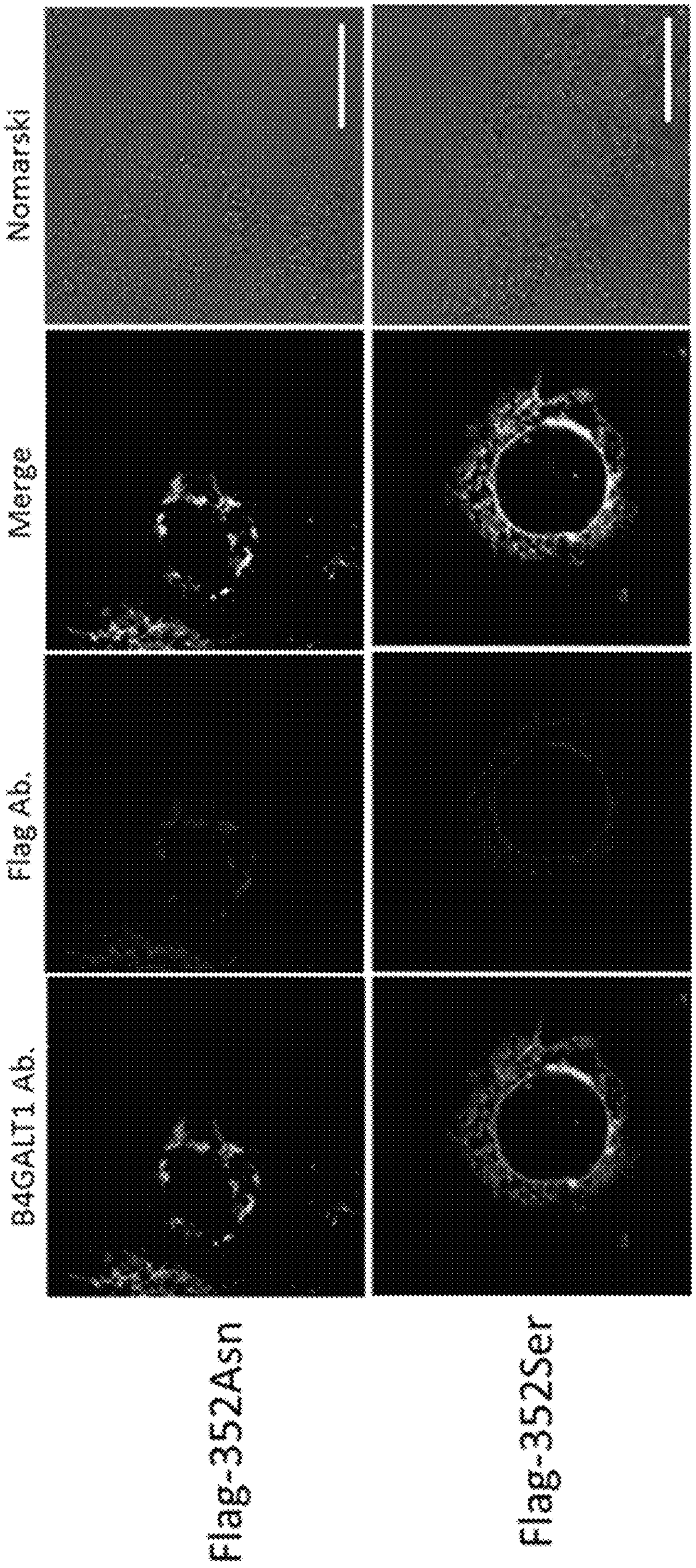
FIG. 15 shows confocal microscopy images of Flag-352Asn or Flag-352Ser subcellular localization.
Figure 16:
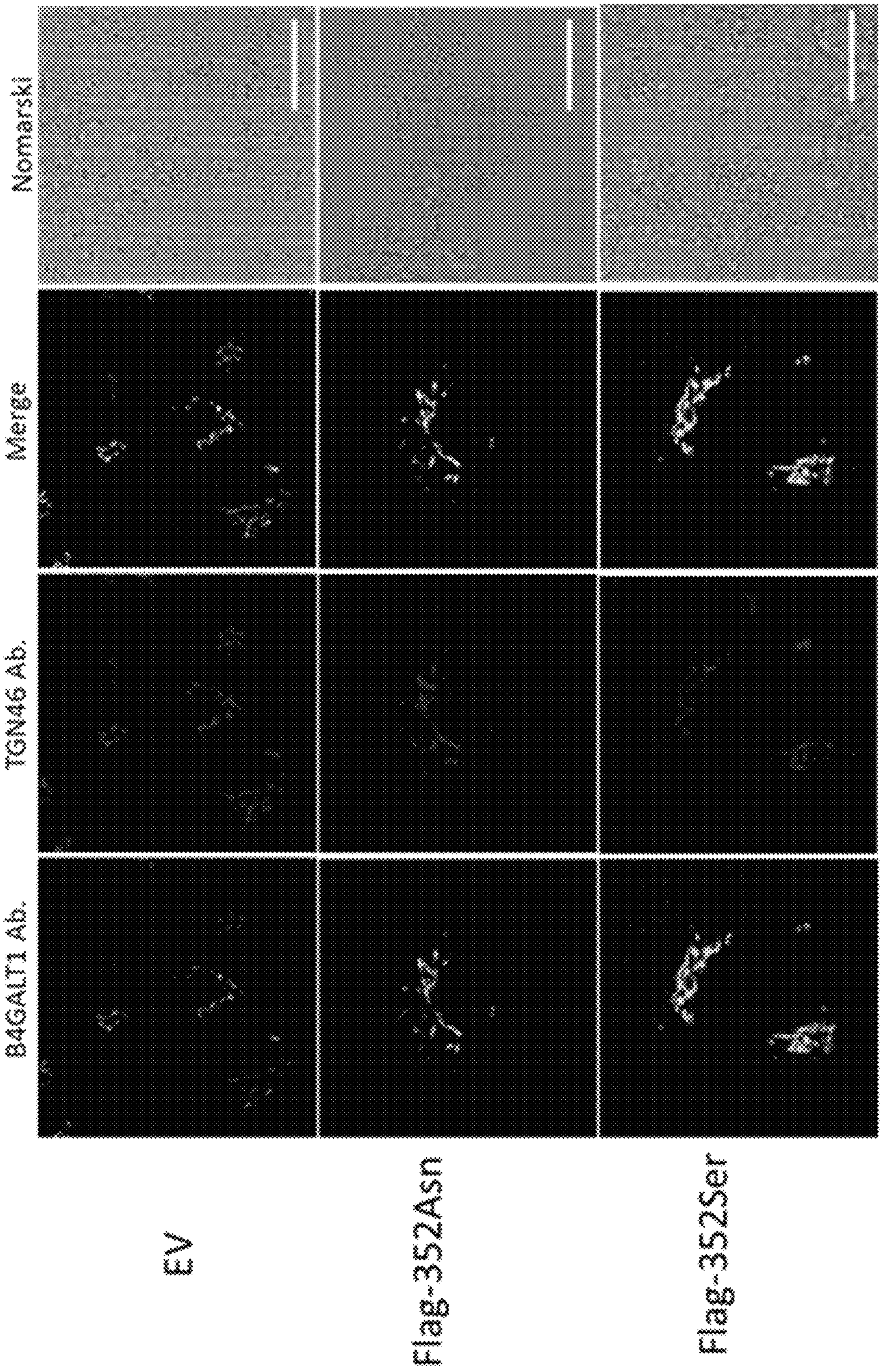
FIG. 16 shows confocal microscopy images of endogenous B4GALT1, Flag-352Asn, and Flag-352Se sub-cellular localization in relation with the trans Golgi Network marker TGN46.

Example 9: B4GALT1 N3525 Causes Reduced Enzymatic Activity in Absence of Change in Protein Stability or Cellular Localization Investigations of the properties of B4GALT1 were carried out in COS-7 and Huh7 cells overexpressing human epitope-tagged Flag-B4GALT1 352Asn or epitope-tagged Flag-B4GALT1 352Ser (FIGS. 15 and 16). Referring to FIG. 15, confocal microscopy images of Flag-352Asn or Flag-352Ser using B4GALT1 or Flag antibodies indicate an identical pattern of staining (scale bars=10 μm). Referring to FIG. 16, subcellular localization by indirect immunofluorescence of Huh7 cells showed a co-localization of endogenously expressed B4GALT1 and TGN56, a Golgi apparatus marker. A similar co-localization pattern was observed whether human epitope-tagged Flag-B4GALT1 352Asn or epitope-tagged Flag-B4GALT1 352Ser were over expressed (FIG. 16). Referring to FIG. 16, endogenous B4GALT1, Flag-352Asn, and Flag-352ser overexpressed in human hepatoma Huh7 cells co-localized with the Trans Golgi Network marker TGN46. Shown are confocal microscopy images of endogenous B4GALT1, Flag-352Asn, and Flag-352Se subcellular localization in relation with the trans Golgi Network marker TGN46, with scale bars=10 μm.

Figure 17:
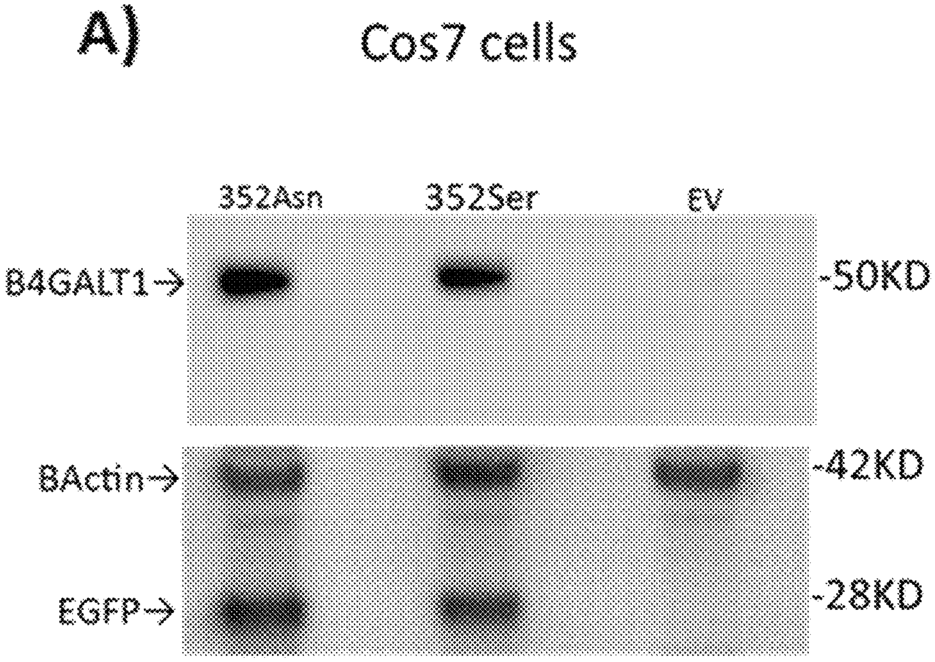
FIG. 17 (Panels A and B) shows the effect of 352Ser on steady-state levels of B4GALT1 protein; (Panel A) COS7 cells expressing either 352Asn or 352Ser Flag tag proteins fusion with free EGFP; and (Panel B) mRNA expression levels for B4GALT1 gene determined by RT-qPCR analysis.
Figure 17:
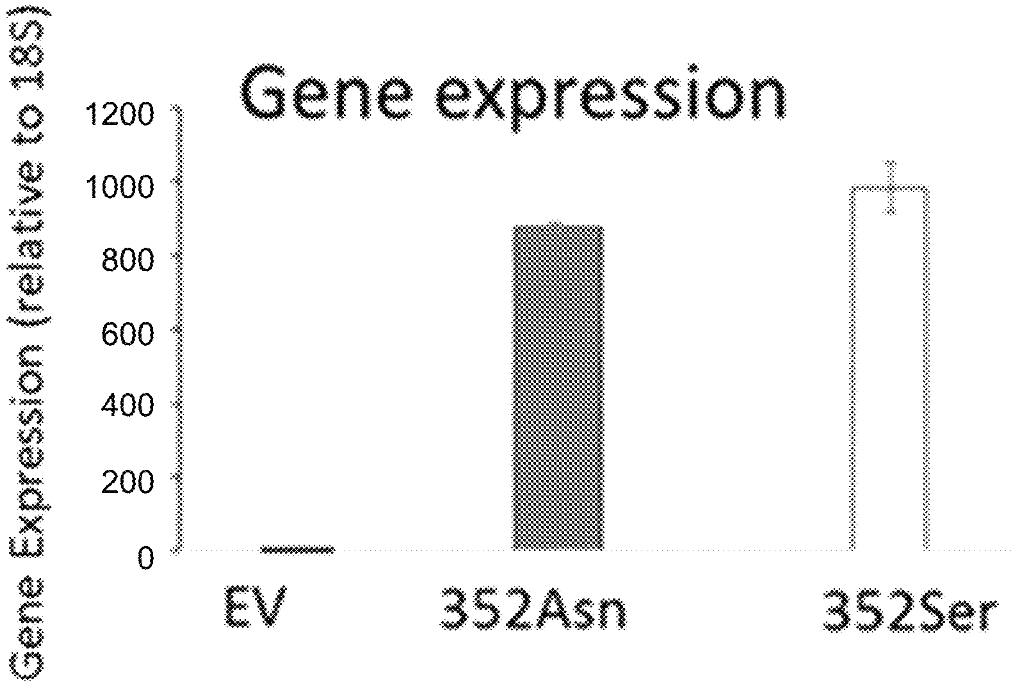

COS-7 cells were observed to have a low content of endogenous B4GALT1 (FIG. 17, Panel B), so this cell line was used to assess the effect of the missense mutation on protein stability and/or steady-state levels, and galactosyltransferase activity. The results showed that the missense mutation does not affect protein stability and/or steady-state levels (by Western blot) (FIG. 17). Referring to FIG. 17, the effect of 352Ser on protein stability and/or steady-state levels is shown. Panel A shows COS7 cells expressing either 352Asn or 352Ser Flag tag proteins fusion with free EGFP were expressed in COS7 cells. Cell lysates were analyzed by Western blot for B4GALT1, Bactin, and EGFP using commercial antibodies. One of four similar experiments is shown. Panel B shows mRNA expression levels for B4GALT1 gene determined by RT-qPCR analysis. Data represent means±S.E. of 4 experiments.

Figure 18:
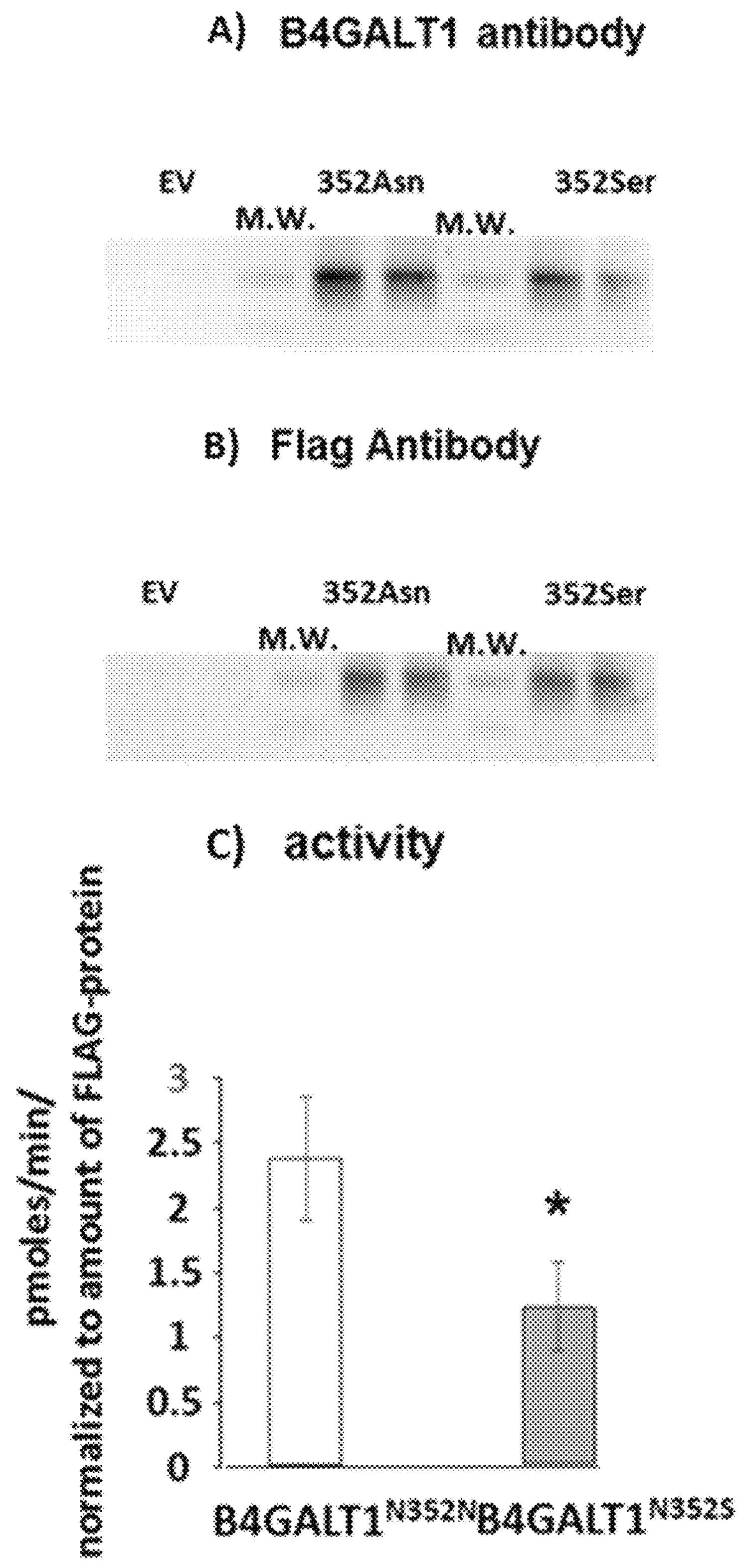
FIG. 18 (Panels A, B, and C) shows the effect of 352Ser mutation on activity; (Panels A and B) COS7 cells expressing either 352Asn or 352Ser Flag tag proteins fusion expressed in COS7 cells and analyzed by Western blot for B4GALT1 or Flag; (Panel C) B4GALT1 activity in the immunoprecipitates.

To determine the catalytic activity of 352Ser, lysates of nontransfected COS-7 cells and COS-7 cells transfected with the expression vector alone or containing the cDNA insert of wild-type or mutant B4GALT1 were analyzed for galactosyltransferase activity. When normalized relative to the expression of FLAG-tagged protein (immunoblotting experiment in FIG. 18, Panels A and B), the enzymatic activity of the 352Ser was approximately 50% decreased in comparison to 352Asn (FIG. 18, Panel C). Referring to FIG. 18, the effect of 352Ser mutation on activity is shown. Panels A and B show COS7 cells expressing either 352Asn or 352Ser Flag tag proteins fusion expressed in COS7 cells. Cell lysates were incubated with rabbit anti-Flag IgG or rabbit pre-immune control IgG. Immunoprecipitates were analyzed by Western blot for B4GALT1 or Flag using commercial antibodies. One of four similar experiments is shown. Panel C shows B4GALT1 activity in the immunoprecipitates measured with a commercial kit (R&D). Each data point represents the average of the calculated ratio of B4GALT1 specific activity with the amount of 352Asn or 352Ser protein recovered in the immnunoprecipitates. Signals from Western blots ECL were quantified by densitometry using ImageJ software. Data represent means±S.E. of 4 experiments (*, p<0.05, 352Asn vs 352Ser).

These experiments show that this missense mutation has no effect on the level of protein expression and its localization, but it leads to lower enzymatic activity.

Example 10: Carbohydrate Deficient Transferrin for Congenital Disorders of Glycosylation (CDG) Test The CDG test was performed using 0.1 ml serum samples from 24 subjects from the 3 genotype groups (8 minor homozygotes, 8 heterozygotes and 8 major homozygotes). Each minor homozygote was matched with a heterozygote and a major homozygote that are either sibs or closely related same sex individual based on the kinship coefficient. The age, and the carrier status were also matched for major lipid-altering gene alleles in $APOB^{R3527Q}$.

Water diluted samples were double washed using an immunoaffinity column. Glycosylation profiling of eluted proteins was performed using a mass spectrometer operated with 2 scan ranges specific for APOCIII and transferrin. Glycoform ratios of each protein were used to determine glycosylation deficiency. The CDG test was performed at the Mayo medical laboratory of the Mayo Clinic.

Figure 19:
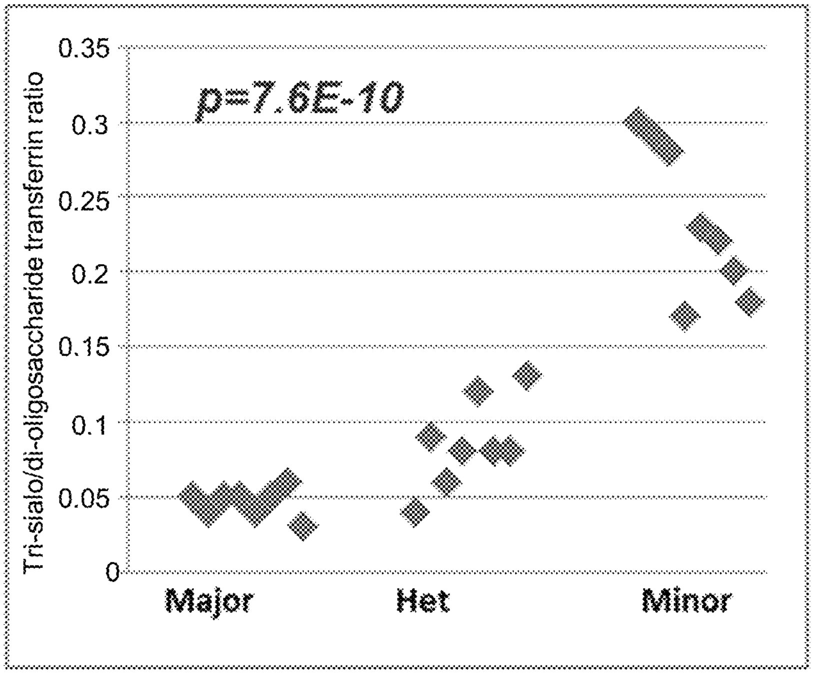
FIG. 19 shows the tri-sialo/di-oligo ratio by B4GALT1 N352S genotype group.

The results showed that all 24 samples had normal levels of the mono-oligosaccharide/di-oligosaccharide transferrin ratio, the a-oligosaccharide/di-oligosaccharide transferrin ratio, the ApoCIII-1/ApoCIII-2 ratio, and the ApoCIII-0/ApoCIII-2 ratio. However, while all wild type samples had normal levels of the tri-sialo/di-oligosaccharide transferrin ratio, the level in all heterozygotes were in the intermediate range and the level in all minor homozygotes was abnormal and significantly higher than matched wild type and heterzygotes (p=7.6 E-10) (FIG. 19). These results show that this missense mutation is associated with defective glycosylation as a result of the decreased enzymatic activity of B4GALT1.

Example 11: Global N-Linked Glycan Analysis of Plasma Glycoproteins

Figure 20A:
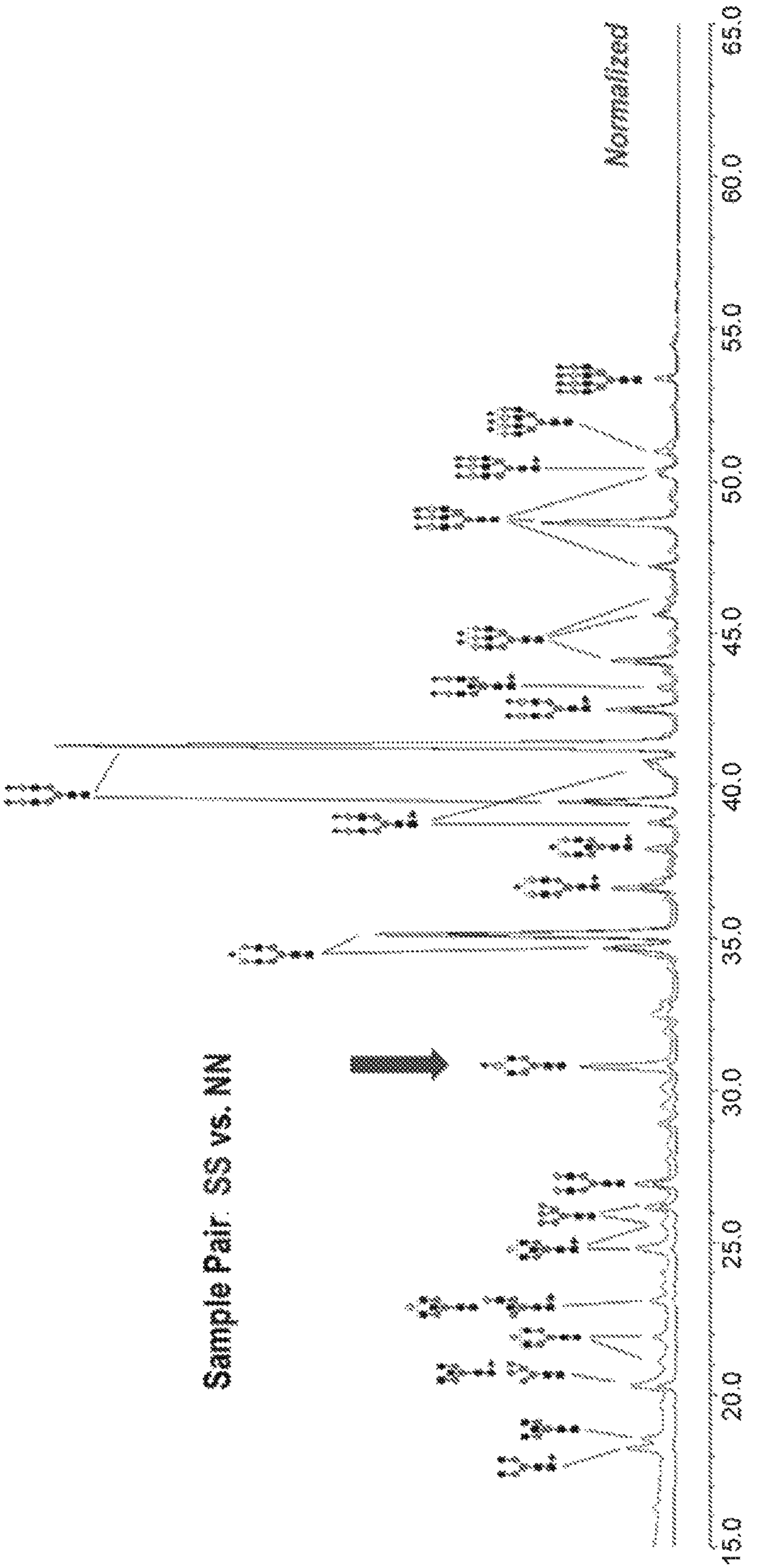
FIGS. 20A and 20B show a representative HILIC-FLR-MS spectrum of N-Glycan analysis of Glycoprotein from a matched pair of minor (SS) and major (NN) homozygotes of B4GALT1 N352S.
Figure 20B:
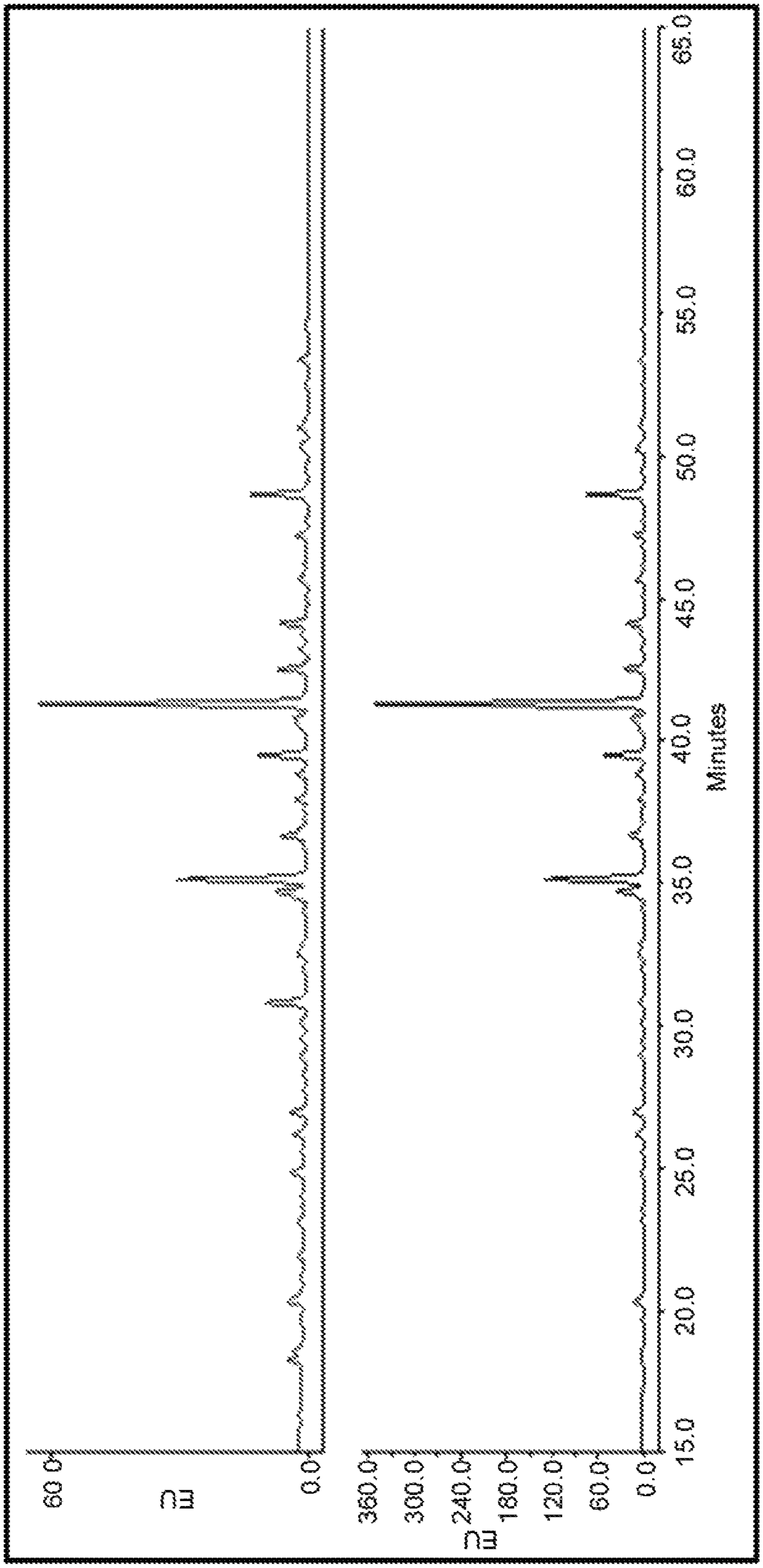

To determine if the desialylation and hypogalactsylation are affecting only transferrin or extending to other glycoproteins, global N-Glycan analysis was performed by the analytical chemistry group at Regneron. Lectin enriched glycoproteins were extracted from serum of 5 pairs of major and minor homozygotes in duplicate, and Global N-linked glycan separation was performed for labeled glycans using hydrophilic interaction chromatography and detected by fluorescence and analyzed by mass spectrometry (HILIC-FLR-MS) (FIG. 20 and Table 5). Referring to FIG. 20, a representative HILIC-FLR-MS spectrum of N-Glycan analysis of Glycoprotein from a matched pair of minor (SS) and major (NN) homozygotes of B4GALT1 N352S is shown. The results showed that the minor homozygotes have significantly higher levels of hypogalactosylated and less sialylated glycans including biantennary glycans with only one galactose and one sialic acid (p=3.1 E-5), asialylated biantennary glycans with one galactose (p=0.001), and truncated biantennary glycans missing both galactoses and sialic acids (p=0.005). On the other hand, the minor homozygotes have significantly lower levels (p=0.001) of biantennary glycans with two galactose and two sialic acid (Table 5). There was a significantly lower overall galactosylation (p=9.2 E-5) and sialylation (p=0.001) among minor homozygotes, while there was no difference in fucosylation level (p=0.5). Both CDT and global N-glycan analysis of serum show significantly increased levels of carbohydrate-deficient glycoproteins in minor homozygotes, indicating that B4GALT1N3525 is leading to defective protein glycosylation.

TABLE 5

Mean (± sd) of % peak area of significantly different glycans between minor and major homozygotes

| Glycan | Major Homozygote | Minor Homozygote | P value |
|---|---|---|---|
| G0F | 0.58 ± 0.34 | 1.84 ± 0.48 | 0.005 |
| G1 | 0.19 ± 0.12 | 0.91 ± 0.16 | 0.001 |
| G1S1 | 0.63 ± 0.16 | 4.7 ± 0.38 | 3.1E−5 |
| G2S2 | 39.3 ± 0.79 | 31.5 ± 1.8 | 0.001 |

The disclosure is not limited to the embodiments described and exemplified above, but is capable of variation and modification within the scope of the appended claims. The disclosure is also not to be limited in any manner by the use of any headers recited herein.

What is claimed is:

1. A method of lowering levels of low density lipoprotein cholesterol (LDL) and/or fibrinogen in a human subject who is not a carrier of a Beta-1,4-galactosyltransferase 1 (B4GALT1) variant having a serine at the position corresponding to position 352 in the B4GALT1 polypeptide having SEQ ID NO:8, comprising introducing into muscle tissue of the subject:

a) a Cas protein or a nucleic acid encoding the Cas protein;

b) a guide RNA or a nucleic acid encoding the guide RNA, wherein the guide RNA forms a complex with the Cas protein and hybridizes to a guide RNA recognition sequence within an endogenous B4GALT1 gene, wherein the guide RNA recognition sequence includes or is within about 1000 nucleotides to a position corresponding to positions 53575 to 53577 of SEQ ID NO: 1, comprises the start codon for the endogenous B4GALT1 gene, is within about 1,000 nucleotides of the start codon, or is selected from SEQ ID NOS: 9-12; and c) an expression vector comprising an exogenous donor sequence comprising a 5' homology arm that hybridizes to a target sequence 5' of the positions corresponding to positions 53575 to 53577 of SEQ ID NO:1, a 3' homology arm that hybridizes to a target sequence 3' of the positions corresponding to positions 53575 to 53577 of SEQ ID NO:1, and a nucleic acid insert comprising a nucleotide sequence encoding a serine at positions corresponding to positions 53575 to 53577 of SEQ ID NO:2 flanked by the 5' homology arm and the 3' homology arm, wherein the Cas protein cleaves the endogenous B4GALT1 gene in a cell in the subject and the exogenous donor sequence recombines with the endogenous B4GALT1 gene in the cell, wherein upon recombination of the exogenous donor sequence with the endogenous B4GALT1 gene, the serine is inserted at nucleotides corresponding to positions 53575 to 53577 of SEQ ID NO: 1.

2. The method according to claim 1, wherein the guide RNA recognition sequence is selected from SEQ ID NOS: 9-12.

3. The method according to claim 1, wherein the guide RNA recognition sequence includes the position corresponding to positions 53575 to 53577 of SEQ ID NO: 1.

4. The method according to claim 1, wherein the exogenous donor sequence is from about 50 nucleotides to about 1 kb in length.

5. The method according to claim 4, wherein the exogenous donor sequence is from about 80 nucleotides to about 200 nucleotides in length.

6. The method according to claim 1, wherein the exogenous donor sequence is a single-stranded oligodeoxynucleotide.

7. A method of lowering levels of low density lipoprotein cholesterol (LDL) and/or fibrinogen in a human subject who is not a carrier of a Beta-1,4-galactosyltransferase 1 (B4GALT1) variant having a serine at the position corresponding to position 352 in the B4GALT1 polypeptide having SEQ ID NO:8, comprising introducing into muscle tissue of the subject:

a) a Cas protein or a nucleic acid encoding the Cas protein;

b) a guide RNA or a nucleic acid encoding the guide RNA, wherein the guide RNA forms a complex with the Cas protein and hybridizes to a guide RNA recognition sequence within an endogenous B4GALT1 gene, wherein the guide RNA recognition sequence comprises the start codon for the endogenous B4GALT1 gene or is within about 1,000 nucleotides of the start codon or is selected from SEQ ID NOS: 9-12; and c) an expression vector comprising a recombinant B4GALT1 gene comprising a nucleotide sequence encoding a serine at positions corresponding to positions 53575 to 53577 of SEQ ID NO:2, wherein the Cas protein cleaves or alters expression of the endogenous B4GALT1 gene in a cell in the subject and the expression vector expresses the recombinant B4GALT1 gene in the cell in the subject.

8. The method according to claim 7, wherein the guide RNA recognition sequence is selected from SEQ ID NOS: 9-12.

9. The method according to claim 7, wherein the Cas protein is a nuclease-active Cas protein.

10. The method according to claim 7, wherein the Cas protein is a nuclease-inactive Cas protein fused to a transcriptional repressor domain.

11. The method according to claim 1, wherein the introduction of the Cas protein or the nucleic acid encoding the Cas protein and the guide RNA or the nucleic acid encoding the guide RNA into muscle tissue is carried out by vector delivery, particle-mediated delivery, exosome-mediated delivery, lipid-nanoparticle-mediated delivery, cell-penetrating-peptide-mediated delivery, or hydrodynamic delivery (HDD).

12. The method according to claim 11, wherein the Cas protein or the nucleic acid encoding the Cas protein and the guide RNA or the nucleic acid encoding the guide RNA are introduced into muscle tissue in a carrier comprising a poly (lactic acid) (PLA) microsphere, a poly (D,L-lactic-coglycolic-acid) (PLGA) microsphere, a liposome, a micelle, an inverse micelle, a lipid cochleate, or a lipid microtubule.

13. The method according to claim 7, wherein the introduction of the Cas protein or the nucleic acid encoding the Cas protein and the guide RNA or the nucleic acid encoding the guide RNA into muscle tissue is carried out by vector delivery, particle-mediated delivery, exosome-mediated delivery, lipid-nanoparticle-mediated delivery, cell-penetrating-peptide-mediated delivery, or hydrodynamic delivery (HDD).

14. The method according to claim 13, wherein the Cas protein or the nucleic acid encoding the Cas protein and the guide RNA or the nucleic acid encoding the guide RNA are introduced into muscle tissue in a carrier comprising a poly (lactic acid) (PLA) microsphere, a poly (D,L-lactic-coglycolic-acid) (PLGA) microsphere, a liposome, a micelle, an inverse micelle, a lipid cochleate, or a lipid microtubule.

* * * * *

SEQUENCE LISTING

<160> NUMBER OF SEQ ID NOS: 17

<210> SEQ ID NO 1
<211> LENGTH: 56718
<212> TYPE: DNA
<213> ORGANISM: Homo sapien
<220> FEATURE:
<223> OTHER INFORMATION: wild-type B4GALT1 genomic sequence

<400> SEQUENCE: 1
gcgcctcggg cggcttctcg ccgctcccag gtctggctgg ctggaggagt 50
ctcagctctc agccgctcgc ccgcccccgc tccgggccct cccctagtcg 100
ccgctgtggg gcagcgcctg gcgggcggcc cgcgggcggg tcgcctcccc 150
tcctgtagcc cacacccttc ttaaagcggc ggcgggaaga tgaggcttcg 200
ggagccgctc ctgagcggca gcgccgcgat gccaggcgcg tccctacagc 250
gggcctgccg cctgctcgtg gccgtctgcg ctctgcacct tggcgtcacc 300
ctcgtttact acctggctgg ccgcgacctg agccgcctgc cccaactggt 350
cggagtctcc acaccgctgc agggcggctc gaacagtgcc gccgccatcg 400
ggcagtcctc cggggagctc cggaccggag gggcccggcc gccgcctcct 450
ctaggcgcct cctcccagcc gcgcccgggt ggcgactcca gcccagtcgt 500
ggattctggc cctggccccg ctagcaactt gacctcggtc ccagtgcccc 550
acaccaccgc actgtcgctg cccgcctgcc ctgaggagtc cccgctgctt 600
ggtaaggact cgggtcggcg ccagtcggag gattgggacc cccccggatt 650
tccccgacag ggtcccccag acattccctc aggctggctc ttctacgaca 700
gccagcctcc ctcttctgga tcagagtttt aaatcccaga cagaggcttg 750
ggactggatg ggagagaagg tttgcgaggt gggtccctgg ggagtcctgt 800
tggaggcgtg gggccgggac cgcacaggga agtcccgagg cccctctagc 850
cccagaacca gagaaggcct tggagacttc cctgctgtgg cccgaggctc 900
aggaagtttt ggagtttggg tctgcttagg gcttcgagca gccttgcact 950
gagaactctg gtagggacct cgagtaatcc actccctttt ggggactgac 1000
gtgaggctcc cggtggggaa ggagactgac ctctcggttc acgtgtcttg 1050
ccatagagcc actctcctga gtgggttttt ctcctgatcg tttgggccaa 1100
gtgacttctc tctgaacctc atatttctct tctgggataa taaatggtca 1150
ccctttcaag ggttgtttt ggaagatatt gtgaacaatg gtaaataagg 1200
gcttaattaa tgagggtaag ccctcagtaa attgtcactg tgtgttcatt 1250
tcttcctctg tgtggatcgt gaccgagagc ccttccccct agcctcctcc 1300
tggtatgggt acccaaaacc taggtgagca gggatctctc ccaggggcag 1350
agagcttgtg tactctgggt gttagagggc taaaatataa ccagtcaaca 1400
ccacgttgcc catttctggt acttccggta gcagcctgag tctcaattat 1450
cttgcccaga tgatctgaac tctgacctct agcctgtttc agcataggca 1500
gagagcttga gtaggtgagt ttgcattcct catagcagct ggctgagcct 1550
agtctggact tctctttgac ctgtaaccta caggcccaca ggcccaaggc 1600

-continued aaccacaggt tgcttccagg gttaccacac aggtggtttc tcatttctaa 1650
tgctaggttt tagataattg ttgtaagtga ggggccctgg caggcaggat 1700
gacatcctgc caataggagt tttctgtcac tttcccacag agccctggct 1750
actacatact cttgctcaat ttcgccagta attgcgtcaa tgtgttcata 1800
tcaagtttgg gaagaacatc ttggaattgg tcagacgtga actgtggtaa 1850
taatgggggc ttgttttttt aagcagataa ttaaattcct ttgcatttga 1900
tgattattct gggaagcaga ctagtcccat aaaatgaaat ggactctgcc 1950
ttgctgctaa gtgtctgact tgagacatgc tatcgagttt ctcaaaatct 2000
cttccttgtg taaaatgtgg ttgtcgatga ttaccttaca ggggtttttt 2050
taagactaaa tgagatcgtg tacattaaat acaggcactc aggctgggca 2100
tggtggctca cgcctgtaat cctagcactt tgggaggctg aggggagtgg 2150
atcacttgag gttaggagtt tgagaccagc ctggccaata tggtgaaaca 2200
ccatcccatc tctacaaaaa tacaaaaaag ttagccaggg gtggtggcat 2250
cgcagctact caggaggccg aggcaggaga attgcttgaa cctgggaggc 2300
agaggttgca gtgagtcaag attgtgccag tacactccag cctgggcgac 2350
gaagcaagac tgtctaaaaa aaaaaaaaaa aaaaaaaata cgggcactca 2400
atacaccgta taataataat atagtaataa tatttgctta ggatctttaa 2450
aaagtttcat tttttcagac tcccacagaa atggctctgc acagcagagt 2500
gaagggggag agagactgag tctccaggcc agaaaaaggc caggtttttt 2550
gcttttgttt ttagttgttg cctggatatt gcacagaaag aaaaaaataat 2600 tagcaagtta aacaaaagta ccgcaaagtt gattacattg gtatttgagt 2650
atcacatctt ctctcagaag cgtaagagac aaggtcgtga ccatacctct 2700
gcttagtttt gttttgtaat ggtgttgcta gtgatcggct tgtcaccagt 2750
tactggtgtt tctaaatgga ctataattgg ctacttgaaa ggacttcctg 2800
agaaagaaca ttttggagga cgaggagaga gtgccttctc tattttggct 2850
gctttcatgt gacatgcaag agaccatgac gtttaggctg ctgctgaggc 2900
agccccagaa atgggggccg agaggtcttt tcttcatttt aatagggtct 2950
gtaggtttgg gtggttaggt acagttctca gaatggaggt tcctggctat 3000
gaggccttga gaaagctgaa agtctccttg ggagtgtgtg ggtgggggga 3050
gtcgagccca tctgttcatg ggcaggtgtc agccaaagcc cttgcgggtg 3100
gttttgaggt tggtgggaga aagcatccgt ggggtttaga gttgtggcct 3150
tttcactact tgcagttcct ttccccgact tggctttact ttctggtgtc 3200
caggggtctg ggccagatgc tgagattcct ctcagctgac aggtgtgggt 3250
tatgggcaaa cccttccctg gaggacataa ggcaccggat tggactgctg 3300
atgggttgct gttggagttg tcagggcctt ggaatagtct tcagatagac 3350
ttgggttagt gtgacctggg gcaggctgca ggtttggagc catagtaccc 3400
cccgccccca caccgggcac cctgctctgg gctaatgtga ggcttgcagg 3450
agtgagtgat gcagtgggaa ggggggcctt tcctgaggat tctacagctt 3500
tctccaggga atcctcccag gtagtttagg cctgcaggtg ctatgctatc 3550
cttctttcct aaccctgtct caggtcctca gcggggccat gcggcatcca 3600

```
cttataaccc tgcagcgagg ccctcttttc tggccacctg ggtgtttgcc        3650
tgctgagatg ggaggaacag tggccttggg cttcttcccc cgtcatgttt        3700
atctctgctc agattgggca gcagctcaat gggacttgac cagctgtggc        3750
actgccagtc tgaagatgag tagggtgatg gggggaggtg ggcagtacct        3800
gaagctgaac tggtgagaga ggcaggctgg cctgggggct cagctggggc        3850
ctgggatggt tggtacagtc ccctcagggg ggtaggggag tgagtgttag        3900
actgcttaag cctcagaggc cgctcttgcc cacctatgct ttgaggagat        3950
cctcttcatt tgttcaaagg gaagactctg atctagagat gggcacttgg        4000
accagcaaac agcagctaca ggtagccagg gcacccgagg agcacttgct        4050
catgagccgg tttccctggt ttttatgggg gctgttgctg agcgtctgcc        4100
agggtttgtg tcctagcact tgctggtctt tgctgggctc tcagctctca        4150
ggtgtttctc taccagcacg tttccccctc cctcatatgc acacatgtgg        4200
acacaagcag gctgcccagg acagagtgta ctttgaggct tgggaaagga        4250
ctctctctcg ccccttttggg gatgagcctt ggaacctcat caccttccgg       4300
cttggggtgg agcttcatcc tgggggttga agctttaggc tcagataact        4350
agtcttgtaa gccagttttg tcctgttgtt tttttcgtgg aaaataatgt        4400
attgacgtat acacagacat tctttgtcta acagtctgag attgagaaat        4450
accctccatg actatttggt ttgctttcat ggtgaaactt ggtcgctttc        4500
ttagacacag cctatggcaa taagagtgat ccctggctgc tgtaattcat        4550
tccagacttt gagcaaacac aaggcaccgc ctccacctgc agtggagcct        4600
ctgatgaacc aaatggaaac tccttgggga atggggagta agagccaaat        4650
gtgggattgg acttaaactg cagcttctta gaactgtagc attccacgat        4700
gggattgtct agtgctcttc ctggaggtta ctattcaata gttggctagt        4750
gcacaggttc aggggtgacc tgatatgccc tagcgtttca gaagatccct        4800
gcaaggtgtg tcttttggtc catctgaagg gtcttgtatg gtgatcttgt        4850
atggatatcc gtgacggcta aggcatctga taacttcatt ccttcagttc        4900
cagcagtgtt cctgtattat gctgggcact agagctacaa agaagaaaac        4950
aaagtgcctc ctcttcagga actcttaatt taggcagggg aggcataatt        5000
gaacagtgct gaggtcatct aggggaacca aagtgtgtat ttatcccctt        5050
ccctatcact cccctccctc cttcatttct tcctttcttc tttcagaaac        5100
tccaagttca tatcaaaatt ctccagccct ggttttattt ggttgtgtga        5150
aaattttcct ctaatttctg aagctatgca ttagttctgc tgagtaatct        5200
ttaacttgct gctttataat gattataatg agatatcact gggtattatg        5250
gtctttgggt agcagcaggg tagggatttc caggctggga ctaagctaat        5300
ttatgggttg ggaattatgg ggcagttaat agcaaggcag tccaagcttt        5350
ccacagattc caccctaggg accatccaga cttaaggaac agggccggca        5400
ggctcatccc ctttgcactc agctgggcta tgggtgtgtg tttgtgaaag        5450
aggtttattc agtagtcata cctgctgatt tccctgctat ctgtttaccc        5500
agtgcctcct gtaccttgtt tcttactctt tgttctctgc tcttactatg        5550
```

```
aagaagcaga gactggaatt ctgcttgaac ccacatctac ctggaaattc      5600
cagtttttct tgtccagtgg agcagcaatc cagttgtttt aggacaaatg      5650
gtctgccctt gaagcttaaa tcctttgagg gcctggcatg gtgacagttt      5700
tacatttggc tttggtatag actggtgtgg tccctgggca gtgaggtcac      5750
tgtaaggcca gccagccaga ccctggctcc taggggaatt aacaaggcat      5800
gggattagac tcacagggtc cctcctgtcc ctaaacttgg taggggttcc      5850
tgggagccag actgcgatta agattgtaga gacctgagac ctgagttgta      5900
ggggcctctg tgttgatctg ggccattgcc gggtgagctg aggcggtcac      5950
tagctcaagg agtgatctca ggatattgtt ctgtaagtca gagacctcca      6000
ggttggagag tggggcttgg gggtggggga cagggtttag tggggagctg      6050
gttctgggtg aatgtggcct aaagggattt gtccttagaa gacagagggg      6100
tgagtcacac actcagtgct tcaggttcca ctttgcggct tggcctcagc      6150
ccgccccttc cctgcacaaa tgaaggccag gggctatata attggctgtt      6200
gctgaattct ttggcagtga ttttaaagtc tggtctgggt gtgttatgta      6250
gctgcttctc tatccactcc ccacacccgc tgcttctcca gagcccctca      6300
caaagcccag gcagagagag agagagagag agagagaatg acttgcctca      6350
cagagatgtt ggggataggg ataggggtat gggtctttgc ttttgccttt      6400
tgagggggga taatctcttc cttcatttta aaagtaaaaa gtaatgcagg      6450
ctcattgaaa ataatttgaa aagttgaaag agatataaaa gcacacccaa      6500
attcctatca cccaaaagaa acataccggc atatttccta ctagtctttt      6550
tcatgtttaa gaatatagct gatatatttt tttttctttt tctttttgag      6600
acagggtttt tgctctgtca cccaggctgg agtgcagtga tcacggctca      6650
ctgcagcctc gacctctcgg gctaagcgat tctcccactt cagtctcccg      6700
agttgctggg accacaggtg cacaccgcca tgcctgacta atttttgtat      6750
tttttgtaga gatggggttt tgccatgttg cctaggctgg tctcgaactc      6800
cagagctcaa gtgattcacc tgccttggcc tcccaaagcg ctgggattat      6850
aggtgtcagt caccacaccc agtgttatag ctgttgtctt tatagatgaa      6900
cagatagatt gacatagatt catgtagata gcctggtgtt cagcattttt      6950
catttaagat tctgtcacag acttgaccct atacctttaa aaatcacaaa      7000
ggcagtatca tagtctgtca gctgaatatg ccataactta aaaaaatcat      7050
tcaactgttg ctgaacacac acatatacat atatagtttt tgtttttttct     7100
tagtgatgta gtgatgcttg tgcagaaagc tttatgtact ttttggatgg      7150
tttctgtagg agagctttct aaaaaaggaa aaaaagtgtt gaatgttttt      7200
tgagaagggc tagattttca agccagtctt acaaaaggat agactcattg      7250
gaaattccag atttgcttag tgctggcaga tgagtatcac ttattgctga      7300
acaatgtgtc tagaattctg attaaaaaag aaactaggtc caggaagtgc      7350
ctgggggcag gggcaaaggg ccaggctgca ggataggctc ttaggatctg      7400
gctgagcaga aatctgctgt gaacagaatc ggtgggggtg atgctttctc      7450
agtaacttct ccatttgttt ctttagcagc taagtccctg tgctggactt      7500
ctgtggacta ctgtggctct ggggctgtgg ttgtgggtga acaacagcta      7550
```

gctaaaccag tgctgttgac atcattgaga tgtgacgcac aggaaggtgg 7600
gagcaagctt gcaaatcaga ttctgaaaca tatagcacag ctctcccacc 7650
tccaggtggt cctgagatct agggaggagc catagtgaga aactttaggt 7700
ttctaggaat tctcttaggg agaagctctc ttagggagag gcagaacctg 7750
gttctcagtt ggggctgatt caggtgggtt agatcaataa agcctcaggc 7800
cagtgtgcca ggctattccc aaggagtata ctttgaagtt actcccttta 7850
gaatgtcctc agtggagata aattctctct gaggagcagt tttgtctgcc 7900
ggggtcattt ggcacaaagc ctggagtgct agggcgaggt tgcactgagg 7950
gaaggggcag gattatgtca gcagtgtgac ggatacagtg tgaggtcagg 8000
ctccttcctg ccccaccacg gggcctaga ggtcatgggg agggtccctg 8050
gcaggggatt caatcattgc ttggccccat gacagagtat attctaaaaa 8100
tgccttaagt ttttttcttt caaagtttct tcctgttttg cataatggcc 8150
ttttgccttt gacatcctga aaccgcagag ctgtcattgg tgttgcagga 8200
cactgccagc ttgaaaaaaa tcaacaacaa aaaaagaaac aggaaaggat 8250
gtggagttca gggtgcggcc tagggaagct ggtatttgcg ttatgggatt 8300
gtggggatgt ggtattaagg tgttgggtag cgcctgacat ttagaggagt 8350
actctgggca gagtccctgc ctgcccaaga ataggtagaa ttgagtcttc 8400
acaccaaagt caggagagac cccctccccc caggaagaga atgaacaggg 8450
actcatttcc tcattcagca aacttttatt ggtaactaca ctatatgaag 8500
tgtgagagat agacatgaac aagagaggcc cccactcttg ggcagtccct 8550
tagtagtagt agatagactc tggcaatatg gtgtggtcag agagaggaag 8600
cctgggtgct ttgagggtac tgaggaggtg cagggagcca aatgggtggt 8650
ctgggccagg gccagagtca gaatgaagga cctctcttcc agacgttgat 8700
tttagcatct ctgtctctca gtatgtttga acagtctccc ttattggaag 8750
ggcaggagtc tactgctaaa agtaacctgc gatttcctct acttgctgtc 8800
atgtggaaag aatactaaag ctgaaattcc aaaagttgca cacctttacc 8850
agcagggcag gagaggaaag gaaatggagg cagagtgagc tgaagatgat 8900
aaaagaaaga gaaggtggtg cagtttggac tgttatggac agaggaagtc 8950
tgagggtagc tggactgagg gatcaaaggg aggcagttga aagggaagag 9000
agctgcagag agggatttct tggtctgcag agggtaggag caagccttga 9050
aggctgctgg agtgaggatt ccgagccctg gtctttattc tttttctaat 9100
tcattacatc attttaggca agtcctaact cctttggtct ctgttgtctt 9150
tctgaaattt gagtgggctg ggcctgctgg tctttagcct ctgtctttct 9200
ctacctccta gattccagtt tggcgagtgg gggggaaaac ctggttgtat 9250
atgcaacgtg aaaggcctct ggaattcctt ttgaagctca ctacccatga 9300
ggcttctgct aaggatttca tcatgtctgt ctaagcagac ataaaaattt 9350
tagcaggtgg atgacccgta gaaatggcac aaggaatgtt tctttctgtc 9400
acactgtggt atttgattta agaaagttgt tatcctctct gtgcctcagt 9450
gttctcactt gtaaaatggc aataacagta tccacctcat agatgttatg 9500

```
aaatacaggt agtagccacg aaagggctta aaacagtgcc taacacagaa    9550
taagttgtga atatatgtta tttattattg gtagtataat gcttatttgt    9600
gaagattttg gcttttgctt tataggacct tttttttttt tagttgaaaa    9650
tacaatgtta ccatgttaaa tgttaaaaaa aattctactt accattgtaa    9700
cagaacatgc tcccacttct gtaacagagc ttgctattac ttttcaaatg    9750
catacatatt ccaatgcata tattccaatg cagttgtaga gtgaaactgt    9800
ttgcatgcag ccatttttat ccaacattat cttataaaat gttatgttgt    9850
ttatgattat cctaattatc ttttgttgct gtctagtatc cttatagata    9900
ttccattagc atacactatt ccaggtttca ctatcgtcga taatctagat    9950
atgaacattt ttgtagtgtg tagctctttg cttcagttga attactttcc   10000
tgggataaat tcctggggaa gaatttctag gccagaggat atggtcatct   10050
tgacaatact gattcacatt gctgcattgc tttccaagag gtttggaatc   10100
attcacaggt tctaaattgg aaaatcctgg cttttgaagt atgtggattc   10150
taagggcgat ttggatctag ctggagcctc acactgacac ttccagccag   10200
tgtgtgtgtg tgtgtgtgtg tgtgtgtgtg tgtgtgtagt tccctatgct   10250
ggacaccgtg tgtgtgtgtg tgtgtgtgtg tgtgtgtgtg tgtgtagttc   10300
cctatgctgg acaccatgtg gcctttctgg acattagggt tttcctgtga   10350
ttgcctcaga gcagttcctg ttgaattcac tctgtgtcca caaaaggagc   10400
cttactgtgg ctctttcaac acccacctac ctttgccaag ttggtttaca   10450
gaaagtaaga acattctttc cttcttcctt gatatgtggc gctaaaccta   10500
tagcatgggg caggctctgg ctttaaaaac ctgacttaaa aataatggtg   10550
ttgatcaaaa agtttgtgga tcagtttttg gaaacactgc atgtagccat   10600
ccatagaaac ttatattctg ttgggctagc ctgggcgcct gatcatttaa   10650
ctcatgtgga tgaacttcta tgtaatagcc ctggtgtatg ggatccagaa   10700
acagggccct aatgaagaaa ggcttttaaa ttatgttgga taaaaataag   10750
ttgttacaat agcccaaagt ctgcaaatat gaattgccag ttctgtcctt   10800
gtagtcatcc accatgtgcc tgcatctttt gtagactctt gtagattcag   10850
aagcccactg aattgcataa atgatggaat gattttagac ttagtgattt   10900
cagtgactaa aagtttacag atcctggccg ggcacagtgg ctcacacccg   10950
tattcccagc actttgggag gccgaggtgg gtggatcacc tgaggtcagg   11000
agtttgagac cagcctggcc aacatggtga aaccttgtct ctactaaaaa   11050
tacaaaaatt agccgggtgt ggtggcatgc acctgttgtc ccagctactt   11100
gggaggctga ggtgggagaa tggcttgaac ctgggaggcg gaggttgcag   11150
tgagcccaca tcaggccact gcactccagc ctgggtgaca gagtgagact   11200
ctgtctccac ctcccccgcc ccccgaaaaa aaaaaaagtt tacagatcca   11250
gcagatgggg catattcaat ttgtgacagc cactcccttc accttatagc   11300
tatgtcatat gtcttcttct cctttgactg cattctgcag cagtcagttg   11350
tgacttaata tggcactctg ggcccactga attaggtcag agctgctagt   11400
agtatattgt tcctagagac ctagggcaag attttcttac tacataaaat   11450
gagggagata atttcttacc tcaagatgtt ggtaagagga gtgaatgagg   11500
```

ttagttatat ggtaatatca gtactctgaa tgtcttttga tcaatgccta 11550
actcatcttc ttgggcacaa aaggcataca gtcagcaccc ttaggccaca 11600
tataaaattc ctccaaatgc aggttttcat ctgccttggg gcagagtcaa 11650
gagaaagaag aggaagaggc gtgaggctct gaccacaact tagggacaga 11700
atatagccca aagcgagtac cccaggccac aaggagaagg ccgctatctt 11750
gttgaatcca cagcactgga aacttggagt gtgtgttccc ctgtgtcagt 11800
tacactggaa ttttatggct gctcacattc ttcccttcag gtggacgttg 11850
ttcatcagta tcctgggcaa gaggccatca taaaccacag acagctgagt 11900
gattaggaag aggagctgaa gagggagcat tagatgtttg attgagtctt 11950
aggtgagaaa gtatatcatt aaaacaaaaa gatagatgta ggcgggctca 12000
gtcttgtgtg cctggtgtgt tggtagaaaa actaaagcac aagcctgtag 12050
ataacctgct ttattctacc tcggggctgg tgttggaatc caggatgcca 12100
gaccctaaag tccagctctc tttccaacct actgaataat ccgagagaaa 12150
tcatgttctc tctctgggcc tcagtttgcc catgtataaa atgagatgaa 12200
ggattggctg ggatgctctc cagagtctct tcctgcctgg agttctgacg 12250
tagccatgta ctcctgctca gcatcgctaa atggctttgt ggtaggacca 12300
ttgagtgctg cctccattag ggccagctat gtaatgctgg ggtggctgtc 12350
actgggccct aagagccagg attggtctta ctggagaaat ccacatccac 12400
ctaaacttaa gacccagggg tgtccaatct tttggcttcc ccaggccaca 12450
ctggaagaag aattgtcttg gaccgcatat aaaatacact aattatagcc 12500
gatgaggtta aaaaaaaaaa actcaatatt ttaagagagt tcatgaattt 12550
gtgttgagct gcattcaaag ccatcctggc cgcatgtggc ccatgggcca 12600
tcggttggac atgcttgctt tagacctccc agcaattcta gtctctaaac 12650
aggaaatcaa aagtcaagat gaatagataa gttggtcagt gtgaaaaagt 12700
aattggtggg agccactgta gatgcagggt tctaggctcc atcaacaacc 12750
acctacatca ctgaacgaaa gataatgctt gttcagcact tattacatgc 12800
caaccatggt aaaaatactt cagatgcatt gttttcatga actctcacag 12850
cagctctttt tcttgcctaa atgccccgtt agaacctcca gtacaatgtt 12900
aaatagatat gctaagagac aacatatgtg tcttgttagg gggaaaatat 12950
ccagtctttg actattaaga atggtgttag cagtgggttt ttcctaggtg 13000
ccctttatca ggttgaggaa gttcctttct attcctggtt tgttgagtat 13050
ttttatcatg aaaaggtgat gggttttgtc aaatgctttt ctgtgtctgt 13100
tgagatgatc atgttttttt gtcatttatt ctattgatat ggtatattat 13150
acattgattt ttcagatatt aatcttgcat acctgggata aatcccactt 13200
ggtcatggtg tataattctt tttatttgtt gctggattga gtttgctagt 13250
attttgttga tttgtattca taacagatag tggtctgtag tctttccctc 13300
cctccctccc tccctccctc cctcccttcc ttccttcctc tctctctctc 13350
tctctcccct cccctccctt cttttcccct cctctcccct ccccttccct 13400
ttcttctctt tcatagttgt ttaccactgt cagaaaaggt ctgttcgttt 13450
tctttcgtcg tgagatcttt gtttggtttt ggtatcaggg taatactgcc 13500
tcaaaaaatg agtagggaag tgttccttcc tcttctgtat tttgagagag 13550
tttgtggtcg gtttttatta attcttcttt aaatatctgg tagcgttcac 13600
cagtaaagcc atctgggcct gatgttttct ttgtggaaaa ctttttgatt 13650
cctaattcag tttctggtta taggtctatt cagaccttct atttttttctt 13700 aagtcagttt tgatagtttg tgtcttccaa ggagtttgct tcatctaagt 13750
catctaattt gttggcatac atttcatagt gattccttat gatccttttt 13800
atttccgtta aagttggtgt agggatagtc cctctttcat tactgattat 13850
aataatttga attttctttt tttcttagtc ttgccaaaag cttgtcattt 13900
ttattgatct tttcagagga ccaactttga gttcattatt tgttctcttt 13950
gttcttattt ttctgcttca ttaacttctc taatctttat tctttcattc 14000
tgcttgcttt tggttaagtt tgctttttct ggtgtcttaa ggtagaaggt 14050
taggttactg atttgagatt taaagatcat gctctttaaa cgttttgata 14100
gatactgtca gtttgccctc tggctttttc tcattaacag tgtataggag 14150
tgcttattcc tcacactcat accagccctg ggtgttacta acctttatat 14200
atttgccagt atcatattca gacatagtat cttgttttaa tatgtttctc 14250
tgattactga tgaagttaag caaattttca cgtgtttatt ggccatctgt 14300
ctttcttttt tcatcctttc tttcaagatg ggagtctttg ccatgttgcc 14350
caggctggac tcgaactcct gggctcaaat gatcttcctg cctcagcctc 14400
ctgagtagct gggactatag gcgtgagcca ccatggctgg cttgcccatt 14450
tgtatttctt atgtgagtat tttttctttt tttttgaagt ggagtctcac 14500
tccatccccc agagtggagt gcagttgtcc gatcttggct cactgcaacc 14550
accgcctccc aggttcaagt gattctcaca ccttagcctc ccaagtatct 14600
gggactatag gtgtgtgcca ccacacctgg ctaatatttg tatttttagc 14650
agagatgggg tttcaccatg ttggccaggc tggtttcaaa ctggcctcaa 14700
gtgattcacc tgcctcggcc tcccaaagtg ctgggattac aggtgtgagc 14750
cactgtgccc agctgacttt ttttttcttt tttttaaccc tttttttttt 14800
ttaccctttt tttggcccat ttttttttac cctttttctt ttaacccatt 14850
tttctattag ttttaaaaat atgtttgcag gagcttttta tattgtggat 14900
ttttcttgtt tattacatat catttgtaaa tatggtctct ccatctgtca 14950
ctcttcttta tctctggttt ctttagctat gtagaagttg ttatgttatg 15000
ttatgttatg ttatgttatg ttatgttatg ttatgttatg ttatgttatt 15050
ttttggagag ggagtcttgc tctgtcgccc aggctggagt gcagtggtga 15100
aatctcggct cactgcaacc tctgcctcct gggttcaagc gattctcctg 15150
cctcagcttc ccgagaagct gtgattacag gcacccgcca ccacacccag 15200
ctaatttttg tgttttagta gagacggggt ttcactatgt aggtcaagct 15250
gatctcaaac tcctgatctc aaatgatcct cccaaagtgc tggggttaca 15300
ggcgtgagcc actgcactcg gccagaagtt ttgaattttt atgtgtttaa 15350
atctatgttt tcctttatga cttcaggttg ctttcatact taagcaggtc 15400
ttcaccatcc caaaatgata aaatttttct cctgagtttt cttctaagtt 15450

```
ggttctttag aagccaccaa cttggcttcg acagcaaaag atgaacagaa      15500
tttctgttca actctcatgc tgcaagaagc tttatgtaat actccaggga      15550
ccctttaagg tcccagagtt ttcctccaaa tctatcagtg attctagtgg      15600
ctaagagtag aaatgtgaaa atttagccat gtgtgctgat agagctgtag      15650
taatttgtaa gctctgaagt tctaaggagt caggggagaa gggaaagtaa      15700
catttattga acatctatta gctcaataag aacatgcgat aagtatgtat      15750
atgtattatt tcacttacat ctgaaaggaa ggcataatta tccccactcc      15800
ttagagaagg aaattggagc tggctacatt taaagtagtc ctgacaccag      15850
agagatattg ccaggagtac ttggctggct gagtgcccag atggcccata      15900
ggagtagtgg gccctccaca gtccaaggtc tggttctagg tggagagaga      15950
aggatgtgct cgtagtcagc accgcagctc cagaaaatct gctggggctc      16000
caaaactgat tagaggggca gctgactcag taataaaact cccaggagac      16050
ttacttacat actggaatgc aaagttgcag ctttactggg aagattagaa      16100
ctgttattga gtagcttaga aatctctggc tgaattcact gcaagggaag      16150
ccgcaggata agctaactgc tggtgagtca gcagtcagag cagggaagtg      16200
aatttaacat tagatgggtc agtctctcgt ggctgatgaa ttcatcccca      16250
caatactgta cacctgcctt agggaccttt gtctggacta ggggttgggg      16300
tccccctcct ttgtacagcc ctggaaggac acatccagct ccatccgcca      16350
tctctccctt acttatttcc ttccttcctt ccttctttcc atccagccat      16400
caagcttcct ttcatggcca ataatcatca ttggggtcta ctcatggact      16450
ctcttgcctc atgtatttgt tttattttgt cctcattccc acttctattt      16500
cccaggtata tcacaggcaa ctattctaac gtatttatag tttgtgtatc      16550
tgtttttgct cttgccaaaa tggaagccac tgctttatac atagatgtat      16600
tcttaacttt aaaaaaaatt tttttagatt aacctacaat aaaattggct      16650
ttttggcata tagtctataa attttaacac atacatattt ttgtgtatct      16700
accaccacaa tcaggataca gaacagttcc atcaccccaa aaaaatccct      16750
cttgtagtca cattctcctc ccacccttaa tcccaggcaa ccactgatct      16800
attcttcatt actattgttt tgtctttttg aggatgtcac ataaatggag      16850
tcacacagta tatatacatt tttttaaaca tatgtaaatg gcattttata      16900
gctcattttg attatatgtt tttcatccag ttctgttttt tttttttatt      16950
tttaaaaagt ttgacataac ttcagactta cagaaaagtt gttagactaa      17000
tacaaagaat tcctggatat cctttggagt ccctaaatgt taacatttta      17050
ctatatttac tttttccttc tctctctctc tctctctcgc tctgtgtgtg      17100
tgtgtgtgtg tgtgtgtgtg tgtgtatcta cctgtagata gatagatatt      17150
aatataattt tagatagatg tatctagatc tctctctctc atatatatgt      17200
gtgtgtgtat atatctatat ctatatctat atatatctcc ttttaccctt      17250
aaatattcag tgtatatttc ctaacaacaa ggtgatttaa aaatatatat      17300
ataaacatag tataattaac aatcaggaca tcaacattga aacatttctg      17350
ctatgtcatc tacaggcctt aggaagactt tgtcaggtgc cccaataata      17400
```

gccttgatgg tagaagaaaa ccatgtgttg tattcagttg tcatgtctct 17450
tagtgtcttg taatctgaaa taattcccaa gccctttgga tttcatgaca 17500
gtgacattgt tgaagagtac aggccagtta ttttgtagaa ggtctctcag 17550
tttaggtctg tctgatgttt cctcctgatc agattcaggt tattcacttt 17600
tgacaggaat accactgaaa tgatgctgag ttcttctcag tgtaacgaga 17650
tctagagaca cacactgtca gtttgttcct tattggcagt gtgaaccttg 17700
aggatttcat tgtagtggca tttggcatta ctccattata gttactattt 17750
taccatttta aattaaaact atctggccgg gcgtagtagc tcatgtctgt 17800
aatcccagca ctttaggagg ctgaggcggg caaattgctt gaggtcagaa 17850
gtttgaaacc atcctagcca acataacatg gtgaaacgcc atctctataa 17900
aaaatacaaa aaattagcct ggcgtggtgg cgcatttgta gttccagcta 17950
ctcaggaggc tgaggcacaa ggcttgcttg agcctgggag gcggaggttg 18000
cagtgagctg aaatcacgcc actgcactct agccagggtg acagagtgag 18050
actctgtctc aaaaaaaaaa agtaaataaa taaaaaaatt ttttaagtat 18100
cttatgggca tatacttgtc ctgttactcc tcaaactttc atccactttt 18150
ttttttttaa atttttttttc ttacctttca tcgttttctt gatatccact 18200
gggttttagc atctacaaat gattcttgcc tgaatcagtt attatggtag 18250
ttgatggttt tctaattcca ttattccttc tatgtttgtt aattttggca 18300
ttcttctata aggaagagct taccctttt ccctattaat taattcatat 18350
attaatgcag acctatgcat tcttacttca ttaaatcata atcctttact 18400
atcattatgt attctgatgt tcagactatc ccagatttag ccaataagat 18450
ccccttcagg ggaatggtct ttgggattcc tctttagagg ttcctggttc 18500
ctgttttctt ttgacatatc ctattactct ttgagcattt ttttttttt 18550
ttttactttt aggcacagca agaagttcca tggtcctctt gttctttccc 18600
caactcagcc ctagagtcag tcacttctcc aatgagctct agttcctttt 18650
agtagagaat cataattaga aaacaagaat cagtgccaag tgtgcacctt 18700
tgtttttaag gtccatccac gttgccgtgt atatgtccag catgttgatt 18750
ctaactgctg aataatacct catgattgtc atccatccca gtgtttcttt 18800
ttcccttctg taatgaggga ctcctggact gcctccagca ttaccttcac 18850
aaatattgct gtgaggaaaa tccttaaacg tttcctttat gggcaacgtg 18900
tgagcatgtt tatgttgatt caggggtgcc agacacagct ccagaatggc 18950
tgcctcagtt tacatttcca ccagcagagc atgacaggct ctgtgtctcc 19000
gtgaataatc agcattaacc agcttcctat tttttgccaa actaatagat 19050
gtgctaggat aactctttgt tttaacttgt ttttctctga ttaccaatga 19100
gctggagcat ttcttcatat gcctgatggt ctttgggatt cctcttaggt 19150
aaattgctta ttcattataa tcctttgcct gtttttcact ggagttctta 19200
tatttttctt gaagatatgc aggaattcct tatacatcct agatattaat 19250
cccttcctgg tctcagacat tgcagatatc ttctgaatct gttatttact 19300
tatttattta caattttttt tttaagagtt ggggttttgc tctgtcaccc 19350
agactggagt gcagtggtat gatcatgact cattgtggcc tcgcaatcct 19400

```
gggcttaagc gatcctccca cctcagcctc ctgagtagtt gggactacag      19450
gtatgcacca ccagacttgg ctaattttat tttatttttt agagatggaa      19500
gtcttaatat gttgctcagg ccaatcttga actcctggcc tcaagcaatc      19550
tttccacctc agcctcctgc atctattata tatatgttca ctttgctcat      19600
gctgtatttt gttgcaacat aaaactattt ttcccattgt tttgtgcagt      19650
ctctcaccag cactcttctt tttctgtaac tgtgttaatg ccctttgttc      19700
ttccatatgt taggtatgct ggtatagttg aactctgctg actctcctca      19750
gtaaacagtc tctttttatg acaccttatc ctctactgaa ttctctctat      19800
caagaatgac ttggccgggc atgggggctc atgcctgtaa tcccagcatt      19850
ctgggaggcc gaggtgggca gatcacccga ggtcagaagt tcaagaccag      19900
cccggccaac acggtgaaac cctgtctcta tgaaaataca aaaatcagct      19950
gggcgtggtg gcaggtgcct gtaatcccag ctacttggga ggctgaggcg      20000
ggagaatcac ttgaacctga gggggaggtt gcagtaagcc gggatggcac      20050
attgcactcc agactgggtg atggagaaac tccatctcag gggaaaaaaa      20100
aaaaaaaaaa aaagaatgac ttgtcttcct cttagagtgt gaggtctaca      20150
tacaaatatt attcttgtat tcagcaaatg tatgtcatag gcctagtgtg      20200
tgttaggaac tgtgctgtca ccaacaaagt ttagagaggt tataaaactt      20250
gactgtagct ttttagaggt ggaggagtga tttgaaacct aggctgtaat      20300
tccttcctcc tgtgattcct tcctactgtg ttgccttccc ttgaaaattg      20350
catttggggg ccaggtgtgg tggctctcgc ctgtaatccc agcactttgg      20400
gaggctgagg cgggtggatc acctgaggtc aggagttcaa gaccagcctg      20450
gccaacatgg cgaaaccccg tctttactaa aaatacaaaa attagctgga      20500
tgtggtgtgt ggtgacatgc acctatattc ccaggtactc agtaggctga      20550
ggcaagagaa tcacttgaac ccaggaggca gaggctgcag tgagctgaaa      20600
ttgcaccact gcactccagc ctgagtgaca gagtgagact ctgtctcaaa      20650
aaaaaaaaaa agaaaagaaa gaaaattgca tttagttcct gtagactgtg      20700
tgtcaaatgt ctaaatctct tctaacaaat ggcctaagga ggtgcaaagc      20750
gaagcatcct caccagcatc ctgacttggc agtgaggcat gggaccctgg      20800
agggagtagt ggtaagtgtg actctggaat tcttcctggg ctacttgtca      20850
gtgactggct ccagattgag aggagagccc agaggacaca ggtggctgcc      20900
ccagcctgga ggtgaaagtc ttaaaataaa atgccagatg cctagaccat      20950
tctaaacctt tctgagaagc tgaaatcatc ccttctggaa gcgctctagt      21000
tctaaaagga cagatataca gcaagatctt cctggggcta atatggagtt      21050
tataggcaag taggcctcag aacctttccc tggtagtgat atctgtgggc      21100
aggcacagtt tccacacttt ccagaaattc cagcggaagg agtgagaagg      21150
aggaatctgc ccttgagtga ggaccaaaga aagcagaaat tcctcttggg      21200
aatttttcct ccagagacca aacactactt gggagcttgt ttactgggct      21250
ttaaaagctt gtgaccccca gtcactcttt cttgacccca aggctttgca      21300
tttctgtggc ttccccactg gacagaagtg gaactgtcat gctgcctgtt      21350
```

ctggggtctc ccagaggttt ccccatgtcc tctccttgct tctactgccc 21400
cacagaattg gggatctgtg accacatatg gtatagaatt aatgcttgag 21450
aatggtttag ttcagtgatg tcaaataaga ttcactttta tgccacctcc 21500
atcagttgaa ggcccccctg gcccctaaat tggaaaagat tctgagacag 21550
aatccccgtg ggtacagcgc agggacagta aaggcacgtg tgctgtgatt 21600
tgctatccac tgtgtggatg catccaggaa tatcagaacc ctggaagatt 21650
atttaagggg aagttaggac agcttttttg ccaatccaag ggtgttcttg 21700
aggaagtctg tcttcctgta tggccttcag tttctttcct gtgtaaccat 21750
ggggccaaca cataattccc acagctctat tggcccttgt ctgccaggat 21800
tctctagggt ctgattcgag gtggatcctg gccctttgag gtggcagaat 21850
ctgatcatgg tgctgtttcc ttagatttag gccttgatac ccttggcgag 21900
agcatcctgg gctgagtgac cacctgaggt ttttctggtg attttgtgac 21950
ccatgtaaaa ctttgagctt tgggattatt ctctcaagga aatagtgaca 22000
tttggtgaag agcctgtttg gtgtggctat gtgaggctta gccaagaaaa 22050
tgcaccattt ttattaggag gttaggccat ccgttgccac aaagtgtcag 22100
atgctaggcc tagagcctgg agaaaactta ttttaaaatt gatggggtgc 22150
tggaggggtt ggggggtggt ggctgtagct catgaatcag gtgctaaacc 22200
tagaaacaaa aggcctcatg tggcagactg tttctgagca cagatgaatg 22250
gatgagcaac tggcgcaact ttgcccagtt ggtccagctt cccacttggc 22300
cacctaggct tgctgtgaag acctcgtctg gcagaaatga gagtgttttt 22350
gccccatctt gatcttaact gtaatttaag actaaaatct tagattctaa 22400
aacatcaaag gcaagatggc tcccagctct gtgagctcag cttctcacct 22450
cttagttgaa caagtgcagt gtgggtcaat acatgattgc tgctcttgct 22500
gccaggaact gtcccagcat agaaaggaat gggacacaat ccctgccgtc 22550
aagattctaa gggaggaagc aggcaggtcg actggtgcct catctctgca 22600
gggctccagc caaggtttgt gaaggatttt gcaggcatat ggagtgggga 22650
ctgattgatc ccgagagggg actggggaaa gctctgaaga ggggatgaca 22700
tttggtttga actccaaaaa atggttgctt tacctgtttc ctgaagtttt 22750
tgaggtggct tataagaaca tataccataa aaaggaccaa tataaattta 22800
aaatcagaaa aagagaaaat gggctgggca tggtggctca tgcctgtaat 22850
cccagcactt tgggaggcca aggtgggtgg atcgtgaggt caggagatcg 22900
agaccatcct gcctggccaa catggtgaaa ccccggctct actaaaaata 22950
caaaaaatta gctgggtgtg gtggcacatg cctgtagtcc cacctacttg 23000
ggaggctgag gcaggagaat cgcttgaaac ctgggaggcg gaggttgcag 23050
tgagctgaga tcgcaccact gcactccagc ctgggcgaca gagtgagact 23100
cctcctcaaa aataaataaa taaagagaaa atggaactta gaaaattaag 23150
aggaagagtg aaaaggtaga tatttagtca ggcacagtgg ctcatgcctg 23200
taatcccaac actttgggag gccaagacag gaaaatctct tgagaccagg 23250
agcttgagac ttgcctggca acatctcagg tgagacctta tctctacaaa 23300
aaatttaaaa attagctgag ctgtgtggct cgtgactgtg atcccagcta 23350
ctcaggaggc cgagaccaca gcccaggagg atcgcttggg cccagcagtt 23400
tgaggctgca gtgagctggc accactgcaa ttcagcctgg gctacagagc 23450
aagacccagt ttaaaaaaaa aaaaaaagat attcaaacca tgggtcccaa 23500
cgtagttatt atatttgacc atttgcaaaa gctgaaagca aaacatgtta 23550
cacattttca gagaggaaaa tacacagtag ttcctgagtg taagttgttt 23600
ttcttgacct cattcttaaa ttgcttcatg agggtgggag ggaagtggta 23650
gttaataagt gaacctgtaa accagcgttt ctcaaaatgt agtccaggga 23700
attgcatcaa aattgcagtt acctacagtg cttgttaaaa tgcagattcc 23750
tgggcccctg ccccaggctt atcaaatcaa tctggtgagt aggactcaag 23800
aacctgtaaa ttcacatact tctgcagatg attcttcttg cactgcacag 23850
catgaaagcc tctgcaatag acagaaagct accagcattg cgaaagcaac 23900
ttgagtgctt ggcctttgaa ggttgagtgg gactttaatg agggagagag 23950
taaggcatga gaaatggcag ttccactgag gtcagtcagt ggttcattgc 24000
tgacgaagtc acttttaagt catgttttag aagaactacc aagtgtggca 24050
ggtcaggcat gtggcaggac tgtttctgag cacagatgaa tggatgagca 24100
cctggcccca ctgtgcccag ttggtctagc ttcccacttg gccacctacg 24150
gtctgctgtg tggaccttgt ctggcagtct cctttaattt attttttatt 24200
atttttttct ttttgagatg gagtcttgct ttgttgccca ggctagagtg 24250
cagtggcatg atctcggctc actgcagcct ccacttccca ggttccagcg 24300
attctcctgc ctcagcctcc caggtagctg ggatcacagg caagtgccac 24350
cacgcccagc taatttttgt atttttaata gagacatggt tttaccatgt 24400
tggccaggct ggtctcgaac tcctgacctc aggtgatcca cccatctcag 24450
cctcccaaaa tgctggaatt acaggtgtga gccaccgcac ctggcctatt 24500
tttttcagc aaattctttg tttttctctc tgttcccaaa tgcagggtac 24550
tgagaccaca gatgtattct gtttcctgtt gaaaaaatgt ttctcactta 24600
gctgggtgtg gtagcatgca ctgcagtccc acgggaggct gaggcgagag 24650
gattgcttga gcccaggagt tcgataatca tgccattgca ctctggtctg 24700
ggtaacagag cgagaaactg tctcttaaaa aaaagaaaaa gaaaaagagg 24750
tcctagggaa agaaacaaat agtggcttgg atggtgagtt ggtggaaaga 24800
acagtgggtg ttgggggtgt tgaacttgtg tttgtgtgtg gtgtacccaa 24850
gacatatcat gtcagcatta agaatagact attcctgttt tctggtcact 24900
gagttgtatg ttttgacatc cttattttgg aagatacttc cttactagga 24950
atgggatagg gagggggtca cctttcccat ctgtgggtca tattttaaaa 25000
tatttattgt tcaagtttaa agatataacc aaaggtataa agaaaaatac 25050
cacaaacatc tgatttaaga aacaaaccag ccgagcgcgg tggctcgtgc 25100
ctgtaatccc agcactgtgg gaggccgagg caggcagatc atgaggtcaa 25150
gagatcgaga ccatcctggc caacatggtg aaaccccgtc tctactgaaa 25200
atacaaaaat taactggtca tggtggtgtg tgcctgtagt cccagctact 25250
cgggaggctg tggcaggaga atcgcttgaa cccaggaggc ggaggttgta 25300
gtgagccaag attgtgccac tgcattctag cctggcgaca gagtgagact 25350
ccgtctcaaa aagaaaaaaa aaagaaagaa atcatttcct acaccttcga 25400
agccttcatg agttagattt tgaaacagtg caaaatgctt cacgtgagaa 25450
tcgagagtcc cttctggtgg ctctccatcc cctgctcttc tgtcaggttt 25500
tcttgtaggt ttatggaaac ctttgttact tgtgcaggtg gcagagaagc 25550
agagaggata gctgcgcgcc acccacacag ctaggattta ttggcgtact 25600
cccacgtgca tggcagccaa gtggacacaa ctctgtgatg aatcctccca 25650
agagaactga ggggccctga tggaggagct gcttctttgc aaagctttcc 25700
ttgactctct tcctgtcccc tagttgattc cccttctgtg ctagttttag 25750
cttattgttt gttacctgtc acacttagca gtactgttgg ctttgctggt 25800
ctccttgact actgggggta aagacctttt gttgttgttg ttgagacaga 25850
gtcttgctct gtcgcccagg ctggagtgca atggcgtgat ttcggctcac 25900
tgcaaccttc acctcccagg ttcaagagat tctcctgcct cagcctccta 25950
agtagctggg attacagcta caccacaccc ggttaatttt tgtattttta 26000
atagagatgg ggtttagtag agatggggtt tcaccatgtt ggccaggctg 26050
gtctcaagcc cctgacctca aggtgacctg cctgtctcag cctcccaaag 26100
tgctgggatt acagacatga gccaccatgc ccagcctcaa agacctcttc 26150
tttacttgct caccctgccg cccactcccc taccaacccc tgcatgccct 26200
ataccacctg gcacatgata catactaact gggtacatgt ttgaatatga 26250
atggatgtgg tgctgtgaat gcttagggga agtgggtgaa atgcttaaga 26300
accaaccttg agtggtctgg gaaggcttcc tgggagggtg gtgtttgagc 26350
taaggccagg cagctgttag atttgttaga ctgaagccct tgcagactta 26400
gagagcttgt gctcttccca gaatgacggg tgagccacgt acagtaaatg 26450
gtgcttctca tttctagccc aaggggcctc aaggggcacc gtgatttcac 26500
gagaatgctg caagcaaatc ttttctcaag ctggggaatt tggtggtaat 26550
gcctggctca gcttgcggtg cgcacctggc ctttggaaga ttggtacaga 26600
gagaagcggc ccatccacat gagcctgtgg aacagcactg gtgggggagc 26650
tgatttgtga agaggggctg tgcagtgtac tgtcaggtct gagacccagg 26700
aagaaattcc agtatcccag ctctcagaat cacagagttc taggcactgc 26750
ctagttccac gtgttcccaa atgtttcctg aatacttgga tttcctgtcc 26800
agagaatttt caaaacaaac ttagaggcct gacccatggc tgccaaggaa 26850
ggattttttt tttaaattaa attttaaaaa tcagtccagc atgaaaatct 26900
atgatgattt cataagagaa aggacatttt aatattcaaa gagtaagaag 26950
cacttaatct tggaagaaag ggcattccta tactttgatt acctttagtt 27000
taattaaaaa acacctacat ggtctttact tctgtgattt cattcctggg 27050
ctagtgaaac attgtcacaa taaagcatca ggccaacgct tctttcgacc 27100
cactggccaa tcagttgaca aacagtgact agatgtttca gcctattttg 27150
ctgaggctaa aggattgaac tagtgcttca gccagcatga aaaccagtca 27200
ggagtccgtg ctggtgttgg cttagattag cagggccttt gatggagggg 27250
catgtatgtg tttgggtttg ctgtgccagg caggggagca gtggaatttg 27300

```
tctgaattga gctcacacat tgaagttatt gagcgactta catgcaaggc    27350
catgacctgg actcccagcc gagaggccca cgtggcgggg cttgagctgg    27400
gggagccgag gacagcttac atctgctcat ctgcttacgt aaccctgcct    27450
cccagcttcc agagccaaga aaacacacaa gccagcccag cggggccgag    27500
agcctgtggt agcacacgcc atgcgccgca cagcaagggc gccttggctc    27550
ggcttgaggc ctgtcatgaa gccctcagcc ctctgcctcc tcccagagct    27600
tctccccacc accccaggca gtggctctga aacctggtcg caggtctgca    27650
tgattctgaa cagaggtagt cgttgccttc ctggagtctg agctctctgg    27700
agtttctcac tgggacagag ccaggtgtgt agcagagcat ggtccctgca    27750
gtatggcagg aggtgtgcag ggcattcagg aggcctcctg gctggcactc    27800
gacccaatta gtcattcaac gccaggtctg gggctgctgt ctgttgtctc    27850
aaaggtgtga gctgcaagat ccttagagtt gtggagaaaa aattgccaga    27900
ttggcaagaa gggcaggatt gggggtcaag gtgtctcagt gtgttggaag    27950
catgatgggg gttgtgcaag gggcacagcg agttcagaag ggagcaggag    28000
agtgagaaga ggctgttcag tgataaagct ctgcacagag ccattggagg    28050
agcaagctcc ttgaccatcc ttaaaccagg gtaattttca tttaggttct    28100
gccacacgct cagcagggaa ctcctggaag gcaggatttg tcttgtccat    28150
cctccctccc tacctcaacc cactcctcct tgggctggca cacagtaggt    28200
acccagaaag tatcaattga aacaaattga aagtggtctt gatacatatc    28250
acagggcaag tttgcagtta acagacattt cagagtaaag actctctggc    28300
ttggtgctcg atcggcttct gtgggttgtc agcatgctgt ggacagcccc    28350
ggcatgggag cgagtgggcg tgtgtgtgtg tgtatgtgag ggtgagagag    28400
cgttagtgtg tgtgttgggg ttggggagag aggaggggga atagaagatg    28450
gaccacccgg gtatcagctt ctgccctggg gagatggtgg tgtcagttgc    28500
tgagggaatc ctgagaagca ggtctggctg taggtggtga tggtggtggg    28550
gttgcatgag aatccatttg gggcaggttg aatttgaggt gcccatgaca    28600
tatggctagc catgttctgt tggctgtgag gtcaggagag agacatgaga    28650
tggaaacaga ggtttgggaa ctgtcatgtg cttaaaccaa agacctgggt    28700
atagggagag tgagaagaga agggggcaaa gatggacatc caagaaagaa    28750
gctgagaaag cctaggaatt tgaggtaaga ggagacgtag gtaaatgtga    28800
cgcttggtga tcaaggcttc tttccacctc tcctatgctg gacactcacg    28850
tctcctgtct gcttggaaat tcatgctgag ggcagggaag gtgggagcaa    28900
ggatttgtct aaagatcttg ctttggatcc ctgcactcct cctggtttac    28950
caagtgtcac tggacacgtc agggcgttct gagaccttag agagcatcca    29000
gtcctgtccc tgcagtttac aaatgaggaa accagtaccc tgagagtggc    29050
tgtactatcc actctcagga taccaaagat catctggaaa gtcactggtg    29100
gagctggacc ggggcccagg catctcttct cctgtccggg gctcttgact    29150
tcaggaccac ctttctgaaa cccatgatgg ggcaacacca ggacactttc    29200
cagcctgcag gtgtctgtcc cgcggaagcg agccaggcca catgtgaatt    29250
```

```
cctgttttct gggtgggttt cagaaggtac gagcaagtcg gcagggtgac      29300
agcccaggtg cttcttgggt tccccaaaac gcggttatgt ttagcagcat      29350
cctcagaacc aaaggtgggg tgggggctgc agatgttgtg ggggccctct      29400
gaagtgaaaa gagccctgtg acagatcttt tcttcatgtt tttcacaagt      29450
tcactgtgca gcagggcccc cccagtagcc tttgcccagg gttgggtgtt      29500
gggcagccca ggcctggctg accttgtggg gaagggtgtg aatggtggga      29550
atccccgagg gccctctttg cccgaaagcc ctaagccttg acatcagatg      29600
cccatcagat ggtccatcgg agccctacta cccagcttgc ccagtgagaa      29650
tcatctgggc tccttgttag gtagccattt aggtccttcc caaaatccac      29700
agactctcta agggaagggc ccgagatgct gtacttgtac taacttcctc      29750
aagcaattct tgtgataggt ttgggaaaaa cttgtccagg gtgaccactg      29800
actgagtcct ggtcttctct gaagagcaca gtgcctgctc actttagggc      29850
accctgggag gtgggagctg gctcagcagg cagtcttata agggactgag      29900
cttcaaggcc tctgtccctc caggagggag gtgcatgacc agagagggag      29950
gcctgaggat cttcttccct gccccagagg gtctgctgcc tgagctctgt      30000
gatagcgcag agagtaaaag gatcaagctt gattgaggcc tatctctcaa      30050
tgcgaaagtt tgctagttaa gaggagagtg ggaagggcat ttctggcaaa      30100
gagaaaagtg tggacaggca tggcttaagg gatggggagg gagacagaca      30150
gagctgaggg tgaagggcct tttgctcagc tgtgggcctt ggccttccct      30200
tgtgcaggga cacacagcct tagagccact ggaggtttta gtgggaaagt      30250
aatatggtcg gggctgtatc tcagaagaaa acaaactaat gggaacaggt      30300
cctgtgatgg tggacctggg tcagctacgg agggagggaa gatgtgagat      30350
gtgtactggg gaagggggtg gaagtggcag ctatctggtg agaggaagca      30400
ggcccacagc tttttttctc aagctgttga attcagaagg gcgagtgatt      30450
ccgggagtag gggtgcttgg gagagccacg cgttattgat aaacagggca      30500
ggctgaagcc tgctcactgg ccctgggcgg gttctcacca gcatgtttca      30550
ggttttgatc tgtgcttgtg gttggtgttc ctacctgttc tctaggttcc      30600
ttcctttgtt cttgtggctc atttgcttca caggtgaagc tggttacact      30650
agagtaacag ttcccaaagt gtgttccctg gaaaaatggt tctgtagcca      30700
aataagcttg ggaaatggtg ggttaaatat aacgaagggg gtttttcgac      30750
tgcacaactt ctcagagcct ttggtgtgtg tcgtgacttt gcagaagcag      30800
gatttaatac gcagcattcc cgttcttatt tgaccacgag acatgttttt      30850
ccattaagca tcttgctggg tctgatgttt tctggaaccc attttgaggc      30900
ggtctggtct gcagagagta tggggagcct gggttcaagc cttggctctt      30950
gactctcagc agagccttga ttccctgtgt tgcctggact gcaccacgtg      31000
taccacatac ccggtatgtg acgttttcct catccctctt cccacctgcc      31050
gttacctcac aatccacaat ctgcacctca tccatttttc ttctgaggca      31100
agcactctct tactaactta cttatctcat ctgcatccat gttcttctag      31150
gccagaaact tgggagtcat ccctccctct ttgttacttc ttcttcctct      31200
ttgttacttt atcccctctg ttactaaaca ttcttctgtg tttccagcta      31250
```

```
tttcttttat tttccctcgg tctcctttgg ggtttctttg cctccatctc      31300
tcccagacct tggttcacct tccatcgagt cccttcctgg gacatgggca      31350
ctcatgccac tcctgctacc ttccacttcg aagctaactc cctccacact      31400
gacgtcccca acatgcatgc atacacacac acacacacac acacacatac      31450
acacacacac acacacactt ccccagttag gctagaatca gagagatgat      31500
gtcagccatt tgtccaaggc cacgcagctg ggaggtcaca gagctaagtc      31550
tcaacctcag gggttttgag aaattgcctt ctcatccgtg atcactgatt      31600
tctacaacag cctgtcagga agtctgggta gaaattactt ccattttaca      31650
gtggagtcag agcggggagg gtcctgggca ggcgagtgct tcacagagtg      31700
accaaccatc taggtttgcc ccacactgaa gggggtttct ggggatggtt      31750
ggtcacccta atgctggatg tggtgcctga tgctgggcag gagggccctc      31800
tccgtggcca cgttgcctcc caggaggaga catttcctct gcagctgcag      31850
ctgcagcctg gccatctgat gcagcctgtg gagcggtggc gagtcctgtg      31900
gcctgctaac ttctccctcc ctccacctct ctagtgggcc ccatgctgat      31950
tgagtttaac atgcctgtgg acctggagct cgtggcaaag cagaacccaa      32000
atgtgaagat gggcggccgc tatgccccca gggactgcgt ctctcctcac      32050
aaggtggcca tcatcattcc attccgcaac cggcaggagc acctcaagta      32100
ctggctatat tatttgcacc cagtcctgca gcgccagcag ctggactatg      32150
gcatctatgt tatcaaccag gtgaggcctg ggaaggtgga atgagagagg      32200
gtgtgtgtgc atgcagatgt gtatcagatg tgtgtgtaat gagggcaggg      32250
gaaggggagt gatttcacag acacctggca cttacagcga ggaaccagcc      32300
ccccagccac caccagtgca gatgaggtaa acgccaaaca gtgtgcttgc      32350
ctattgctgt caactctata gccaagggaa atgctggagt gttttcgttg      32400
ttctgttttt gttttctgga agtagccttc cagcaagatt gggaaaaaag      32450
acaaccctaa ttattccaaa gtacacactg attattccct ggctttgtgt      32500
agctgtgtat tttcctttta aaaataaaac caccatttag atgtcagact      32550
tttaggtaac ttcaaagttt atccagtcag tcagagcgtg tctcctgggg      32600
cacctggaga cagtgccctt agttcaggtc acatgcctac atgccagccc      32650
ctggtgaaat atctggagaa gtctgattcg tgggccatct gagagttatg      32700
tggactgggc cgagtctgag aaaaagtttc tcactgctcg tctgatccat      32750
atgtgttggg ctttagccct gcttaggaaa gtaatgctaa ggataggtca      32800
actttcatca ccatggcatg gagaatcaga ttgatctaag aggcatcttt      32850
attgaaataa atttttcagt ttatttgagg agcattattt tcccaagagt      32900
ataactttga tatttcaaga ttacccctaa cacttaaatt catgttttta      32950
gactataacc tcctaggtgc aatgacacat ctaacttatc taagcaccca      33000
gtttcattga aattcatttg aagagtctga gtacgcccat ttctacaagg      33050
cccaatgtcc atttcatttc gagataaact ctgctttagg taggaggatt      33100
gttggcagtt tacggcttcc atcaaggtca aggaactctg tgcaccttcc      33150
ctatgacccc aggggaagca ctcgaggact gctgtggcat tgtgctgcat      33200
```

```
cacttgctgc agggagattc tgaagaagtg taaggtctca gtcctgccct          33250
gtcccgaagc ctccaaccca cttctggcaa gtgggacctt cccagggaac          33300
aatttgttaa cagacccaaa tatcctgtga ttggatggtg gctgccaaat          33350
gctttggaag ctcagaggaa ggagagagag caatggcttg gaagaaccag          33400
gatataaact aggttctaaa gtctgcaggg agatgggctt ctcagctggg          33450
gccagtgagc agggacctta aggcagaaag gagccttgca tgttcctgga          33500
aattgagatg cccactgggg taggaaagca ccagaagctc tgggaccagg          33550
tgtcagagtt aagcctgtga ggcaggagag agcagaacaa gccctgttac          33600
aaggaaactg aagcaggaga gcaggtggtg ggcaaacccc ttgaggctgt          33650
ttgaattctt cggccaagtg aggtacagac cagggcccta tgaacacctg          33700
caagcaagac agccacgcag ttgtgggtca ccttggaaga atattggaga          33750
atgcaagaga gaacaggtaa atgtcctgca aaatgcgggt cactttaacc          33800
caacacatat tcatttaaga aaagctctgt gattgagaaa catttgtctg          33850
atgccagtta gcacatacca atgacggcaa gattcaggag cctgttatta          33900
aagcagtggc agcgagcacc tggaagaggc ggccaccatc accaggagcc          33950
agcagggatg actaataagc cgtgccagct gcatctcgtt tctctcttga          34000
cagttgctat gccagtagat gagggatgta ctgtggatac aatgctgtca          34050
tatcttattc agcagggcat ctgatagcat cccacaaatc tgcctgagta          34100
gaagacagac agctgtggtc tgggtgccat ataggtaggt taaaatatat          34150
atttgggcct aggcgcagtg gctcatgcct gtaatcccag cactttggga          34200
ggccaaggca ggcggatcac ttgaagtcag gagttcaaga ccagcctggc          34250
caacatggcg aaaccccgtc tctactaaaa atacaaaaat tagctggaca          34300
tagtggtggg cggctgtaat cccagctact cgggaggctg aggcaggaga          34350
atctcttgaa cccaggaggc agaggttgca gtgagccgag atcatgccac          34400
tgcactccag cctgggcaac agagtgagac tctgtctcaa aaaaataaaa          34450
taaataaata aataaataaa atatatactt gggtaaagag gataaaagag          34500
ttagcgatga tgctgaattt ttgaactgag gtggctgttt tcaaggaaga          34550
ctggagggtg ggatgctacg tctagatatg ttgcagttta ggtgaatgtg          34600
agacttccct gttttgaagt caaatattgg accagtaaaa tctagccatc          34650
agcttaaatt cctatgatac aatttacata ctccccaggc tcaacacagt          34700
agatttctga atgtcctctg ccagctacat gctcctgccc acctcaatcc          34750
gagtagatgg aacaactaac caagccagct cagaccggtg gcacagctgt          34800
gctggctaac actgggcacc acctaagaga gtgcttctcc aaaagtgtgc          34850
ttccccaaat ggagcgaaat acgcttgagg aatgttgggt tgaaccatgt          34900
aaagcaggtc tcattcccgc agagcctttg gtaccccggt gtacactgta          34950
accccagaag tgtttcctga gcttgcctga cgagacaact tttccaagaa          35000
ccgtctcaag tgatgagtgt tttgtgagtc acactttggg gaaagcgggc          35050
ctaagttagc atctcctccc agctgcctcc ctgctttccc tggaacacta          35100
ggaactgccc gtcctccctc cctccctcct cttcccactt cacaacttag          35150
catcaggaat attttagttt tggtttttca aacatatata cctccttttt          35200
```

```
tcttatcttg tcaatatcat cttttttttt tctttgcttt tcctcatact      35250
ttttttctc ttcatccttt ccttctccaa gggttaactt tccaccttag      35300
gagaatcttt tctgcttttt ctcccacttc cccagctact ctcttatcat      35350
ctgctccaat ctcaccctaa ttgatcattt tgggaaaata tggtcagagt      35400
ccagataact aagttgagaa atgcttaaac tctgccatac ctttccagta      35450
aagaatatta cctaataaat aataaaatgg taatgggaaa cctgaaccct      35500
gaaaaaaaag aggtggaagg agaaacattt ggagcacatc ctgtctacaa      35550
attaggaact gcctgtgtta tctgttttat ggttatattc tagaagaaga      35600
aagggatttt gtagcacctg gttttgacct ttctgcactg tttgttgagc      35650
aaataaacct tatgggctgt tagccctctt tatagcctct cagcttatcc      35700
ctggcccaga caccctgctg tcattttgac ttttcattcc cacacacaca      35750
tacacatgca cacacatgta cacacacaca cataccattt aagattagac      35800
agaagtaatg ctcaaaatgg agtggcttct gagacattta gtccaagggt      35850
tcccaaacag gcttttcagt atcagatttc tttctgcccc attgaaatgc      35900
tacacaacct tccgcttaca gcaggtcaca agggtttcat tctacttgaa      35950
gtaggggcca tgtcccattt ccacttcctt ggcttcccat tcagtcactg      36000
ctaggatttg cctagacccc tgaggccaga caatgtagaa acttctgctc      36050
catgtcacag gtgaggaaac aggctcagag agggacaggc tccgaaagtc      36100
acatagacaa cagtagggct gcggctcaaa ccccagcgtc tgactccagg      36150
tttagtgcct tctcagggca tcagtgacac tcctcatggc cagggtgccc      36200
ccagtgttgc tcacagtctg gtatccaggg ctgagagtgt gctgtgtgct      36250
cagactgcct gggttcagtc ctggcactgc cactttacag tcagtgacct      36300
caggcaggtt acttaagctc tgcaggcctc agtttcctcc ttggtgggga      36350
gggttatgag gcatccttct catggtaaac cttcagtaaa taccagccgt      36400
tactaggagg gtccactcct gcctctccac tctccattca tcctgcctgt      36450
ttcctctgcc tgcttcctct gcctgcttct gtggtggtga attcttcatg      36500
gctcccaccg cctcctgctg cacccccact cagggcccgc atcaggaccc      36550
ttcctcctat tggtttgaac tccttggagt cagagggtaa tggatagtgg      36600
agtgagccag gtggcagaat ctcagaggcc atcccgggcc tataagcctc      36650
ttcaaaatag ggccacgtat caagctttac acacaggagt gaactttcac      36700
aagttgttat gactcatact ctgtctatag taagctgtta accactccca      36750
tttggcttat gcctctgtaa ttattgtact aacttatatc ttaaaataag      36800
gatattgaag gaatgagccg ggagaggctt tcctggttga gatatagaag      36850
aacaagagtt gctctttttc cttaaggtct ctcctcccac ccctgacctt      36900
agctcaccag catgggagaa tactatttga ctccttgtac tctgagacgt      36950
ggatttcaag atatagcatt ccaacttcaa cggcagcaag aaaagaagca      37000
acagaaggag aagacatcat agcaaacagg gatgcatgct gcatttccta      37050
atactcaaac ccggaaacga gacttcactc aaggtgaagg gagggcaggt      37100
caccacctgg tagcactagc cctaaattaa ggaatgcaga atgtttgtgg      37150
```

gattgcccat cataaaaatt acaaaatgag taaggaatgc aggcacagct 37200
ggccaggtgg gtttgtcaca accatggcag ccctttgccc cacagccagt 37250
acacagaact ggtctctcca attccgattg catatcttct ggcacctctg 37300
ttcctctccc tcagctgccc aggatttttc tggttctgac catgttactt 37350
cctcttttaa acctgttagc atttcacgac tgcctacagg caacggtcta 37400
aatggtcgga aggcccaagc ttagcatccg agaccctgac ctacctccag 37450
ccacttcctc ctcctctcca cttcactgga ctccccatct ccacccagac 37500
acctctgttc tcccctctgt gtgcctttgc ttatgctgtc ccctgtgttc 37550
ctagtgtgtc tctggctatc ttttaagctt ccctccccaa cctcattagt 37600
tctgtggagc ccctggaata gagctgactt ctccttccct gctgctccca 37650
ggctgctcag aactttctgg aaagggatga ttatctgagt tccagcctca 37700
ccccagcccc cggactctga gtccctcatg tctgcctccc ttctttctct 37750
ctgaccacac agctggtaca tagtcagtac agacgcagtc agtgagtgga 37800
gcacggggct tctctccagg attcctgccc ctttgtttat ccctagtctc 37850
aggactccct actcctggtc ttctgcctaa atctgtgcct cttggaagtg 37900
aagcctccgt tcccagtggg gccaggtcct gacccttggg aacttgcagg 37950
atccctccct tgggcctctc cccgaagctt ccagctcaat gctgaccaga 38000
gcacaggctg cctgtgacag tccttggggt gacctccctt atcaggaaaa 38050
atgcagaaaa cctattaata ccttagcctt gtgattgtta atggtcacaa 38100
aactccttta gggtcctttg gactcagcac ctttatggtc tcactttgaa 38150
ttttgaacct cccacctccc cccatccccc agagtaaggc aaatggtctt 38200
ctgattgttc ctgcagaggg aaggctccac aggtaagcac acgatggcca 38250
ggaagcagag ctggagcctg cctgaaaggc tgtggagaaa tggagggagg 38300
gctgccctga ggactctgtc tggctttgaa gttttctact gtttcctttt 38350
cttctgtgca ctgttttagg atgatggggt gatagttcca ggctggttga 38400
ggatggattt ggagacagtc ctttgtaccc tcagtgagca agagtatctg 38450
tcaccctacc tcagcagttg tctctgtcac tggtccaagc agctggttcc 38500
tacacaaggt caagatcaac tggggagaag cagactcctg ggtctatccc 38550
attagtgagg acagctgcct gggcttatgg cctcattggt ttggtttcta 38600
tcttgatcat ctctaccatc cccccatccc ggccttccat tttctacctc 38650
agctgtcagt gcacagattg atgtgtgtgg gaacggagct tgggaggagt 38700
ggggtagggc tggtcctgtc ctgtagcctc cccttccttc gggcacttgg 38750
accctttgga gcttgccggg gtggggaatg ggagtgggaa ggccagggag 38800
tgtctctgca ccatcactgt ttgagtgttg ccccttttgct gtgtgcccca 38850 cctagtctat gtgtgtctct gttctctggg gactcaattt gctggtgaat 38900
tgcttccatg gacattgttc tgggaaatgc catttttttct gctcacccat 38950 gactctgtga caaggaatga cagcttatta ggaatttgtt tttgcattgg 39000
aacagtggtc atcagaatgg gccccttttc ccttgcagct ttgacatttg 39050
cctctctttt cctcacctct ctcccttgca tccacccttt tctctttttc 39100
ttcttttttg ttttccttct agcaggggcc ttttaccttt acttgttaat 39150
cctgtttgta gcaaagcaag tggaaggagg agttcctctc tgatctgctt 39200
cttattctcc acctaccttc tcttctgtac tttccgcctc ctagagagag 39250
agagagagag aggaatgccg acctaactac cgctgccact gctgctgcca 39300
ccaccgctgc caccaccacc ctggtaatgt tcacatgtcc tcaaatcaac 39350
ccagagccag ggccctgctg gtcaggggga ggctatgtaa ataatcccat 39400
gagtgtgcca tcctcaggcc ctggggtctc ctaggcaaga ccagggcctc 39450
tgtgggctct ctcggaaatg ctgaggttgc tggaagccag cccgtcatac 39500
agggtctgag agtttaactt cttttaaatt aaaccacagt tgagctcatg 39550
ctgtgtgtgt ataaactttt gtatcctgct ttttccttaa attctttatc 39600
atcagcatct tcccatgtta tttcatagtc ttcatcatca tcactttcca 39650
taccttcata gtagttgatc gtagaattcc atcataatta acttgtcttt 39700
tctctcttag aagtccctta ggtaatgtcc aattttccgt gagtgtaagt 39750
aataccataa tgaacatctt ggagtctgaa gtttattctg tgttggtttg 39800
ttccacattt aggatcattt tcccaggcta gattttcaga tgtgggatta 39850
tgggttcaga tatggtttac acatttttat agttcttaat acagatggcc 39900
aaattgcttt ctgaaagaga agcttttctt aagtattttt ctccaacttg 39950
tatcttaaac atcctgaaca tgcttagcac cactgtcttg atatatctgc 40000
ggaaagccac gtctccactt ttcagtgtgt cgggccctgg gagaggcagg 40050
catcctgcgc tggctccttg gagctgggtt taaaattgtc tcctctggct 40100
gggcgtggtg gctcacacct gtaatcccag tactttggga ggccgaggtg 40150
ggcggatcac taggtcagga gatcgagacc atcctggcta acatggtgaa 40200
accccgtctc tactaaaaat acaaaaaatt agccgggcgt ggtggcgggc 40250
acttgaaaag tcccagctac tcgggaggct gaggcaggag aatgatatga 40300
acccgggagg cggagcttgc agtgagccga gatcgcgcca ctgcactcca 40350
gcctgggcga cagagtgaga ctccatttta aaaaaacaaa caaacaaaac 40400
aaaaaaacaa acaaacaaaa actgtctctt ctgtgctcac ttcacccaga 40450
atccctgttg ggctcttcaa ggagctcagt tctctctgaa agcaacttta 40500
tagcctcagt ccagtctgtg ttcctgtgtg gcaggggtca agggtatgct 40550
cactcttgag agtggtgtct ttggttgacc aagaaccact cccatagcct 40600
ggtccctaac ccttgaaggc ccatctctct cactcactgg ggtgaagagt 40650
ttaaatctca gatccaagtt ttgttgagag ctctgagcta ccatattgct 40700
atggttaaca atagttaaca atgttaacaa tggttaacta tggttaacaa 40750
tagttaacaa tgtttaacaa ctagagccca gctgggtgtg gtggcatgtg 40800
ctaacagtcc cagcttctca agaggctgag gtgagaagat tgctggagtc 40850
caggagctca aggccagcct gggcaacatg gcgagaccct gtctcccctg 40900
caaaaaaaca acaacaacaa aagcaaaact agagcccaac tgctgtgaac 40950
tcatggctga gtagatatta ttagccctcc acaaactcag catttgtata 41000
atcccaggct gtttccagta attctctggg gatcatctcc cagcctgtcc 41050
actgttccag gatccacact taggcctata ggaatgcccc gtcagagctt 41100
ctgctgccgc tgatctgtta ctgtttcatg caacccactc ggcctagttc 41150
cttcctctta ctgtctcagt gggcacagaa aagcatacag agggtgtttc 41200
agcaaacatt gccactggct gcagacctgc cccggatct gtcctgttga 41250 gagcttagtg ctgcgttctt gcatggtggg gaggggtgtg gctctgtgat 41300
gagccagggc atgtgtatag gagcaacagt gtctctctta tcacgtagaa 41350
gttctgactc attgcgagtc ttggctttgg gttaatggtt ccagccatgt 41400
tgctgctgtg tcttttggtg caggagaggc tgggcacagt tggtccctaa 41450
gccattatgg ataagggatg tgtctgctga tatacacaca tggacctgac 41500
atccagggaa ggcagggtga ttggacagaa cagttcttcc agaagctgtt 41550
ggaacttgga caagagtggc ccttggcttt ctgtagttgg tcatctgtcc 41600
cctgttgcaa tcaggggaag gccacacttg ccttccttaa ccacagttag 41650
gattttcttg ggattagac cagattctag cacctgtcct gaacctctcg 41700
ccccgcccct acaaaggctg cttgcaagtg tagtgcacat acacagggag 41750
caggtggggc atggaagtgg aagtggagcc cctgcctttg gcccttgggg 41800
gaggcactgt ctgcttaccc acggttgttg cctcatagga atcatacaac 41850
agcttcctaa ctggtctcct tgccttcagt tggattgggg cacaaatccc 41900
tccttgacat ataaaccatg gtttaaggct ccctgtggcc taaataaaga 41950
taaagcttaa gtatcttaac aagcacctaa cccttctccc cagcctcggt 42000
gatttggctc atcgctgcct tcatgtttca ttctggcttc actcattcgg 42050
aatttcttgt agttccttgg ctgttctctt ttccttaccg cctttacaaa 42100
tgctctcacc atgcatgctt ttctctgctc ctacagatgc cttctctccc 42150
agcaccgcct ccagagtcta tgtctggtcg attctgtctg ctgtctccag 42200
tccccatctt gtggcagtct ctgctcaatc atttggggat tttatatgtt 42250
ttctggcctt tcttttgggg gcctgtcttc tccttctaaa agcagccagt 42300
tgacctagaa ggaagggata actgtaactc ttgtctacca acataagatt 42350
aggcccaccc tttaaaagct gcgtctttga aagggacacc tgcacccagc 42400
atgctggctt ctcttcacca agcgtgactt cctacgcatt tcacaggcct 42450
ccagaggtcc ccctgactct cttctgctgt gagaaactct aatcatgtaa 42500
gccacaggct aattcccttg agccttaaat gtttttagta atttcccatt 42550
catcagagaa gcaggatttg ggaggaattt tgaagcaaac actacagaag 42600
gcagagtctc caggtaggat atctaagaga catttggaat ggtctgactg 42650
ttcaagatgg atgggaaagc ctcttcctgt aatgatagta gccaacattt 42700
gttgtcaggc agtggggccc catttttgag atggggtctc tgtcacccag 42750
gttggagtgc ggtggtgctg tcatggctca ctgcaacctc agcctccccg 42800
ggctgggtct tcttaattct gaaaaaccca gcttttaaag ggtggaccta 42850
atcttatgtt ggtagacaat gttgtctcat ttaatacaat gcacatgctc 42900
tccccataac acaaaagagg gaactgaggc ctggaggtgt gatgtacccc 42950
aagtcacata gctaataaat aaagaagcca gcattcctgg gattaaaaat 43000
gcatgtgtct gtcactgtgg tgtatttggt gcttgatcaa tgtttacttg 43050
agcaaatgga ggggcagagg taccgatgag tgtgctcagt gaggagggca 43100
ggagtgaagc tgggcgtctt cccgcctctt gtgagtggtg gggcttggtg 43150
agcttgccag ggcctgtctt tcttatcaaa gaaggtgtgt gccccagtgt 43200
tacagcattt cacccaaagc agcctagaaa atgcttgact tttctgtcat 43250
tccggggagg acactttcct cctccactgt tctgctggcc tggtgtaccc 43300
acggcccctg atagatgata gcacctgcta aagtgcacca tgcccttccg 43350
tctcactgca tcccacagat gaggccaggc tgggatgagg gagaaaggga 43400
gggatatata gttcaggtta ttttggaaaa ctgcctgacc aattttaagt 43450
ctgggccgga cactggggca tctcaccacg ttgaaagggc cgtggcaccc 43500
cgggcggtga aaggggctgg aaccaggtct gcttcttggg cttctcctcc 43550
agggtgccat tgctcatggg ccttggctgc agaggtgctc attcgtggtt 43600
ccaaaattcc aattcctggg agaggaaaaa tgcttagttc agtctcagtt 43650
aggcctctgc ttagatcaaa cagccaaggc cagtaggccc agtcctatgg 43700
tagagacatg gcctcaaaga gccctctgct gcagttgttg gggagtgtac 43750
caagagaagg gagcattgtc ctgggctggg cagccctggg ggtctagtgc 43800
atagatgtag aaaggctctg ttggtatacc tccctttgct tgttggaaag 43850
tgctcaacgg ggctgaattg tgtttgacag tgtaagtctg ggctggggtg 43900
agggttgtta caagattgtc aagatgatta aatgaaatgc catttgaaac 43950
acttatccat gccttgtgta tggtatcccc accagtgaat attcacagta 44000
tattataata attccaacaa cttcataatt ttcatatgca atttctaaac 44050
tttgaacttt tttttttttt tttttttttt tgagacagtg tctcgctctg 44100
ttgcccaggc tggagtgcag tggcgcaatc ttggctcact gcaacctcca 44150
cctcccggct tcaagtgatt ctcctgcctc agcctcctga gtagctagga 44200
atccaggcgc ccgccaccac acccagctaa tttttgtatt tttagtagag 44250
acgggctttc gccatgttgg ccaggctggt ctcaaactcc tgacctgagg 44300
tgatccaccg ccttggcctt ccaaagtgct aggattacat acgtgagcca 44350
ctgtgcccgg caatttttttg tgtttttagt agagatgggg tttcaccatg 44400
ttggccaggc tggtctcgaa ctcctgacct caagtgatct gcccgcctca 44450
gcctccctaa tgctgggatt acaggtgtga gccaccacgc ccagcctaaa 44500
ctttgaattt ctttgaaccc atgacttaca cagaattagc tgaacgcaga 44550
attccaaatc aactcagcct gtgggacagc caaaaaacac agtgtgcctt 44600
tgggctcctt cactcaccac gcggggttag aaaactttgt cagaggcttt 44650
aaaaaaggag ctcttgtgtg taaaatgttt ccttgattct ctttctggtg 44700
cctctctttc tctaagtggt ttgcttcccc aagttcccca cctgagtctg 44750
ggtggctgtg gcacatctgt gcattctgta cgcacacagg cagccttttg 44800
gagtgccagt ttccaggtct tggttttatt tatttattta tttatttttt 44850
tgagatgggg gtctcactct gccgcccagg ctggagtgca gtggtgccgt 44900
catggctcac tgcaacctca acctccctgg gatcagttga gcctcctacc 44950
tcagcctcca gagtactagg gaccaccatg cctggcaaat tttgtaatt 45000
ttttgtagag gcagagtctc accatgttgc tcaggctggt ctcgagctcc 45050

```
tagactcaag tgatctgccc accttggcct cccaagtgtt aggattacaa    45100
gtgtgagcca ccatgcccag cccaggtcat cttttgaggg catggagaga    45150
agactttgag catcccactt ttgagattgt gtaccagtcg caagccccta    45200
tgacacactt tttccccaaa gtagagggct ctgactatgt tgatcccaag    45250
agagatggga aagagcattg aatgaggatt ccaaagtatt gggccttagt    45300
tcgtttcctc atgttggtgt tgtgaagatt ctggttagga taacagcatg    45350
tgtgcaggag gctttgtgaa ctgctgagag tgaggcgtgg caatgtcagt    45400
gctaggtttg tccttactaa cctggggcca tgggaattga taagaccaga    45450
ttcccaactc taccccacaa tgtgatccct gtggtgaccc ctcacagggc    45500
tctttggtcg agcttcccag aagggatcac catctgccat tgtatgttga    45550
accccattca ttcattcatt cattcagcca accagcaact atttgttgag    45600
ctcttattgt gtgagaagca gtcttcaagg aactgggtga ataaaaaaaa    45650
caaaacatcc taaccttcat tgagcttaca ttcttactga aagaaaacaa    45700
ataaaacata catgtaatcc tagcactttg ggaggccaag gcaggcggat    45750
cacttgaggt caggaatttg aaaccagcct ggccaacgtg aaacccatct    45800
ctactgaaaa ttaaaaaaaa aaaaaaaaaa aagccgggca tggtggcaca    45850
tgcctgtaat cccagctact cgcgaggcta aggcaggaga atcgcttgaa    45900
tcctggaggc agaggttgca gtgagccaag atcataccat tatactccag    45950
cctcagtgat gaagcaagac tccatctcaa aaataaaaaa taaaaataaa    46000
aatatgcatt ccctttgcac cagcacactt ggtgcctggg gacctcgtgg    46050
ttggcaccct gaagcaggtg tccctcttct gtcttgcaca ccttgcttct    46100
gtcctggtgt gtatggcatg gccttctgcc ctccatggtg agcactgtga    46150
gggcagaggt tgagttgggt ttgctgtatt tctcaggtgc ctaggtttgt    46200
gcttgacagg tagatggaag gcacacaatg tggtcatcaa acctcagtca    46250
accatataag gaaggtagaa gtgaaaagtc ccataggtac ccaactaatg    46300
tcaccagttt cctggatacc tttcctggag tttatttata gtgtgtataa    46350
ataaatgatg tatgtgttta aatgcctttt tcacctttcc ttttagagct    46400
gcctcttttt aacagttcca ttccattgta tggatgtact atgatttatt    46450
gaaccagttc cctactgatt attctgtttt ttgcagtctt ttgttatgat    46500
gaacattcca cagtgacaat gttgttcata gtcattcaca cacatgcaag    46550
tccttctgca ggatatattt ctagagggga attgctgact cagaggtttt    46600
ggtactctgt gttgattgta gagtgacggc agaaaagtga ggcccaagag    46650
tttcctagtg accatgtgta gtggacaagt caccagtccc tgtgagtgtt    46700
tggcccaaag gctttaaggc atttgatatc actgtttttg tttctgcacc    46750
aggcgggaga cactatattc aatcgtgcta agctcctcaa tgttggcttt    46800
caagaagcct tgaaggacta tgactacacc tgctttgtgt ttagtgacgt    46850
ggacctcatt ccaatgaatg accataatgc gtacaggtgt ttttcacagc    46900
cacggcacat ttccgttgca atggataagt ttggattcag gtaagagata    46950
ctcagtcaga atctgtggta aacatgtctc tctcatgtgt tgactaggaa    47000
atgcagtcct ggcagctcaa gagtgcctct ttaagctctg gagcagaatg    47050
```

```
cctcctctga gaaatgggtg ctttgtatta gttgagatgg aaagaagaga 47100
ccagaaatgc ctgtagtctc tgcacatcca gacaaaaaca aattttcccc 47150
cctttttttt ttttgtttgt tttttgagac agggtctggc tctgtcaccc 47200
aggctggagt gcagtgccgt gatcttggct caccgcaacc tctgcctccc 47250
gggttcatgc catcctgtca cctcagcctc ctgagtagct gggactacaa 47300
acacttgcca ccatgcgcag ctaatttttg tatattttgt agagatgggg 47350
ttttgctgta ttgcccagtc tggtctcgaa ctcctgagct caagcaatcc 47400
atctgccttg gcctctcgaa gtgctggatt ataggcatgt ggcaccatgc 47450
ctggcctaag aacagttttt agcatttggg aggggctctc atctttaagc 47500
tccaaatgat actgtatttt cttgcttttt tctttctctt gccccacaag 47550
ttttggaaag taaattggaa tagttttccc ccactgaatt atttagcttg 47600
tatacctcag cagatgttcc ttggcctgtt ttgttttgtt tttgagacag 47650
ggtcttgctc tgtcacccag gctggagtgc agtgacacaa tcatggctca 47700
ctgcagcctt gactgcctgg gctcaatcca tcctgcagcc tcagcctcct 47750
gagtagttgg gactacaggc atgagccagc atgtccagct aatttttat 47800
ttttagtgga gatgaggtct ggctatgttg cccaagctgg gcttgaactc 47850
ttgggctcaa gtgatcctct cacctcagcc ttccaaagca ttgggattac 47900
aggtgtgaac cactgctccc gcccttggcc ctataagaag gaatgtgatt 47950
ctgttttcca gcagggcaca aacttctgct taaatacaaa gcccaaattt 48000
ttccaccaaa atgcccctag tgaagtggcc agcccagatg cccgactagc 48050
gtattatcca aagcatattg tcattggtgg aaaatggcct tatagtccat 48100
tgttttgtct taaaagtaaa tatataaata aacttgtata ttgtttccta 48150
attccgtgtt tatattaaca taaaagtgtt ttaaattacc tgtcagtggc 48200
caggtgcagt ggctcgtgcc tgtaatcgca gcactttggg aggccgaggc 48250
gggcagatca cctgaggtca ggagttcgag accagcctga ccagcatggt 48300
gaaaccctgt ctctactaaa aatacaaaaa ttagccaggt gtggtggcag 48350
gtgcctgtaa tcccagctac tcgggaagct gaggcaggag aattgcttga 48400
acccgggagg cagaggttgc agtgagttga gatcgcgcca ttgaacttca 48450
acttgggcaa cagagcaaga ctctgtctca gagaaagaaa aaaaaaaacc 48500
tatcagttga ataacaaaac cctttccttc cttgctttaa gtgaatctga 48550
agatccagga gctgtgctgc aggtaccctc tatgttgggt acccctggtt 48600
taggctgact agtacagtgt ggttggctca tgtagacagc agaccettta 48650
ttttagatac aacttttttt ctttttcttt tatttttttt gagacagagt 48700
cttgcttgtc acccagcctg gagtgcagtg gcgtgatcat ggctcactat 48750
agccttaaac tccctggctc aagtgatcct ctcacctcgg ctttcctagt 48800
agctgggacc acaggtgtgg gccagcaccc ctggctgatt taaaaaaaaa 48850
aaaatttttt tttttagaga tgtctcacta tgttacccag gctggtcttg 48900
aactcctggg ggctcaagca atcctcctgc tttgacctcc caaagtgctg 48950
ggatgacagg catgaactac tgcacctgct gagatgcaac agctttctgt 49000
```

```
cagactcatt ttattctcat catttcttcc tgtcctccct tgctgggagc 49050
atgagagctg tgatgggaat ataggaatgt atgaagtcct tctcccagat 49100
caaaaatcct aacttcttgt cttaaaggga ggaaaatttg aatgtaacct 49150
tacttttaga ctcttcagaa atccttctat acccttccgt ccccgctttc 49200
acccttcctc cctctccgtg tgtgtatctt cttctcttga aacacacagg 49250
tttataccct gacccctctt gattcatccc ttgaagcaca gtggtgaaca 49300
aggaaggggc ccgtgatgcc ctaattcttt gccacagcac catgtttgtt 49350
tcacaaggag cctggcaggt ttgggcttgg ggcagatagg ggagagaaag 49400
cagcagagac agcaaaacca aatcatgtca gcttggcatg tacttccctc 49450
tgaaatagct aagaatccat ttctgtaaaa gcactgatta tcagaaaacc 49500
ttattggcct ggccaccttt ggttcaaacc ctcacattaa taatgtggac 49550
agtagtatga ggtgtgccaa aggtggatga ctcagcacct aagtgatgac 49600
acctaattac gaataggttc attaaagcag accccctggg gacctttgct 49650
tgaggatcct tacagtcaga attcctgaat atatttgaaa ataataattg 49700
catctttatt ttcatatgtt ctgtatggtt tggctgactt ccccctcaaa 49750
gtctgagtta gagttttcct taatttatgt gatgggtttg gtctttttgg 49800
attccagaaa gagctgggtg tggtttggag ctgcactcag agtcacacaa 49850
aaccacagcc tttagagaac ccacaggaag gctttggggc acgtcctgat 49900
tcttgacatt tctcatcagt gctgactttg tatcccttag gagttcacaa 49950
ttcataacca ctgaaatatt aaaatacaaa aagttttgga aggatgagag 50000
cccagatgct ctactacttg aaaatatgtt aaaacataag ttcatcatta 50050
tacattttgc taaatcagga taaagtctga agtttcaaag aagttttatt 50100
ttagcaaatt ttcagaaaca ctgcctcaac tgttagggcc agtgttctag 50150
tcagtatgcc tttggaagca tgaaagctgg attggtcgat aggatgggtg 50200
tggaaggggg gctgtgactg ggtgggtaca gagaggctct gaaacaatct 50250
cagattccag gagttcctgg ataaggactt catgtgcggg aacagagcac 50300
aggagaagca gattcctgag ccactcagga agaactgggc ctaggcctgc 50350
tcttgtcact gactggcttt ctacataacc acagaaacag cactgtgttg 50400
tagaaagagg aagatcatac tttttgatat ctgtgtctaa tttaaggtca 50450
tctgagccct gatagaaaag caaaacagac aaaacccttg taactgctcc 50500
ctcccacccc acccaccatc aaaaaagctt tagagaggct ggacatggtg 50550
gctcttgcct gtgatcccag cactttggga ggctaaggtg ggtggatcac 50600
ctgaggtcag gagttcgaga ccagcctgac caatatggtg aaaccccatc 50650
tgtactaaaa atacaaaaat tagccaggtg tggtggcaca cgcctgtagt 50700
cccagctact tgggaggctg agacaggaga attacttgaa aacctgggag 50750
gcggaggttg cagtgagccg agatcacgcc attgtactcc agcctgggct 50800
acagagcgag actccttcaa aaaaaaaaaa aaaaaaagat ccggtttggt 50850
gtcttacaac tgtaatccca gcactttggg aggccgaggc cggtggatca 50900
cgaggttaag agatcaagac catcctgacc aacatggtga aaccctgtct 50950
ctactaaaaa ttagctgggc gtggtggcag gcgcctgtag tcccagctcc 51000
```

```
tcaggaggct gaggcagaag aatcgcttga acccgggagg cggaagttgc      51050
agtgagccta gatcgcgccc ctgcactcca gcctggcaac agagcaagac      51100
tacgtctcaa aaaaaaaata aataaaaact ctagagaagc aaaaagaata      51150
actttaaaag tgtttatgtt ctcagcaagc tttattttgg ggatgtcaga      51200
acttaactaa ccactgctcc ttctgtgtgt atgtttttcc tccagcctac      51250
cttatgttca gtattttgga ggtgtctctg ctctaagtaa acaacagttt      51300
ctaaccatca atggatttcc taataattat tggggctggg gaggagaaga      51350
tgatgacatt tttaacaggt aatggtcata acttagatat ctttctcctc      51400
tgtcaacctt cacttccagt tttttaacca atgcttggtt gttccccaag      51450
gactgaccct cagatgggat gcacccctag tcagcccaca ttcttaggtg      51500
tggcttccta caggtcctgc aggtgctaaa agggatctgt aggaaaatga      51550
gtttctgaga tttttgtatt ggcctggaaa aatgtcaaat gggaaccaag      51600
tgacggggca agtttacttt gacttgctgc atgccgtttt gtactcaagg      51650
agtaaaccaa tgtcctttgt aaaaatccct cctttcatta tggtcccctt      51700
tcactgtgaa acaagtttcc ttgagcagaa tcctaactgt cttcacagaa      51750
gctttgtgtt atatttttat tttggagtat tttcacatat acaaaagaga      51800
tactgtagta taataaacct ttgaggacct atccagcccc agcaaccatt      51850
atggcctggt cagttctgtc ccatccacat cctggggctc tttttaagct      51900
ggtaaatcat tatgatgtgg gttgtcattt acagtggtaa aaaacatcta      51950
tcagtagcat ttgaaagaac attctgctca gtcctctggc tgtagaggct      52000
tcaaccccac cagccaccga tgagcacctt ctccctccag gagccagtct      52050
gagctcatta ctgagtttaa tatcagaata caccctggtg cagcctttct      52100
aaattgcagt accagttaac agaaggtgtc tgtcagagca acacccaagt      52150
cattcaagtt accattgtgt gcaaacttaa cagagaccca cgtcttcaat      52200
ataagccttg aaggaaactc cagttttagt atgtagatgg ggtatcaagt      52250
gtgtgcacat tgaacatctg ctgcatacag agcactgtgc caggcaggcc      52300
caggacactg aaaacctgga catagggtcc agacagaagc aagcctgctt      52350
ccacagaggc actcctgggc agacactctg gactgatatg acagtgtgca      52400
gggccgacag gataccacag gtctgaatgg tcagaacagc tggggaggga      52450
gggagcatcc gcaggcatct agtcccatgc taacgcagtg gcactagaag      52500
gatgggtggt gtgtggagca actttcttga aagataaagg acctaacact      52550
ttctatgcac cacttactgt gtgccaggca aggccaggaa tgtttaagtg      52600
gtctgggatc agccagttct gcctcttaac taactttgct gtcctgctct      52650
ccaggctttc attttggtcc tcattccttt tccttggacc aacacagaat      52700
cctccaccct gttctggctg cctctagtct tgttctcagc cctccatttg      52750
tttttttctg ccttttccca catgttctga agccctccat tcgtatacta      52800
ctttccagag acttccccat ggctaaaagc attttggaaa tactgtatat      52850
taggcccctt tcagatactg gcaaccgttt gtgggatgct ctgagaaggc      52900
ctctgtgact tagcctggcc cttttcagcc catcacctgc cacgtcctac      52950
```

cccagaccct tgtcaccagt ccccaggagc ttacgttgct ccctgagggc 53000
actaggcttg ctctcacttc catgcctttg cctgtgccat cctggctgcc 53050
caaaatgcta tggcagatac ctgttcatcc tcaactgggc tctgcctagg 53100
cttgctccag cagaggttac aaactctatg cttcttcctc tgtgtctcca 53150
acctcatctt cctcttctca cctccatcct ggccctaaag gccctatgtt 53200
tgaagcattc acactgtata ttctgtgggg cacacggccc cagtgtctgg 53250
cacatggtag tcaacaccac aaaccgcaga accagttgta aaaggacatg 53300
gagtcggaat gtgagtttta accagggtca tgctgggctg ggttctggca 53350
tgatgctggg ttgtgggctg agtgagaaca gcaagggtga tggtggatgg 53400
agcaacagtc ttgcagccgg ggctctcagg ccaagtgtat ggcagctctg 53450
tgataatgac tttcccttta ctctttgcag attagttttt agaggcatgt 53500
ctatatctcg cccaaatgct gtggtcggga ggtgtcgcat gatccgccac 53550
tcaagagaca agaaaaatga acccaatcct cagaggtgca ttctttgttt 53600
attcatactc cttccccctt taggatgagg taggctgcag gtccgaggct 53650
ctgggcctag agggaaattg aggtggtcag gttacagtgg agagggagga 53700
ggaagtacgt gtgatgattt cttcttaaga tttttgtttt aagacaatct 53750
ccttgtgctc ttttccttgt aggtttgacc gaattgcaca cacaaaggag 53800
acaatgctct ctgatggttt gaactcactc acctaccagg tgctggatgt 53850
acagagatac ccattgtata cccaaatcac agtggacatc gggacaccga 53900
gctagcgttt tggtacacgg ataagagacc tgaaattagc cagggacctc 53950
tgctgtgtgt ctctgccaat ctgctgggct ggtccctctc atttttacca 54000
gtctgagtga caggtcccct tcgctcatca ttcagatggc tttccagatg 54050
accaggacga gtgggatatt ttgcccccaa cttggctcgg catgtgaatt 54100
cttagctctg caaggtgttt atgcctttgc gggtttcttg atgtgttcgc 54150
agtgtcaccc cagagtcaga actgtacaca tcccaaaatt tggtggccgt 54200
ggaacacatt cccggtgata gaattgctaa attgtcgtga aataggttag 54250
aatttttctt taaattatgg ttttcttatt cgtgaaaatt cggagagtgc 54300
tgctaaaatt ggattggtgt gatctttttg gtagttgtaa tttaacagaa 54350
aaacacaaaa tttcaaccat tcttaatgtt acgtcctccc cccacccccct 54400 tctttcagtg gtatgcaacc actgcaatca ctgtgcatat gtcttttctt 54450
agcaaaagga ttttaaaact tgagccctgg accttttgtc ctatgtgtgt 54500
ggattccagg gcaactctag catcagagca aaagccttgg gtttctcgca 54550
ttcagtggcc tatctccaga ttgtctgatt tctgaatgta aagttgttgt 54600
gttttttttt aaatagtagt ttgtagtatt ttaaagaaag aacagatcga 54650
gttctaatta tgatctagct tgattttgtg ttgatccaaa tttgcatagc 54700
tgtttaatgt taagtcatga caatttattt ttcttggcat gctatgtaaa 54750
cttgaatttc ctatgtattt ttattgtggt gttttaaata tggggagggg 54800
tattgagcat tttttaggga gaaaaataaa tatatgctgt agtggccaca 54850
aataggccta tgatttagct ggcaggccag gttttctcaa gagcaaaatc 54900
accctctggc cccttggcag gtaaggcctc ccggtcagca ttatcctgcc 54950
agacctcggg gaggatacct gggagacaga agcctctgca cctactgtgc 55000
agaactctcc acttccccaa ccctccccag gtgggcaggg cggagggagc 55050
ctcagcctcc ttagactgac ccctcaggcc cctaggctgg ggggttgtaa 55100
ataacagcag tcaggttgtt taccagccct ttgcacctcc ccaggcagag 55150
ggagcctctg ttctggtggg ggccacctcc ctcagaggct ctgctagcca 55200
cactccgtgg cccacccttt gttaccagtt cttcctcctt cctcttttcc 55250
cctgcctttc tcattccttc cttcgtctcc ctttttgttc ctttgcctct 55300
tgcctgtccc ctaaaacttg actgtggcac tcagggtcaa acagactatc 55350
cattccccag catgaatgtg ccttttaatt agtgatctag aaagaagttc 55400
agccgaaccc acaccccaac tccctcccaa gaacttcggt gcctaaagcc 55450
tcctgttcca cctcaggttt tcacaggtgc tcccacccca gttgaggctc 55500
ccacccacag ggctgtctgt cacaaaccca cctctgttgg gagctattga 55550
gccacctggg atgagatgac acaaggcact cctaccactg agcgcctttg 55600
ccaggtccag cctgggctca ggttccaaga ctcagctgcc taatcccagg 55650
gttgagcctt gtgctcgtgg cggaccccaa accactgccc tcctgggtac 55700
cagccctcag tgtggaggct gagctggtgc ctggccccag tcttatctgt 55750
gcctttactg ctttgcgcat ctcagatgct aacttggttc tttttccaga 55800
agcctttgta ttggttaaaa attattttcc attgcagaag cagctggact 55850
atgcaaaaag tatttctctg tcagttcccc actctatacc aaggatatta 55900
ttaaaactag aaatgactgc attgagaggg agttgtggga aataagaaga 55950
atgaaagcct ctctttctgt ccgcagatcc tgacttttcc aaagtgcctt 56000
aaaagaaatc agacaaatgc cctgagtggt aacttctgtg ttattttact 56050
cttaaaacca aactctacct tttcttgttg tttttttttt tttttttttt 56100
ttttttttgg ttaccttctc attcatgtca agtatgtggt tcattcttag 56150
aaccaaggga aatactgctc cccccatttg ctgacgtagt gctctcatgg 56200
gctcacctgg gcccaaggca cagccagggc acagttaggc ctggatgttt 56250
gcctggtccg tgagatgccg cgggtcctgt ttccttactg gggatttcag 56300
ggctgggggt tcagggagca tttccttttc ctgggagtta tgaccgcgaa 56350
gttgtcatgt gccgtgccct tttctgtttc tgtgtatcct attgctggtg 56400
actctgtgtg aactggcctt tgggaaagat cagagagggc agaggtggca 56450
caggacagta aaggagatgc tgtgctggcc ttcagcctgg acagggtctc 56500
tgctgactgc caggggcggg ggctctgcat agccaggatg acggctttca 56550
tgtcccagag acctgttgtg ctgtgtattt tgatttcctg tgtatgcaaa 56600
tgtgtgtatt taccattgtg tagggggctg tgtctgatct tggtgttcaa 56650
aacagaactg tatttttgcc tttaaaatta aataatataa cgtgaataaa 56700
tgaccctatc tttgtaac 56718

<210> SEQ ID NO 2
<211> LENGTH: 56718
<212> TYPE: DNA
<213> ORGANISM: Homo sapien
<220> FEATURE:

<223> OTHER INFORMATION: variant B4GALT1 genomic sequence

<400> SEQUENCE: 2

```
gcgcctcggg cggcttctcg ccgctcccag gtctggctgg ctggaggagt        50
ctcagctctc agccgctcgc ccgcccccgc tccgggccct cccctagtcg       100
ccgctgtggg gcagcgcctg gcgggcggcc cgcgggcggg tcgcctcccc       150
tcctgtagcc cacacccttc ttaaagcggc ggcgggaaga tgaggcttcg       200
ggagccgctc ctgagcggca gcgccgcgat gccaggcgcg tccctacagc       250
gggcctgccg cctgctcgtg gccgtctgcg ctctgcacct tggcgtcacc       300
ctcgtttact acctggctgg ccgcgacctg agccgcctgc cccaactggt       350
cggagtctcc acaccgctgc agggcggctc gaacagtgcc gccgccatcg       400
ggcagtcctc cggggagctc cggaccggag gggcccggcc gccgcctcct       450
ctaggcgcct cctcccagcc gcgcccgggt ggcgactcca gcccagtcgt       500
ggattctggc cctggccccg ctagcaactt gacctcggtc ccagtgcccc       550
acaccaccgc actgtcgctg cccgcctgcc ctgaggagtc cccgctgctt       600
ggtaaggact cgggtcggcg ccagtcggag gattgggacc cccccggatt       650
tccccgacag ggtcccccag acattccctc aggctggctc ttctacgaca       700
gccagcctcc ctcttctgga tcagagtttt aaatcccaga cagaggcttg       750
ggactggatg ggagagaagg tttgcgaggt gggtccctgg ggagtcctgt       800
tggaggcgtg gggccgggac cgcacaggga agtcccgagg cccctctagc       850
cccagaacca gagaaggcct tggagacttc cctgctgtgg cccgaggctc       900
aggaagtttt ggagtttggg tctgcttagg gcttcgagca gccttgcact       950
gagaactctg gtagggacct cgagtaatcc actccctttt ggggactgac      1000
gtgaggctcc cggtggggaa ggagactgac ctctcggttc acgtgtcttg      1050
ccatagagcc actctcctga gtgggttttt ctcctgatcg tttgggccaa      1100
gtgacttctc tctgaacctc atatttctct tctgggataa taaatggtca      1150
ccctttcaag gggttgtttt ggaagatatt gtgaacaatg gtaaataagg      1200
gcttaattaa tgagggtaag ccctcagtaa attgtcactg tgtgttcatt      1250
tcttcctctg tgtggatcgt gaccgagagc ccttcccccct agcctcctcc     1300
tggtatgggt acccaaaacc taggtgagca gggatctctc ccaggggcag      1350
agagcttgtg tactctgggt gttagagggc taaaatataa ccagtcaaca      1400
ccacgttgcc catttctggt acttccggta gcagcctgag tctcaattat      1450
cttgcccaga tgatctgaac tctgacctct agcctgtttc agcataggca      1500
gagagcttga gtaggtgagt ttgcattcct catagcagct ggctgagcct      1550
agtctggact tctctttgac ctgtaaccta caggcccaca ggcccaaggc      1600
aaccacaggt tgcttccagg gttaccacac aggtggtttc tcatttctaa      1650
tgctaggttt tagataattg ttgtaagtga ggggccctgg caggcaggat      1700
gacatcctgc caataggagt tttctgtcac tttcccacag agccctggct      1750
actacatact cttgctcaat ttcgccagta attgcgtcaa tgtgttcata      1800
tcaagtttgg gaagaacatc ttggaattgg tcagacgtga actgtggtaa      1850
taatgggggc ttgttttttt aagcagataa ttaaattcct ttgcatttga      1900
```

```
tgattattct gggaagcaga ctagtcccat aaaatgaaat ggactctgcc    1950
ttgctgctaa gtgtctgact tgagacatgc tatcgagttt ctcaaaatct    2000
cttccttgtg taaaatgtgg ttgtcgatga ttaccttaca ggggtttttt    2050
taagactaaa tgagatcgtg tacattaaat acaggcactc aggctgggca    2100
tggtggctca cgcctgtaat cctagcactt tgggaggctg aggggagtgg    2150
atcacttgag gttaggagtt tgagaccagc ctggccaata tggtgaaaca    2200
ccatcccatc tctacaaaaa tacaaaaaag ttagccaggg gtggtggcat    2250
cgcagctact caggaggccg aggcaggaga attgcttgaa cctgggaggc    2300
agaggttgca gtgagtcaag attgtgccag tacactccag cctgggcgac    2350
gaagcaagac tgtctaaaaa aaaaaaaaaa aaaaaaaata cgggcactca    2400
atacaccgta taataataat atagtaataa tatttgctta ggatctttaa    2450
aaagtttcat tttttcagac tcccacagaa atggctctgc acagcagagt    2500
gaagggggag agagactgag tctccaggcc agaaaaaggc caggtttttt    2550
gcttttgttt ttagttgttg cctggatatt gcacagaaag aaaaaaataat    2600
tagcaagtta aacaaaagta ccgcaaagtt gattacattg gtatttgagt    2650
atcacatctt ctctcagaag cgtaagagac aaggtcgtga ccatacctct    2700
gcttagtttt gttttgtaat ggtgttgcta gtgatcggct tgtcaccagt    2750
tactggtgtt tctaaatgga ctataattgg ctacttgaaa ggacttcctg    2800
agaaagaaca ttttggagga cgaggagaga gtgccttctc tattttggct    2850
gctttcatgt gacatgcaag agaccatgac gtttaggctg ctgctgaggc    2900
agccccagaa atgggggccg agaggtcttt tcttcatttt aatagggtct    2950
gtaggtttgg gtggttaggt acagttctca gaatggaggt tcctggctat    3000
gaggccttga gaaagctgaa agtctccttg ggagtgtgtg ggtgggggga    3050
gtcgagccca tctgttcatg ggcaggtgtc agccaaagcc cttgcgggtg    3100
gttttgaggt tggtgggaga aagcatccgt ggggtttaga gttgtggcct    3150
tttcactact tgcagttcct ttccccgact tggctttact ttctggtgtc    3200
caggggtctg ggccagatgc tgagattcct ctcagctgac aggtgtgggt    3250
tatgggcaaa cccttccctg gaggacataa ggcaccggat tggactgctg    3300
atgggttgct gttggagttg tcagggcctt ggaatagtct tcagatagac    3350
ttgggttagt gtgacctggg gcaggctgca ggtttggagc catagtaccc    3400
cccgccccca caccgggcac cctgctctgg gctaatgtga ggcttgcagg    3450
agtgagtgat gcagtgggaa ggggggcctt tcctgaggat tctacagctt    3500
tctccaggga atcctcccag gtagtttagg cctgcaggtg ctatgctatc    3550
cttctttcct aaccctgtct caggtcctca gcggggccat gcggcatcca    3600
cttataaccc tgcagcgagg ccctcttttc tggccacctg ggtgtttgcc    3650
tgctgagatg ggaggaacag tggccttggg cttcttcccc cgtcatgttt    3700
atctctgctc agattgggca gcagctcaat gggacttgac cagctgtggc    3750
actgccagtc tgaagatgag tagggtgatg gggggaggtg ggcagtacct    3800
gaagctgaac tggtgagaga ggcaggctgg cctgggggct cagctggggc    3850
```

```
ctgggatggt tggtacagtc ccctcagggg ggtaggggag tgagtgttag      3900
actgcttaag cctcagaggc cgctcttgcc cacctatgct ttgaggagat      3950
cctcttcatt tgttcaaagg gaagactctg atctagagat gggcacttgg      4000
accagcaaac agcagctaca ggtagccagg gcacccgagg agcacttgct      4050
catgagccgg tttccctggt tttatggggg gctgttgctg agcgtctgcc      4100
agggtttgtg tcctagcact tgctggtctt tgctgggctc tcagctctca      4150
ggtgtttctc taccagcacg tttccccctc cctcatatgc acacatgtgg      4200
acacaagcag gctgcccagg acagagtgta ctttgaggct tgggaaagga      4250
ctctctctcg cccttttggg gatgagcctt ggaacctcat caccttccgg      4300
cttggggtgg agcttcatcc tgggggttga agctttaggc tcagataact      4350
agtcttgtaa gccagttttg tcctgttgtt tttttcgtgg aaaataatgt      4400
attgacgtat acacagacat tctttgtcta acagtctgag attgagaaat      4450
accctccatg actatttggt ttgctttcat ggtgaaactt ggtcgctttc      4500
ttagacacag cctatggcaa taagagtgat ccctggctgc tgtaattcat      4550
tccagacttt gagcaaacac aaggcaccgc ctccacctgc agtggagcct      4600
ctgatgaacc aaatggaaac tccttgggga atggggagta agagccaaat      4650
gtgggattgg acttaaactg cagcttctta gaactgtagc attccacgat      4700
gggattgtct agtgctcttc ctggaggtta ctattcaata gttggctagt      4750
gcacaggttc aggggtgacc tgatatgccc tagcgtttca gaagatccct      4800
gcaaggtgtg tcttttggtc catctgaagg gtcttgtatg gtgatcttgt      4850
atggatatcc gtgacggcta aggcatctga taacttcatt ccttcagttc      4900
cagcagtgtt cctgtattat gctgggcact agagctacaa agaagaaaac      4950
aaagtgcctc ctcttcagga actcttaatt taggcagggg aggcataatt      5000
gaacagtgct gaggtcatct aggggaacca aagtgtgtat ttatcccctt      5050
ccctatcact cccctccctc cttcatttct tcctttcttc tttcagaaac      5100
tccaagttca tatcaaaatt ctccagccct ggttttattt ggttgtgtga      5150
aaatttcct ctaatttctg aagctatgca ttagttctgc tgagtaatct       5200
ttaacttgct gctttataat gattataatg agatatcact gggtattatg      5250
gtctttgggt agcagcaggg tagggatttc caggctggga ctaagctaat      5300
ttatgggttg ggaattatgg ggcagttaat agcaaggcag tccaagcttt      5350
ccacagattc caccctaggg accatccaga cttaaggaac agggccggca      5400
ggctcatccc ctttgcactc agctgggcta tgggtgtgtg tttgtgaaag      5450
aggtttattc agtagtcata cctgctgatt tccctgctat ctgtttaccc      5500
agtgcctcct gtaccttgtt tcttactctt tgttctctgc tcttactatg      5550
aagaagcaga gactggaatt ctgcttgaac ccacatctac ctggaaattc      5600
cagtttttct tgtccagtgg agcagcaatc cagttgtttt aggacaaatg      5650
gtctgccctt gaagcttaaa tcctttgagg gcctggcatg gtgacagttt      5700
tacatttggc tttggtatag actggtgtgg tccctgggca gtgaggtcac      5750
tgtaaggcca gccagccaga ccctggctcc taggggaatt aacaaggcat      5800
gggattagac tcacagggtc cctcctgtcc ctaaacttgg taggggttcc      5850
```

tgggagccag actgcgatta agattgtaga gacctgagac ctgagttgta 5900
ggggcctctg tgttgatctg ggccattgcc gggtgagctg aggcggtcac 5950
tagctcaagg agtgatctca ggatattgtt ctgtaagtca gagacctcca 6000
ggttggagag tggggcttgg gggtggggga cagggtttag tggggagctg 6050
gttctgggtg aatgtggcct aaagggattt gtccttagaa gacagagggg 6100
tgagtcacac actcagtgct tcaggttcca ctttgcggct tggcctcagc 6150
ccgccccttc cctgcacaaa tgaaggccag ggctatata attggctgtt 6200 gctgaattct ttggcagtga ttttaaagtc tggtctgggt gtgttatgta 6250
gctgcttctc tatccactcc ccacacccgc tgcttctcca gagcccctca 6300
caaagcccag gcagagagag agagagagag agagagaatg acttgcctca 6350
cagagatgtt ggggataggg ataggggtat gggtctttgc ttttgccttt 6400 tgaggggga taatctcttc cttcatttta aaagtaaaaa gtaatgcagg 6450
ctcattgaaa ataatttgaa aagttgaaag agatataaaa gcacacccaa 6500
attcctatca cccaaaagaa acataccggc atatttccta ctagtctttt 6550
tcatgtttaa gaatatagct gatatatttt tttttctttt tctttttgag 6600
acagggtttt tgctctgtca cccaggctgg agtgcagtga tcacggctca 6650
ctgcagcctc gacctctcgg gctaagcgat tctcccactt cagtctcccg 6700
agttgctggg accacaggtg cacaccgcca tgcctgacta atttttgtat 6750
tttttgtaga gatggggttt tgccatgttg cctaggctgg tctcgaactc 6800
cagagctcaa gtgattcacc tgccttggcc tcccaaagcg ctgggattat 6850
aggtgtcagt caccacaccc agtgttatag ctgttgtctt tatagatgaa 6900
cagatagatt gacatagatt catgtagata gcctggtgtt cagcattttt 6950
catttaagat tctgtcacag acttgaccct atacctttaa aaatcacaaa 7000
ggcagtatca tagtctgtca gctgaatatg ccataactta aaaaaatcat 7050
tcaactgttg ctgaacacac acatatacat atatagtttt tgtttttttct 7100 tagtgatgta gtgatgcttg tgcagaaagc tttatgtact ttttggatgg 7150
tttctgtagg agagctttct aaaaaaggaa aaaaagtgtt gaatgttttt 7200
tgagaagggc tagattttca agccagtctt acaaaaggat agactcattg 7250
gaaattccag atttgcttag tgctggcaga tgagtatcac ttattgctga 7300
acaatgtgtc tagaattctg attaaaaaag aaactaggtc caggaagtgc 7350
ctgggggcag gggcaaaggg ccaggctgca ggataggctc ttaggatctg 7400
gctgagcaga aatctgctgt gaacagaatc ggtgggggtg atgctttctc 7450
agtaacttct ccatttgttt ctttagcagc taagtccctg tgctggactt 7500
ctgtggacta ctgtggctct ggggctgtgg ttgtgggtga acaacagcta 7550
gctaaaccag tgctgttgac atcattgaga tgtgacgcac aggaaggtgg 7600
gagcaagctt gcaaatcaga ttctgaaaca tatagcacag ctctcccacc 7650
tccaggtggt cctgagatct agggaggagc catagtgaga aactttaggt 7700
ttctaggaat tctcttaggg agaagctctc ttagggagag gcagaacctg 7750
gttctcagtt ggggctgatt caggtgggtt agatcaataa agcctcaggc 7800
cagtgtgcca ggctattccc aaggagtata ctttgaagtt actcccttta 7850
gaatgtcctc agtggagata aattctctct gaggagcagt tttgtctgcc 7900
ggggtcattt ggcacaaagc ctggagtgct agggcgaggt tgcactgagg 7950
gaaggggcag gattatgtca gcagtgtgac ggatacagtg tgaggtcagg 8000
ctccttcctg ccccaccacg gggcctaga ggtcatgggg agggtccctg 8050
gcaggggatt caatcattgc ttggccccat gacagagtat attctaaaaa 8100
tgccttaagt ttttttcttt caaagtttct tcctgttttg cataatggcc 8150
ttttgccttt gacatcctga aaccgcagag ctgtcattgg tgttgcagga 8200
cactgccagc ttgaaaaaaa tcaacaacaa aaaaagaaac aggaaaggat 8250
gtggagttca gggtgcggcc tagggaagct ggtatttgcg ttatgggatt 8300
gtggggatgt ggtattaagg tgttgggtag cgcctgacat ttagaggagt 8350
actctgggca gagtccctgc ctgcccaaga ataggtagaa ttgagtcttc 8400
acaccaaagt caggagagac cccctccccc caggaagaga atgaacaggg 8450
actcatttcc tcattcagca aacttttatt ggtaactaca ctatatgaag 8500
tgtgagagat agacatgaac aagagaggcc cccactcttg ggcagtccct 8550
tagtagtagt agatagactc tggcaatatg gtgtggtcag agagaggaag 8600
cctgggtgct ttgagggtac tgaggaggtg cagggagcca aatgggtggt 8650
ctgggccagg gccagagtca gaatgaagga cctctcttcc agacgttgat 8700
tttagcatct ctgtctctca gtatgtttga acagtctccc ttattggaag 8750
ggcaggagtc tactgctaaa agtaacctgc gatttcctct acttgctgtc 8800
atgtggaaag aatactaaag ctgaaattcc aaaagttgca cacctttacc 8850
agcagggcag gagaggaaag gaaatggagg cagagtgagc tgaagatgat 8900
aaaagaaaga gaaggtggtg cagtttggac tgttatggac agaggaagtc 8950
tgagggtagc tggactgagg gatcaaaggg aggcagttga aagggaagag 9000
agctgcagag agggatttct tggtctgcag agggtaggag caagccttga 9050
aggctgctgg agtgaggatt ccgagccctg gtctttattc tttttctaat 9100
tcattacatc attttaggca agtcctaact cctttggtct ctgttgtctt 9150
tctgaaattt gagtgggctg ggcctgctgg tctttagcct ctgtctttct 9200
ctacctccta gattccagtt tggcgagtgg gggggaaaac ctggttgtat 9250
atgcaacgtg aaaggcctct ggaattcctt ttgaagctca ctacccatga 9300
ggcttctgct aaggatttca tcatgtctgt ctaagcagac ataaaaattt 9350
tagcaggtgg atgacccgta gaaatggcac aaggaatgtt tctttctgtc 9400
acactgtggt atttgattta agaaagttgt tatcctctct gtgcctcagt 9450
gttctcactt gtaaaatggc aataacagta tccacctcat agatgttatg 9500
aaatacaggt agtagccacg aaagggctta aaacagtgcc taacacagaa 9550
taagttgtga atatatgtta tttattattg gtagtataat gcttatttgt 9600
gaagattttg gcttttgctt tataggacct tttttttttt tagttgaaaa 9650
tacaatgtta ccatgttaaa tgttaaaaaa aattctactt accattgtaa 9700
cagaacatgc tcccacttct gtaacagagc ttgctattac ttttcaaatg 9750
catacatatt ccaatgcata tattccaatg cagttgtaga gtgaaactgt 9800

```
ttgcatgcag ccatttttat ccaacattat cttataaaat gttatgttgt      9850
ttatgattat cctaattatc ttttgttgct gtctagtatc cttatagata      9900
ttccattagc atacactatt ccaggtttca ctatcgtcga taatctagat      9950
atgaacattt ttgtagtgtg tagctctttg cttcagttga attactttcc     10000
tgggataaat tcctggggaa gaatttctag gccagaggat atggtcatct     10050
tgacaatact gattcacatt gctgcattgc tttccaagag gtttggaatc     10100
attcacaggt tctaaattgg aaaatcctgg cttttgaagt atgtggattc     10150
taagggcgat ttggatctag ctggagcctc acactgacac ttccagccag     10200
tgtgtgtgtg tgtgtgtgtg tgtgtgtgtg tgtgtgtagt tccctatgct     10250
ggacaccgtg tgtgtgtgtg tgtgtgtgtg tgtgtgtgtg tgtgtagttc     10300
cctatgctgg acaccatgtg gcctttctgg acattagggt tttcctgtga     10350
ttgcctcaga gcagttcctg ttgaattcac tctgtgtcca caaaaggagc     10400
cttactgtgg ctctttcaac acccacctac ctttgccaag ttggtttaca     10450
gaaagtaaga acattctttc cttcttcctt gatatgtggc gctaaaccta     10500
tagcatgggg caggctctgg ctttaaaaac ctgacttaaa aataatggtg     10550
ttgatcaaaa agtttgtgga tcagtttttg gaaacactgc atgtagccat     10600
ccatagaaac ttatattctg ttgggctagc ctgggcgcct gatcatttaa     10650
ctcatgtgga tgaacttcta tgtaatagcc ctggtgtatg ggatccagaa     10700
acagggccct aatgaagaaa ggcttttaaa ttatgttgga taaaaataag     10750
ttgttacaat agcccaaagt ctgcaaatat gaattgccag ttctgtcctt     10800
gtagtcatcc accatgtgcc tgcatctttt gtagactctt gtagattcag     10850
aagcccactg aattgcataa atgatggaat gattttagac ttagtgattt     10900
cagtgactaa aagtttacag atcctggccg ggcacagtgg ctcacacccg     10950
tattcccagc actttgggag gccgaggtgg gtggatcacc tgaggtcagg     11000
agtttgagac cagcctggcc aacatggtga aaccttgtct ctactaaaaa     11050
tacaaaaatt agccgggtgt ggtggcatgc acctgttgtc ccagctactt     11100
gggaggctga ggtgggagaa tggcttgaac ctgggaggcg gaggttgcag     11150
tgagcccaca tcaggccact gcactccagc ctgggtgaca gagtgagact     11200
ctgtctccac ctcccccgcc ccccgaaaaa aaaaaaagtt tacagatcca     11250
gcagatgggg catattcaat ttgtgacagc cactcccttc accttatagc     11300
tatgtcatat gtcttcttct cctttgactg cattctgcag cagtcagttg     11350
tgacttaata tggcactctg ggcccactga attaggtcag agctgctagt     11400
agtatattgt tcctagagac ctagggcaag attttcttac tacataaaat     11450
gagggagata atttcttacc tcaagatgtt ggtaagagga gtgaatgagg     11500
ttagttatat ggtaatatca gtactctgaa tgtcttttga tcaatgccta     11550
actcatcttc ttgggcacaa aaggcataca gtcagcaccc ttaggccaca     11600
tataaaattc ctccaaatgc aggttttcat ctgccttggg gcagagtcaa     11650
gagaaagaag aggaagaggc gtgaggctct gaccacaact tagggacaga     11700
atatagccca aagcgagtac cccaggccac aaggagaagg ccgctatctt     11750
```

-continued gttgaatcca cagcactgga aacttggagt gtgtgttccc ctgtgtcagt 11800
tacactggaa ttttatggct gctcacattc ttcccttcag gtggacgttg 11850
ttcatcagta tcctgggcaa gaggccatca taaaccacag acagctgagt 11900
gattaggaag aggagctgaa gagggagcat tagatgtttg attgagtctt 11950
aggtgagaaa gtatatcatt aaaacaaaaa gatagatgta ggcgggctca 12000
gtcttgtgtg cctggtgtgt tggtagaaaa actaaagcac aagcctgtag 12050
ataacctgct ttattctacc tcggggctgg tgttggaatc caggatgcca 12100
gaccctaaag tccagctctc tttccaacct actgaataat ccgagagaaa 12150
tcatgttctc tctctgggcc tcagtttgcc catgtataaa atgagatgaa 12200
ggattggctg ggatgctctc cagagtctct tcctgcctgg agttctgacg 12250
tagccatgta ctcctgctca gcatcgctaa atggctttgt ggtaggacca 12300
ttgagtgctg cctccattag ggccagctat gtaatgctgg ggtggctgtc 12350
actgggccct aagagccagg attggtctta ctggagaaat ccacatccac 12400
ctaaacttaa gacccagggg tgtccaatct tttggcttcc ccaggccaca 12450
ctggaagaag aattgtcttg gaccgcatat aaaatacact aattatagcc 12500
gatgaggtta aaaaaaaaaa actcaatatt ttaagagagt tcatgaattt 12550
gtgttgagct gcattcaaag ccatcctggc cgcatgtggc ccatgggcca 12600
tcggttggac atgcttgctt tagacctccc agcaattcta gtctctaaac 12650
aggaaatcaa aagtcaagat gaatagataa gttggtcagt gtgaaaaagt 12700
aattggtggg agccactgta gatgcagggt tctaggctcc atcaacaacc 12750
acctacatca ctgaacgaaa gataatgctt gttcagcact tattacatgc 12800
caaccatggt aaaaatactt cagatgcatt gttttcatga actctcacag 12850
cagctctttt tcttgcctaa atgccccgtt agaacctcca gtacaatgtt 12900
aaatagatat gctaagagac aacatatgtg tcttgttagg gggaaaatat 12950
ccagtctttg actattaaga atggtgttag cagtgggttt ttcctaggtg 13000
ccctttatca ggttgaggaa gttcctttct attcctggtt tgttgagtat 13050
ttttatcatg aaaaggtgat gggttttgtc aaatgctttt ctgtgtctgt 13100
tgagatgatc atgttttttt gtcatttatt ctattgatat ggtatattat 13150
acattgattt ttcagatatt aatcttgcat acctgggata aatcccactt 13200
ggtcatggtg tataattctt tttatttgtt gctggattga gtttgctagt 13250
attttgttga tttgtattca taacagatag tggtctgtag tctttccctc 13300
cctccctccc tccctccctc cctcccttcc ttccttcctc tctctctctc 13350
tctctcccct cccctccctt cttttcccct cctctcccct ccccttccct 13400
ttcttctctt tcatagttgt ttaccactgt cagaaaaggt ctgttcgttt 13450
tctttcgtcg tgagatcttt gtttggtttt ggtatcaggg taatactgcc 13500
tcaaaaaatg agtagggaag tgttccttcc tcttctgtat tttgagagag 13550
tttgtggtcg gtttttatta attcttcttt aaatatctgg tagcgttcac 13600
cagtaaagcc atctgggcct gatgttttct ttgtggaaaa ctttttgatt 13650
cctaattcag tttctggtta taggtctatt cagaccttct atttttttctt 13700
aagtcagttt tgatagtttg tgtcttccaa ggagtttgct tcatctaagt 13750
catctaattt gttggcatac atttcatagt gattccttat gatccttttt 13800
atttccgtta aagttggtgt agggatagtc cctctttcat tactgattat 13850
aataatttga attttctttt tttcttagtc ttgccaaaag cttgtcattt 13900
ttattgatct tttcagagga ccaactttga gttcattatt tgttctcttt 13950
gttcttattt ttctgcttca ttaacttctc taatctttat tctttcattc 14000
tgcttgcttt tggttaagtt tgctttttct ggtgtcttaa ggtagaaggt 14050
taggttactg atttgagatt taaagatcat gctctttaaa cgttttgata 14100
gatactgtca gtttgccctc tggctttttc tcattaacag tgtataggag 14150
tgcttattcc tcacactcat accagccctg ggtgttacta acctttatat 14200
atttgccagt atcatattca gacatagtat cttgttttaa tatgtttctc 14250
tgattactga tgaagttaag caaattttca cgtgtttatt ggccatctgt 14300
ctttcttttt tcatcctttc tttcaagatg ggagtctttg ccatgttgcc 14350
caggctggac tcgaactcct gggctcaaat gatcttcctg cctcagcctc 14400
ctgagtagct gggactatag gcgtgagcca ccatggctgg cttgcccatt 14450
tgtatttctt atgtgagtat tttttctttt tttttgaagt ggagtctcac 14500
tccatccccc agagtggagt gcagttgtcc gatcttggct cactgcaacc 14550
accgcctccc aggttcaagt gattctcaca ccttagcctc ccaagtatct 14600
gggactatag gtgtgtgcca ccacacctgg ctaatatttg tatttttagc 14650
agagatgggg tttcaccatg ttggccaggc tggtttcaaa ctggcctcaa 14700
gtgattcacc tgcctcggcc tcccaaagtg ctgggattac aggtgtgagc 14750
cactgtgccc agctgacttt ttttttcttt tttttaaccc tttttttttt 14800
ttaccctttt tttggcccat ttttttttac cctttttctt ttaacccatt 14850
tttctattag ttttaaaaat atgtttgcag gagcttttta tattgtggat 14900
ttttcttgtt tattacatat catttgtaaa tatggtctct ccatctgtca 14950
ctcttcttta tctctggttt ctttagctat gtagaagttg ttatgttatg 15000
ttatgttatg ttatgttatg ttatgttatg ttatgttatg ttatgttatt 15050
ttttggagag ggagtcttgc tctgtcgccc aggctggagt gcagtggtga 15100
aatctcggct cactgcaacc tctgcctcct gggttcaagc gattctcctg 15150
cctcagcttc ccgagaagct gtgattacag gcacccgcca ccacacccag 15200
ctaatttttg tgttttagta gagacggggt ttcactatgt aggtcaagct 15250
gatctcaaac tcctgatctc aaatgatcct cccaaagtgc tggggttaca 15300
ggcgtgagcc actgcactcg gccagaagtt ttgaattttt atgtgtttaa 15350
atctatgttt tcctttatga cttcaggttg ctttcatact taagcaggtc 15400
ttcaccatcc caaaatgata aaatttttct cctgagtttt cttctaagtt 15450
ggttctttag aagccaccaa cttggcttcg acagcaaaag atgaacagaa 15500
tttctgttca actctcatgc tgcaagaagc tttatgtaat actccaggga 15550
ccctttaagg tcccagagtt ttcctccaaa tctatcagtg attctagtgg 15600
ctaagagtag aaatgtgaaa atttagccat gtgtgctgat agagctgtag 15650
taatttgtaa gctctgaagt tctaaggagt caggggagaa gggaaagtaa 15700
catttattga acatctatta gctcaataag aacatgcgat aagtatgtat 15750
atgtattatt tcacttacat ctgaaaggaa ggcataatta tccccactcc 15800
ttagagaagg aaattggagc tggctacatt taaagtagtc ctgacaccag 15850
agagatattg ccaggagtac ttggctggct gagtgcccag atggcccata 15900
ggagtagtgg gccctccaca gtccaaggtc tggttctagg tggagagaga 15950
aggatgtgct cgtagtcagc accgcagctc cagaaaatct gctggggctc 16000
caaaactgat tagaggggca gctgactcag taataaaact cccaggagac 16050
ttacttacat actggaatgc aaagttgcag ctttactggg aagattagaa 16100
ctgttattga gtagcttaga aatctctggc tgaattcact gcaagggaag 16150
ccgcaggata agctaactgc tggtgagtca gcagtcagag cagggaagtg 16200
aatttaacat tagatgggtc agtctctcgt ggctgatgaa ttcatcccca 16250
caatactgta cacctgcctt agggaccttt gtctggacta ggggttgggg 16300
tccccctcct ttgtacagcc ctggaaggac acatccagct ccatccgcca 16350
tctctccctt acttatttcc ttccttcctt ccttctttcc atccagccat 16400
caagcttcct ttcatggcca ataatcatca ttggggtcta ctcatggact 16450
ctcttgcctc atgtatttgt tttattttgt cctcattccc acttctattt 16500
cccaggtata tcacaggcaa ctattctaac gtatttatag tttgtgtatc 16550
tgtttttgct cttgccaaaa tggaagccac tgctttatac atagatgtat 16600
tcttaacttt aaaaaaaatt tttttagatt aacctacaat aaaattggct 16650
ttttggcata tagtctataa attttaacac atacatattt ttgtgtatct 16700
accaccacaa tcaggataca gaacagttcc atcaccccaa aaaaatccct 16750
cttgtagtca cattctcctc ccacccttaa tcccaggcaa ccactgatct 16800
attcttcatt actattgttt tgtctttttg aggatgtcac ataaatggag 16850
tcacacagta tatatacatt tttttaaaca tatgtaaatg gcattttata 16900
gctcattttg attatatgtt tttcatccag ttctgttttt tttttttatt 16950
tttaaaaagt ttgacataac ttcagactta cagaaaagtt gttagactaa 17000
tacaaagaat tcctggatat cctttggagt ccctaaatgt taacatttta 17050
ctatatttac tttttccttc tctctctctc tctctctcgc tctgtgtgtg 17100
tgtgtgtgtg tgtgtgtgtg tgtgtatcta cctgtagata gatagatatt 17150
aatataattt tagatagatg tatctagatc tctctctctc atatatatgt 17200
gtgtgtgtat atatctatat ctatatctat atatatctcc ttttaccctt 17250
aaatattcag tgtatatttc ctaacaacaa ggtgatttaa aaatatatat 17300
ataaacatag tataattaac aatcaggaca tcaacattga aacatttctg 17350
ctatgtcatc tacaggcctt aggaagactt tgtcaggtgc cccaataata 17400
gccttgatgg tagaagaaaa ccatgtgttg tattcagttg tcatgtctct 17450
tagtgtcttg taatctgaaa taattcccaa gccctttgga tttcatgaca 17500
gtgacattgt tgaagagtac aggccagtta ttttgtagaa ggtctctcag 17550
tttaggtctg tctgatgttt cctcctgatc agattcaggt tattcacttt 17600
tgacaggaat accactgaaa tgatgctgag ttcttctcag tgtaacgaga 17650
tctagagaca cacactgtca gtttgttcct tattggcagt gtgaaccttg 17700
aggatttcat tgtagtggca tttggcatta ctccattata gttactattt 17750
taccatttta aattaaaact atctggccgg gcgtagtagc tcatgtctgt 17800
aatcccagca ctttaggagg ctgaggcggg caaattgctt gaggtcagaa 17850
gtttgaaacc atcctagcca acataacatg gtgaaacgcc atctctataa 17900
aaaatacaaa aaattagcct ggcgtggtgg cgcatttgta gttccagcta 17950
ctcaggaggc tgaggcacaa ggcttgcttg agcctgggag gcggaggttg 18000
cagtgagctg aaatcacgcc actgcactct agccagggtg acagagtgag 18050
actctgtctc aaaaaaaaaa agtaaataaa taaaaaaatt ttttaagtat 18100
cttatgggca tatacttgtc ctgttactcc tcaaactttc atccactttt 18150
ttttttttaa attttttttc ttacctttca tcgttttctt gatatccact 18200
gggttttagc atctacaaat gattcttgcc tgaatcagtt attatggtag 18250
ttgatggttt tctaattcca ttattccttc tatgtttgtt aattttggca 18300
ttcttctata aggaagagct taccctttttt ccctattaat taattcatat 18350
attaatgcag acctatgcat tcttacttca ttaaatcata atcctttact 18400
atcattatgt attctgatgt tcagactatc ccagatttag ccaataagat 18450
ccccttcagg ggaatggtct ttgggattcc tctttagagg ttcctggttc 18500
ctgttttctt ttgacatatc ctattactct ttgagcattt tttttttttt 18550
ttttactttt aggcacagca agaagttcca tggtcctctt gttctttccc 18600
caactcagcc ctagagtcag tcacttctcc aatgagctct agttcctttt 18650
agtagagaat cataattaga aaacaagaat cagtgccaag tgtgcacctt 18700
tgtttttaag gtccatccac gttgccgtgt atatgtccag catgttgatt 18750
ctaactgctg aataatacct catgattgtc atccatccca gtgtttcttt 18800
ttcccttctg taatgaggga ctcctggact gcctccagca ttaccttcac 18850
aaatattgct gtgaggaaaa tccttaaacg tttcctttat gggcaacgtg 18900
tgagcatgtt tatgttgatt caggggtgcc agacacagct ccagaatggc 18950
tgcctcagtt tacatttcca ccagcagagc atgacaggct ctgtgtctcc 19000
gtgaataatc agcattaacc agcttcctat tttttgccaa actaatagat 19050
gtgctaggat aactctttgt tttaacttgt ttttctctga ttaccaatga 19100
gctggagcat ttcttcatat gcctgatggt ctttgggatt cctcttaggt 19150
aaattgctta ttcattataa tcctttgcct gtttttcact ggagttctta 19200
tatttttctt gaagatatgc aggaattcct tatacatcct agatattaat 19250
cccttcctgg tctcagacat tgcagatatc ttctgaatct gttatttact 19300
tatttattta caattttttt tttaagagtt ggggttttgc tctgtcaccc 19350
agactggagt gcagtggtat gatcatgact cattgtggcc tcgcaatcct 19400
gggcttaagc gatcctccca cctcagcctc ctgagtagtt gggactacag 19450
gtatgcacca ccagacttgg ctaattttat tttatttttt agagatggaa 19500
gtcttaatat gttgctcagg ccaatcttga actcctggcc tcaagcaatc 19550
tttccacctc agcctcctgc atctattata tatatgttca ctttgctcat 19600
gctgtatttt gttgcaacat aaaactattt ttcccattgt tttgtgcagt 19650

```
ctctcaccag cactcttctt tttctgtaac tgtgttaatg ccctttgttc 19700
ttccatatgt taggtatgct ggtatagttg aactctgctg actctcctca 19750
gtaaacagtc tctttttatg acaccttatc ctctactgaa ttctctctat 19800
caagaatgac ttggccgggc atgggggctc atgcctgtaa tcccagcatt 19850
ctgggaggcc gaggtgggca gatcacccga ggtcagaagt tcaagaccag 19900
cccggccaac acggtgaaac cctgtctcta tgaaaataca aaaatcagct 19950
gggcgtggtg gcaggtgcct gtaatcccag ctacttggga ggctgaggcg 20000
ggagaatcac ttgaacctga gggggaggtt gcagtaagcc gggatggcac 20050
attgcactcc agactgggtg atggagaaac tccatctcag gggaaaaaaa 20100
aaaaaaaaaa aaagaatgac ttgtcttcct cttagagtgt gaggtctaca 20150
tacaaatatt attcttgtat tcagcaaatg tatgtcatag gcctagtgtg 20200
tgttaggaac tgtgctgtca ccaacaaagt ttagagaggt tataaaactt 20250
gactgtagct ttttagaggt ggaggagtga tttgaaacct aggctgtaat 20300
tccttcctcc tgtgattcct tcctactgtg ttgccttccc ttgaaaattg 20350
catttggggg ccaggtgtgg tggctctcgc ctgtaatccc agcactttgg 20400
gaggctgagg cgggtggatc acctgaggtc aggagttcaa gaccagcctg 20450
gccaacatgg cgaaaccccg tctttactaa aaatacaaaa attagctgga 20500
tgtggtgtgt ggtgacatgc acctatattc ccaggtactc agtaggctga 20550
ggcaagagaa tcacttgaac ccaggaggca gaggctgcag tgagctgaaa 20600
ttgcaccact gcactccagc ctgagtgaca gagtgagact ctgtctcaaa 20650
aaaaaaaaaa agaaaagaaa gaaaattgca tttagttcct gtagactgtg 20700
tgtcaaatgt ctaaatctct tctaacaaat ggcctaagga ggtgcaaagc 20750
gaagcatcct caccagcatc ctgacttggc agtgaggcat gggaccctgg 20800
agggagtagt ggtaagtgtg actctggaat tcttcctggg ctacttgtca 20850
gtgactggct ccagattgag aggagagccc agaggacaca ggtggctgcc 20900
ccagcctgga ggtgaaagtc ttaaaataaa atgccagatg cctagaccat 20950
tctaaacctt tctgagaagc tgaaatcatc ccttctggaa gcgctctagt 21000
tctaaaagga cagatataca gcaagatctt cctggggcta atatggagtt 21050
tataggcaag taggcctcag aacctttccc tggtagtgat atctgtgggc 21100
aggcacagtt tccacacttt ccagaaattc cagcggaagg agtgagaagg 21150
aggaatctgc ccttgagtga ggaccaaaga aagcagaaat tcctcttggg 21200
aatttttcct ccagagacca aacactactt gggagcttgt ttactgggct 21250
ttaaaagctt gtgaccccca gtcactcttt cttgacccca aggctttgca 21300
tttctgtggc ttccccactg gacagaagtg gaactgtcat gctgcctgtt 21350
ctggggtctc ccagaggttt ccccatgtcc tctccttgct tctactgccc 21400
cacagaattg gggatctgtg accacatatg gtatagaatt aatgcttgag 21450
aatggtttag ttcagtgatg tcaaataaga ttcactttta tgccacctcc 21500
atcagttgaa ggcccccctg gcccctaaat tggaaaagat tctgagacag 21550
aatccccgtg ggtacagcgc agggacagta aaggcacgtg tgctgtgatt 21600
tgctatccac tgtgtggatg catccaggaa tatcagaacc ctggaagatt 21650
```

```
atttaagggg aagttaggac agctttttttg ccaatccaag ggtgttcttg    21700
aggaagtctg tcttcctgta tggccttcag tttctttcct gtgtaaccat    21750
ggggccaaca cataattccc acagctctat tggcccttgt ctgccaggat    21800
tctctagggt ctgattcgag gtggatcctg gccctttgag gtggcagaat    21850
ctgatcatgg tgctgtttcc ttagatttag gccttgatac ccttggcgag    21900
agcatcctgg gctgagtgac cacctgaggt ttttctggtg attttgtgac    21950
ccatgtaaaa ctttgagctt tgggattatt ctctcaagga aatagtgaca    22000
tttggtgaag agcctgtttg gtgtggctat gtgaggctta gccaagaaaa    22050
tgcaccattt ttattaggag gttaggccat ccgttgccac aaagtgtcag    22100
atgctaggcc tagagcctgg agaaaactta ttttaaaatt gatggggtgc    22150
tggaggggtt ggggggtggt ggctgtagct catgaatcag gtgctaaacc    22200
tagaaacaaa aggcctcatg tggcagactg tttctgagca cagatgaatg    22250
gatgagcaac tggcgcaact ttgcccagtt ggtccagctt cccacttggc    22300
cacctaggct tgctgtgaag acctcgtctg gcagaaatga gagtgttttt    22350
gccccatctt gatcttaact gtaatttaag actaaaatct tagattctaa    22400
aacatcaaag gcaagatggc tcccagctct gtgagctcag cttctcacct    22450
cttagttgaa caagtgcagt gtgggtcaat acatgattgc tgctcttgct    22500
gccaggaact gtcccagcat agaaaggaat gggacacaat ccctgccgtc    22550
aagattctaa gggaggaagc aggcaggtcg actggtgcct catctctgca    22600
gggctccagc caaggtttgt gaaggatttt gcaggcatat ggagtgggga    22650
ctgattgatc ccgagagggg actggggaaa gctctgaaga ggggatgaca    22700
tttggtttga actccaaaaa atggttgctt tacctgtttc ctgaagtttt    22750
tgaggtggct tataagaaca tataccataa aaaggaccaa tataaattta    22800
aaatcagaaa aagagaaaat gggctgggca tggtggctca tgcctgtaat    22850
cccagcactt tgggaggcca aggtgggtgg atcgtgaggt caggagatcg    22900
agaccatcct gcctggccaa catggtgaaa ccccggctct actaaaaata    22950
caaaaaatta gctgggtgtg gtggcacatg cctgtagtcc cacctacttg    23000
ggaggctgag gcaggagaat cgcttgaaac ctgggaggcg gaggttgcag    23050
tgagctgaga tcgcaccact gcactccagc ctgggcgaca gagtgagact    23100
cctcctcaaa aataaataaa taaagagaaa atggaactta gaaaattaag    23150
aggaagagtg aaaaggtaga tatttagtca ggcacagtgg ctcatgcctg    23200
taatcccaac actttgggag gccaagacag gaaaatctct tgagaccagg    23250
agcttgagac ttgcctggca acatctcagg tgagacctta tctctacaaa    23300
aaatttaaaa attagctgag ctgtgtggct cgtgactgtg atcccagcta    23350
ctcaggaggc cgagaccaca gcccaggagg atcgcttggg cccagcagtt    23400
tgaggctgca gtgagctggc accactgcaa ttcagcctgg gctacagagc    23450
aagacccagt ttaaaaaaaa aaaaaaagat attcaaacca tgggtcccaa    23500
cgtagttatt atatttgacc atttgcaaaa gctgaaagca aaacatgtta    23550
cacattttca gagaggaaaa tacacagtag ttcctgagtg taagttgttt    23600
```

-continued

```
ttcttgacct cattcttaaa ttgcttcatg agggtgggag ggaagtggta      23650
gttaataagt gaacctgtaa accagcgttt ctcaaaatgt agtccaggga      23700
attgcatcaa aattgcagtt acctacagtg cttgttaaaa tgcagattcc      23750
tgggcccctg ccccaggctt atcaaatcaa tctggtgagt aggactcaag      23800
aacctgtaaa ttcacatact tctgcagatg attcttcttg cactgcacag      23850
catgaaagcc tctgcaatag acagaaagct accagcattg cgaaagcaac      23900
ttgagtgctt ggcctttgaa ggttgagtgg gactttaatg agggagagag      23950
taaggcatga gaaatggcag ttccactgag gtcagtcagt ggttcattgc      24000
tgacgaagtc acttttaagt catgttttag aagaactacc aagtgtggca      24050
ggtcaggcat gtggcaggac tgtttctgag cacagatgaa tggatgagca      24100
cctggcccca ctgtgcccag ttggtctagc ttcccacttg gccacctacg      24150
gtctgctgtg tggaccttgt ctggcagtct cctttaattt atttttttatt     24200
attttttttct ttttgagatg gagtcttgct ttgttgccca ggctagagtg     24250
cagtggcatg atctcggctc actgcagcct ccacttccca ggttccagcg      24300
attctcctgc ctcagcctcc caggtagctg ggatcacagg caagtgccac      24350
cacgcccagc taatttttgt atttttaata gagacatggt tttaccatgt      24400
tggccaggct ggtctcgaac tcctgacctc aggtgatcca cccatctcag      24450
cctcccaaaa tgctggaatt acaggtgtga gccaccgcac ctggcctatt      24500
tttttcagc aaattctttg tttttctctc tgttcccaaa tgcagggtac      24550
tgagaccaca gatgtattct gtttcctgtt gaaaaaatgt ttctcactta      24600
gctgggtgtg gtagcatgca ctgcagtccc acgggaggct gaggcgagag      24650
gattgcttga gcccaggagt tcgataatca tgccattgca ctctggtctg      24700
ggtaacagag cgagaaactg tctcttaaaa aaaagaaaaa gaaaaagagg      24750
tcctagggaa agaaacaaat agtggcttgg atggtgagtt ggtggaaaga      24800
acagtgggtg ttgggggtgt tgaacttgtg tttgtgtgtg gtgtacccaa      24850
gacatatcat gtcagcatta agaatagact attcctgttt tctggtcact      24900
gagttgtatg ttttgacatc cttattttgg aagatacttc cttactagga      24950
atgggatagg gagggggtca cctttcccat ctgtgggtca tattttaaaa      25000
tatttattgt tcaagtttaa agatataacc aaaggtataa agaaaaatac      25050
cacaaacatc tgatttaaga aacaaaccag ccgagcgcgg tggctcgtgc      25100
ctgtaatccc agcactgtgg gaggccgagg caggcagatc atgaggtcaa      25150
gagatcgaga ccatcctggc caacatggtg aaaccccgtc tctactgaaa      25200
atacaaaaat taactggtca tggtggtgtg tgcctgtagt cccagctact      25250
cgggaggctg tggcaggaga atcgcttgaa cccaggaggc ggaggttgta      25300
gtgagccaag attgtgccac tgcattctag cctggcgaca gagtgagact      25350
ccgtctcaaa aagaaaaaaa aaagaaagaa atcatttcct acaccttcga      25400
agccttcatg agttagattt tgaaacagtg caaaatgctt cacgtgagaa      25450
tcgagagtcc cttctggtgg ctctccatcc cctgctcttc tgtcaggttt      25500
tcttgtaggt ttatggaaac ctttgttact tgtgcaggtg gcagagaagc      25550
agagaggata gctgcgcgcc acccacacag ctaggattta ttggcgtact      25600
```

cccacgtgca tggcagccaa gtggacacaa ctctgtgatg aatcctccca 25650
agagaactga ggggccctga tggaggagct gcttctttgc aaagctttcc 25700
ttgactctct tcctgtcccc tagttgattc cccttctgtg ctagttttag 25750
cttattgttt gttacctgtc acacttagca gtactgttgg ctttgctggt 25800
ctccttgact actgggggta aagacctttt gttgttgttg ttgagacaga 25850
gtcttgctct gtcgcccagg ctggagtgca atggcgtgat ttcggctcac 25900
tgcaaccttc acctcccagg ttcaagagat tctcctgcct cagcctccta 25950
agtagctggg attacagcta caccacaccc ggttaatttt tgtattttta 26000
atagagatgg ggtttagtag agatggggtt tcaccatgtt ggccaggctg 26050
gtctcaagcc cctgacctca aggtgacctg cctgtctcag cctcccaaag 26100
tgctgggatt acagacatga gccaccatgc ccagcctcaa agacctcttc 26150
tttacttgct caccctgccg cccactcccc taccaacccc tgcatgccct 26200
ataccacctg gcacatgata catactaact gggtacatgt ttgaatatga 26250
atggatgtgg tgctgtgaat gcttagggga agtgggtgaa atgcttaaga 26300
accaaccttg agtggtctgg gaaggcttcc tgggagggtg gtgtttgagc 26350
taaggccagg cagctgttag atttgttaga ctgaagccct tgcagactta 26400
gagagcttgt gctcttccca gaatgacggg tgagccacgt acagtaaatg 26450
gtgcttctca tttctagccc aaggggcctc aaggggcacc gtgatttcac 26500
gagaatgctg caagcaaatc ttttctcaag ctggggaatt tggtggtaat 26550
gcctggctca gcttgcggtg cgcacctggc ctttggaaga ttggtacaga 26600
gagaagcggc ccatccacat gagcctgtgg aacagcactg gtgggggagc 26650
tgatttgtga agaggggctg tgcagtgtac tgtcaggtct gagacccagg 26700
aagaaattcc agtatcccag ctctcagaat cacagagttc taggcactgc 26750
ctagttccac gtgttcccaa atgtttcctg aatacttgga tttcctgtcc 26800
agagaatttt caaaacaaac ttagaggcct gacccatggc tgccaaggaa 26850
ggattttttt tttaaattaa attttaaaaa tcagtccagc atgaaaatct 26900
atgatgattt cataagagaa aggacatttt aatattcaaa gagtaagaag 26950
cacttaatct tggaagaaag ggcattccta tactttgatt acctttagtt 27000
taattaaaaa acacctacat ggtctttact tctgtgattt cattcctggg 27050
ctagtgaaac attgtcacaa taaagcatca ggccaacgct tctttcgacc 27100
cactggccaa tcagttgaca aacagtgact agatgtttca gcctattttg 27150
ctgaggctaa aggattgaac tagtgcttca gccagcatga aaaccagtca 27200
ggagtccgtg ctggtgttgg cttagattag cagggccttt gatggagggg 27250
catgtatgtg tttgggtttg ctgtgccagg caggggagca gtggaatttg 27300
tctgaattga gctcacacat tgaagttatt gagcgactta catgcaaggc 27350
catgacctgg actcccagcc gagaggccca cgtggcgggg cttgagctgg 27400
gggagccgag gacagcttac atctgctcat ctgcttacgt aaccctgcct 27450
cccagcttcc agagccaaga aaacacacaa gccagcccag cggggccgag 27500
agcctgtggt agcacacgcc atgcgccgca cagcaagggc gccttggctc 27550
ggcttgaggc ctgtcatgaa gccctcagcc ctctgcctcc tcccagagct 27600
tctccccacc accccaggca gtggctctga aacctggtcg caggtctgca 27650
tgattctgaa cagaggtagt cgttgccttc ctggagtctg agctctctgg 27700
agtttctcac tgggacagag ccaggtgtgt agcagagcat ggtccctgca 27750
gtatggcagg aggtgtgcag ggcattcagg aggcctcctg gctggcactc 27800
gacccaatta gtcattcaac gccaggtctg ggctgctgt ctgttgtctc 27850 aaaggtgtga gctgcaagat ccttagagtt gtggagaaaa aattgccaga 27900
ttggcaagaa gggcaggatt gggggtcaag gtgtctcagt gtgttggaag 27950
catgatgggg gttgtgcaag gggcacagcg agttcagaag ggagcaggag 28000
agtgagaaga ggctgttcag tgataaagct ctgcacagag ccattggagg 28050
agcaagctcc ttgaccatcc ttaaaccagg gtaattttca tttaggttct 28100
gccacacgct cagcagggaa ctcctggaag gcaggatttg tcttgtccat 28150
cctccctccc tacctcaacc cactcctcct tgggctggca cacagtaggt 28200
acccagaaag tatcaattga aacaaattga aagtggtctt gatacatatc 28250
acagggcaag tttgcagtta acagacattt cagagtaaag actctctggc 28300
ttggtgctcg atcggcttct gtgggttgtc agcatgctgt ggacagcccc 28350
ggcatgggag cgagtgggcg tgtgtgtgtg tgtatgtgag ggtgagagag 28400
cgttagtgtg tgtgttgggg ttggggagag aggaggggga atagaagatg 28450
gaccacccgg gtatcagctt ctgccctggg gagatggtgg tgtcagttgc 28500
tgagggaatc ctgagaagca ggtctggctg taggtggtga tggtggtggg 28550
gttgcatgag aatccatttg gggcaggttg aatttgaggt gcccatgaca 28600
tatggctagc catgttctgt tggctgtgag gtcaggagag agacatgaga 28650
tggaaacaga ggtttgggaa ctgtcatgtg cttaaaccaa agacctgggt 28700
atagggagag tgagaagaga agggggcaaa gatggacatc caagaaagaa 28750
gctgagaaag cctaggaatt tgaggtaaga ggagacgtag gtaaatgtga 28800
cgcttggtga tcaaggcttc tttccacctc tcctatgctg gacactcacg 28850
tctcctgtct gcttggaaat tcatgctgag ggcagggaag gtgggagcaa 28900
ggatttgtct aaagatcttg ctttggatcc ctgcactcct cctggtttac 28950
caagtgtcac tggacacgtc agggcgttct gagaccttag agagcatcca 29000
gtcctgtccc tgcagtttac aaatgaggaa accagtaccc tgagagtggc 29050
tgtactatcc actctcagga taccaaagat catctggaaa gtcactggtg 29100
gagctggacc ggggcccagg catctcttct cctgtccggg gctcttgact 29150
tcaggaccac ctttctgaaa cccatgatgg ggcaacacca ggacactttc 29200
cagcctgcag gtgtctgtcc cgcggaagcg agccaggcca catgtgaatt 29250
cctgttttct gggtgggttt cagaaggtac gagcaagtcg gcagggtgac 29300
agcccaggtg cttcttgggt tccccaaaac gcggttatgt ttagcagcat 29350
cctcagaacc aaaggtgggg tgggggctgc agatgttgtg ggggccctct 29400
gaagtgaaaa gagccctgtg acagatcttt tcttcatgtt tttcacaagt 29450
tcactgtgca gcagggcccc cccagtagcc tttgcccagg gttgggtgtt 29500
gggcagccca ggcctggctg accttgtggg gaagggtgtg aatggtggga 29550
atccccgagg gccctctttg cccgaaagcc ctaagccttg acatcagatg 29600
cccatcagat ggtccatcgg agccctacta cccagcttgc ccagtgagaa 29650
tcatctgggc tccttgttag gtagccattt aggtccttcc caaaatccac 29700
agactctcta agggaagggc ccgagatgct gtacttgtac taacttcctc 29750
aagcaattct tgtgataggt ttgggaaaaa cttgtccagg gtgaccactg 29800
actgagtcct ggtcttctct gaagagcaca gtgcctgctc actttagggc 29850
accctgggag gtgggagctg gctcagcagg cagtcttata agggactgag 29900
cttcaaggcc tctgtccctc caggagggag gtgcatgacc agagagggag 29950
gcctgaggat cttcttccct gccccagagg gtctgctgcc tgagctctgt 30000
gatagcgcag agagtaaaag gatcaagctt gattgaggcc tatctctcaa 30050
tgcgaaagtt tgctagttaa gaggagagtg ggaagggcat ttctggcaaa 30100
gagaaaagtg tggacaggca tggcttaagg gatggggagg gagacagaca 30150
gagctgaggg tgaagggcct tttgctcagc tgtgggcctt ggccttccct 30200
tgtgcaggga cacacagcct tagagccact ggaggtttta gtgggaaagt 30250
aatatggtcg gggctgtatc tcagaagaaa acaaactaat gggaacaggt 30300
cctgtgatgg tggacctggg tcagctacgg agggagggaa gatgtgagat 30350
gtgtactggg gaagggggtg gaagtggcag ctatctggtg agaggaagca 30400
ggcccacagc ttttttctc aagctgttga attcagaagg gcgagtgatt 30450
ccgggagtag gggtgcttg gagagccacg cgttattgat aaacagggca 30500
ggctgaagcc tgctcactgg ccctgggcgg gttctcacca gcatgtttca 30550
ggttttgatc tgtgcttgtg gttggtgttc ctacctgttc tctaggttcc 30600
ttcctttgtt cttgtggctc atttgcttca caggtgaagc tggttacact 30650
agagtaacag ttcccaaagt gtgttccctg gaaaaatggt tctgtagcca 30700
aataagcttg ggaaatggtg ggttaaatat aacgaagggg gtttttcgac 30750
tgcacaactt ctcagagcct ttggtgtgtg tcgtgacttt gcagaagcag 30800
gatttaatac gcagcattcc cgttcttatt tgaccacgag acatgttttt 30850
ccattaagca tcttgctggg tctgatgttt tctggaaccc attttgaggc 30900
ggtctggtct gcagagagta tggggagcct gggttcaagc cttggctctt 30950
gactctcagc agagccttga ttccctgtgt tgcctggact gcaccacgtg 31000
taccacatac ccggtatgtg acgttttcct catccctctt cccacctgcc 31050
gttacctcac aatccacaat ctgcacctca tccatttttc ttctgaggca 31100
agcactctct tactaactta cttatctcat ctgcatccat gttcttctag 31150
gccagaaact tgggagtcat ccctccctct ttgttacttc ttcttcctct 31200
ttgttacttt atcccctctg ttactaaaca ttcttctgtg tttccagcta 31250
tttcttttat tttccctcgg tctcctttgg ggtttctttg cctccatctc 31300
tcccagacct tggttcacct tccatcgagt cccttcctgg gacatgggca 31350
ctcatgccac tcctgctacc ttccacttcg aagctaactc cctccacact 31400
gacgtcccca acatgcatgc atacacacac acacacacac acacacatac 31450
acacacacac acacacactt ccccagttag gctagaatca gagagatgat 31500
gtcagccatt tgtccaaggc cacgcagctg ggaggtcaca gagctaagtc 31550
tcaacctcag gggttttgag aaattgcctt ctcatccgtg atcactgatt 31600
tctacaacag cctgtcagga agtctgggta gaaattactt ccattttaca 31650
gtggagtcag agcggggagg gtcctgggca ggcgagtgct tcacagagtg 31700
accaaccatc taggtttgcc ccacactgaa gggggtttct ggggatggtt 31750
ggtcacccta atgctggatg tggtgcctga tgctgggcag gagggccctc 31800
tccgtggcca cgttgcctcc caggaggaga catttcctct gcagctgcag 31850
ctgcagcctg gccatctgat gcagcctgtg gagcggtggc gagtcctgtg 31900
gcctgctaac ttctccctcc ctccacctct ctagtgggcc ccatgctgat 31950
tgagtttaac atgcctgtgg acctggagct cgtggcaaag cagaacccaa 32000
atgtgaagat gggcggccgc tatgccccca gggactgcgt ctctcctcac 32050
aaggtggcca tcatcattcc attccgcaac cggcaggagc acctcaagta 32100
ctggctatat tatttgcacc cagtcctgca gcgccagcag ctggactatg 32150
gcatctatgt tatcaaccag gtgaggcctg ggaaggtgga atgagagagg 32200
gtgtgtgtgc atgcagatgt gtatcagatg tgtgtgtaat gagggcaggg 32250
gaaggggagt gatttcacag acacctggca cttacagcga ggaaccagcc 32300
ccccagccac caccagtgca gatgaggtaa acgccaaaca gtgtgcttgc 32350
ctattgctgt caactctata gccaagggaa atgctggagt gttttcgttg 32400
ttctgttttt gttttctgga agtagccttc cagcaagatt gggaaaaaag 32450
acaaccctaa ttattccaaa gtacacactg attattccct ggctttgtgt 32500
agctgtgtat tttcctttta aaaataaaac caccatttag atgtcagact 32550
tttaggtaac ttcaaagttt atccagtcag tcagagcgtg tctcctgggg 32600
cacctggaga cagtgccctt agttcaggtc acatgcctac atgccagccc 32650
ctggtgaaat atctggagaa gtctgattcg tgggccatct gagagttatg 32700
tggactgggc cgagtctgag aaaaagtttc tcactgctcg tctgatccat 32750
atgtgttggg ctttagccct gcttaggaaa gtaatgctaa ggataggtca 32800
actttcatca ccatggcatg gagaatcaga ttgatctaag aggcatcttt 32850
attgaaataa atttttcagt ttatttgagg agcattattt tcccaagagt 32900
ataactttga tatttcaaga ttacccctaa cacttaaatt catgttttta 32950
gactataacc tcctaggtgc aatgacacat ctaacttatc taagcaccca 33000
gtttcattga aattcatttg aagagtctga gtacgcccat ttctacaagg 33050
cccaatgtcc atttcatttc gagataaact ctgctttagg taggaggatt 33100
gttggcagtt tacggcttcc atcaaggtca aggaactctg tgcaccttcc 33150
ctatgacccc aggggaagca ctcgaggact gctgtggcat tgtgctgcat 33200
cacttgctgc agggagattc tgaagaagtg taaggtctca gtcctgccct 33250
gtcccgaagc ctccaaccca cttctggcaa gtgggacctt cccagggaac 33300
aatttgttaa cagacccaaa tatcctgtga ttggatggtg gctgccaaat 33350
gctttggaag ctcagaggaa ggagagagag caatggcttg gaagaaccag 33400
gatataaact aggttctaaa gtctgcaggg agatgggctt ctcagctggg 33450
gccagtgagc agggacctta aggcagaaag gagccttgca tgttcctgga 33500
aattgagatg cccactgggg taggaaagca ccagaagctc tgggaccagg 33550
tgtcagagtt aagcctgtga ggcaggagag agcagaacaa gccctgttac 33600
aaggaaactg aagcaggaga gcaggtggtg ggcaaacccc ttgaggctgt 33650
ttgaattctt cggccaagtg aggtacagac cagggcccta tgaacacctg 33700
caagcaagac agccacgcag ttgtgggtca ccttggaaga atattggaga 33750
atgcaagaga gaacaggtaa atgtcctgca aaatgcgggt cactttaacc 33800
caacacatat tcatttaaga aaagctctgt gattgagaaa catttgtctg 33850
atgccagtta gcacatacca atgacggcaa gattcaggag cctgttatta 33900
aagcagtggc agcgagcacc tggaagaggc ggccaccatc accaggagcc 33950
agcagggatg actaataagc cgtgccagct gcatctcgtt tctctcttga 34000
cagttgctat gccagtagat gagggatgta ctgtggatac aatgctgtca 34050
tatcttattc agcagggcat ctgatagcat cccacaaatc tgcctgagta 34100
gaagacagac agctgtggtc tgggtgccat ataggtaggt taaaatatat 34150
atttgggcct aggcgcagtg gctcatgcct gtaatcccag cactttggga 34200
ggccaaggca ggcggatcac ttgaagtcag gagttcaaga ccagcctggc 34250
caacatggcg aaaccccgtc tctactaaaa atacaaaaat tagctggaca 34300
tagtggtggg cggctgtaat cccagctact cgggaggctg aggcaggaga 34350
atctcttgaa cccaggaggc agaggttgca gtgagccgag atcatgccac 34400
tgcactccag cctgggcaac agagtgagac tctgtctcaa aaaaataaaa 34450
taaataaata aataaataaa atatatactt gggtaaagag gataaaagag 34500
ttagcgatga tgctgaattt ttgaactgag gtggctgttt tcaaggaaga 34550
ctggagggtg ggatgctacg tctagatatg ttgcagttta ggtgaatgtg 34600
agacttccct gttttgaagt caaatattgg accagtaaaa tctagccatc 34650
agcttaaatt cctatgatac aatttacata ctccccaggc tcaacacagt 34700
agatttctga atgtcctctg ccagctacat gctcctgccc acctcaatcc 34750
gagtagatgg aacaactaac caagccagct cagaccggtg gcacagctgt 34800
gctggctaac actgggcacc acctaagaga gtgcttctcc aaaagtgtgc 34850
ttccccaaat ggagcgaaat acgcttgagg aatgttgggt tgaaccatgt 34900
aaagcaggtc tcattcccgc agagcctttg gtaccccggt gtacactgta 34950
accccagaag tgtttcctga gcttgcctga cgagacaact tttccaagaa 35000
ccgtctcaag tgatgagtgt tttgtgagtc acactttggg gaaagcgggc 35050
ctaagttagc atctcctccc agctgcctcc ctgctttccc tggaacacta 35100
ggaactgccc gtcctccctc cctccctcct cttcccactt cacaacttag 35150
catcaggaat attttagttt tggtttttca aacatatata cctccttttt 35200
tcttatcttg tcaatatcat cttttttttt tctttgcttt tcctcatact 35250
tttttttctc ttcatccttt ccttctccaa gggttaactt tccaccttag 35300
gagaatcttt tctgcttttt ctcccacttc cccagctact ctcttatcat 35350
ctgctccaat ctcaccctaa ttgatcattt tgggaaaata tggtcagagt 35400
ccagataact aagttgagaa atgcttaaac tctgccatac ctttccagta 35450

-continued

```
aagaatatta cctaataaat aataaaatgg taatgggaaa cctgaaccct          35500
gaaaaaaaag aggtggaagg agaaacattt ggagcacatc ctgtctacaa          35550
attaggaact gcctgtgtta tctgttttat ggttatattc tagaagaaga          35600
aagggatttt gtagcacctg gttttgacct ttctgcactg tttgttgagc          35650
aaataaacct tatgggctgt tagccctctt tatagcctct cagcttatcc          35700
ctggcccaga caccctgctg tcattttgac ttttcattcc cacacacaca          35750
tacacatgca cacacatgta cacacacaca cataccattt aagattagac          35800
agaagtaatg ctcaaaatgg agtggcttct gagacattta gtccaagggt          35850
tcccaaacag gcttttcagt atcagatttc tttctgcccc attgaaatgc          35900
tacacaacct tccgcttaca gcaggtcaca agggtttcat tctacttgaa          35950
gtaggggcca tgtcccattt ccacttcctt ggcttcccat tcagtcactg          36000
ctaggatttg cctagacccc tgaggccaga caatgtagaa acttctgctc          36050
catgtcacag gtgaggaaac aggctcagag agggacaggc tccgaaagtc          36100
acatagacaa cagtagggct gcggctcaaa ccccagcgtc tgactccagg          36150
tttagtgcct tctcagggca tcagtgacac tcctcatggc cagggtgccc          36200
ccagtgttgc tcacagtctg gtatccaggg ctgagagtgt gctgtgtgct          36250
cagactgcct gggttcagtc ctggcactgc cactttacag tcagtgacct          36300
caggcaggtt acttaagctc tgcaggcctc agtttcctcc ttggtgggga          36350
gggttatgag gcatccttct catggtaaac cttcagtaaa taccagccgt          36400
tactaggagg gtccactcct gcctctccac tctccattca tcctgcctgt          36450
ttcctctgcc tgcttcctct gcctgcttct gtggtggtga attcttcatg          36500
gctcccaccg cctcctgctg cacccccact cagggcccgc atcaggaccc          36550
ttcctcctat tggtttgaac tccttggagt cagagggtaa tggatagtgg          36600
agtgagccag gtggcagaat ctcagaggcc atcccgggcc tataagcctc          36650
ttcaaaatag ggccacgtat caagctttac acacaggagt gaactttcac          36700
aagttgttat gactcatact ctgtctatag taagctgtta accactccca          36750
tttggcttat gcctctgtaa ttattgtact aacttatatc ttaaaataag          36800
gatattgaag gaatgagccg ggagaggctt tcctggttga gatatagaag          36850
aacaagagtt gctctttttc cttaaggtct ctcctcccac ccctgacctt          36900
agctcaccag catgggagaa tactatttga ctccttgtac tctgagacgt          36950
ggatttcaag atatagcatt ccaacttcaa cggcagcaag aaaagaagca          37000
acagaaggag aagacatcat agcaaacagg gatgcatgct gcatttccta          37050
atactcaaac ccggaaacga gacttcactc aaggtgaagg gagggcaggt          37100
caccacctgg tagcactagc cctaaattaa ggaatgcaga atgtttgtgg          37150
gattgcccat cataaaaatt acaaaatgag taaggaatgc aggcacagct          37200
ggccaggtgg gtttgtcaca accatggcag ccctttgccc cacagccagt          37250
acacagaact ggtctctcca attccgattg catatcttct ggcacctctg          37300
ttcctctccc tcagctgccc aggatttttc tggttctgac catgttactt          37350
cctcttttaa acctgttagc atttcacgac tgcctacagg caacggtcta          37400
aatggtcgga aggcccaagc ttagcatccg agaccctgac ctacctccag          37450
```

ccacttcctc ctcctctcca cttcactgga ctccccatct ccacccagac 37500
acctctgttc tcccctctgt gtgcctttgc ttatgctgtc ccctgtgttc 37550
ctagtgtgtc tctggctatc ttttaagctt ccctccccaa cctcattagt 37600
tctgtggagc ccctggaata gagctgactt ctccttccct gctgctccca 37650
ggctgctcag aactttctgg aaagggatga ttatctgagt tccagcctca 37700
ccccagcccc cggactctga gtccctcatg tctgcctccc ttctttctct 37750
ctgaccacac agctggtaca tagtcagtac agacgcagtc agtgagtgga 37800
gcacggggct tctctccagg attcctgccc ctttgtttat ccctagtctc 37850
aggactccct actcctggtc ttctgcctaa atctgtgcct cttggaagtg 37900
aagcctccgt tcccagtggg gccaggtcct gacccttggg aacttgcagg 37950
atccctccct tgggcctctc cccgaagctt ccagctcaat gctgaccaga 38000
gcacaggctg cctgtgacag tccttggggt gacctccctt atcaggaaaa 38050
atgcagaaaa cctattaata ccttagcctt gtgattgtta atggtcacaa 38100
aactccttta gggtcctttg gactcagcac ctttatggtc tcactttgaa 38150
ttttgaacct cccacctccc cccatccccc agagtaaggc aaatggtctt 38200
ctgattgttc ctgcagaggg aaggctccac aggtaagcac acgatggcca 38250
ggaagcagag ctggagcctg cctgaaaggc tgtggagaaa tggagggagg 38300
gctgccctga ggactctgtc tggctttgaa gttttctact gtttcctttt 38350
cttctgtgca ctgttttagg atgatggggt gatagttcca ggctggttga 38400
ggatggattt ggagacagtc ctttgtaccc tcagtgagca agagtatctg 38450
tcaccctacc tcagcagttg tctctgtcac tggtccaagc agctggttcc 38500
tacacaaggt caagatcaac tggggagaag cagactcctg ggtctatccc 38550
attagtgagg acagctgcct gggcttatgg cctcattggt ttggtttcta 38600
tcttgatcat ctctaccatc cccccatccc ggccttccat tttctacctc 38650
agctgtcagt gcacagattg atgtgtgtgg gaacggagct tgggaggagt 38700
ggggtagggc tggtcctgtc ctgtagcctc cccttccttc gggcacttgg 38750
accctttgga gcttgccggg gtggggaatg ggagtgggaa ggccagggag 38800
tgtctctgca ccatcactgt ttgagtgttg cccctttgct gtgtgcccca 38850
cctagtctat gtgtgtctct gttctctggg gactcaattt gctggtgaat 38900
tgcttccatg gacattgttc tgggaaatgc catttttttct gctcacccat 38950 gactctgtga caaggaatga cagcttatta ggaatttgtt tttgcattgg 39000
aacagtggtc atcagaatgg gccccttttc ccttgcagct ttgacatttg 39050
cctctctttt cctcacctct ctcccttgca tccacccttt tctctttttc 39100
ttcttttttg ttttccttct agcaggggcc ttttaccttt acttgttaat 39150
cctgtttgta gcaaagcaag tggaaggagg agttcctctc tgatctgctt 39200
cttattctcc acctaccttc tcttctgtac tttccgcctc ctagagagag 39250
agagagagag aggaatgccg acctaactac cgctgccact gctgctgcca 39300
ccaccgctgc caccaccacc ctggtaatgt tcacatgtcc tcaaatcaac 39350
ccagagccag ggccctgctg gtcaggggga ggctatgtaa ataatcccat 39400
gagtgtgcca tcctcaggcc ctggggtctc ctaggcaaga ccagggcctc 39450
tgtgggctct ctcggaaatg ctgaggttgc tggaagccag cccgtcatac 39500
agggtctgag agtttaactt cttttaaatt aaaccacagt tgagctcatg 39550
ctgtgtgtgt ataaactttt gtatcctgct ttttccttaa attctttatc 39600
atcagcatct tcccatgtta tttcatagtc ttcatcatca tcactttcca 39650
taccttcata gtagttgatc gtagaattcc atcataatta acttgtcttt 39700
tctctcttag aagtccctta ggtaatgtcc aattttccgt gagtgtaagt 39750
aataccataa tgaacatctt ggagtctgaa gtttattctg tgttggtttg 39800
ttccacattt aggatcattt tcccaggcta gattttcaga tgtgggatta 39850
tgggttcaga tatggtttac acatttttat agttcttaat acagatggcc 39900
aaattgcttt ctgaaagaga agcttttctt aagtattttt ctccaacttg 39950
tatcttaaac atcctgaaca tgcttagcac cactgtcttg atatatctgc 40000
ggaaagccac gtctccactt ttcagtgtgt cgggccctgg gagaggcagg 40050
catcctgcgc tggctccttg gagctgggtt taaaattgtc tcctctggct 40100
gggcgtggtg gctcacacct gtaatcccag tactttggga ggccgaggtg 40150
ggcggatcac taggtcagga gatcgagacc atcctggcta acatggtgaa 40200
accccgtctc tactaaaaat acaaaaaatt agccgggcgt ggtggcgggc 40250
acttgaaaag tcccagctac tcgggaggct gaggcaggag aatgatatga 40300
acccgggagg cggagcttgc agtgagccga gatcgcgcca ctgcactcca 40350
gcctgggcga cagagtgaga ctccatttta aaaaaacaaa caaacaaaac 40400
aaaaaaacaa acaaacaaaa actgtctctt ctgtgctcac ttcacccaga 40450
atccctgttg ggctcttcaa ggagctcagt tctctctgaa agcaacttta 40500
tagcctcagt ccagtctgtg ttcctgtgtg gcaggggtca agggtatgct 40550
cactcttgag agtggtgtct ttggttgacc aagaaccact cccatagcct 40600
ggtccctaac ccttgaaggc ccatctctct cactcactgg ggtgaagagt 40650
ttaaatctca gatccaagtt ttgttgagag ctctgagcta ccatattgct 40700
atggttaaca atagttaaca atgttaacaa tggttaacta tggttaacaa 40750
tagttaacaa tgtttaacaa ctagagccca gctgggtgtg gtggcatgtg 40800
ctaacagtcc cagcttctca agaggctgag gtgagaagat tgctggagtc 40850
caggagctca aggccagcct gggcaacatg gcgagaccct gtctcccctg 40900
caaaaaaaca acaacaacaa aagcaaaact agagcccaac tgctgtgaac 40950
tcatggctga gtagatatta ttagccctcc acaaactcag catttgtata 41000
atcccaggct gtttccagta attctctggg gatcatctcc cagcctgtcc 41050
actgttccag gatccacact taggcctata ggaatgcccc gtcagagctt 41100
ctgctgccgc tgatctgtta ctgtttcatg caacccactc ggcctagttc 41150
cttcctctta ctgtctcagt gggcacagaa aagcatacag agggtgtttc 41200
agcaaacatt gccactggct gcagacctgc ccccggatct gtcctgttga 41250
gagcttagtg ctgcgttctt gcatggtggg gaggggtgtg gctctgtgat 41300
gagccagggc atgtgtatag gagcaacagt gtctctctta tcacgtagaa 41350
gttctgactc attgcgagtc ttggctttgg gttaatggtt ccagccatgt 41400
tgctgctgtg tcttttggtg caggagaggc tgggcacagt tggtccctaa 41450
gccattatgg ataagggatg tgtctgctga tatacacaca tggacctgac 41500
atccagggaa ggcagggtga ttggacagaa cagttcttcc agaagctgtt 41550
ggaacttgga caagagtggc ccttggcttt ctgtagttgg tcatctgtcc 41600
cctgttgcaa tcaggggaag gccacacttg ccttccttaa ccacagttag 41650
gattttcttg ggattagac cagattctag cacctgtcct gaacctctcg 41700
ccccgcccct acaaaggctg cttgcaagtg tagtgcacat acacagggag 41750
caggtggggc atggaagtgg aagtggagcc cctgcctttg gcccttgggg 41800
gaggcactgt ctgcttaccc acggttgttg cctcatagga atcatacaac 41850
agcttcctaa ctggtctcct tgccttcagt tggattgggg cacaaatccc 41900
tccttgacat ataaaccatg gtttaaggct ccctgtggcc taaataaaga 41950
taaagcttaa gtatcttaac aagcacctaa cccttctccc cagcctcggt 42000
gatttggctc atcgctgcct tcatgtttca ttctggcttc actcattcgg 42050
aatttcttgt agttccttgg ctgttctctt ttccttaccg cctttacaaa 42100
tgctctcacc atgcatgctt ttctctgctc ctacagatgc cttctctccc 42150
agcaccgcct ccagagtcta tgtctggtcg attctgtctg ctgtctccag 42200
tccccatctt gtggcagtct ctgctcaatc atttggggat tttatatgtt 42250
ttctggcctt tcttttgggg gcctgtcttc tccttctaaa agcagccagt 42300
tgacctagaa ggaagggata actgtaactc ttgtctacca acataagatt 42350
aggcccaccc tttaaaagct gcgtctttga aagggacacc tgcacccagc 42400
atgctggctt ctcttcacca agcgtgactt cctacgcatt tcacaggcct 42450
ccagaggtcc ccctgactct cttctgctgt gagaaactct aatcatgtaa 42500
gccacaggct aattcccttg agccttaaat gtttttagta atttcccatt 42550
catcagagaa gcaggatttg ggaggaattt tgaagcaaac actacagaag 42600
gcagagtctc caggtaggat atctaagaga catttggaat ggtctgactg 42650
ttcaagatgg atgggaaagc ctcttcctgt aatgatagta gccaacattt 42700
gttgtcaggc agtggggccc catttttgag atggggtctc tgtcacccag 42750
gttggagtgc ggtggtgctg tcatggctca ctgcaacctc agcctccccg 42800
ggctgggtct tcttaattct gaaaaaccca gcttttaaag ggtggaccta 42850
atcttatgtt ggtagacaat gttgtctcat ttaatacaat gcacatgctc 42900
tccccataac acaaaagagg gaactgaggc ctggaggtgt gatgtacccc 42950
aagtcacata gctaataaat aaagaagcca gcattcctgg gattaaaaat 43000
gcatgtgtct gtcactgtgg tgtatttggt gcttgatcaa tgtttacttg 43050
agcaaatgga ggggcagagg taccgatgag tgtgctcagt gaggagggca 43100
ggagtgaagc tgggcgtctt cccgcctctt gtgagtggtg gggcttggtg 43150
agcttgccag ggcctgtctt tcttatcaaa gaaggtgtgt gccccagtgt 43200
tacagcattt cacccaaagc agcctagaaa atgcttgact tttctgtcat 43250
tccggggagg acactttcct cctccactgt tctgctggcc tggtgtaccc 43300
acggcccctg atagatgata gcacctgcta aagtgcacca tgcccttccg 43350

```
tctcactgca tcccacagat gaggccaggc tgggatgagg gagaaaggga 43400
gggatatata gttcaggtta ttttggaaaa ctgcctgacc aattttaagt 43450
ctgggccgga cactggggca tctcaccacg ttgaaagggc cgtggcaccc 43500
cgggcggtga aaggggctgg aaccaggtct gcttcttggg cttctcctcc 43550
agggtgccat tgctcatggg ccttggctgc agaggtgctc attcgtggtt 43600
ccaaaattcc aattcctggg agaggaaaaa tgcttagttc agtctcagtt 43650
aggcctctgc ttagatcaaa cagccaaggc cagtaggccc agtcctatgg 43700
tagagacatg gcctcaaaga gccctctgct gcagttgttg gggagtgtac 43750
caagagaagg gagcattgtc ctgggctggg cagccctggg ggtctagtgc 43800
atagatgtag aaaggctctg ttggtatacc tccctttgct tgttggaaag 43850
tgctcaacgg ggctgaattg tgtttgacag tgtaagtctg ggctggggtg 43900
agggttgtta caagattgtc aagatgatta aatgaaatgc catttgaaac 43950
acttatccat gccttgtgta tggtatcccc accagtgaat attcacagta 44000
tattataata attccaacaa cttcataatt ttcatatgca atttctaaac 44050
tttgaacttt tttttttttt ttttttttt tgagacagtg tctcgctctg 44100
ttgcccaggc tggagtgcag tggcgcaatc ttggctcact gcaacctcca 44150
cctcccggct tcaagtgatt ctcctgcctc agcctcctga gtagctagga 44200
atccaggcgc ccgccaccac acccagctaa tttttgtatt tttagtagag 44250
acgggctttc gccatgttgg ccaggctggt ctcaaactcc tgacctgagg 44300
tgatccaccg ccttggcctt cccaaagtgct aggattacat acgtgagcca 44350
ctgtgcccgg caatttttttg tgtttttagt agagatgggg tttcaccatg 44400
ttggccaggc tggtctcgaa ctcctgacct caagtgatct gcccgcctca 44450
gcctccctaa tgctgggatt acaggtgtga gccaccacgc ccagcctaaa 44500
ctttgaattt ctttgaaccc atgacttaca cagaattagc tgaacgcaga 44550
attccaaatc aactcagcct gtgggacagc caaaaaacac agtgtgcctt 44600
tgggctcctt cactcaccac gcggggttag aaaactttgt cagaggcttt 44650
aaaaaaggag ctcttgtgtg taaaatgttt ccttgattct ctttctggtg 44700
cctctctttc tctaagtggt ttgcttcccc aagttcccca cctgagtctg 44750
ggtggctgtg gcacatctgt gcattctgta cgcacacagg cagccttttg 44800
gagtgccagt ttccaggtct tggttttatt tatttattta tttatttttt 44850
tgagatgggg gtctcactct gccgcccagg ctggagtgca gtggtgccgt 44900
catggctcac tgcaacctca acctccctgg gatcagttga gcctcctacc 44950
tcagcctcca gagtactagg gaccaccatg cctggcaaat tttgtaatt 45000
ttttgtagag gcagagtctc accatgttgc tcaggctggt ctcgagctcc 45050
tagactcaag tgatctgccc accttggcct cccaagtgtt aggattacaa 45100
gtgtgagcca ccatgcccag cccaggtcat cttttgaggg catggagaga 45150
agactttgag catcccactt ttgagattgt gtaccagtcg caagccccta 45200
tgacacactt tttccccaaa gtagagggct ctgactatgt tgatcccaag 45250
agagatggga aagagcattg aatgaggatt ccaaagtatt gggccttagt 45300
tcgtttcctc atgttggtgt tgtgaagatt ctggttagga taacagcatg 45350
```

```
tgtgcaggag gctttgtgaa ctgctgagag tgaggcgtgg caatgtcagt          45400
gctaggtttg tccttactaa cctggggcca tgggaattga taagaccaga          45450
ttcccaactc taccccacaa tgtgatccct gtggtgaccc ctcacagggc          45500
tctttggtcg agcttcccag aagggatcac catctgccat tgtatgttga          45550
accccattca ttcattcatt cattcagcca accagcaact atttgttgag          45600
ctcttattgt gtgagaagca gtcttcaagg aactgggtga ataaaaaaaa          45650
caaaacatcc taaccttcat tgagcttaca ttcttactga aagaaaacaa          45700
ataaaacata catgtaatcc tagcactttg ggaggccaag gcaggcggat          45750
cacttgaggt caggaatttg aaaccagcct ggccaacgtg aaacccatct          45800
ctactgaaaa ttaaaaaaaa aaaaaaaaaa aagccgggca tggtggcaca          45850
tgcctgtaat cccagctact cgcgaggcta aggcaggaga atcgcttgaa          45900
tcctggaggc agaggttgca gtgagccaag atcataccat tatactccag          45950
cctcagtgat gaagcaagac tccatctcaa aaataaaaaa taaaaataaa          46000
aatatgcatt ccctttgcac cagcacactt ggtgcctggg gacctcgtgg          46050
ttggcaccct gaagcaggtg tccctcttct gtcttgcaca ccttgcttct          46100
gtcctggtgt gtatggcatg gccttctgcc ctccatggtg agcactgtga          46150
gggcagaggt tgagttgggt ttgctgtatt tctcaggtgc ctaggtttgt          46200
gcttgacagg tagatggaag gcacacaatg tggtcatcaa acctcagtca          46250
accatataag gaaggtagaa gtgaaaagtc ccataggtac ccaactaatg          46300
tcaccagttt cctggatacc tttcctggag tttatttata gtgtgtataa          46350
ataaatgatg tatgtgttta aatgcctttt tcacctttcc ttttagagct          46400
gcctcttttt aacagttcca ttccattgta tggatgtact atgatttatt          46450
gaaccagttc cctactgatt attctgtttt ttgcagtctt ttgttatgat          46500
gaacattcca cagtgacaat gttgttcata gtcattcaca cacatgcaag          46550
tccttctgca ggatatattt ctagagggga attgctgact cagaggtttt          46600
ggtactctgt gttgattgta gagtgacggc agaaaagtga ggcccaagag          46650
tttcctagtg accatgtgta gtggacaagt caccagtccc tgtgagtgtt          46700
tggcccaaag gctttaaggc atttgatatc actgtttttg tttctgcacc          46750
aggcgggaga cactatattc aatcgtgcta agctcctcaa tgttggcttt          46800
caagaagcct tgaaggacta tgactacacc tgctttgtgt ttagtgacgt          46850
ggacctcatt ccaatgaatg accataatgc gtacaggtgt tttcacagc           46900
cacggcacat ttccgttgca atggataagt ttggattcag gtaagagata          46950
ctcagtcaga atctgtggta aacatgtctc tctcatgtgt tgactaggaa          47000
atgcagtcct ggcagctcaa gagtgcctct ttaagctctg gagcagaatg          47050
cctcctctga gaaatgggtg ctttgtatta gttgagatgg aaagaagaga          47100
ccagaaatgc ctgtagtctc tgcacatcca gacaaaaaca aattttcccc          47150
ccttttttt ttttgtttgt tttttgagac agggtctggc tctgtcaccc           47200
aggctggagt gcagtgccgt gatcttggct caccgcaacc tctgcctccc          47250
gggttcatgc catcctgtca cctcagcctc ctgagtagct gggactacaa          47300
```

```
acacttgcca ccatgcgcag ctaatttttg tatattttgt agagatgggg 47350
ttttgctgta ttgcccagtc tggtctcgaa ctcctgagct caagcaatcc 47400
atctgccttg gcctctcgaa gtgctggatt ataggcatgt ggcaccatgc 47450
ctggcctaag aacagttttt agcatttggg aggggctctc atctttaagc 47500
tccaaatgat actgtatttt cttgcttttt tctttctctt gccccacaag 47550
ttttggaaag taaattggaa tagttttccc ccactgaatt atttagcttg 47600
tatacctcag cagatgttcc ttggcctgtt ttgttttgtt tttgagacag 47650
ggtcttgctc tgtcacccag gctggagtgc agtgacacaa tcatggctca 47700
ctgcagcctt gactgcctgg gctcaatcca tcctgcagcc tcagcctcct 47750
gagtagttgg gactacaggc atgagccagc atgtccagct aattttttat 47800
ttttagtgga gatgaggtct ggctatgttg cccaagctgg gcttgaactc 47850
ttgggctcaa gtgatcctct cacctcagcc ttccaaagca ttgggattac 47900
aggtgtgaac cactgctccc gcccttggcc ctataagaag gaatgtgatt 47950
ctgttttcca gcagggcaca aacttctgct taaatacaaa gcccaaattt 48000
ttccaccaaa atgcccctag tgaagtggcc agcccagatg cccgactagc 48050
gtattatcca aagcatattg tcattggtgg aaaatggcct tatagtccat 48100
tgttttgtct taaaagtaaa tatataaata aacttgtata ttgtttccta 48150
attccgtgtt tatattaaca taaaagtgtt ttaaattacc tgtcagtggc 48200
caggtgcagt ggctcgtgcc tgtaatcgca gcactttggg aggccgaggc 48250
gggcagatca cctgaggtca ggagttcgag accagcctga ccagcatggt 48300
gaaaccctgt ctctactaaa aatacaaaaa ttagccaggt gtggtggcag 48350
gtgcctgtaa tcccagctac tcgggaagct gaggcaggag aattgcttga 48400
acccgggagg cagaggttgc agtgagttga gatcgcgcca ttgaacttca 48450
acttgggcaa cagagcaaga ctctgtctca gagaaagaaa aaaaaaaacc 48500
tatcagttga ataacaaaac cctttccttc cttgctttaa gtgaatctga 48550
agatccagga gctgtgctgc aggtaccctc tatgttgggt acccctggtt 48600
taggctgact agtacagtgt ggttggctca tgtagacagc agaccctta 48650
ttttagatac aactttttttt ctttttcttt tattttttttt gagacagagt 48700
cttgcttgtc acccagcctg gagtgcagtg gcgtgatcat ggctcactat 48750
agccttaaac tccctggctc aagtgatcct ctcacctcgg ctttcctagt 48800
agctgggacc acaggtgtgg gccagcaccc ctggctgatt taaaaaaaaa 48850
aaaatttttt tttttagaga tgtctcacta tgttacccag gctggtcttg 48900
aactcctggg ggctcaagca atcctcctgc tttgacctcc caaagtgctg 48950
ggatgacagg catgaactac tgcacctgct gagatgcaac agctttctgt 49000
cagactcatt ttattctcat catttcttcc tgtcctccct tgctgggagc 49050
atgagagctg tgatgggaat ataggaatgt atgaagtcct tctcccagat 49100
caaaaatcct aacttcttgt cttaaaggga ggaaaatttg aatgtaacct 49150
tacttttaga ctcttcagaa atccttctat acccttccgt ccccgctttc 49200
acccttcctc cctctccgtg tgtgtatctt cttctcttga aacacacagg 49250
tttataccct gacccctctt gattcatccc ttgaagcaca gtggtgaaca 49300
```

aggaaggggc ccgtgatgcc ctaattcttt gccacagcac catgtttgtt 49350
tcacaaggag cctggcaggt ttgggcttgg ggcagatagg ggagagaaag 49400
cagcagagac agcaaaacca aatcatgtca gcttggcatg tacttccctc 49450
tgaaatagct aagaatccat ttctgtaaaa gcactgatta tcagaaaacc 49500
ttattggcct ggccaccttt ggttcaaacc ctcacattaa taatgtggac 49550
agtagtatga ggtgtgccaa aggtggatga ctcagcacct aagtgatgac 49600
acctaattac gaataggttc attaaagcag accccctggg gacctttgct 49650
tgaggatcct tacagtcaga attcctgaat atatttgaaa ataataattg 49700
catctttatt ttcatatgtt ctgtatggtt tggctgactt ccccctcaaa 49750
gtctgagtta gagttttcct taatttatgt gatgggtttg gtctttttgg 49800
attccagaaa gagctgggtg tggtttggag ctgcactcag agtcacacaa 49850
aaccacagcc tttagagaac ccacaggaag gctttggggc acgtcctgat 49900
tcttgacatt tctcatcagt gctgactttg tatcccttag gagttcacaa 49950
ttcataacca ctgaaatatt aaaatacaaa aagttttgga aggatgagag 50000
cccagatgct ctactacttg aaaatatgtt aaaacataag ttcatcatta 50050
tacattttgc taaatcagga taaagtctga agtttcaaag aagttttatt 50100
ttagcaaatt ttcagaaaca ctgcctcaac tgttagggcc agtgttctag 50150
tcagtatgcc tttggaagca tgaaagctgg attggtcgat aggatgggtg 50200
tggaaggggg gctgtgactg ggtgggtaca gagaggctct gaaacaatct 50250
cagattccag gagttcctgg ataaggactt catgtgcggg aacagagcac 50300
aggagaagca gattcctgag ccactcagga agaactgggc ctaggcctgc 50350
tcttgtcact gactggcttt ctacataacc acagaaacag cactgtgttg 50400
tagaaagagg aagatcatac tttttgatat ctgtgtctaa tttaaggtca 50450
tctgagccct gatagaaaag caaaacagac aaaacccttg taactgctcc 50500
ctcccacccc acccaccatc aaaaaagctt tagagaggct ggacatggtg 50550
gctcttgcct gtgatcccag cactttggga ggctaaggtg ggtggatcac 50600
ctgaggtcag gagttcgaga ccagcctgac caatatggtg aaaccccatc 50650
tgtactaaaa atacaaaaat tagccaggtg tggtggcaca cgcctgtagt 50700
cccagctact tgggaggctg agacaggaga attacttgaa aacctgggag 50750
gcggaggttg cagtgagccg agatcacgcc attgtactcc agcctgggct 50800
acagagcgag actccttcaa aaaaaaaaaa aaaaaaagat ccggtttggt 50850
gtcttacaac tgtaatccca gcactttggg aggccgaggc cggtggatca 50900
cgaggttaag agatcaagac catcctgacc aacatggtga aaccctgtct 50950
ctactaaaaa ttagctgggc gtggtggcag gcgcctgtag tcccagctcc 51000
tcaggaggct gaggcagaag aatcgcttga acccgggagg cggaagttgc 51050
agtgagccta gatcgcgccc ctgcactcca gcctggcaac agagcaagac 51100
tacgtctcaa aaaaaaaata aataaaaact ctagagaagc aaaaagaata 51150
actttaaaag tgtttatgtt ctcagcaagc tttattttgg ggatgtcaga 51200
acttaactaa ccactgctcc ttctgtgtgt atgtttttcc tccagcctac 51250

```
cttatgttca gtattttgga ggtgtctctg ctctaagtaa acaacagttt      51300
ctaaccatca atggatttcc taataattat tggggctggg gaggagaaga      51350
tgatgacatt tttaacaggt aatggtcata acttagatat ctttctcctc      51400
tgtcaacctt cacttccagt tttttaacca atgcttggtt gttccccaag      51450
gactgaccct cagatgggat gcacccctag tcagcccaca ttcttaggtg      51500
tggcttccta caggtcctgc aggtgctaaa agggatctgt aggaaaatga      51550
gtttctgaga tttttgtatt ggcctggaaa aatgtcaaat gggaaccaag      51600
tgacggggca agtttacttt gacttgctgc atgccgtttt gtactcaagg      51650
agtaaaccaa tgtcctttgt aaaaatccct cctttcatta tggtcccctt      51700
tcactgtgaa acaagtttcc ttgagcagaa tcctaactgt cttcacagaa      51750
gctttgtgtt atatttttat tttggagtat tttcacatat acaaaagaga      51800
tactgtagta taataaacct ttgaggacct atccagcccc agcaaccatt      51850
atggcctggt cagttctgtc ccatccacat cctggggctc tttttaagct      51900
ggtaaatcat tatgatgtgg gttgtcattt acagtggtaa aaaacatcta      51950
tcagtagcat ttgaaagaac attctgctca gtcctctggc tgtagaggct      52000
tcaaccccac cagccaccga tgagcacctt ctccctccag gagccagtct      52050
gagctcatta ctgagtttaa tatcagaata caccctggtg cagcctttct      52100
aaattgcagt accagttaac agaaggtgtc tgtcagagca acacccaagt      52150
cattcaagtt accattgtgt gcaaacttaa cagagaccca cgtcttcaat      52200
ataagccttg aaggaaactc cagttttagt atgtagatgg ggtatcaagt      52250
gtgtgcacat tgaacatctg ctgcatacag agcactgtgc caggcaggcc      52300
caggacactg aaaacctgga catagggtcc agacagaagc aagcctgctt      52350
ccacagaggc actcctgggc agacactctg gactgatatg acagtgtgca      52400
gggccgacag gataccacag gtctgaatgg tcagaacagc tggggaggga      52450
gggagcatcc gcaggcatct agtcccatgc taacgcagtg gcactagaag      52500
gatgggtggt gtgtggagca actttcttga aagataaagg acctaacact      52550
ttctatgcac cacttactgt gtgccaggca aggccaggaa tgtttaagtg      52600
gtctgggatc agccagttct gcctcttaac taactttgct gtcctgctct      52650
ccaggctttc attttggtcc tcattccttt tccttggacc aacacagaat      52700
cctccaccct gttctggctg cctctagtct tgttctcagc cctccatttg      52750
tttttttctg ccttttccca catgttctga agccctccat tcgtatacta      52800
ctttccagag acttccccat ggctaaaagc attttggaaa tactgtatat      52850
taggcccctt tcagatactg gcaaccgttt gtgggatgct ctgagaaggc      52900
ctctgtgact tagcctggcc cttttcagcc catcacctgc cacgtcctac      52950
cccagaccct tgtcaccagt ccccaggagc ttacgttgct ccctgagggc      53000
actaggcttg ctctcacttc catgcctttg cctgtgccat cctggctgcc      53050
caaaatgcta tggcagatac ctgttcatcc tcaactgggc tctgcctagg      53100
cttgctccag cagaggttac aaactctatg cttcttcctc tgtgtctcca      53150
acctcatctt cctcttctca cctccatcct ggccctaaag gccctatgtt      53200
tgaagcattc acactgtata ttctgtgggg cacacggccc cagtgtctgg      53250
```

cacatggtag tcaacaccac aaaccgcaga accagttgta aaaggacatg 53300
gagtcggaat gtgagtttta accagggtca tgctgggctg ggttctggca 53350
tgatgctggg ttgtgggctg agtgagaaca gcaagggtga tggtggatgg 53400
agcaacagtc ttgcagccgg ggctctcagg ccaagtgtat ggcagctctg 53450
tgataatgac tttcccttta ctctttgcag attagttttt agaggcatgt 53500
ctatatctcg cccaaatgct gtggtcggga ggtgtcgcat gatccgccac 53550
tcaagagaca agaaaaatga acccagtcct cagaggtgca ttctttgttt 53600
attcatactc cttccccctt taggatgagg taggctgcag gtccgaggct 53650
ctgggcctag agggaaattg aggtggtcag gttacagtgg agagggagga 53700
ggaagtacgt gtgatgattt cttcttaaga tttttgtttt aagacaatct 53750
ccttgtgctc ttttccttgt aggtttgacc gaattgcaca cacaaaggag 53800
acaatgctct ctgatggttt gaactcactc acctaccagg tgctggatgt 53850
acagagatac ccattgtata cccaaatcac agtggacatc gggacaccga 53900
gctagcgttt tggtacacgg ataagagacc tgaaattagc cagggacctc 53950
tgctgtgtgt ctctgccaat ctgctgggct ggtccctctc atttttacca 54000
gtctgagtga caggtcccct tcgctcatca ttcagatggc tttccagatg 54050
accaggacga gtgggatatt ttgcccccaa cttggctcgg catgtgaatt 54100
cttagctctg caaggtgttt atgcctttgc gggtttcttg atgtgttcgc 54150
agtgtcaccc cagagtcaga actgtacaca tcccaaaatt tggtggccgt 54200
ggaacacatt cccggtgata gaattgctaa attgtcgtga aataggttag 54250
aatttttctt taaattatgg ttttcttatt cgtgaaaatt cggagagtgc 54300
tgctaaaatt ggattggtgt gatctttttg gtagttgtaa tttaacagaa 54350
aaacacaaaa tttcaaccat tcttaatgtt acgtcctccc cccacccccct 54400 tctttcagtg gtatgcaacc actgcaatca ctgtgcatat gtcttttctt 54450
agcaaaagga ttttaaaact tgagccctgg accttttgtc ctatgtgtgt 54500
ggattccagg gcaactctag catcagagca aaagccttgg gtttctcgca 54550
ttcagtggcc tatctccaga ttgtctgatt tctgaatgta aagttgttgt 54600
gttttttttt aaatagtagt ttgtagtatt ttaaagaaag aacagatcga 54650
gttctaatta tgatctagct tgattttgtg ttgatccaaa tttgcatagc 54700
tgtttaatgt taagtcatga caatttattt ttcttggcat gctatgtaaa 54750
cttgaatttc ctatgtattt ttattgtggt gttttaaata tggggagggg 54800
tattgagcat tttttaggga gaaaaataaa tatatgctgt agtggccaca 54850
aataggccta tgatttagct ggcaggccag gttttctcaa gagcaaaatc 54900
accctctggc cccttggcag gtaaggcctc ccggtcagca ttatcctgcc 54950
agacctcggg gaggatacct gggagacaga agcctctgca cctactgtgc 55000
agaactctcc acttccccaa ccctccccag gtgggcaggg cggagggagc 55050
ctcagcctcc ttagactgac ccctcaggcc cctaggctgg ggggttgtaa 55100
ataacagcag tcaggttgtt taccagccct ttgcacctcc ccaggcagag 55150
ggagcctctg ttctggtggg ggccacctcc ctcagaggct ctgctagcca 55200

```
cactccgtgg cccacccttt gttaccagtt cttcctcctt cctcttttcc          55250

cctgcctttc tcattccttc cttcgtctcc ctttttgttc ctttgcctct          55300

tgcctgtccc ctaaaacttg actgtggcac tcagggtcaa acagactatc          55350

cattccccag catgaatgtg ccttttaatt agtgatctag aaagaagttc          55400

agccgaaccc acaccccaac tccctcccaa gaacttcggt gcctaaagcc          55450

tcctgttcca cctcaggttt tcacaggtgc tcccacccca gttgaggctc          55500

ccacccacag ggctgtctgt cacaaaccca cctctgttgg gagctattga          55550

gccacctggg atgagatgac acaaggcact cctaccactg agcgcctttg          55600

ccaggtccag cctgggctca ggttccaaga ctcagctgcc taatcccagg          55650

gttgagcctt gtgctcgtgg cggaccccaa accactgccc tcctgggtac          55700

cagccctcag tgtggaggct gagctggtgc ctggccccag tcttatctgt          55750

gcctttactg ctttgcgcat ctcagatgct aacttggttc tttttccaga          55800

agcctttgta ttggttaaaa attattttcc attgcagaag cagctggact          55850

atgcaaaaag tatttctctg tcagttcccc actctatacc aaggatatta          55900

ttaaaactag aaatgactgc attgagaggg agttgtggga aataagaaga          55950

atgaaagcct ctctttctgt ccgcagatcc tgacttttcc aaagtgcctt          56000

aaaagaaatc agacaaatgc cctgagtggt aacttctgtg ttattttact          56050

cttaaaacca aactctacct tttcttgttg tttttttttt tttttttttt          56100

ttttttttgg ttaccttctc attcatgtca agtatgtggt tcattcttag          56150

aaccaaggga aatactgctc cccccatttg ctgacgtagt gctctcatgg          56200

gctcacctgg gcccaaggca cagccagggc acagttaggc ctggatgttt          56250

gcctggtccg tgagatgccg cgggtcctgt ttccttactg gggatttcag          56300

ggctgggggt tcagggagca tttccttttc ctgggagtta tgaccgcgaa          56350

gttgtcatgt gccgtgccct tttctgtttc tgtgtatcct attgctggtg          56400

actctgtgtg aactggcctt tgggaaagat cagagagggc agaggtggca          56450

caggacagta aaggagatgc tgtgctggcc ttcagcctgg acagggtctc          56500

tgctgactgc caggggcggg ggctctgcat agccaggatg acggctttca          56550

tgtcccagag acctgttgtg ctgtgtattt tgatttcctg tgtatgcaaa          56600

tgtgtgtatt taccattgtg tagggggctg tgtctgatct tggtgttcaa          56650

aacagaactg tatttttgcc tttaaaatta aataatataa cgtgaataaa          56700

tgaccctatc tttgtaac                                             56718
```

<210> SEQ ID NO 3
<211> LENGTH: 4214
<212> TYPE: DNA
<213> ORGANISM: Homo sapien
<220> FEATURE:
<223> OTHER INFORMATION: wild-type B4GALT1 mRNA sequence

<400> SEQUENCE: 3

```
gcgccucggg cggcuucucg ccgcucccag gucuggcugg cuggaggagu             50

cucagcucuc agccgcucgc ccgcccccgc uccgggcccu ccccuagucg            100

ccgcuguggg gcagcgccug gcgggcggcc cgcgggcggg ucgccucccc            150

uccuguagcc cacacccuuc uuaaagcggc ggcgggaaga ugaggcuucg            200
```

```
ggagccgcuc cugagcggca gcgccgcgau gccaggcgcg ucccuacagc     250
gggccugccg ccugcucgug gccgucugcg cucugcaccu uggcgucacc     300
cucguuuacu accuggcugg ccgcgaccug agccgccugc cccaacuggu     350
cggagucucc acaccgcugc agggcggcuc gaacagugcc gccgccaucg     400
ggcaguccuc cggggagcuc cggaccggag gggcccggcc gccgccuccu     450
cuaggcgccu ccucccagcc gcgcccgggu ggcgacucca gcccagucgu     500
ggauucuggc ccuggccccg cuagcaacuu gaccucgguc ccagugcccc     550
acaccaccgc acugucgcug cccgccugcc cugaggaguc cccgcugcuu     600
gugggcccca ugcugauuga guuuaacaug ccuguggacc uggagcucgu     650
ggcaaagcag aacccaaaug ugaagauggg cggccgcuau gcccccaggg     700
acugcgucuc uccucacaag guggccauca ucauuccauu ccgcaaccgg     750
caggagcacc ucaaguacug gcuauauuau uugcacccag uccugcagcg     800
ccagcagcug gacuauggca ucuauguuau caaccaggcg ggagacacua     850
uauucaaucg ugcuaagcuc cucaauguug gcuuucaaga agccuugaag     900
gacuaugacu acaccugcuu uguguuuagu gacguggacc ucauuccaau     950
gaaugaccau aaugcguaca gguguuuuuc acagccacgg cacauuuccg    1000
uugcaaugga uaaguuugga uucagccuac cuuauguuca guauuuugga    1050
ggugucucug cucuaaguaa acaacaguuu cuaaccauca auggauuucc    1100
uaauaauuau uggggcuggg gaggagaaga ugaugacauu uuuaacagau    1150
uaguuuuuag aggcaugucu auaucucgcc caaaugcugu ggucgggagg    1200
ugucgcauga uccgccacuc aagagacaag aaaaaugaac ccaauccuca    1250
gagguuugac cgaauugcac acacaaagga gacaaugcuc ucugaugguu    1300
ugaacucacu caccuaccag gugcuggaug uacagagaua cccauuguau    1350
acccaaauca caguggacau cgggacaccg agcuagcguu uugguacacg    1400
gauaagagac cugaaauuag ccagggaccu cugcugugug ucucugccaa    1450
ucugcugggc ugguccucu cauuuuuacc agucugagug acagguccccc    1500
uucgcucauc auucagaugg cuuuccagau gaccaggacg agugggauau    1550
uuugcccccca acuuggcucg gcaugugaau ucuuagcucu gcaagguguu    1600
uaugccuuug cggguuucuu gauguguucg cagugucacc ccagagucag    1650
aacuguacac aucccaaaau uugguggccg uggaacacau ucccggugau    1700
agaauugcua aauugucgug aaauagguua gaauuuuucu uuaaauuaug    1750
guuuucuuau ucgugaaaau ucggagagug cugcuaaaau uggauuggug    1800
ugaucuuuuu gguaguugua auuuaacaga aaaacacaaa auuucaacca    1850
uucuuaaugu uacguccucc ccccaccccc uucuuucagu gguaugcaac    1900
cacugcaauc acugugcaua ugucuuuucu uagcaaaagg auuuuaaaac    1950
uugagcccug gaccuuuugu ccuaugugug uggauuccag ggcaacucua    2000
gcaucagagc aaaagccuug gguuucucgc auucaguggc cuaucuccag    2050
auugucugau uucugaaugu aaaguuguug uguuuuuuuu uaaauaguag    2100
uuuguaguau uuuaaagaaa gaacagaucg aguucuaauu augaucuagc    2150
```

-continued uugauuuugu guugauccaa auuugcauag cuguuuaaug uuaagucaug 2200
acaauuuauu uuucuuggca ugcuauguaa acuugaauuu ccuauguauu 2250
uuuauugugg uguuuuaaau auggggaggg guauugagca uuuuuuaggg 2300
agaaaaauaa auauaugcug uaguggccac aaauaggccu augauuuagc 2350
uggcaggcca gguuuucuca agagcaaaau cacccucugg ccccuuggca 2400
gguaaggccu cccggucagc auuauccugc cagaccucgg ggaggauacc 2450
ugggagacag aagccucugc accuacugug cagaacucuc cacuucccca 2500
acccucccca ggugggcagg gcggagggag ccucagccuc cuuagacuga 2550
ccccucaggc cccuaggcug gggggguugua aauaacagca gucagguugu 2600
uuaccagccc uuugcaccuc cccaggcaga gggagccucu guucuggugg 2650
gggccaccuc ccucagaggc ucugcuagcc acacuccgug gcccacccuu 2700
uguuaccagu ucuuccuccu uccucuuuuc cccugccuuu cucauuccuu 2750
ccuucgucuc ccuuuuuguu ccuuugccuc uugccugucc ccuaaaacuu 2800
gacuguggca cucaggguca aacagacuau ccauucccca gcaugaaugu 2850
gccuuuuaau uagugaucua gaaagaaguu cagccgaacc cacaccccaa 2900
cucccuccca agaacuucgg ugccuaaagc cuccuguucc accucagguu 2950
uucacaggug cucccacccc aguugaggcu cccacccaca gggcugucug 3000
ucacaaaccc accucuguug ggagcuauug agccaccugg gaugagauga 3050
cacaaggcac uccuaccacu gagcgccuuu gccaggucca gccugggcuc 3100
agguuccaag acucagcugc cuaaucccag gguugagccu ugugcucgug 3150
gcggacccca aaccacugcc cuccugggua ccagcccuca guguggaggc 3200
ugagcuggug ccuggcccca gucuuaucug ugccuuuacu gcuuugcgca 3250
ucucagaugc uaacuugguu cuuuuuccag aagccuuugu auugguuaaa 3300
aauuauuuuc cauugcagaa gcagcuggac uaugcaaaaa guauuucucu 3350
gucaguuccc cacucuauac caaggauauu auuaaaacua gaaaugacug 3400
cauugagagg gaguuguggg aaauaagaag aaugaaagcc ucucuuucug 3450
uccgcagauc cugacuuuuc caaagugccu uaaaagaaau cagacaaaug 3500
cccugagugg uaacuucugu guuauuuuac ucuuaaaacc aaacucuacc 3550
uuuucuuguu guuuuuuuuu uuuuuuuuuu uuuuuuuuug guuaccuucu 3600
cauucauguc aaguaugugg uucauucuua gaaccaaggg aaauacugcu 3650
ccccccauuu gcugacguag ugcucucaug ggcucaccug ggcccaaggc 3700
acagccaggg cacaguuagg ccuggauguu ugccuggucc gugagaugcc 3750
gcggguccug uuuccuuacu ggggauuuca gggcuggggg uucagggagc 3800
auuuccuuuu ccugggaguu augaccgcga aguugucaug ugccgugccc 3850
uuuucuguuu cuguguaucc uauugcuggu gacucugugu gaacuggccu 3900
uugggaaaga ucagagaggg cagagguggc acaggacagu aaaggagaug 3950
cugugcuggc cuucagccug gacagggucu cugcugacug ccaggggcgg 4000
gggcucugca uagccaggau gacggcuuuc augucccaga gaccuguugu 4050
gcuguguauu uugauuuccu guguaugcaa augugugugauu uuaccauugu 4100 guagggggcu gugucugauc uuggguguca aaacagaacu guauuuuugc 4150
cuuuaaaauu aaauaauaua acgugaauaa augacccuau cuuuguaaca 4200
aaaaaaaaaa aaaa 4214

<210> SEQ ID NO 4
<211> LENGTH: 4214
<212> TYPE: DNA
<213> ORGANISM: Homo sapien
<220> FEATURE:
<223> OTHER INFORMATION: variant B4GALT1 mRNA sequence

<400> SEQUENCE: 4
gcgccucggg cggcuucucg ccgcucccag gucuggcugg cuggaggagu 50
cucagcucuc agccgcucgc ccgcccccgc uccgggcccu ccccuagucg 100
ccgcuguggg gcagcgccug gcgggcggcc cgcgggcggg ucgccucccc 150
uccuguagcc cacacccuuc uuaaagcggc ggcgggaaga ugaggcuucg 200
ggagccgcuc cugagcggca gcgccgcgau gccaggcgcg ucccuacagc 250
gggccugccg ccugcucgug gccgucugcg cucugcaccu uggcgucacc 300
cucguuuacu accuggcugg ccgcgaccug agccgccugc cccaacuggu 350
cggagucucc acaccgcugc agggcggcuc gaacagugcc gccgccaucg 400
ggcaguccuc cggggagcuc cggaccggag gggcccggcc gccgccuccu 450
cuaggcgccu ccucccagcc gcgcccgggu ggcgacucca gcccagucgu 500
ggauucuggc ccuggccccg cuagcaacuu gaccucgguc ccagugcccc 550
acaccaccgc acugucgcug cccgccugcc cugaggaguc cccgcugcuu 600
gugggcccca ugcugauuga guuuaacaug ccuguggacc uggagcucgu 650
ggcaaagcag aacccaaaug ugaagauggg cggccgcuau gcccccaggg 700
acugcgucuc ucccucacaag guggccauca ucauuccauu ccgcaaccgg 750
caggagcacc ucaaguacug gcuauauuau uugcacccag uccugcagcg 800
ccagcagcug gacuauggca ucuauguuau caaccaggcg ggagacacua 850
uauucaaucg ugcuaagcuc cucaauguug gcuuucaaga agccuugaag 900
gacuaugacu acaccugcuu uguguuuagu gacguggacc ucauuccaau 950
gaaugaccau aaugcguaca gguguuuuuc acagccacgg cacauuuccg 1000
uugcaaugga uaaguuugga uucagccuac cuuauguuca guauuuugga 1050
ggugucucug cucuaaguaa acaacaguuu cuaaccauca auggauuucc 1100
uaauaauuau uggggcuggg gaggagaaga ugaugacauu uuuaacagau 1150
uaguuuuuag aggcaugucu auaucucgcc caaaugcugu ggucgggagg 1200
ugucgcauga uccgccacuc aagagacaag aaaaaugaac ccaguccuca 1250
gagguuugac cgaauugcac acacaaagga gacaaugcuc ucugaugguu 1300
ugaacucacu caccuaccag gugcuggaug uacagagaua cccauuguau 1350
acccaaauca caguggacau cgggacaccg agcuagcguu uugguacacg 1400
gauaagagac cugaaauuag ccagggaccu cugcugugug ucucugccaa 1450
ucugcugggc ugguccucu cauuuuuacc agucugagug acaggucccc 1500
uucgcucauc auucagaugg cuuuccagau gaccaggacg agugggauau 1550
uuugccccca acuuggcucg gcaugugaau ucuuagcucu gcaagguguu 1600
uaugccuuug cggguuucuu gauguguucg cagugucacc ccagagucag 1650
aacuguacac aucccaaaau uugguggccg uggaacacau ucccggugau 1700
agaauugcua aauugucgug aaauagguua gaauuuuucu uuaaauuaug 1750
guuuucuuau ucgugaaaau ucggagagug cugcuaaaau uggauuggug 1800
ugaucuuuuu gguaguugua auuuaacaga aaaacacaaa auuucaacca 1850
uucuuaaugu uacguccucc ccccaccccc uucuuucagu gguaugcaac 1900
cacugcaauc acugugcaua ugucuuuucu uagcaaaagg auuuuaaaac 1950
uugagcccug gaccuuuugu ccuaugugug uggauuccag ggcaacucua 2000
gcaucagagc aaaagccuug gguuucucgc auucaguggc cuaucuccag 2050
auugucugau uucugaaugu aaaguuguug uguuuuuuuu uaaauaguag 2100
uuuguaguau uuuaaagaaa gaacagaucg aguucuaauu augaucuagc 2150
uugauuuugu guugauccaa auuugcauag cuguuuaaug uuaagucaug 2200
acaauuuauu uuucuuggca ugcuauguaa acuugaauuu ccuauguauu 2250
uuuauugugg uguuuuaaau auggggaggg guauugagca uuuuuuaggg 2300
agaaaaauaa auauaugcug uaguggccac aaauaggccu augauuuagc 2350
uggcaggcca gguuuucuca agagcaaaau cacccucugg ccccuuggca 2400
gguaaggccu cccggucagc auuauccugc cagaccucgg ggaggauacc 2450
ugggagacag aagccucugc accuacugug cagaacucuc cacuucccca 2500
acccucccca ggugggcagg gcggagggag ccucagccuc cuuagacuga 2550
ccccucaggc cccuaggcug gggguugua aauaacagca gucagguugu 2600
uuaccagccc uuugcaccuc cccaggcaga gggagccucu guucuggugg 2650
gggccaccuc ccucagaggc ucugcuagcc acacuccgug gcccacccuu 2700
uguuaccagu ucuuccuccu uccucuuuuc cccugccuuu cucauuccuu 2750
ccuucgucuc ccuuuuuguu ccuuugccuc uugccugucc ccuaaaacuu 2800
gacuguggca cucaggguca aacagacuau ccauucccca gcaugaaugu 2850
gccuuuuaau uagugaucua gaaagaaguu cagccgaacc cacaccccaa 2900
cuccccucca agaacuucgg ugccuaaagc cuccuguucc accucagguu 2950
uucacaggug cucccacccc aguugaggcu cccacccaca gggcugucug 3000
ucacaaaccc accucuguug ggagcuauug agccaccugg gaugagauga 3050
cacaaggcac uccuaccacu gagcgccuuu gccaggucca gccugggcuc 3100
agguuccaag acucagcugc cuaaucccag gguugagccu ugugcucgug 3150
gcggacccca aaccacugcc cuccugggua ccagcccuca guguggaggc 3200
ugagcuggug ccuggcccca gucuuaucug ugccuuuacu gcuuugcgca 3250
ucucagaugc uaacuugguu cuuuuuccag aagccuuugu auugguuaaa 3300
aauuauuuuc cauugcagaa gcagcuggac uaugcaaaaa guauuucucu 3350
gucaguuccc cacucuauac caaggauauu auuaaaacua gaaaugacug 3400
cauugagagg gaguuguggg aaauaagaag aaugaaagcc ucucuuucug 3450
uccgcagauc cugacuuuuc caaagugccu uaaaagaaau cagacaaaug 3500
cccugagugg uaacuucugu guuauuuuac ucuuaaaacc aaacucuacc 3550
uuuucuuguu guuuuuuuuu uuuuuuuuuu uuuuuuuuug guuaccuucu 3600
cauucauguc aaguaugugg uucauucuua gaaccaaggg aaauacugcu 3650
ccccccauuu gcugacguag ugcucucaug ggcucaccug ggcccaaggc 3700
acagccaggg cacaguuagg ccuggauguu ugccuggucc gugagaugcc 3750
gcggguccug uuuccuuacu ggggauuuca gggcuggggg uucagggagc 3800
auuuccuuuu ccugggaguu augaccgcga aguugucaug ugccgugccc 3850
uuuucuguuu cuguguaucc uauugcuggu gacucugugu gaacuggccu 3900
uugggaaaga ucagagaggg cagagguggc acaggacagu aaaggagaug 3950
cugugcuggc cuucagccug gacagggucu cugcugacug ccaggggcgg 4000
gggcucugca uagccaggau gacggcuuuc augucccaga gaccuguugu 4050
gcuguguauu uugauuuccu guguaugcaa augugugauu uuaccauugu 4100
guagggggcu gugucugauc uuggguguuca aaacagaacu guauuuuugc 4150
cuuuaaaauu aaauaauaua acgugaauaa augacccuau cuuuguaaca 4200
aaaaaaaaaa aaaa 4214

<210> SEQ ID NO 5
<211> LENGTH: 1197
<212> TYPE: DNA
<213> ORGANISM: Homo sapien
<220> FEATURE:
<223> OTHER INFORMATION: wild-type B4GALT1 cDNA sequence

<400> SEQUENCE: 5
atgaggcttc gggagccgct cctgagcggc agcgccgcga tgccaggcgc 50
gtccctacag cgggcctgcc gcctgctcgt ggccgtctgc gctctgcacc 100
ttggcgtcac cctcgtttac tacctggctg gccgcgacct gagccgcctg 150
ccccaactgg tcggagtctc cacaccgctg cagggcggct cgaacagtgc 200
cgccgccatc gggcagtcct ccggggagct ccggaccgga ggggcccggc 250
cgccgcctcc tctaggcgcc tcctcccagc cgcgcccggg tggcgactcc 300
agcccagtcg tggattctgg ccctggcccc gctagcaact tgacctcggt 350
cccagtgccc cacaccaccg cactgtcgct gcccgcctgc cctgaggagt 400
ccccgctgct tgtgggcccc atgctgattg agtttaacat gcctgtggac 450
ctggagctcg tggcaaagca gaacccaaat gtgaagatgg gcggccgcta 500
tgcccccagg gactgcgtct ctcctcacaa ggtggccatc atcattccat 550
tccgcaaccg gcaggagcac ctcaagtact ggctatatta tttgcaccca 600
gtcctgcagc gccagcagct ggactatggc atctatgtta tcaaccaggc 650
gggagacact atattcaatc gtgctaagct cctcaatgtt ggctttcaag 700
aagccttgaa ggactatgac tacacctgct ttgtgtttag tgacgtggac 750
ctcattccaa tgaatgacca taatgcgtac aggtgttttt cacagccacg 800
gcacatttcc gttgcaatgg ataagtttgg attcagccta ccttatgttc 850
agtattttgg aggtgtctct gctctaagta aacaacagtt tctaaccatc 900
aatggatttc ctaataatta ttggggctgg ggaggagaag atgatgacat 950
ttttaacaga ttagttttta gaggcatgtc tatatctcgc ccaaatgctg 1000
tggtcgggag gtgtcgcatg atccgccact caagagacaa gaaaaatgaa 1050
cccaatcctc agaggtttga ccgaattgca cacacaaagg agacaatgct 1100
ctctgatggt ttgaactcac tcacctacca ggtgctggat gtacagagat 1150
acccattgta tacccaaatc acagtggaca tcgggacacc gagctag 1197

<210> SEQ ID NO 6
<211> LENGTH: 1197
<212> TYPE: DNA
<213> ORGANISM: Homo sapien
<220> FEATURE:
<223> OTHER INFORMATION: variant B4GALT1 cDNA sequence

<400> SEQUENCE: 6
atgaggcttc gggagccgct cctgagcggc agcgccgcga tgccaggcgc 50
gtccctacag cgggcctgcc gcctgctcgt ggccgtctgc gctctgcacc 100
ttggcgtcac cctcgtttac tacctggctg gccgcgacct gagccgcctg 150
ccccaactgg tcggagtctc cacaccgctg cagggcggct cgaacagtgc 200
cgccgccatc gggcagtcct ccggggagct ccggaccgga ggggcccggc 250
cgccgcctcc tctaggcgcc tcctcccagc cgcgcccggg tggcgactcc 300
agcccagtcg tggattctgg ccctggcccc gctagcaact tgacctcggt 350
cccagtgccc cacaccaccg cactgtcgct gcccgcctgc cctgaggagt 400
ccccgctgct tgtgggcccc atgctgattg agtttaacat gcctgtggac 450
ctggagctcg tggcaaagca gaacccaaat gtgaagatgg gcggccgcta 500
tgcccccagg gactgcgtct ctcctcacaa ggtggccatc atcattccat 550
tccgcaaccg gcaggagcac ctcaagtact ggctatatta tttgcaccca 600
gtcctgcagc gccagcagct ggactatggc atctatgtta tcaaccaggc 650
gggagacact atattcaatc gtgctaagct cctcaatgtt ggctttcaag 700
aagccttgaa ggactatgac tacacctgct ttgtgtttag tgacgtggac 750
ctcattccaa tgaatgacca taatgcgtac aggtgttttt cacagccacg 800
gcacatttcc gttgcaatgg ataagtttgg attcagccta ccttatgttc 850
agtattttgg aggtgtctct gctctaagta aacaacagtt tctaaccatc 900
aatggatttc ctaataatta ttggggctgg ggaggagaag atgatgacat 950
ttttaacaga ttagttttta gaggcatgtc tatatctcgc ccaaatgctg 1000
tggtcgggag gtgtcgcatg atccgccact caagagacaa gaaaaatgaa 1050
cccagtcctc agaggtttga ccgaattgca cacacaaagg agacaatgct 1100
ctctgatggt ttgaactcac tcacctacca ggtgctggat gtacagagat 1150
acccattgta tacccaaatc acagtggaca tcgggacacc gagctag 1197

<210> SEQ ID NO 7
<211> LENGTH: 398
<212> TYPE: PRT
<213> ORGANISM: Homo sapien
<220> FEATURE:
<223> OTHER INFORMATION: wild-type B4GALT1 sequence

<400> SEQUENCE: 7

Met Arg Leu Arg Glu Pro Leu Leu Ser Gly Ser Ala Ala Met Pro Gly
1 5 10 15

Ala Ser Leu Gln Arg Ala Cys Arg Leu Leu Val Ala Val Cys Ala Leu
20 25 30

```
His Leu Gly Val Thr Leu Val Tyr Tyr Leu Ala Gly Arg Asp Leu Ser
        35                  40                  45

Arg Leu Pro Gln Leu Val Gly Val Ser Thr Pro Leu Gln Gly Gly Ser
    50                  55                  60

Asn Ser Ala Ala Ala Ile Gly Gln Ser Ser Gly Glu Leu Arg Thr Gly
65                  70                  75                  80

Gly Ala Arg Pro Pro Pro Pro Leu Gly Ala Ser Ser Gln Pro Arg Pro
                85                  90                  95

Gly Gly Asp Ser Ser Pro Val Val Asp Ser Gly Pro Gly Pro Ala Ser
            100                 105                 110

Asn Leu Thr Ser Val Pro Val Pro His Thr Thr Ala Leu Ser Leu Pro
        115                 120                 125

Ala Cys Pro Glu Glu Ser Pro Leu Leu Val Gly Pro Met Leu Ile Glu
    130                 135                 140

Phe Asn Met Pro Val Asp Leu Glu Leu Val Ala Lys Gln Asn Pro Asn
145                 150                 155                 160

Val Lys Met Gly Gly Arg Tyr Ala Pro Arg Asp Cys Val Ser Pro His
                165                 170                 175

Lys Val Ala Ile Ile Ile Pro Phe Arg Asn Arg Gln Glu His Leu Lys
            180                 185                 190

Tyr Trp Leu Tyr Tyr Leu His Pro Val Leu Gln Arg Gln Gln Leu Asp
        195                 200                 205

Tyr Gly Ile Tyr Val Ile Asn Gln Ala Gly Asp Thr Ile Phe Asn Arg
    210                 215                 220

Ala Lys Leu Leu Asn Val Gly Phe Gln Glu Ala Leu Lys Asp Tyr Asp
225                 230                 235                 240

Tyr Thr Cys Phe Val Phe Ser Asp Val Asp Leu Ile Pro Met Asn Asp
                245                 250                 255

His Asn Ala Tyr Arg Cys Phe Ser Gln Pro Arg His Ile Ser Val Ala
            260                 265                 270

Met Asp Lys Phe Gly Phe Ser Leu Pro Tyr Val Gln Tyr Phe Gly Gly
        275                 280                 285

Val Ser Ala Leu Ser Lys Gln Gln Phe Leu Thr Ile Asn Gly Phe Pro
    290                 295                 300

Asn Asn Tyr Trp Gly Trp Gly Gly Glu Asp Asp Asp Ile Phe Asn Arg
305                 310                 315                 320

Leu Val Phe Arg Gly Met Ser Ile Ser Arg Pro Asn Ala Val Val Gly
                325                 330                 335

Arg Cys Arg Met Ile Arg His Ser Arg Asp Lys Lys Asn Glu Pro Asn
            340                 345                 350

Pro Gln Arg Phe Asp Arg Ile Ala His Thr Lys Glu Thr Met Leu Ser
        355                 360                 365

Asp Gly Leu Asn Ser Leu Thr Tyr Gln Val Leu Asp Val Gln Arg Tyr
    370                 375                 380

Pro Leu Tyr Thr Gln Ile Thr Val Asp Ile Gly Thr Pro Ser
385                 390                 395
```

<210> SEQ ID NO 8
<211> LENGTH: 398
<212> TYPE: PRT
<213> ORGANISM: Homo sapien
<220> FEATURE:
<223> OTHER INFORMATION: variant B4GALT1 sequence

<400> SEQUENCE: 8

```
Met Arg Leu Arg Glu Pro Leu Leu Ser Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Ser
        35                  40                  45

Arg Leu Pro Gln Leu Val Gly Val Ser Thr Pro Leu Gln Gly Gly Ser
    50                  55                  60

Asn Ser Ala Ala Ala Ile Gly Gln Ser Ser Gly Glu Leu Arg Thr Gly
65                  70                  75                  80

Gly Ala Arg Pro Pro Pro Pro Leu Gly Ala Ser Ser Gln Pro Arg Pro
                85                  90                  95

Gly Gly Asp Ser Ser Pro Val Val Asp Ser Gly Pro Gly Pro Ala Ser
            100                 105                 110

Asn Leu Thr Ser Val Pro Val Pro His Thr Thr Ala Leu Ser Leu Pro
        115                 120                 125

Ala Cys Pro Glu Glu Ser Pro Leu Leu Val Gly Pro Met Leu Ile Glu
    130                 135                 140

Phe Asn Met Pro Val Asp Leu Glu Leu Val Ala Lys Gln Asn Pro Asn
145                 150                 155                 160

Val Lys Met Gly Gly Arg Tyr Ala Pro Arg Asp Cys Val Ser Pro His
                165                 170                 175

Lys Val Ala Ile Ile Ile Pro Phe Arg Asn Arg Gln Glu His Leu Lys
            180                 185                 190

Tyr Trp Leu Tyr Tyr Leu His Pro Val Leu Gln Arg Gln Gln Leu Asp
        195                 200                 205

Tyr Gly Ile Tyr Val Ile Asn Gln Ala Gly Asp Thr Ile Phe Asn Arg
    210                 215                 220

Ala Lys Leu Leu Asn Val Gly Phe Gln Glu Ala Leu Lys Asp Tyr Asp
225                 230                 235                 240

Tyr Thr Cys Phe Val Phe Ser Asp Val Asp Leu Ile Pro Met Asn Asp
                245                 250                 255

His Asn Ala Tyr Arg Cys Phe Ser Gln Pro Arg His Ile Ser Val Ala
            260                 265                 270

Met Asp Lys Phe Gly Phe Ser Leu Pro Tyr Val Gln Tyr Phe Gly Gly
        275                 280                 285

Val Ser Ala Leu Ser Lys Gln Gln Phe Leu Thr Ile Asn Gly Phe Pro
    290                 295                 300

Asn Asn Tyr Trp Gly Trp Gly Gly Glu Asp Asp Asp Ile Phe Asn Arg
305                 310                 315                 320

Leu Val Phe Arg Gly Met Ser Ile Ser Arg Pro Asn Ala Val Val Gly
                325                 330                 335

Arg Cys Arg Met Ile Arg His Ser Arg Asp Lys Lys Asn Glu Pro Ser
            340                 345                 350

Pro Gln Arg Phe Asp Arg Ile Ala His Thr Lys Glu Thr Met Leu Ser
        355                 360                 365

Asp Gly Leu Asn Ser Leu Thr Tyr Gln Val Leu Asp Val Gln Arg Tyr
    370                 375                 380

Pro Leu Tyr Thr Gln Ile Thr Val Asp Ile Gly Thr Pro Ser
385                 390                 395
```

<210> SEQ ID NO 9
<211> LENGTH: 20

<212> TYPE: DNA
<213> ORGANISM: Artificial Sequence
<220> FEATURE:
<223> OTHER INFORMATION: guide RNA recognition sequences

<400> SEQUENCE: 9
attagttttt agaggcatgt 20

<210> SEQ ID NO 10
<211> LENGTH: 20
<212> TYPE: DNA
<213> ORGANISM: Artificial Sequence
<220> FEATURE:
<223> OTHER INFORMATION: guide RNA recognition sequences

<400> SEQUENCE: 10
ggctctcagg ccaagtgtat 20

<210> SEQ ID NO 11
<211> LENGTH: 20
<212> TYPE: DNA
<213> ORGANISM: Artificial Sequence
<220> FEATURE:
<223> OTHER INFORMATION: guide RNA recognition sequences

<400> SEQUENCE: 11
tactccttcc ccctttagga 20

<210> SEQ ID NO 12
<211> LENGTH: 20
<212> TYPE: DNA
<213> ORGANISM: Artificial Sequence
<220> FEATURE:
<223> OTHER INFORMATION: guide RNA recognition sequences

<400> SEQUENCE: 12
gtccgaggct ctgggcctag 20

<210> SEQ ID NO 13
<211> LENGTH: 6
<212> TYPE: DNA
<213> ORGANISM: Artificial Sequence
<220> FEATURE:
<223> OTHER INFORMATION: PAM for Cas9 from S. aureus
<220> FEATURE:
<221> NAME/KEY: n is A, G, C, or T
<222> LOCATION: (1) .. (2)
<220> FEATURE:
<221> NAME/KEY: r is A or G
<222> LOCATION: (4) .. (5)

<400> SEQUENCE: 13 nngrrt 6

<210> SEQ ID NO 14
<211> LENGTH: 5
<212> TYPE: DNA
<213> ORGANISM: Artificial Sequence
<220> FEATURE:
<223> OTHER INFORMATION: PAM for Cas9 from S. aureus
<220> FEATURE:
<221> NAME/KEY: n is A, G, C, or T
<222> LOCATION: (1) .. (2)
<220> FEATURE:
<221> NAME/KEY: r is A or G
<222> LOCATION: (4) .. (5)

<400> SEQUENCE: 14

```
nngrr                                                          5


<210> SEQ ID NO 15
<211> LENGTH: 23
<212> TYPE: DNA
<213> ORGANISM: Artificial Sequence
<220> FEATURE:
<223> OTHER INFORMATION: target motif preceding NGG recognized by Cas9
      protein
<220> FEATURE:
<221> NAME/KEY: n is A, G, C, or T
<222> LOCATION: (2) .. (21)

<400> SEQUENCE: 15

gnnnnnnnnn nnnnnnnnnn ngg                                     23


<210> SEQ ID NO 16
<211> LENGTH: 23
<212> TYPE: DNA
<213> ORGANISM: Artificial Sequence
<220> FEATURE:
<223> OTHER INFORMATION: target motif preceding NGG recognized by Cas9
      protein
<220> FEATURE:
<221> NAME/KEY: n is A, G, C, or T
<222> LOCATION: (1) .. (21)

<400> SEQUENCE: 16

nnnnnnnnnn nnnnnnnnnn ngg                                     23


<210> SEQ ID NO 17
<211> LENGTH: 25
<212> TYPE: DNA
<213> ORGANISM: Artificial Sequence
<220> FEATURE:
<223> OTHER INFORMATION: RNA recognition sequence
<220> FEATURE:
<221> NAME/KEY: n is A, G, C, or T
<222> LOCATION: (3) .. (23)

<400> SEQUENCE: 17

ggnnnnnnnn nnnnnnnnnn nnngg                                   25
```